US 11,981,914 B2
May 14, 2024

(12) United States Patent
McCoy et al.

(54) RECOMBINANT ADENO-ASSOCIATED VIRUS VECTORS

(71) Applicant: Ginkgo Bioworks, Inc., Boston, MA (US)

(72) Inventors: Daniel McCoy, Durham, NC (US); Garrett E. Berry, Durham, NC (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,334

(22) Filed: Sep. 25, 2023

(65) Prior Publication Data

US 2024/0067986 A1 Feb. 29, 2024

Related U.S. Application Data

(63) Continuation of application No. 17/479,577, filed on Sep. 20, 2021, which is a continuation of application No. PCT/US2020/023877, filed on Mar. 20, 2020.

(60) Provisional application No. 62/821,710, filed on Mar. 21, 2019.

(51) Int. Cl.
| | | |
|---|---|---|
| C12N 15/864 | (2006.01) |
| A61K 48/00 | (2006.01) |
| C07K 14/005 | (2006.01) |
| C12N 7/00 | (2006.01) |
| C12N 9/22 | (2006.01) |
| C12N 15/11 | (2006.01) |
| C12N 15/86 | (2006.01) |

(52) U.S. Cl.
CPC ............ *C12N 15/86* (2013.01); *C07K 14/005* (2013.01); *A61K 48/00* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | |
|---|---|---|
| 4,039,388 A | 8/1977 | Gal et al. |
| 4,501,729 A | 2/1985 | Boucher et al. |
| 4,968,603 A | 11/1990 | Slamon et al. |
| 5,139,941 A | 8/1992 | Muzyczka et al. |
| 5,328,470 A | 7/1994 | Nabel et al. |
| 5,399,346 A | 3/1995 | Anderson et al. |
| 5,478,745 A | 12/1995 | Samulski et al. |
| 5,658,776 A | 8/1997 | Flotte et al. |
| 5,686,240 A | 11/1997 | Schuchman et al. |
| 5,863,541 A | 1/1999 | Samulski et al. |
| 5,869,248 A | 2/1999 | Yuan et al. |
| 5,877,022 A | 3/1999 | Stinchcomb et al. |
| 5,905,040 A | 5/1999 | Mazzara et al. |
| 5,916,563 A | 6/1999 | Young et al. |
| 5,962,313 A | 10/1999 | Podsakoff et al. |
| 6,013,487 A | 1/2000 | Mitchell |
| 6,040,183 A | 3/2000 | Ferrari et al. |
| 6,083,702 A | 7/2000 | Mitchell et al. |
| 6,093,570 A | 7/2000 | Ferrari et al. |
| 6,156,303 A | 12/2000 | Russell et al. |
| 6,180,613 B1 | 1/2001 | Kaplitt et al. |
| 6,426,198 B1 | 7/2002 | Carstea et al. |
| 6,468,524 B1 | 10/2002 | Chiorini et al. |
| 6,468,798 B1 | 10/2002 | Debs et al. |
| 6,503,888 B1 | 1/2003 | Kaplitt et al. |
| 6,544,785 B1 | 4/2003 | Palese et al. |
| 6,562,958 B1 | 5/2003 | Breton et al. |
| 6,733,757 B2 | 5/2004 | Patel et al. |
| 6,822,071 B1 | 11/2004 | Stephens et al. |
| 6,962,815 B2 | 11/2005 | Bartlett |
| 6,984,517 B1 | 1/2006 | Chiorini et al. |
| 7,045,675 B2 | 5/2006 | Carstea et al. |
| 7,071,172 B2 | 7/2006 | McCown et al. |
| 7,105,345 B2 | 9/2006 | Wilson et al. |
| 7,198,951 B2 | 4/2007 | Gao et al. |
| 7,201,898 B2 | 4/2007 | Monahan et al. |
| 7,214,786 B2 | 5/2007 | Kovalic et al. |
| 7,252,997 B1 | 8/2007 | Hallek et al. |
| 7,259,151 B2 | 8/2007 | Arbetman et al. |
| 7,282,199 B2 | 10/2007 | Gao et al. |
| 7,314,912 B1 | 1/2008 | Hallek et al. |
| 7,473,531 B1 | 1/2009 | Domon et al. |
| 7,588,772 B2 | 9/2009 | Kay et al. |
| 7,712,893 B2 | 5/2010 | Dobashi |
| 7,718,424 B2 | 5/2010 | Chiorini et al. |
| 7,749,492 B2 | 7/2010 | Bartlett et al. |

(Continued)

FOREIGN PATENT DOCUMENTS

| | | |
|---|---|---|
| EP | 1033405 A2 | 9/2000 |
| EP | 1777296 A2 | 4/2007 |

(Continued)

OTHER PUBLICATIONS

ACS on STN, BD Registry, 1182714-10-8 [online] [retrieved on Apr. 30, 2019], 2009215879, Aug. 27, 2009, SEQ ID No. 7, 1 page.

(Continued)

*Primary Examiner* — Maria Marvich
(74) *Attorney, Agent, or Firm* — Foley Hoag LLP; Brendan T. Jones; Tracy L. Vrablik

(57) ABSTRACT

AAV capsid proteins comprising a modification in the amino acid sequence and virus vectors comprising the modified AAV capsid protein are described. Also described are methods of administering the virus vectors and virus capsids to a cell or to a subject in vivo.

20 Claims, 9 Drawing Sheets

Specification includes a Sequence Listing.

(56) References Cited

U.S. PATENT DOCUMENTS

| | | |
|---|---|---|
| 7,777,097 B2 | 8/2010 | Glazebrook et al. |
| 7,790,449 B2 | 9/2010 | Gao et al. |
| 7,867,484 B2 | 1/2011 | Samulski et al. |
| 7,892,809 B2 | 2/2011 | Bowles et al. |
| 7,906,111 B2 | 3/2011 | Wilson et al. |
| 8,067,014 B2 | 11/2011 | Kay et al. |
| 8,299,321 B2 | 10/2012 | Cao |
| 8,318,480 B2 | 11/2012 | Gao et al. |
| 8,343,764 B2 | 1/2013 | Abad et al. |
| 8,445,267 B2 | 5/2013 | Zhong et al. |
| 8,628,966 B2 | 1/2014 | Chatterjee et al. |
| 8,664,475 B2 | 3/2014 | Puzio et al. |
| 8,679,837 B2 | 3/2014 | Zolotukhin et al. |
| 8,734,809 B2 | 5/2014 | Gao et al. |
| 8,802,440 B2 | 8/2014 | Zhong et al. |
| 8,889,641 B2 | 11/2014 | Asokan et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,952,217 B2 | 2/2015 | Puzio et al. |
| 8,962,332 B2 | 2/2015 | Gao et al. |
| 9,012,224 B2 | 4/2015 | Bowles et al. |
| 9,066,966 B2 | 6/2015 | Puccio et al. |
| 9,157,098 B2 | 10/2015 | Zhong et al. |
| 9,409,953 B2 | 8/2016 | Asokan et al. |
| 9,441,244 B2 | 9/2016 | Schaffer et al. |
| 9,475,845 B2 | 10/2016 | Asokan et al. |
| 9,567,376 B2 | 2/2017 | Cronin et al. |
| 9,585,971 B2 | 3/2017 | Deverman et al. |
| 9,587,250 B2 | 3/2017 | Gao et al. |
| 9,598,468 B2 | 3/2017 | Weigel-Van Aken et al. |
| 9,611,302 B2 | 4/2017 | Srivastava et al. |
| 9,623,120 B2 | 4/2017 | Chatterjee et al. |
| 9,677,088 B2 | 6/2017 | Nakai et al. |
| 9,677,089 B2 | 6/2017 | Gao et al. |
| 9,683,268 B2 | 6/2017 | Barouch et al. |
| 9,695,220 B2 | 7/2017 | Vandenberghe et al. |
| 9,719,070 B2 | 8/2017 | Vandenberghe et al. |
| 9,725,485 B2 | 8/2017 | Srivastava et al. |
| 9,737,618 B2 | 8/2017 | Wilson et al. |
| 9,737,619 B2 | 8/2017 | Ansell et al. |
| 9,775,918 B2 | 10/2017 | Zhong et al. |
| 9,777,291 B2 | 10/2017 | Chatterjee et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 9,834,789 B2 | 12/2017 | Chatterjee et al. |
| 9,839,696 B2 | 12/2017 | Chatterjee et al. |
| 9,879,275 B2 | 1/2018 | Nadzan et al. |
| 9,890,396 B2 | 2/2018 | Chatterjee et al. |
| 9,909,142 B2 | 3/2018 | Yazicioglu et al. |
| 9,920,097 B2 | 3/2018 | Zhong et al. |
| 9,944,908 B2 | 4/2018 | Vatèn et al. |
| 9,976,157 B2 | 5/2018 | Poraty-Gavra et al. |
| 10,011,640 B2 | 7/2018 | Srivastava et al. |
| 10,072,251 B2 | 9/2018 | Gao et al. |
| 10,077,291 B2 | 9/2018 | Asokan et al. |
| 10,081,659 B2 | 9/2018 | Chiorini et al. |
| 10,119,125 B2 | 11/2018 | Vandenberghe et al. |
| 10,214,566 B2 | 2/2019 | Schaffer et al. |
| 10,337,027 B2 | 7/2019 | Puccio et al. |
| 10,369,193 B2 | 8/2019 | Passini et al. |
| 10,385,320 B2 | 8/2019 | Kay et al. |
| 10,392,632 B2 | 8/2019 | Wright et al. |
| 10,406,244 B2 | 9/2019 | Kay et al. |
| 10,414,803 B2 | 9/2019 | Nathwani et al. |
| 10,426,844 B2 | 10/2019 | Agbandje-McKenna et al. |
| 10,526,627 B2 | 1/2020 | Skuratowicz et al. |
| 10,668,094 B2 | 6/2020 | Karlish et al. |
| 10,745,447 B2 | 8/2020 | Asokan et al. |
| 10,907,176 B2 | 2/2021 | Asokan et al. |
| 11,077,128 B2 | 8/2021 | Karlish et al. |
| 2002/0192189 A1 | 12/2002 | Xiao et al. |
| 2003/0017131 A1 | 1/2003 | Park et al. |
| 2003/0053990 A1 | 3/2003 | Rabinowitz et al. |
| 2003/0225017 A1 | 12/2003 | Murdin et al. |
| 2004/0013645 A1 | 1/2004 | Monahan et al. |
| 2004/0031072 A1 | 2/2004 | La Rosa et al. |
| 2004/0071659 A1 | 4/2004 | Chang et al. |
| 2004/0166519 A1 | 8/2004 | Cargill et al. |
| 2004/0214272 A1 | 10/2004 | La Rosa et al. |
| 2005/0287122 A1 | 12/2005 | Bartlett et al. |
| 2006/0107345 A1 | 5/2006 | Alexandrov et al. |
| 2006/0123505 A1 | 6/2006 | Kikuchi et al. |
| 2006/0171926 A1 | 8/2006 | Passini et al. |
| 2006/0236419 A1 | 10/2006 | La Rosa et al. |
| 2007/0015238 A1 | 1/2007 | Snyder et al. |
| 2007/0124833 A1 | 5/2007 | Abad et al. |
| 2007/0196338 A1 | 8/2007 | Samulski et al. |
| 2007/0243526 A1 | 10/2007 | Kay et al. |
| 2008/0229439 A1 | 9/2008 | La Rosa et al. |
| 2009/0215879 A1 | 8/2009 | Diprimio et al. |
| 2009/0221620 A1 | 9/2009 | Luke et al. |
| 2009/0275107 A1 | 11/2009 | Lock et al. |
| 2009/0317417 A1 | 12/2009 | Vandenberghe et al. |
| 2010/0037352 A1 | 2/2010 | Alexandrov et al. |
| 2010/0047174 A1 | 2/2010 | Kay et al. |
| 2010/0095387 A1 | 4/2010 | Smith et al. |
| 2011/0061124 A1 | 3/2011 | Nadzan et al. |
| 2011/0067143 A2 | 3/2011 | Rosa et al. |
| 2011/0124048 A1 | 5/2011 | Yun |
| 2011/0131679 A2 | 6/2011 | La Rosa et al. |
| 2011/0209246 A1 | 8/2011 | Kovalic et al. |
| 2011/0214206 A1 | 9/2011 | La Rosa et al. |
| 2011/0236353 A1 | 9/2011 | Wilson et al. |
| 2011/0294218 A1 | 12/2011 | Chatterjee et al. |
| 2012/0009268 A1 | 1/2012 | Asokan et al. |
| 2012/0137379 A1 | 5/2012 | Gao et al. |
| 2012/0216318 A1 | 8/2012 | La Rosa et al. |
| 2012/0255046 A1 | 10/2012 | Kay et al. |
| 2012/0322861 A1 | 12/2012 | Byrne et al. |
| 2013/0096182 A1 | 4/2013 | Chatterjee et al. |
| 2013/0152224 A1 | 6/2013 | Abad et al. |
| 2013/0185831 A1 | 7/2013 | Kovalic et al. |
| 2013/0195801 A1 | 8/2013 | Gao et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0225666 A1 | 8/2013 | Kaspar et al. |
| 2013/0326723 A1 | 12/2013 | La Rosa et al. |
| 2014/0017212 A1 | 1/2014 | Rebar |
| 2014/0037585 A1 | 2/2014 | Wright et al. |
| 2014/0050701 A1 | 2/2014 | Zhong et al. |
| 2014/0056854 A1 | 2/2014 | Asokan et al. |
| 2014/0057969 A1 | 2/2014 | Frost et al. |
| 2014/0130203 A1 | 5/2014 | La Rosa et al. |
| 2014/0162319 A2 | 6/2014 | Hareendran et al. |
| 2014/0199313 A1 | 7/2014 | Plesch et al. |
| 2014/0223605 A1 | 8/2014 | Puzio et al. |
| 2014/0259218 A1 | 9/2014 | Kovalic et al. |
| 2014/0296486 A1 | 10/2014 | Gao et al. |
| 2014/0335054 A1 | 11/2014 | Gao et al. |
| 2014/0341852 A1 | 11/2014 | Srivastava et al. |
| 2015/0050302 A1 | 2/2015 | Thess |
| 2015/0079038 A1 | 3/2015 | Deverman et al. |
| 2015/0082481 A1 | 3/2015 | La Rosa et al. |
| 2015/0126588 A1 | 5/2015 | Nakai et al. |
| 2015/0133530 A1 | 5/2015 | Srivastava et al. |
| 2015/0184189 A1 | 7/2015 | Abad et al. |
| 2015/0191739 A1 | 7/2015 | La Rosa et al. |
| 2015/0197763 A1 | 7/2015 | La Rosa et al. |
| 2015/0238550 A1 | 8/2015 | McCown et al. |
| 2015/0344911 A1 | 12/2015 | Chatterjee et al. |
| 2016/0017295 A1 | 1/2016 | Schaffer et al. |
| 2016/0025657 A1 | 1/2016 | Shahbazmohamadi et al. |
| 2016/0106865 A1 | 4/2016 | Zhong et al. |
| 2016/0215024 A1 | 7/2016 | Vandenberghe et al. |
| 2016/0222067 A1 | 8/2016 | Gao et al. |
| 2016/0256571 A1 | 9/2016 | Corral-Debrinski et al. |
| 2016/0264984 A1 | 9/2016 | La Rosa et al. |
| 2016/0289275 A1 | 10/2016 | Chiorini et al. |
| 2016/0319294 A1 | 11/2016 | Kovalic et al. |
| 2016/0333372 A1 | 11/2016 | Srivastava et al. |
| 2016/0361439 A1 | 12/2016 | Agbandje-McKenna et al. |

(56) References Cited

U.S. PATENT DOCUMENTS

| | | |
|---|---|---|
| 2016/0369299 A1 | 12/2016 | Boye et al. |
| 2017/0007720 A1 | 1/2017 | Boye et al. |
| 2017/0028082 A1 | 2/2017 | Wilson et al. |
| 2017/0049910 A1 | 2/2017 | Cronin et al. |
| 2017/0067908 A1 | 3/2017 | Nakai et al. |
| 2017/0088852 A1 | 3/2017 | Dangoor et al. |
| 2017/0088858 A1 | 3/2017 | Gao et al. |
| 2017/0096683 A1 | 4/2017 | Scaria et al. |
| 2017/0130245 A1 | 5/2017 | Kotin et al. |
| 2017/0159027 A1 | 6/2017 | Wilson et al. |
| 2017/0166926 A1 | 6/2017 | Deverman et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0240885 A1 | 8/2017 | Deverman et al. |
| 2017/0275337 A1 | 9/2017 | Srivastava et al. |
| 2017/0298323 A1 | 10/2017 | Vandenberghe et al. |
| 2017/0349911 A1 | 12/2017 | Gao et al. |
| 2018/0002722 A1 | 1/2018 | Asokan et al. |
| 2018/0030096 A1 | 2/2018 | Aslanidi et al. |
| 2018/0030479 A1 | 2/2018 | Gao et al. |
| 2018/0036428 A1 | 2/2018 | Zhong et al. |
| 2018/0066022 A1 | 3/2018 | Chalberg et al. |
| 2018/0066285 A1 | 3/2018 | Ojala et al. |
| 2018/0104289 A1 | 4/2018 | Venditti et al. |
| 2018/0105559 A1 | 4/2018 | Srivastava et al. |
| 2018/0112229 A1 | 4/2018 | Nadzan et al. |
| 2018/0119167 A1 | 5/2018 | Abad et al. |
| 2018/0135074 A1 | 5/2018 | Srivastava et al. |
| 2018/0135076 A1 | 5/2018 | Linden |
| 2018/0163227 A1 | 6/2018 | Chatterjee et al. |
| 2018/0214576 A1 | 8/2018 | Fitzgerald et al. |
| 2018/0244727 A1 | 8/2018 | Zhong et al. |
| 2018/0265863 A1 | 9/2018 | Esteves et al. |
| 2018/0355376 A1 | 12/2018 | Chiorini et al. |
| 2018/0362592 A1 | 12/2018 | Gao et al. |
| 2018/0371024 A1 | 12/2018 | Asokan et al. |
| 2019/0048041 A1 | 2/2019 | Asokan et al. |
| 2019/0055524 A1 | 2/2019 | Vandenberghe et al. |
| 2019/0085301 A1 | 3/2019 | Gao et al. |
| 2019/0100560 A1 | 4/2019 | Vandenberghe et al. |
| 2019/0249195 A1 | 8/2019 | Marsic et al. |
| 2019/0255192 A1 | 8/2019 | Kirn et al. |
| 2019/0262373 A1 | 8/2019 | Woodard et al. |
| 2019/0284576 A1 | 9/2019 | Qu et al. |
| 2019/0292561 A1 | 9/2019 | Qu et al. |
| 2019/0367562 A1 | 12/2019 | Asokan et al. |
| 2020/0109418 A1 | 4/2020 | Li et al. |
| 2020/0399321 A1 | 12/2020 | Asokan et al. |
| 2021/0115474 A1 | 4/2021 | McCoy et al. |
| 2021/0128652 A1 | 5/2021 | Dismuke |
| 2021/0324418 A1 | 10/2021 | Thomas et al. |
| 2022/0056478 A1 | 2/2022 | O'Banion |
| 2022/0088152 A1 | 3/2022 | Mikati et al. |
| 2022/0089651 A1 | 3/2022 | Asokan et al. |

FOREIGN PATENT DOCUMENTS

| | | |
|---|---|---|
| EP | 1887081 A2 | 2/2008 |
| EP | 2194140 A2 | 6/2010 |
| EP | 2359869 A2 | 8/2011 |
| EP | 2492347 A1 | 8/2012 |
| EP | 2660325 A2 | 11/2013 |
| EP | 2315833 B1 | 4/2015 |
| EP | 1453547 B1 | 9/2016 |
| EP | 2007795 B1 | 11/2016 |
| EP | 2675484 B1 | 5/2018 |
| EP | 2263692 B1 | 9/2018 |
| EP | 2206728 B9 | 10/2018 |
| EP | 3244931 B1 | 10/2018 |
| EP | 1633767 B1 | 11/2018 |
| EP | 3060575 B1 | 12/2018 |
| EP | 3250239 B1 | 12/2018 |
| EP | 3459965 A1 | 3/2019 |
| EP | 3511021 A1 | 7/2019 |
| EP | 3108000 B1 | 8/2019 |
| JP | 2014-534245 A | 12/2014 |
| RU | 2457252 C2 | 7/2012 |
| WO | WO-90/05142 A1 | 5/1990 |
| WO | WO-98/11244 A2 | 3/1998 |
| WO | WO-99/01555 A1 | 1/1999 |
| WO | WO-99/61601 A2 | 12/1999 |
| WO | WO-00/17377 A2 | 3/2000 |
| WO | WO-99/61601 A9 | 3/2000 |
| WO | WO-00/23477 A2 | 4/2000 |
| WO | WO-00/28004 A1 | 5/2000 |
| WO | WO-00/28061 A2 | 5/2000 |
| WO | WO-00/28061 A9 | 11/2000 |
| WO | WO-01/11034 A2 | 2/2001 |
| WO | WO-01/81581 A2 | 11/2001 |
| WO | WO-2001/92551 A2 | 12/2001 |
| WO | WO-02/10210 A2 | 2/2002 |
| WO | WO-03/000906 A2 | 1/2003 |
| WO | WO-03/008540 A2 | 1/2003 |
| WO | WO-03/033515 A1 | 4/2003 |
| WO | WO-03/042361 A2 | 5/2003 |
| WO | WO-2003/052051 A2 | 6/2003 |
| WO | WO-03/095647 A2 | 11/2003 |
| WO | WO-2004/027019 A2 | 4/2004 |
| WO | WO-2006/021724 A2 | 3/2006 |
| WO | WO-2006/029319 A2 | 3/2006 |
| WO | WO-2006/066066 A2 | 6/2006 |
| WO | WO-2006/073052 A1 | 7/2006 |
| WO | WO-2006/119137 A1 | 11/2006 |
| WO | WO-2006/119432 A2 | 11/2006 |
| WO | WO-2007/084773 A2 | 7/2007 |
| WO | WO-2007/089632 A2 | 8/2007 |
| WO | WO-2007/092563 A2 | 8/2007 |
| WO | WO-2007/100465 A2 | 9/2007 |
| WO | WO-2007/120542 A2 | 10/2007 |
| WO | WO-2007/127264 A2 | 11/2007 |
| WO | WO-2008/088895 A2 | 7/2008 |
| WO | WO-2009/037279 A1 | 3/2009 |
| WO | WO-2009/043936 A1 | 4/2009 |
| WO | WO-2009/105612 A2 | 8/2009 |
| WO | WO-2009/108274 A2 | 9/2009 |
| WO | WO-2010/093784 A2 | 8/2010 |
| WO | WO-2010/129021 A1 | 11/2010 |
| WO | WO-2010/138263 A2 | 12/2010 |
| WO | WO-2011/020118 A1 | 2/2011 |
| WO | WO-2011/020710 A2 | 2/2011 |
| WO | WO-2011/122950 A1 | 10/2011 |
| WO | WO-2011/133890 A1 | 10/2011 |
| WO | WO-2012/061744 A2 | 5/2012 |
| WO | WO-2012/064960 A2 | 5/2012 |
| WO | WO-2012/112578 A2 | 8/2012 |
| WO | WO-2013/016315 A1 | 1/2013 |
| WO | WO-2013/027223 A2 | 2/2013 |
| WO | WO-2013/158879 A1 | 10/2013 |
| WO | WO-2013/170078 A1 | 11/2013 |
| WO | WO-2013/173512 A2 | 11/2013 |
| WO | WO-2013/190059 A1 | 12/2013 |
| WO | WO-2014/007858 A1 | 1/2014 |
| WO | WO-2014/045674 A1 | 3/2014 |
| WO | WO-2014/124282 A1 | 8/2014 |
| WO | WO-2014/144229 A1 | 9/2014 |
| WO | WO-2014/153083 A1 | 9/2014 |
| WO | WO-2014/193716 A2 | 12/2014 |
| WO | WO-2014/194132 A1 | 12/2014 |
| WO | WO-2015/013313 A1 | 1/2015 |
| WO | WO-2015/018860 A1 | 2/2015 |
| WO | WO-2015/038958 A1 | 3/2015 |
| WO | WO-2015/054653 A2 | 4/2015 |
| WO | WO-2015/062516 A1 | 5/2015 |
| WO | WO-2015/121501 A1 | 8/2015 |
| WO | WO-2015/164757 A1 | 10/2015 |
| WO | WO-2015/168666 A2 | 11/2015 |
| WO | WO-2015/181823 A1 | 12/2015 |
| WO | WO-2015/191508 A1 | 12/2015 |
| WO | WO-2016/054557 A1 | 4/2016 |
| WO | WO-2016/065001 A1 | 4/2016 |
| WO | WO-2016/115382 A1 | 7/2016 |

(56) References Cited

FOREIGN PATENT DOCUMENTS

| | | |
|---|---|---|
| WO | WO-2016/115503 A1 | 7/2016 |
| WO | WO-2016/128558 A1 | 8/2016 |
| WO | WO-2016/128559 A1 | 8/2016 |
| WO | WO-2016/134338 A1 | 8/2016 |
| WO | WO-2016/150964 A1 | 9/2016 |
| WO | WO-2016/164642 A1 | 10/2016 |
| WO | WO-2016/172008 A1 | 10/2016 |
| WO | WO-2016/172155 A1 | 10/2016 |
| WO | WO-2016/179644 A1 | 11/2016 |
| WO | WO-2017/015102 A1 | 1/2017 |
| WO | WO-2017/058892 A2 | 4/2017 |
| WO | WO-2017/066764 A2 | 4/2017 |
| WO | WO-2017/070516 A1 | 4/2017 |
| WO | WO-2017/077451 A1 | 5/2017 |
| WO | WO-2017/096164 A1 | 6/2017 |
| WO | WO-2017/106236 A1 | 6/2017 |
| WO | WO-2017/139643 A1 | 8/2017 |
| WO | WO-2017/143100 A1 | 8/2017 |
| WO | WO-2017/147123 A1 | 8/2017 |
| WO | WO-2017/180854 A1 | 10/2017 |
| WO | WO-2017/192750 A1 | 11/2017 |
| WO | WO-2017/201248 A1 | 11/2017 |
| WO | WO-2018/022608 A2 | 2/2018 |
| WO | WO-2018/035213 A1 | 2/2018 |
| WO | WO-2018/049226 A1 | 3/2018 |
| WO | WO-2018/064624 A1 | 4/2018 |
| WO | WO-2018/075798 A1 | 4/2018 |
| WO | WO-2018/119330 A2 | 6/2018 |
| WO | WO-2018/152333 A1 | 8/2018 |
| WO | WO-2018/160582 A1 | 9/2018 |
| WO | WO-2018/170310 A1 | 9/2018 |
| WO | WO-2018/204764 A1 | 11/2018 |
| WO | WO-2018/209154 A1 | 11/2018 |
| WO | WO-2018/226785 A1 | 12/2018 |
| WO | WO-2018/237066 A1 | 12/2018 |
| WO | WO-2019/006418 A2 | 1/2019 |
| WO | WO-2019/025984 A1 | 2/2019 |
| WO | WO-2019/141765 A1 | 7/2019 |
| WO | WO-2019/168961 A1 | 9/2019 |
| WO | WO-2019/169004 A1 | 9/2019 |
| WO | WO-2019/169132 A1 | 9/2019 |
| WO | WO-2019/173434 A1 | 9/2019 |
| WO | WO-2019/173538 A1 | 9/2019 |
| WO | WO-2019/178412 A1 | 9/2019 |
| WO | WO-2019/195423 A1 | 10/2019 |
| WO | WO-2019/195444 A1 | 10/2019 |
| WO | WO-2019/195449 A1 | 10/2019 |
| WO | WO-2020/016318 A1 | 1/2020 |
| WO | WO-2020/106916 A1 | 5/2020 |
| WO | WO-2020/142653 A1 | 7/2020 |
| WO | WO-2020/191300 A1 | 9/2020 |
| WO | WO-2020/232297 A1 | 11/2020 |
| WO | WO-2021/076911 A1 | 4/2021 |
| WO | WO-2021/076925 A1 | 4/2021 |

OTHER PUBLICATIONS

ACS on STN, BD Registry, 1182714-97-1 [online] [retrieved on Apr. 30, 2019], 2009215879, Aug. 27, 2009, SEQ ID No. 210, 1 page.
Adachi et al., "Drawing a high-resolution functional map of adeno-associated virus capsid by massively parallel sequencing," Nature Communications 5(1): 14 pages (2013).
Agbandje et al. "The Structure of Human Parvovirus B19 at 8 A; Resolution" Virology 203(1):106-115 (1994).
Agbandje-McKenna et al. "AAV Capsid Structure and Cell Interactions" Methods in Molecular Biology, 807:47-92 (2011).
Albright et al., "Mapping the Structural Determinants Required for AAVrh.10 Transport across the Blood-Brain Barrier," Molecular Therapy 26(2), p. 1-14 (2017).
Albright, "Modulation of Sialic Acid Dependence Influences the Central Nervous System Transduction Profile of Adeno-associated Viruses," Journal of Virology 93(11), pp. 1-15 (2019).
Altschul et al. "Basic Local Alignment Search Tool" Journal of Molecular Biology 215:403-410 (1990).
Altschul et al. "Local Alignment Statistics" Methods in Enzymology 266:460-480 (1996).
Altschul et al., "Gapped BLAST and PSI-BLAST: a new generation of protein database search programs," Nucleic Acids Res. (1997) 25(17):3389-3402.
Altschul, SF et al., 'Issues in searching molecular sequence databases,' Nat. Genet., vol. 6, pp. 119-129, (Feb. 1994).
Andino et al. "AAV-mediated knockdown of phospholamban leads to improved contractility and calcium handling in cardiomyocytes" The Journal of Gene Medicine 10:132-142 (2008).
Arnold et al., "A calcium responsive element that regulates expression of two calcium binding proteins in Purkinje cells," Proc Natl Acad Sci USA 94(16):8842-8847 (1997).
Arruda et al., "Regional intravascular delivery of AAV-2-F.IX to skeletal muscle achieves longterm correction of hemophilia B in a large animal model," Blood 105:3458-3464 (2005).
Asokan et al. "Adeno-Associated Virus Type 2 Contains an Integrin a5 1 Binding Domain Essential for Viral Cell Entry" Journal of Virology, 80(18):8961-8969 (2006).
Asokan et al., "The AW Vector Toolkit: Poised at the Clinical Crossroads," Molecular Therapy 20(4):699-708 (2012).
Asokan, et al., "Reengineering a receptor footprint of adeno-associated virus enables selective and systemic gene transfer to muscle", Nat Biotechnol, (Jan. 2010); 28(1): 79-82.
Asuri et al., Directed Evolution of adeno-associated Virus for Enhanced Gene Delivery and Gene Targeting in Human Pluripotent Stem Cells, Molecular Therapy, Nature Publishing Group GB 20(2):329-338 (2013).
Ballabh et al. "The blood-brain barrier: an overview: structure, regulation, and clinical implications" Neurobiology of Disease, 16:1-13 (2004).
Bantel-Schaal et al. "Human adeno-Associated Virus Type 5 Is Only Distantly Related to Other Known Primate Helper-Dependent Parvovirus" Journal of Virology 73(2):939-947 (1999).
Bantel-Schaal et al., "Adeno-associated virus type 5 exploits two different entry pathways in human embryo fibroblast," J Virology 73:939 (1999).
Bartlett, JS et al., 'Selective and Rapid Uptake of Adeno-Associated Virus Type 2 in Brain,' Hum. Gene Ther., 9(8):1181-1186, (May 1998).
Bell et al. "Identification of the Galactose Binding Domain of the Adeno-Associated Virus Serotype 9 Capsid" Journal of Virology, 86(13):7326-7333 (2012).
Bennett et al. "AAV6 K531 serves a dual function in selective receptor and antibody ADK6 recognition" Virology, 18:369-376 (2018).
Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).
Bordoli et al. "Protein structure homology modeling using SWISS-MODEL workspace" Nature Protocols, 4(1):1-13 (2008).
Bowie, et al., "Deciphering the Message in Protein Sequences: Tolerance to Amino Acid Substitutions." Science (1990); 247: 1306-1310.
Bowles et al. "Phase 1 Gene Therapy for Duchenne Muscular Dystrophy Using a Translational Optimized AAV Vector" Molecular Therapy, 20(2):443-455 (2012).
Brichard et al. ""The Tyrosinase Gene Codes for an Antigen Recognized by Autologous Cytolytic T Lymphocytes on HLA-AZ Melanomas"" Journal of Experimental Medicine 178:489-495 (1993).
Brown et al. "Chimeric Parvovirus 19 Capsids for the Presentation of Foreign Epitopes" Virology 198(2):477-488 (1994).
Brown et al. "Erythrocyte P Antigen: Cellular Receptor for B19 Parvovirus" Science 262(5130):114-117 (1993).
Carrillo-Tripp et al. "VIPERdb2: an enhanced and web API enabled relational database for structural virology" Nucleic Acids Research, 37:D436-D442 (2009).
Carstea, ED et al. 'Niemann-Pick C1 Disease Gene: Homology to Mediators of Cholesterol Homeostasis,' Science, 277(5323): 228-231 (Jul. 1997).

(56) References Cited

OTHER PUBLICATIONS

Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).
Cearley, C.N. et al. (2008). "Expanded repertoire of AAV vector serotypes mediate unique patterns of transduction in mouse brain," Mol. Ther. 16:1710-1718.
Chai et al., "Nab Escaping AAV Mutants Isolated from Mouse Muscles." Bio Protoc., vol. 98, No. 9, pages Article: e2841 Section on "Procedure" (2018).
Chandler et al., "Systemic AAV9 gene therapy improves the lifespan of mice with Niemann-Pick disease, type C1 ," Human Molecular Genetics 26(1):52-64 (2017).
Chao et al. "Several Log Increase in Therapeutic Transgene Delivery by Distinct Adeno-Associated Viral Serotype Vectors" Molecular Therapy 2(6):619-623 (2000).
Chapman et al. "Structure, Sequence, and Function Correlations among Parvoviruses" Virology 194(2):491-508 (1993).
Chen et al. "Efficient Transduction of Vascular Endothelial Cells with Recombinant Adeno-Associated Virus Serotype 1 and 5 Vectors" Human Gene Therapy, 16(2):235-247 (2005).
Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).
Chiorini et al. "Cloning and Characterization of adeno-Associated Virus Type 5" Journal of Virology 73(2):1309-1319 (1999).
Chiorini et al. "Cloning of adeno-Associated Virus Type 4 (AAV4). and Generation of Recombinant AAV4 Particles" Journal of Virology 71 (9):6823-6833 (1997).
Chipman et al. ""Cryo-electron microscopy studies of empty capsids of human parvovirus 819 complexed with its cellular receptor"" Proceedings of the National Academy of Sciences 93:7502-7506 (1996).
Chirmule et al., "Humoral immunity to adeno-associated virus type 2 vectors following administration to murine and nonhuman primate muscle," Journal of Virology, The American Society for Microbiology, 74(5):2420-2425 (2000).
Choi et al., "Optimization of AAV expression cassettes to improve packaging capacity and transgene expression in neurons," Molecular Brain, Biomed Central Ltd, London UK, 7(1):17 pp. 1-10 (2014).
Choudhury et al., "In Vivo Selection Yields AAV-B1 Capsid for Central Nervous System and Muscle Gene Therapy." Mol Ther, vol. 24, No. 7, pp. 1247-1257 (2016).
Clapcote SJ, et al., "Mutation 1810N in the alpha3 isoform of Na+, K+-ATPase causes impairments in the sodium pump and hyperexcitability in the CNS," Proc Natl Acad Sci USA. 106(33):14085-14090 (2009).
Clark, KR et al., 'Highly Purified Recombinant Adeno-Associated Virus Vectors Are Biologically Active and Free of Detectable Helper and Wild-Type Viruses,' Hum. Gene Ther., 10(6):1031-1039, (Apr. 1999).
Conway et al. "High-titer recombinant adeno-associated virus production utilizing a recombinant herpes simplex virus type 1 vector expressing AAV-2 Rep and Cap" Gene Therapy 6:986-993 (1999).
Corpet et al., 'Multiple sequence alignment with hierarchical clustering,' Nucleic Acids Research, vol. 16 No. 22, pp. 10881-10890, (Oct. 1988).
Cotmore et al.,"The Family Parvoviridae," Archives of Virology 159:1239-1247 (2014).
DataBase GenBank: ABS91093.1, Aug. 10, 2007, [online] [retrieved on Feb. 14, 2020] Retrieved from Internet: https://www.ncbi.nlm.nih.gov/protein/ABS91093.1.
DataBase GenBank: ACW56705.1, Sep. 24, 2009, [online] [retrieved on May 7, 2019] Retrieved from Internet:https://www.ncbi.nlm.nih.gov/protein/ACW56705.1?report=genbank&log$=prottop&blast_rank= 1&RID=D2CZ8TP9014, 1 page.

De Jesus et al., "Telomerase gene therapy in adult and old mice delays aging and increases longevity without increasing cancer," EMBO Mol. Med. 4(8): 691-704 (2012).
Devereux et al. "A comprehensive set of sequence analysis programs for the VAX" Nucleic Acids Research 12(1):387-395 (1984).
Deverman, BE, Cre-dependent selection yields AAV variants for widespread gene transfer to the adult brain, Nat. Biotechnol., 34(2) :204-209. doi: 10.1038/nbt.3440. PubMed PMID: 26829320 (Epub Feb. 1, 2016).
Dimattia et al. "Structural Insight into the Unique Properties of Adeno-Associated Virus Serotype 9," Journal of Virology, 86(12):6947-6958 (2012).
Dipasquale et al. "Identification of PDGFR as a receptor for MV-5 transduction" Nature Medicine, 9:1306-1312 (2003). (Abstract only).
Diprimio, et al., "Surface loop dynamics in adeno-associated virus capsid assembly", Journal of Virology (2008); vol. 82, No. 11, pp. 5178-5189.
Emsley et al. "Features and development of Coot" Acta Crystallographica Section D: Biological Crystallography, D66:486-501 (2010).
Fang et al., "Stable antibody expression at therapeutic levels using the 2A peptide," Nature Biotechnology 23:584-590 (2005).
Felsenstein, Joseph "Confidence Limits on Phylogenies: An Approach Using the Bootstrap" Evolution, 39 (4):783-791 (1985).
Fisher, KJ et al., 'Transduction with Recombinant Adeno-Associated Virus for Gene Therapy Is Limited by Leading-Strand Synthesis,' J. Virol., 70(1):520-532 (LFU assay) (Jan. 1996).
Foster et al., "Emerging Immunotherapies for Autoimmune Kidney Disease," Hyman Vaccines & Immunotherapeutics 15(4):876-890 (2019).
Foust et al. "Intravascular AAV9 preferentially targets neonatal neurons and adult astrocytes" Nature Biotechnology, 27(1):59-65 (2009).
Gao et al. "Adeno-associated viruses undergo substantial evolution in primates during natural infections" Proceedings of the National Academy of Sciences, 100(10):6081-6086 (2003).
Gao et al. "Clades of adeno-Associated Viruses are Widely Disseminated in Human Tissues" Journal of Virology 78(12):6381-6388 (2004).
Gao et al. "Novel adeno-associated viruses from Rhesus Monkeys as Vectors for human gene therapy," Proceedings of the National Academy of Sciences 99(18):11854-11859 (2002).
Genbank Accession No. AAR26465, Bovine Adeno-Associated Virus, dated May 25, 2004, 2 pages.
Genbank Accession No. AAT46339, capsid protein [Adeno-associated virus 11], dated Nov. 30, 2004, 2 pages.
Genbank Accession No. ABI16639, VP1 [Adeno-associated virus 12, dated Feb. 20, 2008, 2 pages.
GenBank Accession No. AF028704 "Adeno-associated virus 6, complete genome," Jan. 12, 1998 [online]. (Retrieved online Feb. 21, 2019].
GenBank Accession No. AF028705 "adeno-associated Virus 3B, complete genome" NCBI (2 pages). (Jan. 12, 1998).
GenBank Accession No. AF043303 "Adeno-associated virus 2, complete genome," May 20, 2010 [online]. (Retrieved online Feb. 21, 2019].
Genbank Accession No. AF085716, Adeno-associated virus 5 DNA binding trs helicase (Rep22) and capsid protein (VP1) genes, complete cds., dated Feb. 9, 1999, 3 pages.
GenBank Accession No. AF258783.1 'Felis catus Niemann-Pick type C1 disease protein (NPC1) mRNA, complete eds' (2000).
GenBank Accession No. AF288061 "Hamster parvovirus 5' terminal hairpin gene sequence" NCBI (1 page). (Apr. 13, 2001), replaced by AH009962.
GenBank Accession No. AF513851 "Adeno-associated virus 7 nonstructural protein and capsid protein genes, complete cds," Sep. 5, 2002 [online]. (Retrieved online Feb. 21, 2019].
GenBank Accession No. AF513852 "Adeno-associated virus 8 nonstructural protein and capsid protein genes, complete cds," Sep. 5, 2002 [online]. (Retrieved online Feb. 21, 2019].
GenBank Accession No. AY028223 "B19 Virus isolate patient_A. 1.1 genomic sequence" NCB/ (1 page). (Apr. 16, 2001).

(56) References Cited

OTHER PUBLICATIONS

GenBank Accession No. AY028226 "819 Virus isolate patient_A. 2.1 genomic sequence" NCB/ (1 page). (Apr. 16, 2001).
Genbank Accession No. AY186198, Avian adeno-associated virus Atcc VR-865, complete genome, dated Jun. 5, 2003, 3 pages.
Genbank Accession No. AY242997, Non-Human primate Adeno-associated virus isolate AAVrh.8 capsid protein (VP1) gene, complete cds, dated May 14, 2003, 2 pages.
Genbank Accession No. AY242998, Non-Human primate Adeno-associated virus isolate AAVrh.37 capsid protein (VP1) gene, complete cds, dated May 14, 2003, 2 pages.
Genbank Accession No. AY242999, Non-Human primate Adeno-associated virus isolate AAVrh.36 capsid protein (VP1) gene, complete cds, dated May 14, 2003, 2 pages.
Genbank Accession No. AY243000, Non-Human primate Adeno-associated virus isolate AAVrh.35 capsid protein (VP1) gene, complete cds, dated May 14, 2003, 2 pages.
Genbank Accession No. AY243001, Non-Human Primate Adeno-associated Virus Isolate AAVrh.34 capsid protein (VP1) gene, complete cds., dated May 14, 2003, 2 pages.
Genbank Accession No. AY243002, Non-Human Primate Adeno-associated Virus Isolate AAVrh.33 capsid protein (VP1) gene, complete cds. dated May 14, 2003, 2 pages.
Genbank Accession No. AY243003, Non-Human Primate Adeno-associated Virus Isolate AAVrh.32 capsid protein (VP1) gene, complete cds, dated May 14, 2003, 2 pages.
Genbank Accession No. AY243007, Non-Human Primate Adeno-associated Virus Isolate AAVrh.2 capsid protein (VP1) gene, complete cds, dated May 14, 2003, 2 pages.
Genbank Accession No. AY243013, Non-Human primate Adeno-associated virus isolate AAVrh.13 capsid protein (VP1) gene, complete cds, dated May 14, 2003, 2 pages.
Genbank Accession No. AY243015, Non-Human primate Adeno-associated virus isolate AAVrh.10 capsid protein (VP1) gene, complete cds dated May 14, 2003, 2 pages.
Genbank Accession No. AY243016, Non-Human primate Adeno-associated virus isolate AAVcy.6 capsid protein (VP1) gene, complete cds dated May 14, 2003, 2 pages.
Genbank Accession No. AY243017, Non-Human primate Adeno-associated virus isolate AAVcy.5 capsid protein (VP1) gene, complete cds, dated May 14, 2003, 2 pages.
Genbank Accession No. AY243018, Non-Human primate Adeno-associated virus isolate AAVcy.4 capsid protein (VP1) gene, complete cds, dated May 14, 2003, 2 pages.
Genbank Accession No. AY243019, Non-Human primate Adeno-associated virus isolate AAVcy.3 capsid protein (VP1) gene, complete cds, dated May 14, 2003, 2 pages.
Genbank Accession No. AY243020, Non-Human primate Adeno-associated virus isolate AAVcy.2 capsid protein (VP1) gene, complete cds, dated May 14, 2003, 2 pages.
Genbank Accession No. AY243021, Non-Human primate Adeno-associated virus isolate AAVch.5 capsid protein (VP1) gene, complete cds, dated May 14, 2003, 2 pages.
Genbank Accession No. AY243022, Non-Human primate Adeno-associated virus isolate AAVbb.2 capsid protein (VP1) gene, complete cds, dated May 14, 2003, 2 pages.
Genbank Accession No. AY243023, Non-Human primate Adeno-associated virus isolate AAVbb.1 capsid protein (VP1) gene, complete cds, dated May 14, 2003, 2 pages.
Genbank Accession No. AY388617, Bovine adeno-associated virus, complete genome, dated May 25, 2004, 3 pages.
Genbank Accession No. AY530553, Adeno-associated virus isolate pi.1 capsid protein VP1 (cap) gene, complete cds, dated Jun. 24, 2004, 2 pages.
Genbank Accession No. AY530554, Adeno-associated virus isolate pi.2 capsid protein VP1 (cap) gene, complete cds, dated Jun. 24, 2004, 2 pages.
Genbank Accession No. AY530555, Adeno-associated virus isolate pi.3 capsid protein VP1 (cap) gene, complete cds, dated Jun. 24, 2004, 2 pages.
Genbank Accession No. AY530556, Adeno-associated virus isolate rh.1 capsid protein VP1 (cap) gene, complete cds, dated Jun. 24, 2004, 2 pages.
Genbank Accession No. AY530557, Adeno-associated virus isolate rh.25 capsid protein VP1 (cap) gene, complete cds, dated Jun. 24, 2004, 2 pages.
Genbank Accession No. AY530558, Adeno-associated virus isolate rh.38 capsid protein VP1 (cap) gene, complete cds, dated Jun. 24, 2004, 2 pages.
Genbank Accession No. AY530559, Adeno-associated virus isolate rh.40 capsid protein VP1 (cap) gene, complete cds, dated Jun. 24, 2004, 2 pages.
Genbank Accession No. AY530560, Adeno-associated virus isolate rh.43 capsid protein VP1 (cap) gene, complete cds, dated Jun. 24, 2004, 2 pages.
Genbank Accession No. AY530561, Adeno-associated virus isolate rh.48 capsid protein VP1 (cap) gene, complete cds, dated Jun. 24, 2004, 2 pages.
Genbank Accession No. AY530562, Adeno-associated virus isolate rh.49 capsid protein VP1 (cap) gene, complete cds, dated Jun. 24, 2004, 2 pages.
Genbank Accession No. AY530563, Adeno-associated virus isolate rh.50 capsid protein VP1 (cap) gene, complete cds, dated Jun. 24, 2004, 2 pages.
Genbank Accession No. AY530564, Adeno-associated virus isolate rh.51 capsid protein VP1 (cap) gene, complete cds, dated Jun. 24, 2004, 2 pages.
Genbank Accession No. AY530565, Adeno-associated virus isolate rh.52 capsid protein VP1 (cap) gene, complete cds, dated Jun. 24, 2004, 2 pages.
Genbank Accession No. AY530566, Adeno-associated virus isolate rh.53 capsid protein VP1 (cap) gene, complete cds, dated Jun. 24, 2004, 2 pages.
Genbank Accession No. AY530567, Adeno-associated virus isolate rh.54 capsid protein VP1 (cap) gene, complete cds, dated Jun. 24, 2004, 2 pages.
Genbank Accession No. AY530568, Adeno-associated virus isolate rh.55 capsid protein VP1 (cap) gene, complete cds, dated Jun. 24, 2004, 2 pages.
Genbank Accession No. AY530569, Adeno-associated virus isolate rh.57 capsid protein VP1 (cap) gene, complete cds, dated Jun. 24, 2004, 2 pages.
Genbank Accession No. AY530570, Adeno-associated virus isolate rh.58 capsid protein VP1 (cap) gene, complete cds, dated Jun. 24, 2004, 2 pages.
Genbank Accession No. AY530572, Adeno-associated virus isolate rh.61 capsid protein VP1 (cap) gene, complete cds, dated Jun. 24, 2004, 2 pages.
Genbank Accession No. AY530573, Adeno-associated virus isolate rh.62 capsid protein VP1 (cap) gene, complete cds, dated Jun. 24, 2004, 2 pages.
Genbank Accession No. AY530574, Adeno-associated virus isolate rh.64 capsid protein VP1 (cap) gene, complete cds, dated Jun. 24, 2004, 2 pages.
Genbank Accession No. AY530575, Adeno-associated virus isolate hu.1 capsid protein VP1 (cap) gene, complete cds, dated Jun. 24, 2004, 2 pages.
Genbank Accession No. AY530576, Adeno-associated virus isolate hu.10 capsid protein VP1 (cap) gene, complete cds, dated Jun. 24, 2004, 2 pages.
Genbank Accession No. AY530577, Adeno-associated virus isolate hu.11 capsid protein VP1 (cap) gene, complete cds, dated Jun. 24, 2004, 2 pages.
Genbank Accession No. AY530578, Adeno-associated virus isolate hu.13 capsid protein VP1 (cap) gene, complete cds, dated Jun. 24, 2004, 2 pages.
Genbank Accession No. AY530580, Adeno-associated virus isolate hu.15 capsid protein VP1 (cap) gene, complete cds, dated Jun. 24, 2004, 2 pages.
Genbank Accession No. AY530581, Adeno-associated virus isolate hu.16 capsid protein VP1 (cap) gene, complete cds, dated Jun. 24, 2004, 2 pages.

(56) References Cited

OTHER PUBLICATIONS

Genbank Accession No. AY530582, Adeno-associated virus isolate hu.17 capsid protein VP1 (cap) gene, complete cds, dated Jun. 24, 2004, 2 pages.
Genbank Accession No. AY530583, Adeno-associated virus isolate hu.18 capsid protein VP1 (cap) gene, complete cds, dated Jun. 24, 2004, 2 pages.
Genbank Accession No. AY530584, Adeno-associated virus isolate hu.19 capsid protein VP1 (cap) gene, complete cds, dated Jun. 24, 2004, 2 pages.
Genbank Accession No. AY530585, Adeno-associated virus isolate hu.2 capsid protein VP1 (cap) gene, complete cds, dated Jun. 24, 2004, 2 pages.
Genbank Accession No. AY530586, Adeno-associated virus isolate hu.20 capsid protein VP1 (cap) gene, complete cds, dated Jun. 24, 2004, 2 pages.
Genbank Accession No. AY530587, Adeno-associated virus isolate hu.21 capsid protein VP1 (cap) gene, complete cds, dated Jun. 24, 2004, 2 pages.
Genbank Accession No. AY530588, Adeno-associated virus isolate hu.22 capsid protein VP1 (cap) gene, complete cds, dated Jun. 24, 2004, 2 pages.
Genbank Accession No. AY530589, Adeno-associated virus isolate hu.23 capsid protein VP1 (cap) gene, complete cds, dated Jun. 24, 2004, 2 pages.
Genbank Accession No. AY530590, Adeno-associated virus isolate hu.24 capsid protein VP1 (cap) gene, complete cds, dated Jun. 24, 2004, 2 pages.
Genbank Accession No. AY530591, Adeno-associated virus isolate hu.25 capsid protein VP1 (cap) gene, complete cds, dated Jun. 24, 2004, 2 pages.
Genbank Accession No. AY530592, Adeno-associated virus isolate hu.27 capsid protein VP1 (cap) gene, complete cds, dated Jun. 24, 2004, 2 pages.
Genbank Accession No. AY530593, Adeno-associated virus isolate hu.28 capsid protein VP1 (cap) gene, complete cds, dated Jun. 24, 2004, 2 pages.
Genbank Accession No. AY530594, Adeno-associated virus isolate hu.29 capsid protein VP1 (cap) gene, complete cds, dated Jun. 24, 2004, 2 pages.
Genbank Accession No. AY530595, Adeno-associated virus isolate hu.3 capsid protein VP1 (cap) gene, complete cds, dated Jun. 24, 2004, 2 pages.
Genbank Accession No. AY530596, Adeno-associated virus isolate hu.31 capsid protein VP1 (cap) gene, complete cds, dated Jun. 24, 2004, 2 pages.
Genbank Accession No. AY530597, Adeno-associated virus isolate hu.32 capsid protein VP1 (cap) gene, complete cds, dated Jun. 24, 2004, 2 pages.
Genbank Accession No. AY530598, Adeno-associated virus isolate hu.34 capsid protein VP1 (cap) gene, complete cds, dated Jun. 24, 2004, 2 pages.
Genbank Accession No. AY530599, Adeno-associated virus isolate hu.35 capsid protein VP1 (cap) gene, complete cds, dated Jun. 24, 2004, 2 pages.
Genbank Accession No. AY530600, Adeno-associated virus isolate hu.37 capsid protein VP1 (cap) gene, complete cds, dated Jun. 24, 2004, 2 pages.
Genbank Accession No. AY530601, Adeno-associated virus isolate hu.39 capsid protein VP1 (cap) gene, complete cds, dated Jun. 24, 2004, 2 pages.
Genbank Accession No. AY530602, Adeno-associated virus isolate hu.4 capsid protein VP1 (cap) gene, complete cds, dated Jun. 24, 2004, 2 pages.
Genbank Accession No. AY530603, Adeno-associated virus isolate hu.40 capsid protein VP1 (cap) gene, complete cds, dated Jun. 24, 2004, 2 pages.
Genbank Accession No. AY530604, Adeno-associated virus isolate hu.41 capsid protein VP1 (cap) gene, complete cds, dated Jun. 24, 2004, 2 pages.
Genbank Accession No. AY530605, Adeno-associated virus isolate hu.42 capsid protein VP1 (cap) gene, complete cds, dated Jun. 24, 2004, 2 pages.
Genbank Accession No. AY530606, Adeno-associated virus isolate hu.43 capsid protein VP1 (cap) gene, complete cds, dated Jun. 24, 2004, 2 pages.
Genbank Accession No. AY530607, Adeno-associated virus isolate hu.44 capsid protein VP1 (cap) gene, complete cds, dated Jun. 24, 2004, 2 pages.
Genbank Accession No. AY530608, Adeno-associated virus isolate hu.45 capsid protein VP1 (cap) gene, complete cds, dated Jun. 24, 2004, 2 pages.
Genbank Accession No. AY530609, Adeno-associated virus isolate hu.46 capsid protein VP1 (cap) gene, complete cds, dated Jun. 24, 2004, 2 pages.
Genbank Accession No. AY530610, Adeno-associated virus isolate hu.47 capsid protein VP1 (cap) gene, complete cds, dated Jun. 24, 2004, 2 pages.
Genbank Accession No. AY530611, Adeno-associated virus isolate hu.48 capsid protein VP1 (cap) gene, complete cds, dated Jun. 24, 2004, 4 pages.
Genbank Accession No. AY530612, Adeno-associated virus isolate hu.49 capsid protein VP1 (cap) gene, complete cds, dated Jun. 24, 2004, 2 pages.
Genbank Accession No. AY530613, Adeno-associated virus isolate hu.51 capsid protein VP1 (cap) gene, complete cds, dated Jun. 24, 2004, 2 pages.
Genbank Accession No. AY530614, Adeno-associated virus isolate hu.52 capsid protein VP1 (cap) gene, complete cds, dated Jun. 24, 2004, 2 pages.
Genbank Accession No. AY530615, Adeno-associated virus isolate hu.53 capsid protein VP1 (cap) gene, complete cds, dated Jun. 24, 2004, 2 pages.
Genbank Accession No. AY530616, Adeno-associated virus isolate hu.54 capsid protein VP1 (cap) gene, complete cds, dated Jun. 24, 2004, 2 pages.
Genbank Accession No. AY530617, Adeno-associated virus isolate hu.55 capsid protein VP1 (cap) gene, complete cds, dated Jun. 24, 2004, 2 pages.
Genbank Accession No. AY530618, Adeno-associated virus isolate hu.56 capsid protein VP1 (cap) gene, complete cds, dated Jun. 24, 2004, 2 pages.
Genbank Accession No. AY530619, Adeno-associated virus isolate hu.57 capsid protein VP1 (cap) gene, complete cds, dated Jun. 24, 2004, 2 pages.
Genbank Accession No. AY530620, Adeno-associated virus isolate hu.58 capsid protein VP1 (cap) gene, complete cds, dated Jun. 24, 2004, 2 pages.
Genbank Accession No. AY530621, Adeno-associated virus isolate hu.6 capsid protein VP1 (cap) gene, complete cds, dated Jun. 24, 2004, 2 pages.
Genbank Accession No. AY530622, Adeno-associated virus isolate hu.60 capsid protein VP1 (cap) gene, complete cds, dated Jun. 24, 2004, 2 pages.
Genbank Accession No. AY530623, Adeno-associated virus isolate hu.61 capsid protein VP1 (cap) gene, complete cds, dated Jun. 24, 2004, 2 pages.
Genbank Accession No. AY530624, Adeno-associated virus isolate hu.63 capsid protein VP1 (cap) gene, complete cds, dated Jun. 24, 2004, 2 pages.
Genbank Accession No. AY530625, Adeno-associated virus isolate hu.64 capsid protein VP1 (cap) gene, complete cds, dated Jun. 24, 2004, 2 pages.
Genbank Accession No. AY530626, Adeno-associated virus isolate hu.66 capsid protein VP1 (cap) gene, complete cds, dated Jun. 24, 2004, 2 pages.
Genbank Accession No. AY530627, Adeno-associated virus isolate hu.67 capsid protein VP1 (cap) gene, complete cds, dated Jun. 24, 2004, 2 pages.
Genbank Accession No. AY530628, Adeno-associated virus isolate hu.7 capsid protein VP1 (cap) gene, complete cds, dated Jun. 24, 2004, 2 pages.

(56) References Cited

OTHER PUBLICATIONS

Genbank Accession No. AY530629, Adeno-associated virus isolate hu.9 capsid protein VP1 (cap) gene, complete cds, dated Jun. 24, 2004, 2 pages.
Genbank Accession No. AY629583, Avian adeno-associated virus strain DA-1, complete genome, dated Sep. 10, 2004, 3 pages.
Genbank Accession No. AY631966, Adeno-associated virus 11 nonstructural protein and capsid protein genes, complete cds, dated Nov. 30, 2004, 3 pages.
Genbank Accession No. AY695370, Adeno-associated virus isolate hu.T17 capsid protein VP1 (cap) gene, complete cds, dated Nov. 15, 2005, 3 pages.
Genbank Accession No. AY695371, Adeno-associated virus isolate hu.T32 Rep 78 protein and capsid protein VP1 (cap) genes, complete cds, dated Nov. 15, 2005, 3 pages.
Genbank Accession No. AY695372, Adeno-associated virus isolate hu.T40 Rep 78 protein and capsid protein VP1 (cap) genes, complete cds, dated Nov. 15, 2005, 3 pages.
Genbank Accession No. AY695373, Adeno-associated virus isolate hu.T70 Rep 78 protein and capsid protein VP1 (cap) genes, complete cds, dated Nov. 15, 2005, 3 pages.
Genbank Accession No. AY695374, Adeno-associated virus isolate hu.T32 Rep 71 protein and capsid protein VP1 (cap) genes, complete cds, dated Nov. 15, 2005, 3 pages.
Genbank Accession No. AY695375, Adeno-associated virus isolate hu.T88 Rep 78 protein and capsid protein VP1 (cap) genes, complete cds, dated Nov. 15, 2005, 3 pages.
Genbank Accession No. AY695376, Adeno-associated virus isolate hu.S17 Rep 78 protein and capsid protein VP1 (cap) genes, complete cds, dated Nov. 15, 2005, 3 pages.
Genbank Accession No. AY695377, Adeno-associated virus isolate hu.LG15 capsid protein VP1 (cap) gene, complete cds, dated Nov. 15, 2005, 3 pages.
Genbank Accession No. AY695378, Adeno-associated virus isolate hu.T41 capsid protein VP1 (cap) gene, complete cds, dated Nov. 15, 2005, 2 pages.
GenBank Accession No. BC002532 'Homo sapiens Niemann-Pick disease, type C2, mRNA (cDNA clone MGC:1333 Image:3140870), complete cds' (2006).
GenBank Accession No. BC045895 'Dania rerio Niemann-Pick disease, type C2, mRNA (cDNA clone MGC:56070 Image:5409780), complete cds' (2003).
GenBank Accession No. BC054539 'Mus musculus Niemann Pick type C1, mRNA (cDNA clone MGC:62352 Image:6405214), complete cds' (2006).
GenBank Accession No. BC090541 'Dania rerio Niemann-Pick disease, type C1, mRNA (cDNA clone Image:7149020), partial cds' (2016).
GenBank Accession No. BC102504 'Bos taurus Niemann-Pick disease, type C2, mRNA (cDNA clone MGC:127986 Image:7954223), complete cds' (2007).
GenBank Accession No. BC117178 'Homo sapiens NPC1 (Niemann-Pickdisease, type C1, gene)-like 1, mRNA (cDNA clone MGC:150787 Image:40125729), complete cds' (2006).
GenBank Accession No. BC143756 'Homo sapiens NPC1 (Niemann-Pickdisease, type C1, gene)-like 1, mRNA (cDNA clone MGC:177287 Image:9052270), complete cds' (2009).
GenBank Accession No. BC151276 'Bos taurus Niemann-Pick disease, type C1, mRNA (cDNA clone MGC:152602 Image:8433293), complete cds' (2007).
Genbank Accession No. DQ813647, Adeno-Associated Virus 12 Rep 78 and VP1 genes, complete cds., dated Feb. 20, 2008, 3 pages.
GenBank Accession No. J00306 "Human somatostatin I gene and flanks" NCBJ (2 pages). (Jan. 13, 1995).
GenBank Accession No. J01901 "adeno-associated Virus 2, complete genome" NCBJ (3 pages). (Apr. 27, 1993).
GenBank Accession No. J02275 "Minute Virus of mice, complete genome" NCBJ (4 pages). (May 22, 1995).

GenBank Accession No. KJ893081 'Synthetic construct Homo sapiens clone cosb BroadEn 02475 NPC2 gene, encodes complete protein' (2015).
Genbank Accession No. MI332400.1, Sequence 20 from U.S. Pat. No. 9,839,696, dated Feb. 12, 2018, 2 pages.
Genbank Accession No. MI332401.1, Sequence 21 from U.S. Pat. No. 9,839,696, dated Feb. 12, 2018, 2 pages.
Genbank Accession No. MI332402.1, Sequence 22 from U.S. Pat. No. 9,839,696, dated Feb. 12, 2018, 2 pages.
Genbank Accession No. MI332403.1, Sequence 23 from U.S. Pat. No. 9,839,696, dated Feb. 12, 2018, 2 pages.
Genbank Accession No. MI332404.1, Sequence 24 from U.S. Pat. No. 9,839,696, dated Feb. 12, 2018, 2 pages.
Genbank Accession No. MI332405.1, Sequence 25 from U.S. Pat. No. 9,839,696, dated Feb. 12, 2018, 2 pages.
Genbank Accession No. MI332406.1, Sequence 26 from U.S. Pat. No. 9,839,696, dated Feb. 12, 2018, 2 pages.
Genbank Accession No. MI332407.1, Sequence 27 from U.S. Pat. No. 9,839,696, dated Feb. 12, 2018, 2 pages.
Genbank Accession No. MI332408.1, Sequence 28 from U.S. Pat. No. 9,839,696, dated Feb. 12, 2018, 2 pages.
Genbank Accession No. MI332409.1, Sequence 29 from U.S. Pat. No. 9,839,696, dated Feb. 12, 2018, 2 pages.
Genbank Accession No. MI332410.1, Sequence 30 from U.S. Pat. No. 9,839,696, dated Feb. 12, 2018, 2 pages.
Genbank Accession No. MI332411.1, Sequence 31 from U.S. Pat. No. 9,839,696, dated Feb. 12, 2018, 2 pages.
Genbank Accession No. MI332412.1, Sequence 32 from U.S. Pat. No. 9,839,696, dated Feb. 12, 2018, 2 pages.
Genbank Accession No. MI332413.1, Sequence 33 from U.S. Pat. No. 9,839,696, dated Feb. 12, 2018, 2 pages.
Genbank Accession No. MI332414.1, Sequence 34 from U.S. Pat. No. 9,839,696, dated Feb. 12, 2018, 2 pages.
Genbank Accession No. MI332415.1, Sequence 35 from U.S. Pat. No. 9,839,696, dated Feb. 12, 2018, 2 pages.
GenBank Accession No. NC_000883 "Human parvo Virus 819, complete genome" NCBI (4 pages). (Feb. 10, 2015).
GenBank Accession No. NC_001358 "ParvoVirus H1, complete genome" NCBI (3 pages). (Feb. 10, 2015).
GenBank Accession No. NC_001510 "Minute Virus of mice, complete genome" NCBI (5 pages). (Mar. 28, 2016).
Genbank Accession No. NC_001729, Adeno-associated virus-3, complete genome, dated Aug. 13, 2018, 3 pages.
Genbank Accession No. NC_001829, Adeno-associated virus-4, complete genome, dated Aug. 13, 2018, 3 pages.
Genbank Accession No. NC_001863, Adeno-associated virus 3B, complete genome, dated Jan. 12, 2004, 4 pages.
Genbank Accession No. NC_002077, Adeno-associated virus-1, dated Aug. 13, 2018, 3 pages.
Genbank Accession No. NC_004828, Avian adeno-associated virus ATCC VR-865, complete genome, dated Aug. 13, 2018, 3 pages.
Genbank Accession No. NC_005889, Bovine adeno-associated virus, complete genome, dated Aug. 13, 2018, 3 pages.
Genbank Accession No. NC_006148.1, Snake parvovirus 1, complete genome, dated Aug. 13, 2018, 3 pages.
GenBank Accession No. NC_006152 "adeno-associated Virus 5, complete genome" NCBI (3 pages). (Dec. 8, 2008).
GenBank Accession No. NC_006261 "adeno-associated Virus 8, complete genome" NCBI (3 pages). (Mar. 11, 2010).
Genbank Accession No. NC_006263, Avian adeno-associated virus strain DA-1, complete genome, dated Aug. 13, 2018, 3 pages.
GenBank Accession No. NM 000271.4 Homo sapiens cholesterol transporter 1 (NPC1), mRNA (2017).
GenBank Accession No. NM 008720.2 Mus musculus cholesterol transporter 1 (Npc1), mRNA (2017).
GenBank Accession No. NM 023409.4 Mus musculus NPC intracellular cholesterol transporter 2 (Npc2 mRNA' (2017).
GenBank Accession No. NM 173918 Bos taurus NPC intracellular cholesterol transporter 2 NPC2), mRNA-;-(2017).
GenBank Accession No. NM_006432.3 'Homo sapiens NPC intracellular cholesterol transporter 2 (NPC2), mRNA' (2017).

(56) References Cited

OTHER PUBLICATIONS

GenBank Accession No. NM_214206 "Sus scrofa NPC intracellular cholesterol transporter 2 (NPC2), mRNA," dated Jun. 20, 2021, 2 pages.
GenBank Accession No. NP_044927 "capsid [Adeno-associated Virus-4]" NCBI (2 pages). (Jan. 28, 2010).
GenBank Accession No. P01166 "Somatostatin precursor [Contains: Somatostatin 28; Somatostatin-14]" NCBI (2 pages). (Sep. 15, 2003).
GenBank Accession No. P61278 "Somatostatin precursor [Contains: Somatostatin 28; Somatostatin-14]" NCBI (2 pages). (Nov. 13, 2019).
GenBank Accession No. U89790 "Adeno-associated virus 4, complete genome," Aug. 21, 1997 [online]. (Retrieved online Feb. 21, 2019].
GenBank Accession No. X01457 "Parvovirus h-1, complete genome" NCBI (3 pages). (Apr. 18, 2005).
Genbank Accession No. Y18065, adeno-associated virus type 5 partial genome (cap and rep genes complete), dated Jan. 15, 1999, 3 pages.
GenBank Accession No. AH009962 "Hamster parvovirus" NCBI (1 page). (Aug. 25, 2016), replaced AF288061.
GenBank Accession No. AY530579 "adeno-associated Virus 9 isolate hu.14 capsid protein VP1 (cap). gene, complete eds" NCBI (2 pages). (Jun. 24, 2004).
GenBank Accession No. NC_001401 "adeno-associated Virus-2, complete genome" NCBI (5 pages). (Dec. 2, 2014).
GenBank Accession No. NC_001540 "Bovine parvovirus complete genome" NCBI (4 pages). (Nov. 30, 2009).
GenBank Accession No. NC_001701 "Goose parvovirus, complete genome" NCBI (4 pages). (Jan. 28, 2010).
GenBank Accession No. NC_001729 "adeno-associated virus-3, complete genome" NCBI (3 pages). (Jun. 28, 2010).
GenBank Accession No. NC_001829 "adeno-associated Virus 4, complete genome" NCBI (3 pages). (Jan. 28, 2010).
GenBank Accession No. NC_002077 "adeno-associated Virus-1, complete genome" NCBI (3 pages). (Mar. 11, 2010).
Ghusayni R, et al., ""Magnetic resonance imaging volumetric analysis in patients with Alternating hemiplegia of childhood: A pilot study,"" Eur J Paediatr Neural. 26:15-19 (2020).
Gorman et al. "Stable alteration of pre-mRNA splicing patterns by modified U7 small nuclear RNAs" Proceedings of the National Academy of Sciences 95:4929:4934 (1998).
Govindasamy et al, "Structurally mapping the diverse phenotype of adeno-associated virus serotype 4," J. Virol 80:11556-11570 (2006).
Govindasamy et al., "Structural Insights into Adeno-Associated Virus Serotype 5," J. Virology 87: 11187-11199 (2013).
Gray et al. "Preclinical Differences of Intravascular MV9 Delivery to Neurons and Glia: A Comparative Study of Adult Mice and Nonhuman Primates" Molecular Therapy, 19(6):1058-1069 (2011).
Gregorevic et al. "Systemic Microdystrophin Gene Delivery Improves Skeletal Muscle Structure and Function in Old Dystrophic mdx Mice" Molecular Therapy 16(4):657-664 (2008).
Grieger, et al., "Separate Basic Region Motifs within the Adeno-Associated Virus Capsid Proteins Are Essential for infectivity and Assembly." J. Virol. (2006), 80(11): 5199-5210.
Grifman, et al., "Incorporation of tumor-targeting peptides into recombinant adeno-associated virus capsids". Molecular Therapy (2001); vol. 3, No. 6, pp. 964-975.
Grimm D., et al., "In Vitro and in Vivo Gene Therapy Vector Evolution Via Multispecies Interbreeding and Retargeting of Adeno-Associated Viruses," Journal of Virology, Jun. 2008, vol. 82(12), pp. 5887-5911, XP002610286.
Gurda et al. "Capsid Antibodies to Different adeno-Associated Virus Serotypes Bind Common Regions" Journal of Virology, 87(16):9111-9124 (2013).
Gurda et al., "Mapping a Neutralizing Epitope onto the Capsid of Adeno-Associated Virus Serotype 8," Journal of Virology 86(15): 7739-7751 (2012).

Hadaczek et al. "Transduction of Nonhuman Primate Brain with Adeno-Associated Virus Serotype 1: Vector Trafficking and Immune Response" Human Gene Therapy, 20(3):225-237 (2009).
Hajitou et al., "Vascular targeting: recent advances and therapeutic perspectives," TCM 16:80-88 (2006).
Hauck et al. "Characterization of Tissue Tropism Determinants of Adeno-Associated Virus Type 1" Journal of Virology 77(4):2768-2774 (2003).
Heinzen EL, et al., "De nova mutations in ATP1A3 cause alternating hemiplegia of childhood," Nat Genet. 44 (9):1030-1034 (2012).
Helseth AR, et al., "Novel E815K knock-in mouse model of alternating hemiplegia of childhood," Neurobiol Dis. 119:100-112 (2018).
Higgins, Desmond G., and Sharp, Paul M. "CLUSTAL: a package for performing multiple sequence alignment on a microcomputer." Gene (1988); 73.1: 237-244.
Holm R, et al., "B. Neurological disease mutations of a3 Na+, K+-ATPase: Structural and functional perspectives and rescue of compromised function," Biochim Biophys Acta. 1857(11):1807-1828 (2016).
Hoshijima et al. ""Chronic suppression of heart-failure progression by a pseudophosphorylated mutant of phospholamban via in vivo cardiac rAAV gene delivery"" Nature Medicine 8:864-871 (2002).
Huang et al. "Characterization of the adeno-Associated Virus 1 and 6 Sialic Acid Binding Site" Journal of Virology, 9 (11 ):5219-5230 (2016).
Huang et al. "ParvoVirus glycan interactions" Current Opinion in Virology 7:108-118 (2014).
Huang, X et al., 'Dynamic programming algorithms for restriction map comparison,' Cabios, Vo1.8, No. 5., pp. 511-520, (1992).
Hughes et al., "AAV9 intracerebroventricular gene therapy improves lifespan, locomotor function and pathology in a mouse model of Niemann-Pick type C1 disease," Human Molecular Genetics 27(17)3079-3098 (2018).
Hunanyan AS, et al., Knock-in mouse model of alternating hemiplegia of childhood: behavioral and electrophysiologic characterization. Epilepsia. 56(1):82-93 (2015).
Hunanyan AS, et al., "Mechanisms of increased hippocampal excitability in the Mashl+/− mouse model of Na+ /K+-ATPase dysfunction," Epilepsia 59(7):1455-1468 (2018).
Ikeda K, et al., ""Knockout of sodium pump a3 subunit gene (Atp1a3-/-) results in perinatal seizure and defective respiratory rhythm generation,"" Brain Res. 1666:27-37 (2017).
Isaksen T J, et al., "Hypothermia-induced dystonia and abnormal cerebellar activity in a mouse model with a single disease-mutation in the sodium-potassium pump," PLoS Genet. 13(5):e1006763, pp. 1-23 (2017).
Janson, C. et al., 'Clinical protocol. Gene therapy of Canavan disease: AAV-2 vector for neurosurgical delivery of aspartoacylase gene (ASPA) to the human brain,' Hum. Gene Ther., 13(11 ):1391-1412 (Jul. 2002).
Kailasan et al., "Structure of an enteric pathogen, bovine parvovirus," Virology 89:2603-2614 (2015).
Kaplitt, M.G. et al. (1994). "Long-term gene expression and phenotypic correction using adenoassociated virus vectors in the mammalian brain," Nature Genetics 6:148-154.
Karlin et al. "Applications and statistics for multiple high-scoring segments in molecular sequences" Proceedings of National Academy of Sciences 90:5873-5877 (1993).
Kashiwakura et al. "Hepatocyte Growth Factor Receptor Is a Coreceptor for Adeno-Associated Virus Type 2 Infection" Journal of Virology, 79(1).609-614 (2005).
Kauffman et al., "Mechanism Matters: A Taxonomy of Cell Penetrating Peptides," Trends in Biochemcial Sciences, Elsevier, Amsterdam, NL 40(12):749-764 (2015).
Kawakami et al. "Cloning of the gene coding for a shared human melanoma antigen recognized by autologous T cells infiltrating into tumor" Proceedings of the National Academy of Sciences 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).

(56) References Cited

OTHER PUBLICATIONS

Kells, A.P., et al., "AAV-Mediated Gene Delivery of BDNF or GDNF is Neuroprotective in a Model of Huntington Disease," Molecular Therapy, May 2004, vol. 9(5), pp. 682-688.
Kirshenbaum GS, et al., "Alternating hemiplegia of childhood-related neural and behavioural phenotypes in Na+, K+-ATPase a3 missense mutant mice," PLoS One. 8(3):e60141, pp. 1-15 (2013).
Koivunen et al., "Identification of Receptor Ligands with Phage Display Peptide Libraries," J. Nucl. Med. 40:883-888 (1999).
Krissinel et al. "Secondary-structure matching (SSM)., a new tool for fast protein structure alignment in three dimensions" Acta Crystallographica Section D: Biological Crystallography, D60:2256-2268 (2004).
Kuck et al. "Development of AAV serotype-specific ELISAs using novel monoclonal antibodies" Journal of Virological Methods, 140(1-2):17-24 (2007) (Abstract only).
Kumar et al. "MEGA7: Molecular Evolutionary Genetics Analysis Version 7.0 for Bigger Datasets" Molecular Biology and Evolution, 33(7):1870-1874 (2016).
Lein et al. "Genome-wide atlas of gene expression in the adult mouse brain" Nature, 445(7124):168-176 (2007). (Abstract only).
Lerch et al., "The structure of adeno-associated virus serotype 3B (AAV-3B): insights into receptor binding and immune evasion," Virology 403(1):26-36 (2010).
Levine et al. "The Tumor Suppressor Genes" Annual Review of Biochemistry 62:623-651 (1993).
Li et al. "Development of Patient-specific AAV Vectors After Neutralizing Antibody Selection for Enhanced Muscle Gene Transfer" Molecular Therapy, 24(1):53-65 (2016).
Li et al. "Engineering and Selection of Shuffled AAV Genomes: A New Strategy for Producing Targeted Biological Nanoparticles" Molecular Therapy, 16(7):1252-1260 (2008).
Li et al. "Single Amino Acid Modification of adeno-Associated Virus Capsid Changes Transduction and Humeral Immune Profiles" Journal of Virology, 86(15):7752-7759 (2012).
Lisowski L., et al., "Selection and Evaluation of Clinically Relevant AAV Variants in a Xenograft Liver Model," Nature, Feb. 2014, vol. 506 (7488), pp. 382-386, XP055573596.
Loftus, SK et al., 'Murine Model of Niemann-Pick C Disease: Mutation in a Cholesterol Homeostasis Gene,' Science, 277(5323):232-235 (Jul. 1997).
Lux et al. "Green Fluorescent Protein-Tagged Adena-Associated Virus Particles Allow the Study of Cytosolic and Nuclear Trafficking" Journal of Virology, 79(18):11776-11787 (2005).
Madigan et al. "Engineering AAV receptor footprints for gene therapy" Current Opinion in Virology, 18:89-96 (2016).
Margolskee, R. F. "Epstein-Barr Virus Based Expression Vectors" Current Topics in Microbiology and Immunology 158:67-95 (1992).
Masoud M, et al., "Diagnosis and Treatment of Alternating Hemiplegia of Childhood," Curr Treat Options Neural. 19(2):8 (2017).
Mauro et al., "A critical analysis of codon optimization in human therapeutics," Trends in Molecular Medicine, Nov. 2014, vol. 20, No. 11, pp. 604-613.
McCarty, D.M., et al., "Self-complementary recombinant adeno-associated virus (scAAV) vectors promote efficient transduction independently of DNA synthesis," Gene Therapy 8, 1248-1254 (2001).
McCraw et al. "structurE of adeno-associated virus-2 In Complex with Neutralizing Monoclonal antibodY A20" Virology, 431 (1-2):40-49 (2012).
McLaughlin et al., "Adeno-associated virus general transduction vectors: analysis of proviral structures," J. Virol., (1988) 62:1963-1973.
Mikati et al., "Alternating hemiplegia of childhood: clinical manifestations and long-term outcome," Pediatr Neurol. 23(2):134-141 (2000).
Miller et al. "Production, purification and preliminary X-ray crystallographic studies of adenoassociated virus serotype 1" Acta Crystallographica Section F: Structural Biology and Crystallization Communications, 62(Pt 12):1271-1274 (2006).

Mingozzi et al., "Overcoming the Host Immune Response to Adeno-Associated Virus Gene Delivery Vectors: The Race Between Clearance, Tolerance, Neutralization, and Escape," Annual Review of Virology 1(1):511-534 (2017).
Miyamura et al. "ParvoVirus particles at platforms for protein presentation" Proceedings of National Academy of Sciences 91 :8507-8511, 1994.
Mori et al. "Two novel adeno-associated viruses from cynomolgus monkey: pseudotyping characterization of capsid protein" Virology 330:375-383 (2004).
Muller et al. "Random peptide libraries displayed on adeno-associated virus to select for targeted gene therapy vectors", Nat Biotechnol, Sep. 2003; 21(9):1040-6. Epub Aug. 3, 2003.
Muramatsu et al. "Nucleotide Sequencing and Generation of an Infectious Clone of adeno-Associated Virus 3", Virology, 221(0367):208-217 (1996).
Murlidharan et al. "Biology of adeno-associated viral vectors in the central nervous system" Frontiers in Molecular Neuroscience, 7(76):1-9 (2014), pp. 1-12.
Murlidharan et al. "Glymphatic fluid transport controls paravascular clearance of MV vectors from the brain" JCI Insight, 1 (14):e88034 (2016).
Murlidharan et al. "Unique Glycan Signatures Regulate adeno-Associated Virus Tropism in the Developing Brain" Journal of Virology 89(7):3976-3987 (2015).
Muzyczka, N. "Use of adeno-Associated Virus as a General Transduction Vector for Mammalian Cells," Current Topics in Microbiology and Immunology 158:97-129 (1992).
Nam et al. "Structure of Adeno-Associated Virus Serotype 8, a Gene Therapy Vector" Journal of Virology, 81 (22):12260-12271 (2007).
Nathwani et al. "Long-Term Safety and Efficacy of Factor IX Gene Therapy in Hemophilia B" The New England Journal of Medicine, 371 (21):1994-2004 (2014).
Needleman and Wunsch, "A general method applicable to the search for similarities in the amino acid sequence of two proteins." J Mol Biol. (1970); 48(3): 443-453.
Newton et al., Phage Peptide Display in Handbook of Experimental Pharmacology, pp. 145-163, Springer-Verlag, Berlin (2008).
Ng et al. "Structural Characterization of the Dual Glycan Binding adeno-Associated Virus Serotype 6" Journal of Virology, 84(24):12945-12957 (2010).
Nguyen Vu et al., "Cerebellar Purkinje cell activity drives motor learning", Nature Neuroscience 16(12):1734-1736 (2013).
Padron et al. "Structure of adeno-Associated Virus Type 4" Journal of Virology 79(8):5047-5058 (2005).
Palombo et al. "Site-Specific Integration in Mammalian Cells Mediated by a New Hybrid Baculovirus-Adeno-Associated Virus Vector" Journal of Virology72(6):5025-5034 (1998).
Papadakis, ED et al., 'Promoters and Control Elements: Designing Expression Cassettes for Gene Therapy,' Curr. Gene Therapy, vol. 4, No. 1, pp. 89-113, (Mar. 2004).
Partial Supplementary European Search Report issued by the European Patent Office for Application No. 16852471.8, dated Apr. 24, 2019, 17 pages.
Passini, MA et al., 'Distribution of a Lysosomal Enzyme in the Adult Brain by Axonal Transport and by Cells of the Rostral Migratory Stream,' J. Neuroscience, 22(15):6437-6446 (Aug. 2002).
Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).
Pearson et al., "Improved tools for biological sequence comparison," Proc. Natl. Acad. Sci. USA 85, 2444-2448 (1988).
Piguet et al, "Rapid and Complete Reversal of Sensory Ataxia by Gene Therapy in a Novel Model of Friedreich Ataxia", Molecular Therapy, Nature Publishing Group, GB 26(8), pp. 1-13 (2018).
Pillay et al. "An essential receptor for adeno-associated virus infection" Nature, 530(7588):108-112 (2016).
Powell et al. Characterization of a Novel Adena-Associated Viral Vector with Preferential Oligodendrocyte Tropism. Gene Therapy, 2016. 23:807-814.

(56) References Cited

OTHER PUBLICATIONS

Pulicherla et al. "Engineering Liver-detargeted AAV9 Vectors for Cardiac and Musculoskeletal Gene Transfer" Molecular Therapy, 19(6):1070-1078 (2011).
Puttaraju et al. "Spliceosome-mediated RNA trans-splicing as a tool for gene therapy" Nature Biotechnology 17:246-252 (1999).
Robbins et al. "Recognition of Tyrosinase by Tumor-infiltrating Lymphocytes from a Patient Responding to Immunotherapy" Cancer Research 54:3124-3126 (1994).
Rosenberg "The Immunotherapy of Solid Cancers Based on Cloning the Genes Encoding Tumor-Rejection Antigens" Annual Review of Medicine 47:481-491 (1996).
Rosenberg et al. "A New Era for Cancer Immunotherapy Based on the Genes that Encode Cancer Antigens" Immunity 10:281-287 (1999).
Rosenberg et al. "Comparative Efficacy and Safety of Multiple Routes of Direct CNS Administration of Adeno-Associated Virus Gene Transfer Vector Serotype rh.10 Expressing the Human Arylsulfatase A cDNA to Nonhuman Primates" Human Gene Therapy Clinical Development, 25(3):164-177 (2014).
Saitou, N. et al. (1987). "The neighbor-joining method: A new method for reconstructing phylogenetic trees," Mol. Biol. Evol. 4:406-425.
Salinas et al. "A hitchhiker's guide to the nervous system: the complex journey of viruses and toxins" Nature Reviews Microbiology, 8(9):645-655 (2010). (Abstract only).
Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12).1072-1082 (2013).
Severino M, et al., "White matter and cerebellar involvement in alternating hemiplegia of childhood," J Neurol. 267 (5):1300-1311 (2020).
Shade et al. "Nucleotide Sequence and Genome Organization of Human Parvovirus B19 Isolated from the Serum of a Child during Aplastic Crisis" Journal of Virology 28(3):921-936 (1986).
Sharp et al. "RNA Interference" Science 287(5462):2431-2433 (2000).
Shen et al. "Engraftment of a Galactose Receptor Footprint onto adeno-associated Viral Capsids Improves Transduction Efficiency" The Journal of Biological Chemistry, 288(40):28814-28823 (2013).
Shen et al., Multiple Roles for Sialylated Glycans in Determining the Cardiopulmonary Tropism of Adeno-Associated Virus 4, Journal of Virology 87(24):13206-13213 (2013).
Shi et al. "Insertional Mutagenesis at Positions 520 and 584 of adeno-Associated Virus Type 2 (AAV2). Capsid Gene and Generation of AAV2 Vectors with Eliminated Heparin-Binding Ability and Introduced Novel Tropism" Human Gene Therapy 17:353-361 (2006).
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.
Smith et al, "Comparison of Biosequences", Advanced in Applied Mathematics, vol. 2, Issue 4, Dec. 1981, pp. 482-489.
Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).
Srivastava et al. "Nucleotide Sequence and Organization of the Adeno Associated Virus 2 Genome." Journal of Virology (1983); 45:2, p. 555-564.
Summerford et al. "Membrane-Associated Heparan Sulfate Proteoglycan Is a Receptor for adeno-Associated Virus Type 2 Virions" Journal of Virology, 72(2):1438-1445 (1998).
Tellez et al. "Characterization of Naturally-Occurring Humoral Immunity to AAV in Sheep" PLoS ONE, 8(9):e75142 (2013).
Tinsley et al. "Amelioration of the dystrophic phenotype of mdx mice using a truncated utrophin transgene" Nature 384(6607):349-353 (1996).

Titeux et al., "SIN Retroviral Vectors Expressing COL7A1 Under Human Promoters for Ex Vivo Gene Therapy of Recessive Dystrophic Epidermolysis Bullosa," Mol. Ther., 2010 18:1509-1518.
Tsao et al. The Three-Dimensional Structure of Canine ParvoVirus and Its Functional Implications Science 251 (5000):1456-1464 (1991).
Tse et al., "Strategies to Circumvent Humoral Immunity to Adeno-Associated Viral Vectors," Expert Opinion on Biological Therapy 15(6):845-855 (2015).
Tse L.V., et al., "Structure-Guided Evolution of Antigenically Distinct Adeno-Associated Virus Variants for Immune Evasion," Proceedings of the National Academy of Sciences, Jun. 2017, vol. 114(24), pp. E4812-E4821, XP055590029.
Tseng et al. "Adeno-Associated Virus Serotype 1 (AAV1).- and AAV5-Antibody Complex Structures Reveal Evolutionary Commonalities in ParvoVirus Antigenic Reactivity" Journal of Virology, 89(3):1794-1808 (2015).
Tseng et al. "Generation and characterization of anti-adeno-associated Virus serotype 8 (AAV8). and anti-AAV9 monoclonal antibodies" Journal of Virological Methods, 236:105-110 (2016).
Tseng et al. "Mapping the AAV capsid host antibody response toward the development of second generation gene delivery vectors" Frontiers in Immunology, 5(9):1-11 (2014). UniProt Accession No. O15118, dated May 30, 2000, 21 pages.
Urabe et al. "Insect Cells as a Factory to Produce adeno-Associated Virus Type 2 Vectors" Human Gene Therapy 13:1935-1943 (2002).
Various: Abstracts, 20th Annual Meeting of the American-Society-of-Gene-and-Cell-Therapy (ASGCT); Washington, DC, USA; May 10-13. 2017, Molecular Therapy: the Journal of the American Society of Gene Therapy 25:1-363 (2017).
Veldwijk, MR et al., 'Development and optimization of a real-time quantitative PCR-based method for the titration of AAV-2 vector stocks,' Mal. Ther.,6(2):272-8 (Aug. 2002).
Veron et al. ""Humeral and Cellular Capsid-Specific Immune Responses to Adena-Associated Virus Type 1 in andomized Healthy Donors'" The Journal of Immunology, 188:6418-6424 (2012).
Vincent et al. "Long-term correction of mouse dystrophic degeneration by adenovirusmediated transfer of a minidystrophin gene" Nature Genetics 5:130-134 (1993).
Walters et al. "Structure of adeno-Associated Virus Serotype 5" Journal of Virology 78(7):3361-3371 (2004).
Wang et al. "Adeno-associated Virus vector carrying human minidystrophin genes effectively ameliorates muscular dystrophy in mdx mouse model" Proceedings of the National Academy of Sciences 97(25):13714-13719 (2000).
Wang et al. "Expanding the genetic code" Annual Review of Biophysics and Biomolecular Structure 35:225-249 (2006).
Wang et al., "Identification of an adeno-associated Virus binding epitope for AVB sepharose affinity resin," Molecular Therapy—Methods & Clinical Development vol. 2, pp. 1-6 (2015).
Wassif, CA et al., 'High Incidence of Unrecognized Visceral/Neurological Lateonset Niemann-Pick Disease, type C1 Predicted by Analysis of Massively Parallel Sequencing Data Sets,' Genet Med., 18(1):41-48 (Jan. 2016).
Weller et al. "Epidermal growth factor receptor is a co-receptor for adeno-associated virus serotype 6" Nature Medicine, 16(6):662-664 (2010).
Williams et al. ""Monocyte maturation, HIV susceptibility, and transmigration across the blood brain barrier are critical in HIV neuropathogenesis"" Journal of Leukocyte Biology, 91 (3):401-415 (2012).
Winkler et al., "Changing the Antigen Binding Specificity by Single Point Mutations of an Antip24 (HIV-1) Antibody", The Journal of Immunology, 165: 4505-4514 (2000).
Wobus et al. "Monoclonal Antibodies against the Adena-Associated Virus Type 2 (AAV-2) Capsid: Epitope Mapping and Identification of Capsid Domains Involved in AAV-2-Cell Interaction and Neutralization of AAV-2 Infection," J. of Virology, 74(19):9281-9293 (2000).
Work, et al., "Vascular bed-targeted in vivo gene delivery using tropism-modified adenoassociated viruses." Mol. Ther.; vol. 13, No. 4, pp. 683-693 (Apr. 2006).

(56) References Cited

OTHER PUBLICATIONS

Xiao et al. "Gene Therapy Vectors Based on adeno-Associated Virus Type 1" Journal of Virology 73(5):3994-4003 (1999).
Xiao et al. "Interpretation of Electron Density with Stereographic Roadmap Projections" Journal of Structural Biology, 158(2):182-187 (2007).
Xiao et al., "Gene transfer by adeno-associated virus vectors into the central nervous system," Exp. Neurobiol., (1997) 144:113-124.
Xie et al. "Canine ParvoVirus Capsid Structure, Analyzed at 2.9 A Resolution" Journal of Molecular Biology 264(3):497-420 (1996).
Xie et al. "The atomic structure of adeno-associated Virus (AAV-2)., a vector for human gene therapy" Proceeding of the National Academy of Sciences 99(16):10405-10410 (2002).
Xie, J. et al., "Short DNA Hairpins Compromise Recombinant Adeno-Associated Virus Genome Homogeneity," Mol. Ther., 25(6): 1363-1374 (2017).
Yang et al. "Global CNS Transduction of Adult Mice by Intravenously Delivered rAAVrh.8 and rAAVrh.10 and Nonhuman Primates by rAAVrh.10" Molecular Therapy, 22(7):1299-1309 (2014).
Ye Q, et al., "The AAA+ ATPase TRIP13 remodels HORMA domains through N-terminal engagement and unfolding," EMBO J. 36(16):2419-2434 (2017).
Zhang et al. "Recombinant adenoVirus expressing adeno-associated Virus cap and rep proteins supports production of high-titer recombinant adeno-associated virus" Gene Therapy 8:704-712 (2001).
Zhang et al. "Several rAAV Vectors Efficiently Cross the Blood-brain Barrier and Transduce Neurons and Astrocytes in the Neonatal Mouse Central Nervous System" Molecular Therapy, 19(8): 1440-1448 (2011 ).
Zhang, "Endocytic mechanisms and drug discovery in neurodegenerative diseases," Frontiers in Bioscience 13:6086-6105 (2008).
Zhong et al. ""Tyrosine-phosphorylation of AA V2 vectors and its consequences on viral intracellular trafficking and transgene expression"" Virology, 381 (2):194-202 (2008).
Zhong et al. "Next generation of adeno-associated virus 2 vectors: Point mutations in tyrosines lead to high-efficienc ransduction at lower doses" Proceedings of the National Academy of Sciences USA, 105(22):7827-7832 (2008).
Zinn, E. et al., "In Silico Reconstruction of the Viral Evolutionary Lineage Yields a Potent Gene Therapy Vector," Cell Reports, Aug. 2015; 12:1056-1068.
Zolotukhin et al. "Production and purification of serotype 1, 2, and 5 recombinant adeno-associated viral vectors" Methods, 28(2):158-167 (2002) (Abstract only).
Zolotukhin, et al., "Recombinant adeno-associated virus purification using novel methods improves infectious titer and yield." Gene Therapy (1999); vol. 6, pp. 973-985.
Cleves, Ann E. "Protein transport: The nonclassical ins and outs" Current Biology7:R318-R320 (1997).
Ferrari et al. "New developments in the generation of Ad-free high-titer rAAV gene therapy vectors" Nature Medicine 3(11):1295-1297 (1997).
Gonzales, "Cross-Species Evolution of Synthetic A hetis AAV Strains for clinical Translation," ASGCT, abstract #23 2 pages (2020).
Havlik et al, "Co-Evolution of AAV Capsid Antigenecity and Tropism Through a Structure-Guided Approach," ASGCT, pp. 1-17 (2020).
Havlik, Engineering A Humanized AAV8 Capsid Through Iterative Structure-Guided Evolution ASGCT, 24 pages. (2019), abstract #100, 1 page.
Higgins, DG et al., 'Fast and sensitive multiple sequence alignments on a microcomputer,' Comput Appl Biosci., 5(2):151-3, (Apr. 1989).
Li et al. "Construction of phospholamban antisense RNA recombinant adeno-associated Virus vector and its effects in rat cardiomyocytes" Acta Pharmalogica Sinica 26(1).51-55 (2005).
Mingozzi et al. "Immune responses to AAV vectors: overcoming barriers to successful gene therapy" Blood, 122 (1):23-36 (2013).
Murlidharan et al. "265. Polysialic Acid as a Novel Regulator of AAV Tropism in the Developing Brain" Molecular Therapy 23(Supplement 1 ):S106 (2015), 1 page.
Murlidharan et al. "CNS-restricted Transduction and CRISPR/Cas9-mediated Gene pages Deletion with an Engineered AAV Vector" Molecular Therapy: Nucleic Acids, 5:e338 (2016), pp. 1-12.
Smith et al., "Structural Mapping of AAV9 Antigenic Sites and the Engineering of Immune Escape Variants," Molecular Therapy; 20th Annual Meeting of the American Society of Gene and Cell Therapy (ASGCT).; Washington, DC, A; May 10-13, 2017, Nature Publishing Group, GB vol. 25, No. 5, Suppl 1 (2017), abstract #733, 1 page.
Smith, TF et al., 'Identification of Common Molecular Subsequences,' Journal of Molecular Biology, 147:195-197, PMID 7265238. doi:10.1016/0022-2836(81)90087-5, (1981).
Wang et al., "Selection of neutralizing antibody-resistant AAV8 variants with structure-guided site-specific saturated mutagenesis," Molecular Therapy, 2011, vol. 19 Suppl. 1, S129, abstract #333 1 page.
Wu et al. "alpha2,3 and alpha2,6 N-Linked Sialic Acids Facilitate Efficient Binding and Transduction by Adeno-Associated Virus Types 1 and 6" Journal of Virology, 80(18):9093-9103 (2006).

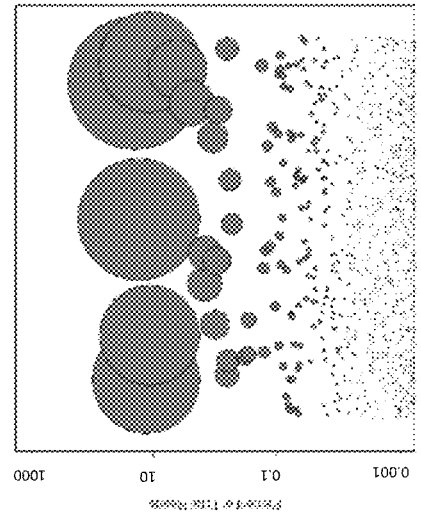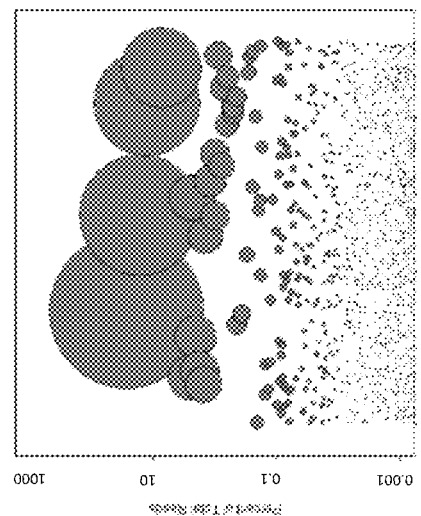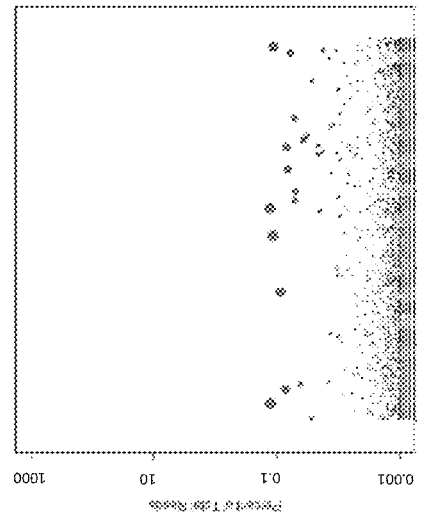

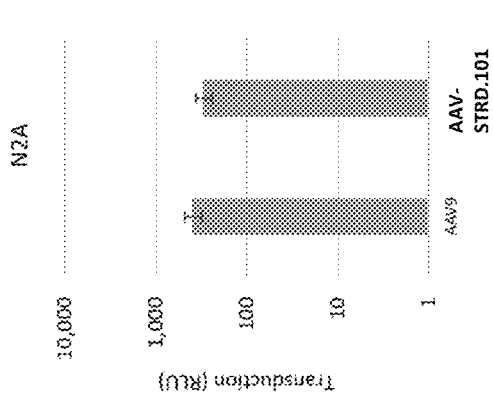
Fig. 4A / Fig. 4B
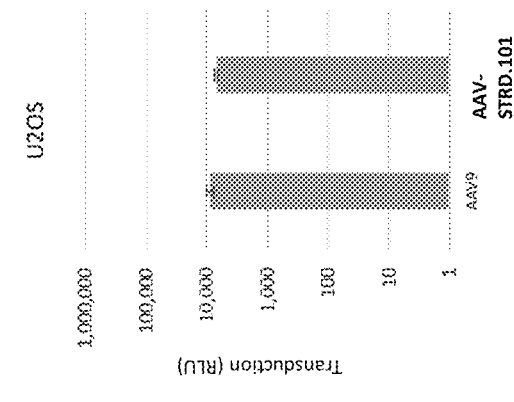
Fig. 4C / Fig. 4D

RECOMBINANT ADENO-ASSOCIATED VIRUS VECTORS

CROSS-REFERENCE TO RELATED APPLICATION

This application is a continuation of U.S. patent application Ser. No. 17/479,577, filed Sep. 20, 2021, which is a continuation of International Patent Application No. PCT/US2020/023877, filed Mar. 20, 2020, which claims the benefit of U.S. Provisional Application No. 62/821,710, filed Mar. 21, 2019, which is incorporated herein by reference in its entirety.

DESCRIPTION OF THE TEXT FILE SUBMITTED ELECTRONICALLY

The instant application contains a Sequence Listing, which has been submitted via Patent Center and is hereby incorporated by reference in its entirety. Said .xml copy, created on Oct. 16, 2023 is named GSB-01302, and is 881,333 bytes in size.

TECHNICAL FIELD

This application relates to adeno-associated virus (AAV) vectors comprising recombinant capsid proteins. In some embodiments, the recombinant AAV vectors evade neutralizing antibodies without decreased transduction efficiency.

BACKGROUND

Host-derived pre-existing antibodies generated upon natural encounter of AAV or recombinant AAV vectors prevent first time as well as repeat administration of AAV vectors as vaccines and/or for gene therapy. Serological studies reveal a high prevalence of antibodies in the human population worldwide with about 67% of people having antibodies against AAV1, 72% against AAV2, and about 40% against AAV5 through AAV9.

In gene therapy, certain clinical scenarios involving gene silencing or tissue degeneration may require multiple AAV vector administrations to sustain long term expression of the transgene. Accordingly, there is a need in the art for recombinant AAV vectors which evade antibody recognition. Such vectors will help a) expand the eligible cohort of subjects suitable for AAV-based gene therapy and b) allow multiple, repeat administrations of AAV-based gene therapy vectors.

BRIEF SUMMARY

Provided herein are recombinant AAV vectors which evade antibody recognition and/or selectively target tissues of the CNS.

In some embodiments, an adeno-associated virus (AAV) vector comprises (i) a recombinant capsid protein and (ii) a cargo nucleic acid encapsidated by the capsid protein, wherein the capsid protein comprises a peptide having the sequence of any one of SEQ ID NO: 12-20.

In some embodiments, an adeno-associated virus (AAV) vector comprises (i) a mutant AAV9 capsid protein and (ii) a cargo nucleic acid encapsidated by the capsid protein, wherein the capsid protein comprises a peptide having the sequence $X^1$-$X^2$-$X^3$-$X^4$-$X^5$-$X^6$-$X^7$-$X^8$ (SEQ ID NO: 158) at amino acids 451-458 of the native AAV9 capsid protein sequence, wherein the peptide does not occur in the native AAV9 capsid protein sequence.

In some embodiments, an adeno-associated virus (AAV) vector comprises (i) a mutant AAV9 capsid protein and (ii) a cargo nucleic acid encapsidated by the capsid protein, wherein the capsid protein comprises a peptide having the sequence $X^1$-$X^2$-$X^3$-$X^4$-$X^5$-$X^6$-$X^7$-$X^8$ (SEQ ID NO: 158) at amino acids 587-594 of the native AAV9 capsid protein sequence, wherein the peptide does not occur in the native AAV9 capsid protein sequence.

In some embodiments, the an adeno-associated virus (AAV) vector comprises (i) a recombinant capsid protein and (ii) a cargo nucleic acid encapsidated by the capsid protein, wherein the capsid protein comprises an amino acid sequence that is at least 95%, at least 96%, at least 97%, at least 98%, or at least 99% identical to any one of SEQ ID NO: 165-187.

Also provided herein are nucleic acid sequences encoding a recombinant capsid protein, and expression vectors comprising the same.

Also provided are cells comprising a nucleic acid, an expression vector, an AAV vector, or an AAV capsid described herein.

Also provided are pharmaceutical compositions comprising a nucleic acid, an expression vector, an AAV vector, an AAV capsid, or a cell described herein.

Also provided are methods for treating a subject in need thereof comprising administering to the subject a therapeutically effective amount of an AAV vector described herein.

Also provided are in vitro method of introducing a nucleic acid molecule into a cell, the methods comprising contacting the cell with an AAV vector described herein.

Also provided is an AAV vector described herein for use as a medicament.

Also provided is an AAV vector described herein for use in a method of treatment of a subject in need thereof.

Also provided is an AAV vector described herein for use in a method of treating or preventing a disease or disorder of the CNS in a subject in need thereof.

These and other embodiments are described in more detail below.

BRIEF DESCRIPTION OF THE DRAWINGS

FIG. 1A-1C. Bubble plots showing analysis of library diversity, directed evolution and enrichment of novel antigenic footprints. Parental (FIG. 1A) and evolved libraries from a first round (FIG. 1B) and a second round (FIG. 1C) of evolution were subjected to high-throughput sequencing using the Illumina MiSeq platform. Following analysis with a custom Perl script, enriched amino acid sequences were plotted. Each bubble represents a distinct capsid amino acid sequence with the radius of the bubble proportional to the number of reads for that variant in the respective library. The y-axis represents the percentage of total reads from the sequencing run. Data are spread along the x-axis for ease of visualization. The percent reduction in unique clones (96.5%) directly demonstrates that numerous "un-fit" sequences were removed after a first and second round of evolution. Dominant isolates were selected for further analysis.

FIG. 4A-4D. Transduction of U87 cells (FIG. 4A), N2A cells (FIG. 4B), Sy5Y cells (FIG. 4C), and U2OS cells (FIG. 4D) by recombinant AAV vectors comprising the STRD.101 capsid and packaging a luciferase transgene, as compared to wildtype AAV9 vectors similarly packaging a luciferase sequence. Error bars represent standard error.

DETAILED DESCRIPTION

Figure 2:
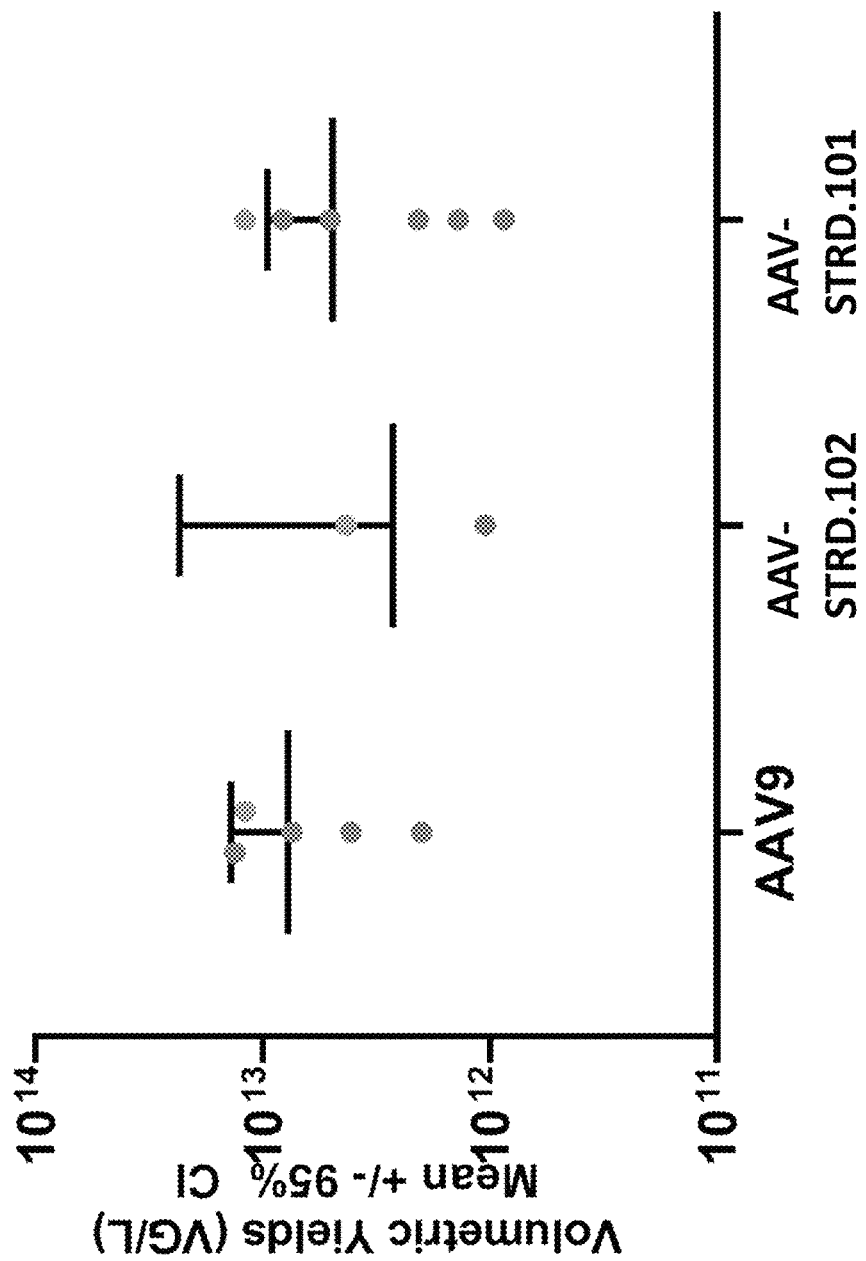
FIG. 2. Volumetric yield of AAV vectors comprising AAV capsid variants STRD.101 and STRD.102, as compared to wildtype AAV9. Bars represent mean+/-95% confidence interval.
Figure 3:
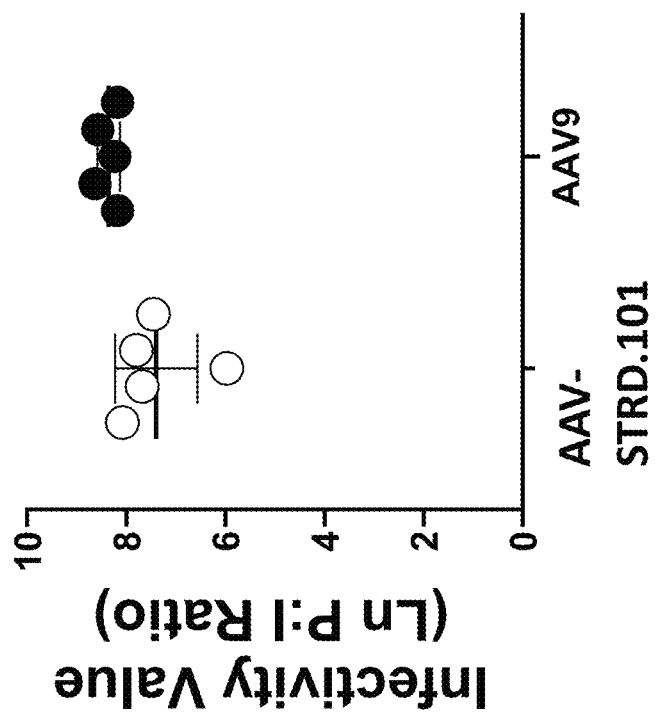
FIG. 3. Infectivity values of AAV-STRD.101 and wild-type AAV9 determined using a standard TCID50 assay. Data are graphed as the natural log of the number of particles required to generate an infectious unit (P:I Ratio). Error bars represent standard deviation.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank or other accession numbers and other references mentioned herein are incorporated by reference in their entirety for all purposes.

The designation of amino acid positions in the AAV capsid proteins in the disclosure and the appended claims is with respect to VP1 capsid subunit numbering. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

Definitions

The following terms are used in the description herein and the appended claims.

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, 10%, 5%, 1%, +0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination. Moreover, in some embodiments, any feature or combination of features set forth herein can be excluded or omitted. To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc., as if each such subcombination is expressly set forth herein. Moreover, such language also indicates that one or more of the specified amino acids can be disclaimed. For example, in some embodiments the amino acid is not A, G or I; is not A; is not G or V; etc., as if each such possible disclaimer is expressly set forth herein.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "increase," "improve," "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

The term "parvovirus" as used herein encompasses the family Parvoviridae, including autonomously replicating parvoviruses and dependoviruses. The autonomous parvoviruses include members of the genera Protoparvovirus, Erythroparvovirus, Bocaparvovirus, and Densovirus subfamily. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al, VIROLOGY, volume 2, chapter 69 (4th ed., Lippincott-Raven Publishers; Cotmore et al. Archives of Virology DOI 10.1007/s00705-013-1914-1).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV2i8, AAV2g9, AAV-LK03, AAV7m8, AAV Anc80, AAV PHP.B, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al, (2004) J. Virology 78:6381-6388; Moris et al, (2004) Virology 33-:375-383; and Table 2). Exemplary AAV capsid sequences for AAV1-9, AAVrh.10 and AAV11 are provided in SEQ ID NO: 1-11.

As used herein, the term "chimeric AAV" refers to an AAV comprising a capsid protein with regions, domains, individual amino acids that are derived from two or more different serotypes of AAV. In some embodiments, a chimeric AAV comprises a capsid protein comprised of a first region that is derived from a first AAV serotype and a second region that is derived from a second AAV serotype. In some embodiments, a chimeric AAV comprises a capsid protein comprised of a first region that is derived from a first AAV serotype, a second region that is derived from a second AAV serotype, and a third region that is derived from a third AAV serotype. In some embodiments, the chimeric AAV may comprise regions, domains, individual amino acids derived from AAV1, AAV2, AAV3, AAV4, AAV5, AAV6, AAV7, AAV8, AAV9, AAV10, AAV11, and/or AAV12. For example, the chimeric AAV may include regions, domains, and/or individual amino acids from a first and a second AAV serotype as shown below (Table 1), wherein AAVX+Y indicates a chimeric AAV including sequences derived from AAVX and AAVY:

TABLE 1

Chimeric AAVs

|  |  | Second AAV Serotype | | | | | | |
|---|---|---|---|---|---|---|---|---|
|  |  | AAV1 | AAV2 | AAV3 | AAV4 | AAV5 | AAV6 | AAV7 |
| First AAV Sertoype | AAV1 | x | AAV1 + 2 | AAV1 + 3 | AAV1 + 4 | AAV1 + 5 | AAV1 + 6 | AAV1 + 7 |
|  | AAV2 | AAV2 + 1 | x | AAV2 + 3 | AAV2 + 4 | AAV2 + 5 | AAV2 + 6 | AAV2 + 7 |
|  | AAV3 | AAV3 + 1 | AAV3 + 2 | x | AAV3 + 4 | AAV3 + 5 | AAV3 + 6 | AAV3 + 7 |
|  | AAV4 | AAV4 + 1 | AAV4 + 2 | AAV4 + 3 | x | AAV4 + 5 | AAV4 + 6 | AAV4 + 7 |
|  | AAV5 | AAV5 + 1 | AAV5 + 2 | AAV5 + 3 | AAV5 + 4 | x | AAV5 + 6 | AAV5 + 7 |
|  | AAV6 | AAV6 + 1 | AAV6 + 2 | IAAV6 + 3 | AAV6 + 4 | AAV6 + 5 | x | AAV6 + 7 |
|  | AAV7 | AAV7 + 1 | AAV7 + 2 | AAV7 + 3 | AAV7 + 4 | AAV7 + 5 | AAV7 + 6 | x |
|  | AAV8 | AAV8 + 1 | AAV8 + 2 | AAV8 + 3 | AAV8 + 4 | AAV8 + 5 | AAV8 + 6 | AAV8 + 7 |
|  | AAV9 | AAV9 + 1 | AAV9 + 2 | AAV9 + 3 | AAV9 + 4 | AAV9 + 5 | AAV9 + 6 | AAV9 + 7 |
|  | AAV10 | AAV10 + 1 | AAV10 + 2 | AAV10 + 3 | AAV10 + 4 | AAV10 + 5 | AAV10 + 6 | AAV10 + 7 |
|  | AAV11 | AAV11 + 1 | AAV11 + 2 | AAV11 + 3 | AAV11 + 4 | AAV11 + 5 | AAV11 + 6 | AAV11 + 7 |
|  | AAV12 | AAV12 + 1 | AAV12 + 2 | AAV12 + 3 | AAV12 + 4 | AAV12 + 5 | AAV12 + 6 | AAV12 + 7 |

|  |  | Second AAV Serotype | | | | |
|---|---|---|---|---|---|---|
|  |  | AAV8 | AAV9 | AAV10 | AAV11 | AAV12 |
| First AAV Sertoype | AAV1 | AAV1 + 8 | AAV1 + 9 | AAV1 + 10 | AAV1 + 11 | AAV1 + 12 |
|  | AAV2 | AAV2 + 8 | AAV2 + 9 | AAV2 + 10 | AAV2 + 11 | AAV2 + 12 |
|  | AAV3 | AAV3 + 8 | AAV3 + 9 | AAV3 + 10 | AAV3 + 11 | AAV3 + 12 |
|  | AAV4 | AAV4 + 8 | AAV4 + 9 | AAV4 + 10 | AAV4 + 11 | AAV4 + 12 |
|  | AAV5 | AAV5 + 8 | AAV5 + 9 | AAV5 + 10 | AAV5 + 11 | AAV5 + 12 |
|  | AAV6 | AAV6 + 8 | AAV6 + 9 | AAV6 + 10 | AAV6 + 11 | AAV6 + 12 |
|  | AAV7 | AAV7 + 8 | AAV7 + 9 | AAV7 + 10 | AAV7 + 11 | AAV7 + 12 |
|  | AAV8 | x | AAV8 + 9 | AAV8 + 10 | AAV8 + 11 | AAV8 + 12 |
|  | AAV9 | AAV9 + 8 | x | AAV9 + 10 | AAV9 + 11 | AAV9 + 12 |
|  | AAV10 | AAV10 + 8 | AAV10 + 9 | x | AAV10 + 11 | AAV10 + 12 |
|  | AAV11 | AAV11 + 8 | AAV11 + 9 | AAV11 + 10 | x | AAV11 + 12 |
|  | AAV12 | AAV12 + 8 | AAV12 + 9 | AAV12 + 10 | AAV12 + 11 | x |

By including individual amino acids or regions from multiple AAV serotypes in one capsid protein, capsid proteins that have multiple desired properties that are separately derived from the multiple AAV serotypes may be obtained.

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) J. Virology 45:555; Chiorini et al, (1998) J Virology 71:6823; Chiorini et al., (1999) J. Virology 73:1309; Bantel-Schaal et al., (1999) J Virology 73:939; Xiao et al., (1999) J Virology 73:3994; Muramatsu et al., (1996) Virology 221:208; Shade et al, (1986) J. Virol. 58:921; Gao et al, (2002) Proc. Nat. Acad. Sci. USA 99:11854; Moris et al, (2004) Virology 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 2. The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) Proc. Nat. Acad. Sci. 99: 10405-10), AAV9 (DiMattia et al., (2012) J. Virol. 86:6947-6958), AAV8 (Nam et al, (2007) J. Virol. 81: 12260-12271), AAV6 (Ng et al., (2010) J. Virol. 84:12945-12957), AAV5 (Govindasamy et al. (2013) J. Virol. 87, 11187-11199), AAV4 (Govindasamy et al. (2006) J. Virol. 80:11556-11570), AAV3B (Lerch et al., (2010) Virology 403:26-36), BPV (Kailasan et al., (2015) J. Virol. 89:2603-2614) and CPV (Xie et al, (1996) J. Mol. Biol. 6:497-520 and Tsao et al, (1991) Science 251:1456-64).

TABLE 2

AAV Serotypes and Clades

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| HSC1 | MI332400.1 |
| HSC2 | MI332401.1 |

TABLE 2-continued

AAV Serotypes and Clades

| | GenBank Accession Number |
|---|---|
| HSC3 | MI332402.1 |
| HSC4 | MI332403.1 |
| HSC5 | MI332405.1 |
| HSC6 | MI332404.1 |
| HSC7 | MI332407.1 |
| HSC8 | MI332408.1 |
| HSC9 | MI332409.1 |
| HSC11 | MI332406.1 |
| HSC12 | MI332410.1 |
| HSC13 | MI332411.1 |
| HSC14 | MI332412.1 |
| HSC15 | MI332413.1 |
| HSC16 | MI332414.1 |
| HSC17 | MI332415.1 |
| Hu68 | |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |
| Others | |
| Rh74 | |
| Bearded Dragon AAV | |
| Snake AAV | NC_006148.1 |

The term "self-complimentary AAV" or "scAAV" refers to a recombinant AAV vector which forms a dimeric inverted repeat DNA molecule that spontaneously anneals, resulting in earlier and more robust transgene expression compared with conventional single-strand (ss) AAV genomes. See, e.g., McCarty, D. M., et al., Gene Therapy 8, 1248-1254 (2001). Unlike conventional ssAAV, scAAV can bypass second-strand synthesis, the rate-limiting step for gene expression. Moreover, double-stranded scAAV is less prone to DNA degradation after viral transduction, thereby increasing the number of copies of stable episomes. Notably, scAAV can typically only hold a genome that is about 2.4 kb, half the size of a conventional AAV vector. In some embodiments, the AAV vectors described herein are self-complementary AAVs.

As used herein, the term "peptide" refers to a short amino acid sequence. The term peptide may be used to refer to portion or region of an AAV capsid amino acid sequence. The peptide may be a peptide that naturally occurs in a native AAV capsid, or a peptide that does not naturally occur in a native AAV capsid. Naturally occurring AAV peptides in an AAV capsid may be substituted by non-naturally occurring peptides. For example, a non-naturally occurring peptide may be substituted into an AAV capsid to provide a modified capsid, such that the naturally-occurring peptide is replaced by the non-naturally occurring peptide.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a transgene of interest.

As used here, "systemic tropism" and "systemic transduction" (and equivalent terms) indicate that the virus capsid or virus vector as described herein exhibits tropism for or transduces, respectively, tissues throughout the body (e.g., brain, lung, skeletal muscle, heart, liver, kidney and/or pancreas). In some embodiments, systemic transduction of muscle tissues (e.g., skeletal muscle, diaphragm and cardiac muscle) is achieved. In some embodiments, systemic transduction of skeletal muscle tissues is achieved. For example, in some embodiments, essentially all skeletal muscles throughout the body are transduced (although the efficiency of transduction may vary by muscle type). In some embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically).

Alternatively, in some embodiments, the capsid or virus vector is delivered locally (e.g., to the footpad, intramuscularly, intradermally, subcutaneously, topically). In some embodiments, the capsid or virus vector is delivered locally to a tissue of the central nervous system (CNS), such as the brain or the spinal cord. In some embodiments, the capsid or virus vector is administered by intrathecal, intracerebral or intracerebroventricular injection.

Unless indicated otherwise, "efficient transduction" or "efficient tropism," or similar terms, can be determined by reference to a suitable control (e.g., at least about 50%, about 60%, about 70%, about 80%, about 85%, about 90%, about 95% or more of the transduction or tropism, respectively, of the control). In some embodiments, the virus vector (e.g., the AVV vector) efficiently transduces or has efficient tropism for skeletal muscle, cardiac muscle, diaphragm muscle, pancreas (including β-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, viral vectors can be identified that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In some embodiments, the virus vector does not efficiently transduce (i.e., does not have efficient tropism) for liver, kidney, gonads and/or germ cells. In some embodiments, undesirable transduction of tissue(s) (e.g., liver) is about 20% or less, about 10% or less, about 5% or less, about 1% or less, about 0.1% or less of the level of transduction of the desired target tissue(s) (e.g., skeletal muscle, diaphragm muscle, cardiac muscle and/or cells of the central nervous system).

As used herein in connection with an AAV vector (or a capsid protein or peptide thereof), the terms "selectively binds," "selective binding" and similar terms, refer to binding of the AAV vector (or a capsid protein or peptide thereof) to a target in a manner dependent upon the presence of a particular molecular structure. In some embodiments, selective binding refers to binding of the AAV predominantly to a specific target, without substantial or significant binding to other targets. In some embodiments, an AAV vector (or capsid protein or peptide thereof) specifically binds to a receptor in a cell or tissue of interest, but does not exhibit substantial or significant binding to other receptors.

A "polynucleotide" is a sequence of nucleotide bases, and may be RNA, DNA or DNA-RNA hybrid sequences (including both naturally occurring and non-naturally occurring nucleotide). In some embodiments, a polynucleotide is either a single or double stranded DNA sequence.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In some embodiments an "isolated" nucleotide is enriched by at least about 10-fold, about 100-fold, about 1000-fold, about 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In some embodiments an "isolated" polypeptide is enriched by at least about 10-fold, about 100-fold, about 1000-fold, about 10,000-fold or more as compared with the starting material.

As used herein, by "isolate" or "purify" (or grammatical equivalents) a virus vector, it is meant that the virus vector is at least partially separated from at least some of the other components in the starting material. In some embodiments an "isolated" or "purified" virus vector is enriched by at least about 10-fold, about 100-fold, about 1000-fold, about 10,000-fold or more as compared with the starting material.

A "therapeutic" polypeptide or protein is one that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the compositions and/or methods described herein. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the compositions and/or methods described herein.

"Therapeutically effective amount" as used herein refers to an amount that, when administered to a subject for treating a disease, or at least one of the clinical symptoms of a disease, is sufficient to affect such treatment of the disease or symptom thereof. The "therapeutically effective amount" may vary depending, for example, on the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone. In some embodiments, the vector genome (e.g., the AAV vector genome) may be comprised in a "cargo nucleic acid." In some embodiments, the vector genome is self-complementary (i.e., double stranded). In some embodiments, the vector genome is not self-complimentary (i.e., single stranded).

A "rAAV vector genome" or "rAAV genome" is an AAV genome (i.e., vDNA) that comprises one or more heterologous nucleic acid sequences. rAAV vectors generally require only the inverted terminal repeat(s) (ITR(s)) in cis to generate virus. All other viral sequences are dispensable and may be supplied in trans (Muzyczka, (1992) Curr. Topics Microbiol. Immunol. 158:97). Typically, the rAAV vector genome will only retain the one or two ITR sequences so as to maximize the size of the transgene that can be efficiently packaged by the vector. The structural and non-structural protein coding sequences may be provided in trans (e.g., from a vector, such as a plasmid, or by stably integrating the sequences into a packaging cell). In some embodiments, the rAAV vector genome comprises at least one ITR sequence (e.g., AAV ITR sequence), optionally two ITRs (e.g., two AAV ITRs), which typically will be at the 5' and 3' ends of the vector genome (i.e., the 5' ITR and the 3' ITR) and flank the heterologous nucleic acid, but need not be contiguous thereto.

The term "inverted terminal repeat" or "ITR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as an ITR, which can further be modified by truncation, substitution, deletion, insertion and/or addition. Further, the ITR can be partially or completely synthetic, such as the "double-D sequence" as described in U.S. Pat. No. 5,478,745.

An "AAV inverted terminal repeat" or "AAV ITR" may be from any AAV, including but not limited to serotypes 1, 2, 3, 4, 5, 6, 7, 8, 9, 10, 11, 12, 13 or any other AAV now known or later discovered (see, e.g., Table 2). An AAV inverted terminal repeat need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors described herein can further be "targeted" virus vectors (e.g., having a directed tropism) and/or "hybrid" virus vectors (i.e., in which the viral ITRs and viral capsid are from different viruses) as described in international patent publication WO00/28004 and Chao et al, (2000) Molecular Therapy 2:619. In some embodiments, the virus vectors are targeted to a cell and/or tissue of the CNS.

The virus vectors described herein can further be duplexed virus particles as described in international patent publication WO 01/92551 (the disclosure of which is incorporated herein by reference in its entirety). Thus, in some embodiments, double stranded (duplex) genomes can be packaged into the virus capsids described herein. Further, the viral capsid or genomic elements can contain other modifications, including insertions, deletions and/or substitutions.

As used herein, the term "amino acid" encompasses any naturally occurring amino acid, modified forms thereof, and synthetic amino acids. Naturally occurring, levorotatory (L-) amino acids are shown in Table 3.

TABLE 3

Amino acid residues and abbreviations.

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 4) and/or can be an amino acid that is modified by post-translation modification (e.g., acetylation, amidation, formylation, hydroxylation, methylation, phosphorylation or sulfatation). Methods of chemically modifying amino acids are known in the art (see, e.g., Greg T. Hermanson, Bioconjugate Techniques, 1$^{st}$ edition, Academic Press, 1996).

TABLE 4

Modified Amino Acid Residues

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |

TABLE 4-continued

Modified Amino Acid Residues

| Modified Amino Acid Residue | Abbreviation |
|---|---|
| 2,4-Diaminobutyric acid | Dbu |
| Desmosine | Des |
| 2,21-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | alle |
| Methionine sulfoxide | MSO |
| N-Methylglycine, sarcosine | MeGly |
| N-Methyl isoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid (as described by Wang et al., Annu Rev Biophys Biomol Struct. 35-225-49 (2006)). These unnatural amino acids can advantageously be used to chemically link molecules of interest to the AAV capsid protein.

Modified AAV Capsid Proteins and AAV Vectors Comprising the Same

AAV Vectors

Additionally provided herein are adeno-associated virus (AAV) vectors comprising (i) a recombinant capsid protein and (ii) a cargo nucleic acid encapsidated by the capsid protein. In some embodiments, the recombinant capsid proteins (VP1, VP2 and/or VP3) may comprise a peptide in their amino acid sequence that does not occur in any native AAV capsid sequence. The inventors have demonstrated that capsid proteins comprising the peptides described herein can confer one or more desirable properties to virus vectors including, without limitation, the ability to evade neutralizing antibodies. Thus, AAV vectors described herein address the limitations associated with conventional AAV vectors.

Accordingly, in some embodiments, the present disclosure provides adeno-associated virus (AAV) vectors comprising (i) a recombinant capsid protein and (ii) a cargo nucleic acid encapsidated by the capsid protein; wherein the capsid protein comprises a peptide having the sequence of any one of SEQ ID NO: 12-20. In some embodiments, the cargo nucleic acid comprises 5' and 3' AAV inverted terminal repeats. In some embodiments, the cargo nucleic acid comprises a transgene. In some embodiments, the cargo nucleic acid is double stranded. In some embodiments, the cargo nucleic acid is single stranded. In some embodiments, the transgene encodes a therapeutic protein or RNA. In some embodiments, the recombinant capsid protein has at least 90%, at least 95%, at least 96%, at least 97%, at least 98%, or at least 99% sequence identity to the native sequence of the AAV1, AAV2, AAV3, AAV4, AAV5, AAV6, AAV7, AAV8, AAV9, AAV10, AAV11, AAV12, AAVrh.8, AAVrh.10, AAVrh32.33, AAVrh74, bovine AAV or avian AAV capsid. In some embodiments, the recombinant capsid protein has at least 90% sequence identity to the native sequence of the AAV9 capsid.

In some embodiments, the peptide is located at the amino acid positions corresponding to amino acids 451-458 of the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and the peptide is selected from any one of SEQ ID NO: 12-18. In some embodiments, the peptide is located at the amino acid positions corresponding to amino acids 587-594 of the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and the peptide is selected from SEQ ID NO: 19 or 20.

In some embodiments, a recombinant capsid protein comprises a) a first peptide having a sequence of any one of SEQ ID NO: 12-18; and b) a second peptide having a sequence of any one of SEQ ID NO: 19-20. In some embodiments, the first peptide is at amino acid positions 451-458, and the second peptide is at amino acids 587-594, wherein the amino acid numbering is based on the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV.

In some embodiments, the peptide inhibits binding of at least one antibody to the capsid protein. In some embodiments, the peptide inhibits neutralization of infectivity of the AAV vector by the antibody.

In some embodiments, the peptide selectively binds to a receptor expressed on the surface of a cell in the central nervous system (CNS). In some embodiments, the cell is in the premotor cortex, the thalamus, the cerebellar cortex, the dentate nucleus, the spinal cord, or the dorsal root ganglion. In some embodiments, the peptide selectively binds to a receptor expressed on the surface of a cell in the heart.

In some embodiments, an adeno-associated virus (AAV) vector comprises (i) a mutant AAV9 capsid protein and (ii) a cargo nucleic acid encapsidated by the capsid protein, wherein the capsid protein comprises a peptide having the sequence $X^1$-$X^2$-$X^3$—$X^4$-$X^5$-$X^6$-$X^7$-$X^8$ (SEQ ID NO: 158) at amino acids 451-458 of the native AAV9 capsid protein sequence, wherein the peptide does not occur in the native AAV9 capsid protein sequence. In some embodiments, $X^1$ is not I, $X^2$ is not N, $X^3$ is not G, $X^4$ is not S, $X^5$ is not G, $X^6$ is not Q, $X^7$ is not N, and/or $X^8$ is not Q. In some embodiments, $X^1$ is S, F, Q, G, K, or R. In some embodiments, $X^2$ is C, G, R, D, T, or Q. In some embodiments, $X^3$ is Q, V, G, Y, R, F, or D. In some embodiments, $X^4$ is P, Q, A, or R. In some embodiments, $X^5$ is T, N, A, P, or I. In some embodiments, $X^6$ is V, Q, A, or I. In some embodiments, $X^7$ is M, P, R, Q, or N. In some embodiments, $X^8$ is N, L, F, E, H, or A. In some embodiments, $X^1$ is S, $X^2$ is C, $X^3$ is Q, $X^4$ is P, $X^5$ is T, $X^6$ is V, $X^7$ is M, and $X^8$ is N. In some embodiments, $X^1$ is F, $X^2$ is G, $X^3$ is V, $X^4$ is P, $X^5$ is N, $X^6$ is Q, $X^7$ is P, and $X^8$ is L. In some embodiments, $X^1$ is Q, $X^2$ is R, $X^3$ is G, $X^4$ is Q, $X^5$ is A, $X^6$ is A, $X^7$ is P, and $X^8$ is F. In some embodiments, $X^1$ is G, $X^2$ is D, $X^3$ is Y, $X^4$ is A, $X^5$ is P, $X^6$ is I, $X^7$ is R, and $X^8$ is E. In some embodiments, $X^1$ is K, $X^2$ is T, $X^3$ is R, $X^4$ is R, $X^5$ is I, $X^6$ is V, $X^7$ is Q, and $X^8$ is H. In some embodiments, $X^1$ is F, $X^2$ is G, $X^3$ is F, $X^4$ is P, $X^5$ is N, $X^6$ is Q, $X^7$ is P, and $X^8$ is L. In some embodiments, $X^1$ is R, $X^2$ is Q, $X^3$ is D, $X^4$ is Q, $X^5$ is P, $X^6$ is I, $X^7$ is N, and $X^8$ is A.

In some embodiments, an adeno-associated virus (AAV) vector comprises (i) a mutant AAV9 capsid protein and (ii) a cargo nucleic acid encapsidated by the capsid protein, wherein the capsid protein comprises a peptide having the sequence $X^1$-$X^2$-$X^3$—$X^4$-$X^5$-$X^6$-$X^7$-$X^8$ (SEQ ID NO: 158) at amino acids 587-594 of the native AAV9 capsid protein sequence, wherein the peptide does not occur in the native AAV9 capsid protein sequence. In some embodiments, $X^1$ is not A, $X^2$ is not Q, $X^3$ is not A, $X^4$ is not Q, $X^5$ is not A, $X^6$ is not Q, $X^7$ is not T, and/or $X^8$ is not G. In some embodiments, $X^1$ is S. In some embodiments, $X^2$ is K or T. In some embodiments, $X^3$ is V. In some embodiments, $X^4$ is E or D. In some embodiments, $X^5$ is S. In some embodiments, $X^6$ is W or I. In some embodiments, $X^7$ is T or A. In some embodiments, $X^8$ is E or I. In some embodiments, $X^1$ is S, $X^2$ is K, $X^3$ is V, $X^4$ is E, $X^5$ is S, $X^6$ is W, $X^7$ is T, and $X^8$ is E. In some embodiments, $X^1$ is S, $X^2$ is T, $X^3$ is V, $X^4$ is D, $X^5$ is S, $X^6$ is I, $X^7$ is A, and $X^8$ is I.

In some embodiments, an adeno-associated virus (AAV) vector comprises (i) a recombinant capsid protein and (ii) a cargo nucleic acid encapsidated by the capsid protein, wherein the capsid protein comprises an amino acid sequence that is at least 95%, at least 96%, at least 97%, at least 98%, or at least 99% identical to any one of SEQ ID NO: 165-187. In some embodiments, the capsid protein comprises the amino acid sequence of any one of SEQ ID NO: 165-187. In some embodiments, the capsid protein comprises the amino acid sequence of SEQ ID NO: 175. In some embodiments, the capsid protein comprises the amino acid sequence of SEQ ID NO: 180.

In some embodiments, an AAV vector selectively delivers the cargo nucleic acid to a cell or tissue of the central nervous system. In some embodiments, the tissue of the central nervous system is the premotor cortex, the thalamus, the cerebellar cortex, the dentate nucleus, the spinal cord, or the dorsal root ganglion. In some embodiments, the AAV vector delivers the cargo nucleic acid to the brain, but does not deliver the AAV vector to the heart. In some embodiments, the AAV vector delivers the cargo nucleic acid to the brain and to the heart. In some embodiments, delivery of the cargo nucleic acid is greater to the brain than to the heart. In some embodiments, delivery of the cargo nucleic acid is approximately equal in the brain and in the heart.

AAV Capsid Proteins

In some embodiments, the disclosure provides an adeno-associated virus (AAV) capsid protein comprising one or more amino acid modifications (e.g., substitutions and/or deletions) compared to a native AAV capsid protein, wherein the one or more modifications modify one or more antigenic sites on the AAV capsid protein. The modification of the one or more antigenic sites results in inhibition of binding by an antibody to the one or more antigenic sites and/or inhibition of neutralization of infectivity of a virus particle comprising the AAV capsid protein. The one or more amino acid modifications (e.g., substitutions and/or deletions) can be in one or more antigenic footprints identified by peptide epitope mapping and/or cryo-electron microscopy studies of AAV-antibody complexes containing AAV capsid proteins. In some embodiments, the one or more antigenic sites are common antigenic motifs or CAMs as described in WO 2017/058892, which is incorporated herein by reference in its entirety. In some embodiments, the antigenic sites are in a variable region (VR) of the AAV capsid protein, such as VR-I, VR-II, VR-III, VR-IV, VR-V, VR-VI, VR-VII, VR-VIII, VR-IX. In some embodiments, one or more antigenic sites is in the HI loop of the AAV capsid protein.

In some embodiments, an AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV capsid protein comprises an amino acid modification (e.g., a substitution or deletion) in one or more of the regions identified in Table 5, below.

TABLE 5

Exemplary antigenic or other regions on various AAV capsids that may be partially or fully substituted/replaced. Respective VP1 numbering of residues in the native AAV capsid sequence is shown.

| AAV1 Sequence (amino acid numbers) | SEQ ID NO | AAV2 Sequence (amino acid numbers) | SEQ ID NO | AAV3 Sequence (amino acid numbers) | SEQ ID NO | AAV4 Sequence (amino acid numbers) | SEQ ID NO | AAV5 Sequence (amino acid numbers) | SEQ ID NO |
|---|---|---|---|---|---|---|---|---|---|
| SASTGAS (262-268) | 2591 | SQSGAS (262-267) | 2601 | SQSGAS (262-267) | 2611 | RLGESLQS (253-260) | 2621 | EIKSGSVDGS (249-258) | 2631 |
| VFMIPQYGYL (370-379) | 2592 | VFMVPQYGYL (369-378) | 2602 | VFMVPQYGYL (369-378) | 2612 | VFMVPQYGYC (360-369) | 2622 | VFTLPQYGYA (360-369 | 2632 |
| NQSGSAQNK (451-459) | 2593 | TPSGTTTQS (450-458) | 2603 | TTSGTTNQS (451-459) | 2613 | GTTLNAGTA (445-453) | 2623 | STNNTGGVQ (440-448) | 2633 |
| SV (472-473) | 2594 | RD (471-472) | 2604 | SL (472-473) | 2614 | SN (466-467 | 2624 | AN (458-459) | 2634 |
| KTDNNNSN (493-500) | 2595 | SADNNNSE (492-499) | 2605 | ANDNNNSN (493-500) | 2615 | ANQNYKIPATGS (487-498) | 2625 | SGVNRAS (479-485) | 2635 |
| KDDEDKF (528-534) | 2596 | KDDEEKF (527-533) | 2606 | KDDEEKF (528-534) | 2616 | GPADSKF (527-533 | 2626 | LQGSNTY (515-521) | 2636 |
| SAGASN (547-552) | 2597 | GSEKTN (546-551) | 2607 | GTTASN (547-552) | 2617 | QNGNTA (545-560) | 2627 | ANPGTTAT (534-541) | 2637 |
| STDPATGDVH (588-597) | 2598 | NRQAATADVN (587-596) | 2608 | NTAPTTGTVN (588-597) | 2618 | SNLPTVDRLT (583-595) | 2628 | TTAPATGTYN (577-586) | 2638 |
| AN (709-710) | 2599 | VN (708-709) | 2609 | VN (709-710) | 2619 | NS (707-708) | 2629 | QF (697-698 | 2639 |
| DNNGLYT (716-722) | 2600 | DTNGVYS (715-721) | 2610 | DTNGVYS (716-722) | 2620 | DAAGKYT (714-720) | 2630 | DSTGEYR (704-710) | 2640 |

| AAV6 (amino acid numbers | SEQ ID NO | AAV7 (amino acid numbers) | SEQ ID NO | AAV8 (amino acid numbers) | SEQ ID NO | AAV9 (amino acid numbers | SEQ ID NO | AAVrh8 (amino acid numbers) | SEQ ID NO |
|---|---|---|---|---|---|---|---|---|---|
| SASTGAS (262-268) | 2641 | SETAGST (263-269) | 2651 | NGTSGGAT (263-270) | 2661 | NSTSGGSS (262-269) | 2671 | NGTSGGST (262-269) | 2681 |
| VFMIPQYGYL (370-379 | 2642 | VFMIPQYGYL (371-380) | 2652 | VFMIPQYGYL (372-381) | 2662 | VFMIPQYGYL (371-380) | 2672 | VFMVPQYGYL (371-380) | 2682 |
| NQSGSAQNK (451-459) | 2643 | NPGGTAGNR (453-461) | 2653 | TTGGTANTQ (453-461) | 2663 | INGSGQNQQ (451-459) | 2673 | QTTGTGGTQ (451-459) | 2683 |
| SV (472-473) | 2644 | AN (474-475) | 2654 | AN (474-475) | 2664 | AV (472-473) | 2674 | AN (472-473) | 2684 |
| KTDNNNSN (493-500) | 2645 | LDQNNNSN (495-502) | 2655 | TGQNNNSN (495-502) | 2665 | VTQNNNSE (493-500) | 2675 | TNQNNNSN (493-500) | 2685 |
| KDDKDKF (528-534) | 2646 | KDDEDRF (530-536) | 2656 | KDDEERF (530-536) | 2666 | KEGEDRF (528-534) | 2676 | KDDDDRF (528-534) | 2686 |
| SAGASN (547-552) | 2647 | GATNKT (549-554) | 2657 | NAARDN (549-554) | 2667 | GTGRDN (547-552) | 2677 | GAGNDG (547-552) | 2687 |
| STDPATGDVH (588-897) | 2648 | NTAAQTQVVN (589-598) | 2658 | NTAPQIGTVNS (590-600) | 2668 | QAQAQTGWVQ (588-597) | 2678 | NTQAQTGLVH (588-597) | 2688 |
| AN (709-710) | 2649 | TG (710-711) | 2659 | TS (711-712) | 2669 | NN (709-710) | 2679 | TN (709-710) | 2689 |
| DNNGLYT (716-722) | 2650 | DSQGVYS (717-723) | 2660 | NTEGVYS (718-724) | 2670 | NTEGVYS (716-722) | 2680 | NTEGVYS (716-722) | 2690 |

| AAVrh10 (amino acid numbers) | SEQ ID NO | AAV10 (amino acid numbers) | SEQ ID NO | AAV11 (amino acid numbers) | SEQ ID NO | AAV12 (amino acid numbers) | SEQ ID NO | AAVrh32.33 (amino acid numbers) | SEQ ID NO |
|---|---|---|---|---|---|---|---|---|---|

TABLE 5-continued

Exemplary antigenic or other regions on various AAV capsids that may be partially or fully substituted/replaced. Respective VP1 numbering of residues in the native AAV capsid sequence is shown.

| | | | | | | | | | |
|---|---|---|---|---|---|---|---|---|---|
| NGTSGGST (263-270) | 2691 | NGTSGGST (263-270) | 2701 | RLGTTSSS (253-260) | 2711 | RIGTTANS (262-269) | 2721 | RLGTTSNS (253-260) | 2731 |
| VFMIPQYGYL (372-381) | 2692 | VFMIPQYGYL (372-381) | 2702 | VFMVPQYGYC (360-369) | 2712 | VFMVPQYGYC (369-378) | 2722 | VFMVPQYGYC (360-369) | 2732 |
| STGGTAGTQ (453-461) | 2693 | STGGTQGTQ (453-461) | 2703 | GETLNQGNA (444-452) | 2713 | GNSLNQGTA (453-461) | 2723 | GETLNQGNA (444-452) | 2733 |
| SA (474-475) | 2694 | SA (474-475) | 2704 | AF (465-466) | 2714 | AY (474-475 | 2724 | AF (465-466) | 2734 |
| LSQNNNSN (495-502) | 2695 | LSQNNNSN (495-502) | 2705 | ASQNYKIPASGG (486-497) | 2715 | ANQNYKIPASGG (495-506) | 2725 | ASQNYKIPASGG (486-497) | 2735 |
| KDDEERF (530-536) | 2696 | KDDEERF (530-536) | 2706 | GPSDGDF (526-532) | 2716 | GAGDSDF (535-541) | 2726 | GPSDGDF (526-532) | 2736 |
| GAGKDN (549-554) | 2697 | GAGRDN (549-554) | 2707 | VTGNTT (544-549) | 2717 | PSGNTT (553-558) | 2727 | VTGNTT (544-549) | 2737 |
| NAAPIVGAVN (590-599) | 2698 | NTGPIVGNVN (590-599) | 2708 | TTAPITGNVT (585-594) | 2718 | TTAPHIANLD (594-503) | 2728 | TTAPITGNVT (585-594) | 2738 |
| TN (711-712) | 2699 | TN (711-712) | 2709 | SS (706-707) | 2719 | NS (715-716) | 2729 | SS (706-707) | 2739 |
| NTDGTYS (718-724) | 2700 | NTEGTYS (718-724) | 2710 | DTTGKYT (713-719) | 2720 | DNAGNYH (722-728) | 2730 | DTTGKYT (713-719) | 2740 |

| Bovine AAV (amino acid numbers) | SEQ ID NO | Avian AAV (amino acid numbers) | SEQ ID NO |
|---|---|---|---|
| RLGSSNAS (255-262) | 2741 | RIQGPSGG (265-272) | 2751 |
| VFMVPQYGYC (362-371) | 2742 | IYTIPQYGYC (375-384) | 2752 |
| GGTLNQGNS (447-455) | 2743 | VSQAGSSGR (454-462) | 2753 |
| SG (468-469) | 2744 | AA (475-476) | 2754 |
| ASQNYKIPQGRN (489-500) | 2745 | ASNITKNNVFSV (496-507) | 2755 |
| ANDATDF (529-535) | 2746 | FSGEPDR (533-539) | 2756 |
| ITGNTT (547-552) | 2747 | VYDQTTAT (552-559) | 2757 |
| TTVPTVDDVD (588-597) | 2748 | VTPGTRAAVN (595-604) | 2758 |
| DS (709-710) | 2749 | AD (716-717) | 2759 |
| DNAGAYK (716-722) | 2750 | SDTGSYS (723-729) | 2760 |

In some embodiments, the amino acid substitution replaces any eight amino acids in an AAV capsid protein from any one of the following serotypes: AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV. For example, the amino acid substitution may replace the following amino acids (VP1 numbering): 355-362, 363-370, 371-378, 379-386, 387-394, 395-402, 403-410, 411-418, 419-426, 427-434, 435-442, 443-450, 451-458, 459-466, 467-474, 475-482, 483-490, 491-498, 499-506, 507-514, 515-522, 523-530, 531-538, 539-546, 547-554, 555-562, 563-570, 571-578, 579-586, 587-594, 595-602, 603-610, 611-618, 619-626, 627-634, 635-642, 643-650, 651-658, 659-666, 667-674, 675-682, 683-690, 691-698, 699-706, 707-714, 715-722 in any of the above-listed AAV serotypes.

In some embodiments, the amino acid substitution is selected from any one of SEQ ID NO: 19-20. In some embodiments, the amino acid substitution has at least 95%, at least 96%, at least 97%, at least 98%, or at least 99% sequence homology with any one of SEQ ID NO: 12-18. In some embodiments, the substitution is at the amino acids corresponding to amino acids 587-594 of the wildtype AAV9 capsid. In some embodiments, the substitution is at the amino acids corresponding to amino acids 587-594 of the wildtype AAV1 capsid. In some embodiments, the substitution is at the amino acids corresponding to amino acids 587-594 of the wildtype AAV6 capsid. In some embodiments, the substitution is at the amino acids corresponding to amino acids 589-596 of the wildtype AAV8 capsid. In some embodiments, the substitution is at the amino acids corresponding to amino acids 587-594 of the wildtype AAVrh8 capsid. In some embodiments, the substitution is at the amino acids corresponding to amino acids 589-596 of the wildtype AAVrh10 capsid.

In some embodiments, the amino acid substitution is selected from any one of SEQ ID NO: 18-20. In some embodiments, the amino acid substitution has at least 95%, at least 96%, at least 97%, at least 98%, or at least 99% sequence homology with any one of SEQ ID NO: 18-20. In some embodiments, the substitution is at the amino acids corresponding to amino acids 451-458 of the wildtype AAV9 capsid.

In some embodiments, an amino acid deletion comprises a deletion of at least one, at least two, at least three, at least four, at least five, at least six, at least seven, at least eight, at least nine, or at least ten amino acids compared to the wildtype capsid.

In some embodiments, an AAV capsid comprises one or more amino acid substitutions and one or more amino acid deletions. In some embodiments, a capsid comprises at least one amino acid substitution and at least one amino acid deletion. In some embodiments, a capsid comprises at least one amino acid substitution and at least one amino acid deletion, wherein the at least one amino acid substitution and the at least one amino acid deletion are immediately adjacent to one another in the capsid amino acid sequence.

In some embodiments, the capsid proteins are modified to produce an AAV capsid that, when present in an AAV virus particle or AAV virus vector, has a phenotype of selectively targeting the CNS (e.g., the brain, the spinal cord). In some embodiments, the capsid proteins are modified to produce an AAV capsid that, when present in an AAV virus particle or AAV virus vector, has a phenotype of evading neutralizing antibodies. The AAV virus particle or vector can also have a phenotype of enhanced or maintained transduction efficiency in addition to the phenotype of evading neutralizing antibodies and/or targeting the CNS.

In some embodiments, the one or more substitutions can introduce one or more sequences from a capsid protein of a first AAV serotype into the capsid protein of a second AAV serotype that is different from the first AAV serotype.

The base AAV capsid protein to which modifications are added can be a capsid protein of an AAV serotype selected from AAV1, AAV2, AAV3, AAV3B, AAV4, AAV5, AAV6, AAV7, AAV8, AAV9, AAV10, AAV11, AAV12, AAVrh.8, AAVrh.10, AAVrh.32.33, AAVrh74, bovine AAV, avian AAV or any other AAV now known or later identified. In some embodiments, the base AAV capsid protein is of the AAV9 serotype. In some embodiments, the base AAV capsid protein is chimeric. In some embodiments, the base AAV capsid protein is an AAV8/9 chimera.

Several examples of a modified AAV capsid protein are provided herein. In the following examples, the capsid protein can comprise the specific substitutions described and, in some embodiments, can comprise fewer or more substitutions than those described. As used herein, "substitution" may refer to a single amino acid substitution, or a substitution of more than one contiguous amino acid. For example in some embodiments, a capsid protein can comprise at least 1, 2, 3, 4, 5, 6, 7, 8, 9, 10, etc., single amino acid substitutions. In some embodiments, a capsid protein can comprise one or more substitutions of multiple contiguous amino acids, such as one or more substitutions of 2, 3, 4, 5, 6, 7, 8, 9, 10, 11, or 12 contiguous amino acids.

Furthermore, in some embodiments described herein wherein an amino acid residue is substituted by any amino acid residue other than the amino acid residue present in the wildtype or native amino acid sequence, the any other amino acid residue can be any natural or non-natural amino acid residue known in the art (see, e.g., Tables 2 and 3). In some embodiments, the substitution can be a conservative substitution and in some embodiments, the substitution can be a nonconservative substitution. In some embodiments, an AAV capsid protein comprises one or more amino acid substitutions, wherein the amino acid substitutions are each individually selected from SEQ ID NO: 12-18 as shown in Table 6.1.

TABLE 6.1

AMINO ACID SUBSTITUTIONS

| Amino Acid Substitution | SEQ ID NO. |
|---|---|
| SCQPTVMN | 12 |
| FGVPNQPL | 13 |
| QRGQAAPF | 14 |
| GDYAPIRE | 15 |
| KTRRIVQH | 16 |
| FGFPNQPL | 17 |
| RQDQPINA | 18 |

In some embodiments, an AAV capsid protein comprises one or more amino acid substitutions, wherein the amino acid substitutions are each selected from SEQ ID NO: 19-20 as shown in Table 6.2.

TABLE 6.2

AMINO ACID SUBSTITUTIONS

| Amino Acid Substitution | SEQ ID NO. |
|---|---|
| SKVESWTE | 19 |
| STVDSIAI | 20 |

In some embodiments, an AAV capsid protein may comprise a first substitution selected from the sequences listed in Table 6.1 and a second substitution selected from the sequences listed in Table 6.2. In some embodiments, an AAV capsid protein may comprise a first substitution, a second substitution as shown in Tables 6.3 and 6.4.

TABLE 6.3

COMBINATIONS OF AMINO ACID SUBSTITUTIONS

| First Substitution (SEQ ID NO) | Second Substitution (SEQ ID NO) |
|---|---|
| 12, 13, 14, 15, 16, 17, or 18 | 19 or 20 |

TABLE 6.4

COMBINATIONS OF AMINO ACID SUBSTITUTIONS

| First Substitution (SEQ ID NO) | Second Substitution (SEQ ID NO) |
|---|---|
| 12 | 19 |
| 12 | 20 |
| 13 | 19 |
| 13 | 20 |
| 14 | 19 |
| 14 | 20 |
| 15 | 19 |
| 15 | 20 |
| 16 | 19 |
| 16 | 20 |

TABLE 6.4-continued

COMBINATIONS OF AMINO ACID SUBSTITUTIONS

| First Substitution (SEQ ID NO) | Second Substitution (SEQ ID NO) |
|---|---|
| 17 | 19 |
| 17 | 20 |
| 18 | 19 |
| 18 | 20 |

In some embodiments, an AAV capsid protein comprises an amino acid modification (e.g., substitution and/or deletion), wherein the amino acid modification modifies one or more surface-exposed regions, such as an antigenic region, on the AAV capsid protein.

In some embodiments, an AAV capsid protein comprises one or more amino acid substitutions, wherein at least one of the amino acid substitutions comprises one of SEQ ID NOs: 19-20. In some embodiments, the substitution replaces the amino acids corresponding to amino acids 587-594 of the wildtype AAV9 capsid.

In some embodiments, an AAV capsid protein comprises one or more amino acid substitutions, wherein at least one of the amino acid substitutions comprises one of SEQ ID NOs: 12-18. In some embodiments, the substitution replaces the amino acids corresponding to amino acids 451-458 of the wildtype AAV9 capsid.

In some embodiments, an AAV capsid protein comprises a substitution comprising a sequence of eight amino acids ($X^1$—$X^2$-$X^3$-$X^4$-$X^5$-$X^6$-$X^7$-$X^8$) (SEQ ID NO: 158) that does not occur in the native capsid protein sequence. In some embodiments, $X^1$ is not I, $X^2$ is not N, $X^3$ is not G, $X^4$ is not S, $X^5$ is not G, $X^6$ is not Q, $X^7$ is not N, and/or $X^8$ is not Q. In some embodiments, $X^1$ is S, F, Q, G, K, or R. In some embodiments, $X^2$ is C, G, R, D, T, or Q. In some embodiments, $X^3$ is Q, V, G, Y, R, F, or D. In some embodiments, $X^4$ is P, Q, A, or R. In some embodiments, $X^5$ is T, N, A, P, or I. In some embodiments, $X^6$ is V, Q, A, or I. In some embodiments, $X^7$ is M, P, R, Q, or N. In some embodiments, $X^8$ is N, L, F, E, H, or A. In some embodiments, $X^1$ is S, $X^2$ is C, $X^3$ is Q, $X^4$ is P, $X^5$ is T, $X^6$ is V, $X^7$ is M, and $X^8$ is N. In some embodiments, $X^1$ is F, $X^2$ is G, $X^3$ is V, $X^4$ is P, $X^5$ is N, $X^6$ is Q, $X^7$ is P, and $X^8$ is L. In some embodiments, $X^1$ is Q, $X^2$ is R, $X^3$ is G, $X^4$ is Q, $X^5$ is A, $X^6$ is A, $X^7$ is P, and $X^8$ is F. In some embodiments, $X^1$ is G, $X^2$ is D, $X^3$ is Y, $X^4$ is A, $X^5$ is P, $X^6$ is I, $X^7$ is R, and $X^8$ is E. In some embodiments, $X^1$ is K, $X^2$ is T, $X^3$ is R, $X^4$ is R, $X^5$ is I, $X^6$ is V, $X^7$ is Q, and $X^8$ is H. In some embodiments, $X^1$ is F, $X^2$ is G, $X^3$ is F, $X^4$ is P, $X^5$ is N, $X^6$ is Q, $X^7$ is P, and $X^8$ is L. In some embodiments, $X^1$ is R, $X^2$ is Q, $X^3$ is D, $X^4$ is Q, $X^5$ is P, $X^6$ is I, $X^7$ is N, and $X^8$ is A.

In some embodiments, $X^1$ is not A, $X^2$ is not Q, $X^3$ is not A, $X^4$ is not Q, $X^5$ is not A, $X^6$ is not Q, $X^7$ is not T, and/or $X^8$ is not G. In some embodiments, $X^1$ is S. In some embodiments, $X^2$ is K or T. In some embodiments, $X^3$ is V. In some embodiments, $X^4$ is E or D. In some embodiments, $X^5$ is S. In some embodiments, $X^6$ is W or I. In some embodiments, $X^7$ is T or A. In some embodiments, $X^8$ is E or I. In some embodiments, $X^1$ is S, $X^2$ is K, $X^3$ is V, $X^4$ is E, $X^5$ is S, $X^6$ is W, $X^7$ is T, and $X^8$ is E. In some embodiments, $X^1$ is S, $X^2$ is T, $X^3$ is V, $X^4$ is D, $X^5$ is S, $X^6$ is I, $X^7$ is A, and $X^8$ is I.

In some embodiments, an AAV capsid protein comprises one or more amino acid deletions, wherein the amino acid deletion comprises a deletion of at least six or at least eight amino acids compared to the wildtype AAV capsid. In some embodiments, an AAV capsid protein comprises a deletion of eight consecutive amino acids compared to the native capsid protein sequence. In some embodiments, an AAV capsid protein comprises a deletion of six consecutive amino acids compared to the native capsid protein sequence.

In some embodiments, an AAV capsid protein comprises the sequence LSKTQTLK (SEQ ID NO: 1374) or the sequence LSKTDPQTLK (SEQ ID NO: 1375). In some embodiments, the AAV capsid protein comprising SEQ ID NO: 1374 or 1375 is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

In some embodiments, an AAV capsid protein comprises a first substitution comprising a sequence selected from SEQ ID NO: 12-18; and a second substitution comprising a sequence selected from SEQ ID NO: 19-20.

In some embodiments, an AAV capsid protein comprises an amino acid deletion and a substitution, wherein the substitution comprises a sequence selected from SEQ ID NO: 12-20.

In some embodiments, a recombinant capsid protein has a sequence that is at least 90%, at least 95%, at least 96%, at least 97%, at least 98%, at least 99% or 100% identical to SEQ ID NO: 9 (AAV9) and comprises one or more of the following amino acid substitutions: 1451S, 1451F, 1451Q, 1451G, 1451K, 1451R, N452C, N452G, N452R, N452D, N452T, N452Q, G453Q, G453V, G453Y, G453R, G453F, G453D, S454P, S454Q, S454A, S454R, G455T, G455N, G455A, G455P, G4551, Q456V, Q456A, Q4561, N457M, N457P, N457R, N457Q, Q458N, Q458L, Q458F, Q458E, Q458H, Q458A, A587S, Q588K, Q588T, A589V, Q590E, Q590D, A591 S, Q592W, Q5921, T593A, G594E, G5941.

Any of the AAV capsids described herein may further comprise a modification (e.g., a substitution or a deletion) in the HI loop. The HI loop is a prominent domain on the AAV capsid surface, between β strands βH and βI, that extends from each viral protein (VP) subunit overlapping the neighboring fivefold VP. In some embodiments, an AAV capsid comprises one, two, three, four, five, six, seven, or eight amino acid substitutions in the HI loop. In some embodiments, the AAV capsid comprises one or more of the following substitutions in the HI loop: P661R, T662S, Q666G, S667D, wherein the numbering corresponds to the wildtype AAV8 capsid (SEQ ID NO: 8). In some embodiments, the AAV capsid comprises one or more of the following substitutions in the HI loop: P659R, T660S, A661T, K664G, wherein the numbering corresponds to the wildtype AAV9 capsid (SEQ ID NO: 9).

In some embodiments, an AAV capsid protein comprises one, two, three, or four amino acid substitutions, wherein each substitution modifies a different antigenic site on the AAV capsid protein, and wherein at least one of the amino acid substitutions modifies the HI loop of the capsid protein.

In some embodiments, an AAV capsid protein comprises a first, a second, a third, and a fourth amino acid substitution. In some embodiments, at least one of the substitutions modifies the HI Loop of the capsid protein. In some embodiments, the AAV capsid comprises one or more of the following substitutions in the HI loop: P661R, T662S, Q666G, S667D, wherein the numbering corresponds to the wildtype AAV8 capsid (SEQ ID NO: 8); or P659R, T660S, A661T, K664G, wherein the numbering corresponds to the wildtype AAV9 capsid (SEQ ID NO: 9). In some embodiments, an AAV capsid protein comprises the amino acid sequence of any one of SEQ ID NO: 185-187. In some embodiments, an AAV capsid protein comprises an amino acid sequence sharing at least 90%, at least 95%, at least 96%, at least 97%, at least 98%, or at least 99% sequence identity to any one of SEQ ID NO: 165-187.

Also provided herein is a nucleotide sequence, or an expression vector comprising the same that encodes one or more of the AAV capsid proteins described herein. The nucleotide sequence may be a DNA sequence or an RNA sequence. In some embodiments, cell comprises one or more nucleotide sequences or expression vectors described herein.

In some embodiments, an AAV capsid comprises an AAV capsid protein as described herein. Further provided herein is a viral vector comprising an AAV capsid as well as a composition comprising the AAV capsid protein, AAV capsid and/or viral vector in a pharmaceutically acceptable carrier.

In some embodiments, modification of one or more antigenic sites results in inhibition of binding by an antibody to the one or more antigenic sites. In some embodiments, modification of the one or more antigenic sites results in inhibition of neutralization of infectivity of a virus particle comprising the AAV capsid protein.

As described herein, the nucleic acid and amino acid sequences of the capsid proteins from a number of AAV are known in the art. Thus, the amino acids "corresponding" to amino acid positions of the native AAV capsid protein can be readily determined for any other AAV (e.g., by using sequence alignments).

The modified capsid proteins can be produced by modifying the capsid protein of any AAV now known or later discovered. Further, the base AAV capsid protein that is to be modified can be a naturally occurring AAV capsid protein (e.g., an AAV2, AAV3a or 3b, AAV4, AAV5, AAV6, AAV7, AAV8, AAV9, AAV10 or AAV11 capsid protein or any of the AAV shown in Table 2) but is not so limited. Those skilled in the art will understand that a variety of manipulations to the AAV capsid proteins are known in the art and the disclosure is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). In some embodiments, the capsid protein may be a chimeric capsid protein. In some embodiments, the capsid protein may be an engineered AAV, such as AAV2i8, AAV2g9, AAV-LK03, AAV7m8, AAV Anc80, AAV PHP.B.

Thus, in some embodiments, the AAV capsid protein to be modified can be derived from a naturally occurring AAV but further comprises one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 2, etc.), it is intended to encompass the native capsid protein as well as capsid proteins that have alterations other than the modifications described herein. Such alterations include substitutions, insertions and/or deletions. In some embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids inserted therein (other than the insertions described herein) as compared with the native AAV capsid protein sequence. In some embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acid substitutions (other than the amino acid substitutions described herein) as compared with the native AAV capsid protein sequence, in some embodiments, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids as compared with the native AAV capsid protein sequence.

In some embodiments, the AAV capsid protein has an amino acid sequence that is at least about 90%, about 95%, about 97%, about 98% or about 99% similar or identical to a native AAV capsid protein sequence.

Methods of determining sequence similarity or identity between two or more amino acid sequences are known in the art. Sequence similarity or identity may be determined using standard techniques, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

In some embodiments, a virus capsid comprises a modified AAV capsid protein as described herein. In some embodiments, the virus capsid is a parvovirus capsid, which may further be an autonomous parvovirus capsid or a dependovirus capsid. Optionally, the virus capsid is an AAV capsid. In some embodiments, the AAV capsid is an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV capsid, avian AAV capsid or any other AAV now known or later identified. A nonlimiting list of AAV serotypes is shown in Table 2. An AAV capsid can be any AAV serotype listed in Table 2 or derived from any of the foregoing by one or more insertions, substitutions and/or deletions. Molecules that can be packaged by the modified virus capsid and transferred into a cell include cargo nucleic acids (e.g., heterologous DNA or RNA), polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In some embodiments the therapeutically useful molecule is covalently linked (i.e., conjugated or chemically coupled) to the capsid proteins. Methods of covalently linking molecules are known by those skilled in the art.

The modified virus capsids also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In some embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to some embodiments, modified virus capsids can be administered to a subject prior to and/or concurrently with a modified virus vector as described herein. Further, the disclosure provides compositions and pharmaceutical formulations comprising the inventive modified virus capsids; optionally, the composition also comprises a modified virus vector as described herein.

In some embodiments, a nucleic acid (optionally, an isolated nucleic acid) encodes the modified virus capsids and capsid proteins described herein. Further provided are vectors comprising the nucleic acids, and cells (in vivo or in culture) comprising the nucleic acids and/or vectors described herein. As one example, a virus vector may comprise: (a) a modified AAV capsid as described herein; and (b) a nucleic acid comprising at least one terminal repeat sequence, wherein the nucleic acid is encapsidated by the AAV capsid.

Other suitable vectors include without limitation viral vectors (e.g., adenovirus, AAV, herpesvirus, vaccinia, poxviruses, baculovirus, lentivirus, coronavirus, and the like), plasmids, phage, YACs, BACs, and the like. Such nucleic acids, vectors and cells can be used, for example, as reagents (e.g., helper packaging constructs or packaging cells) for the production of modified virus capsids or virus vectors as described herein.

Virus capsids described herein can be produced using any method known in the art, e.g., by using a baculovirus system (Brown et al., (1994) Virology 198:477-488).

The modifications to the AAV capsid protein as described herein are "selective" modifications. This approach is in contrast to previous work with whole subunit or large domain swaps between AAV serotypes (see, e.g., international patent publication WO 00/28004 and Hauck et al., (2003) J. Virology 77:2768-2774). In some embodiments, a "selective" modification results in the insertion and/or substitution and/or deletion of less than or equal to about 20, 18, 15, 12, 10, 9, 8, 7, 6, 5, 4 or 3 contiguous amino acids.

The modified capsid proteins and capsids described herein can further comprise any other modification, now known or later identified. For example, the AAV capsid proteins and virus capsids can be chimeric in that they can comprise all or a portion of a capsid subunit from another virus, optionally another parvovirus or AAV, e.g., as described in international patent publication WO 00/28004.

In some embodiments, the virus capsid can be a targeted virus capsid, comprising a targeting sequence (e.g., substituted or inserted in the viral capsid) that directs the virus capsid to interact with cell-surface molecules present on desired target tissue(s) (see, e.g., International patent publication WO 00/28004 and Hauck et al., (2003) J. Virology 77:2768-2774); Shi et al., Human Gene Therapy 17:353-361 (2006) [describing insertion of the integrin receptor binding motif RGD at positions 520 and/or 584 of the AAV capsid subunit]; and U.S. Pat. No. 7,314,912 [describing insertion of the PI peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., Molecular Therapy 3:964-975 (2001)).

For example, a virus capsid as described herein may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., Annu Rev Biophys Biomol Struct. 35:225-49 (2006)) can be incorporated into an AAV capsid subunit as described herein at an orthogonal site as a means of redirecting a low-transduction vector to desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like.

In some embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin or heparan sulfate binding domain (e.g., the respiratory syncytial virus heparin binding domain) may be inserted or substituted into a capsid subunit that does not typically bind HS receptors (e.g., AAV4, AAV5) to confer heparin and/or heparan sulfate binding to the resulting mutant.

B19 infects primary erythroid progenitor cells using globoside as its receptor (Brown et al, (1993) Science 262:114). The structure of B19 has been determined to 8 Å resolution (Agbandje-McKenna et al, (1994) Virology 203:106). The region of the B19 capsid that binds to globoside has been mapped between amino acids 399-406 (Chapman et al, (1993) Virology 194:419), a looped out region between β-barrel structures E and F (Chipman et al, (1996) Proc. Nat. Acad. Sci. USA 93:7502). Accordingly, the globoside receptor binding domain of the B19 capsid may be substituted into an AAV capsid protein to target a virus capsid or virus vector comprising the same to erythroid cells.

In some embodiments, the exogenous targeting sequence may be any amino acid sequence encoding a peptide that alters the tropism of a virus capsid or virus vector comprising the modified AAV capsid protein. In some embodiments, the targeting peptide or protein may be naturally occurring or, alternately, completely or partially synthetic. Exemplary targeting sequences include ligands and other peptides that bind to cell surface receptors and glycoproteins, such as ROD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadolibcrin, corticostatin, β-endorphin, leu-enkephalin, rimorphin, alpha-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as alpha-bungarotoxin, and the like) can be substituted into the capsid protein as a targeting sequence. In some embodiments, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (Current Biology 7:R318 (1997)) into the AAV capsid protein. Also encompassed are peptide motifs that direct uptake by specific cells, e.g., a FVFLP (SEQ ID NO: 22) peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC 1 glycoproteins, carbohydrate components found on membrane glycoproteins, including, mannose, N-acetyl-galactosamine, N-acetyl-glucosamine, fucose, galactose, and the like.

In some embodiments, a heparan sulfate (HS) or heparin binding domain is substituted into the virus capsid (for example, in an AAV capsid that otherwise does not bind to HS or heparin). It is known in the art that HS/heparin binding is mediated by a "basic patch" that is rich in arginines and/or lysines. In some embodiments, a sequence following the motif BXXB (SEQ ID NO: 23), where "B" is a basic residue and X is neutral and/or hydrophobic residue can be employed. As a nonlimiting example, BXXB can be RGNR (SEQ ID NO: 24). As another nonlimiting example, BXXB is substituted for amino acid positions 262 through 265 in the native AAV2 capsid protein or at the corresponding position(s) in the capsid protein of another AAV serotype.

Table 7 shows other non-limiting examples of suitable targeting sequences.

TABLE 7

TARGETING SEQUENCES

| Sequence | SEQ ID NO | Reference |
|---|---|---|
| NSVRDL(G/S) | 25 | Muller et al., Nature Biotechnology 21: 1040-1046 (2003) |
| PRSVTVP | 26 | Muller et al., Nature Biotechnology 21: 1040-1046 (2003) |
| NSVSSX(S/A) | 27 | Muller et al., Nature Biotechnology 21: 1040-1046 (2003) |
| NGR, NGRAHA | 28 | Grifman et al., Molecular Therapy 3: 964-975 (2001) |
| QPEHSST | 29 | Work et al., Molecular Therapy 13: 683-693 (2006) |
| VNTANST | 30 | Work et al., Molecular Therapy 13: 683-693 (2006) |
| HGPMQS | 31 | Work et al., Molecular Therapy 13: 683-693 (2006) |
| PHKPPLA | 32 | Work et al., Molecular Therapy 13: 683-693 (2006) |
| IKNNEMW | 33 | Work et al., Molecular Therapy 13: 683-693 (2006) |
| RNLDTPM | 34 | Work et al., Molecular Therapy 13: 683-693 (2006) |
| VDSHRQS | 35 | Work et al., Molecular Therapy 13: 683-693 (2006) |
| YDSKTKT | 36 | Work et al., Molecular Therapy 13: 683-693 (2006) |
| SQLPHQK | 37 | Work et al., Molecular Therapy 13: 683-693 (2006) |
| STMQQNT | 38 | Work et al., Molecular Therapy 13: 683-693 (2006) |
| TERYMTQ | 39 | Work et al., Molecular Therapy 13: 683-693 (2006) |
| QPEHSST | 40 | Work et al., Molecular Therapy 13: 683-693 (2006) |

TABLE 7-continued

TARGETING SEQUENCES

| Sequence | SEQ ID NO | Reference |
|---|---|---|
| DASLSTS | 41 | Work et al., Molecular Therapy 13: 683-693 (2006) |
| DLPNKT | 42 | Work et al., Molecular Therapy 13: 683-693 (2006) |
| DLTAARL | 43 | Work et al., Molecular Therapy 13: 683-693 (2006) |
| EPHQFNY | 44 | Work et al., Molecular Therapy 13: 683-693 (2006) |
| EPQSNHT | 45 | Work et al., Molecular Therapy 13: 683-693 (2006) |
| MSSWPSQ | 46 | Work et al., Molecular Therapy 13: 683-693 (2006) |
| NPKHNAT | 47 | Work et al., Molecular Therapy 13: 683-693 (2006) |
| PDGMRTT | 48 | Work et al., Molecular Therapy 13: 683-693 (2006) |
| PNNNKTT | 49 | Work et al., Molecular Therapy 13: 683-693 (2006) |
| QSTTHDS | 50 | Work et al., Molecular Therapy 13: 683-693 (2006) |
| TGSKQKQ | 51 | Work et al., Molecular Therapy 13: 683-693 (2006) |
| SLKHQAL | 52 | Work et al., Molecular Therapy 13: 683-693 (2006) |
| SPIDGEQ | 53 | Work et al., Molecular Therapy 13: 683-693 (2006) |
| WIFPWIQL | 54 | Hajitou et al., TCM 16: 80-88 (2006) |
| CDCRGDCFC | 55 | Hajitou et al., TCM 16: 80-88 (2006) |
| CNGRC | 56 | Hajitou et al., TCM 16: 80-88 (2006) |
| CPRECES | 57 | Hajitou et al., TCM 16: 80-88 (2006) |
| CTTHWGFTLC | 58 | Hajitou et al., TCM 16: 80-88 (2006) |
| CGRRAGGSC | 59 | Hajitou et al., TCM 16: 80-88 (2006) |
| CKGGRAKDC | 60 | Hajitou et al., TCM 16: 80-88 (2006) |
| CVPELGHEC | 61 | Hajitou et al., TCM 16: 80-88 (2006) |
| CRRETAWAK | 62 | Koivunen et al., J. Nucl. Med. 40: 883-888 (1999) |
| VSWFSHRYSPFAVS | 63 | Koivunen et al., J. Nucl. Med. 40: 883-888 (1999) |
| GYRDGYAGPILYN | 64 | Koivunen et al., J. Nucl. Med. 40: 883-888 (1999) |
| XXXY*XXX | 65 | Koivunen et al., J. Nucl. Med. 40: 883-888 (1999) |
| Y*E/MNW | 66 | Koivunen et al., J. Nucl. Med. 40: 883-888 (1999) |
| RPLPPLP | 67 | Koivunen et al., J. Nucl. Med. 40: 883-888 (1999) |
| APPLPPR | 68 | Koivunen et al., J. Nucl. Med. 40: 883-888 (1999) |
| DVFYPYPYASGS | 69 | Koivunen et al., J. Nucl. Med. 40: 883-888 (1999) |
| MYWYPY | 70 | Koivunen et al., J. Nucl. Med. 40: 883-888 (1999) |
| DITWDQLWDLMK | 71 | Koivunen et al., J. Nucl. Med. 40: 883-888 (1999) |
| CWDD(G/L)WLC | 72 | Koivunen et al., J. Nucl. Med. 40: 883-888 (1999) |
| EWCEYLGGYLRCYA | 73 | Koivunen et al., J. Nucl. Med. 40: 883-888 (1999) |
| YXCXXGPXTWXCXP | 74 | Koivunen et al., J. Nucl. Med. 40: 883-888 (1999) |
| IEGPTLRQWLAARA | 75 | Koivunen et al., J. Nucl. Med. 40: 883-888 (1999) |
| LWXX(Y/W/F/H) | 76 | Koivunen et al., J. Nucl. Med. 40: 883-888 (1999) |
| XFXXYLW | 77 | Koivunen et al., J. Nucl. Med. 40: 883-888 (1999) |

TABLE 7-continued

TARGETING SEQUENCES

| Sequence | SEQ ID NO | Reference |
|---|---|---|
| RWGLCD | 78 | Koivunen et al., J. Nucl. Med. 40: 883-888 (1999) |
| MSRPACPPNDKYE | 79 | Koivunen et al., J. Nucl. Med. 40: 883-888 (1999) |
| CLRSGRGC | 80 | Koivunen et al., J. Nucl. Med. 40: 883-888 (1999) |
| CHWMFSPWC | 81 | Koivunen et al., J. Nucl. Med. 40: 883-888 (1999) |
| WXXF | 82 | Koivunen et al., J. Nucl. Med. 40: 883-888 (1999) |
| CSSRLDAC | 83 | Koivunen et al., J. Nucl. Med. 40: 883-888 (1999) |
| CLPVASC | 84 | Koivunen et al., J. Nucl. Med. 40: 883-888 (1999) |
| CGFECVRQCPERC | 85 | Koivunen et al., J. Nucl. Med. 40: 883-888 (1999) |
| CVALCREACGEGC | 86 | Koivunen et al., J. Nucl. Med. 40: 883-888 (1999) |
| SWCEPGWCR | 87 | Koivunen et al., J. Nucl. Med. 40: 883-888 (1999) |
| YSGWGW | 88 | Koivunen et al., J. Nucl. Med. 40: 883-888 (1999) |
| GLSGGRS | 89 | Koivunen et al., J. Nucl. Med. 40: 883-888 (1999) |
| LMLPRAD | 90 | Koivunen et al., J. Nucl. Med. 40: 883-888 (1999) |
| CSCFRDVCC | 91 | Koivunen et al., J. Nucl. Med. 40: 883-888 (1999) |
| CRDVVSVIC | 92 | Koivunen et al., J. Nucl. Med. 40: 883-888 (1999) |
| CNGRC | 93 | Koivunen et al., J. Nucl. Med. 40: 883-888 (1999) |
| MARSGL | 94 | Newton & Deutscher, Phage Peptide Display in Handbook of Experimental Pharmacology, pages 145-163, Springer-Verlag, Berlin (2008) |
| MARAKE | 95 | Newton & Deutscher, Phage Peptide Display in Handbook of Experimental Pharmacology, pages 145-163, Springer-Verlag, Berlin (2008) |
| MSRTMS | 96 | Newton & Deutscher, Phage Peptide Display in Handbook of Experimental Pharmacology, pages 145-163, Springer-Verlag, Berlin (2008) |
| KCCYSL | 97 | Newton & Deutscher, Phage Peptide Display in Handbook of Experimental Pharmacology, pages 145-163, Springer-Verlag, Berlin (2008) |
| MYWGDSHWLQYWYE | 98 | Newton & Deutscher, Phage Peptide Display in Handbook of Experimental Pharmacology, pages 145-163, Springer-Verlag, Berlin (2008) |
| MQLPLAT | 99 | Newton & Deutscher, Phage Peptide Display in Handbook of Experimental Pharmacology, pages 145-163, Springer-Verlag, Berlin (2008) |
| EWLS | 100 | Newton & Deutscher, Phage Peptide Display in Handbook of Experimental Pharmacology, pages 145-163, Springer-Verlag, Berlin (2008) |
| SNEW | 101 | Newton & Deutscher, Phage Peptide Display in Handbook of Experimental Pharmacology, pages 145-163, Springer-Verlag, Berlin (2008) |
| TNYL | 102 | Newton & Deutscher, Phage Peptide Display in Handbook of Experimental Pharmacology, pages 145-163, Springer-Verlag, Berlin (2008) |
| WIFPWIQL | 103 | Newton & Deutscher, Phage Peptide Display in Handbook of Experimental Pharmacology, pages 145-163, Springer-Verlag, Berlin (2008) |
| WDLAWMFRLPVG | 104 | Newton & Deutscher, Phage Peptide Display in Handbook of Experimental Pharmacology, pages 145-163, Springer-Verlag, Berlin (2008) |

TABLE 7-continued

TARGETING SEQUENCES

| Sequence | SEQ ID NO | Reference |
|---|---|---|
| CTVALPGGYVRVC | 105 | Newton & Deutscher, Phage Peptide Display in Handbook of Experimental Pharmacology, pages 145-163, Springer-Verlag, Berlin (2008) |
| CVPELGHEC | 106 | Newton & Deutscher, Phage Peptide Display in Handbook of Experimental Pharmacology, pages 145-163, Springer-Verlag, Berlin (2008) |
| CGRRAGGSC | 107 | Newton & Deutscher, Phage Peptide Display in Handbook of Experimental Pharmacology, pages 145-163, Springer-Verlag, Berlin (2008) |
| CVAYCIEHHCWTC | 108 | Newton & Deutscher, Phage Peptide Display in Handbook of Experimental Pharmacology, pages 145-163, Springer-Verlag, Berlin (2008) |
| CVFAHNYDYLVC | 109 | Newton & Deutscher, Phage Peptide Display in Handbook of Experimental Pharmacology, pages 145-163, Springer-Verlag, Berlin (2008) |
| CVFTSNYAFC | 110 | Newton & Deutscher, Phage Peptide Display in Handbook of Experimental Pharmacology, pages 145-163, Springer-Verlag, Berlin (2008) |
| VHSPNKK | 111 | Newton & Deutscher, Phage Peptide Display in Handbook of Experimental Pharmacology, pages 145-163, Springer-Verlag, Berlin (2008) |
| CDCRGDCFC | 112 | Newton & Deutscher, Phage Peptide Display in Handbook of Experimental Pharmacology, pages 145-163, Springer-Verlag, Berlin (2008) |
| CRGDGWC | 113 | Newton & Deutscher, Phage Peptide Display in Handbook of Experimental Pharmacology, pages 145-163, Springer-Verlag, Berlin (2008) |
| XRGCDX | 114 | Newton & Deutscher, Phage Peptide Display in Handbook of Experimental Pharmacology, pages 145-163, Springer-Verlag, Berlin (2008) |
| PXX(S/T) | 115 | Newton & Deutscher, Phage Peptide Display in Handbook of Experimental Pharmacology, pages 145-163, Springer-Verlag, Berlin (2008) |
| CTTHWGFTLC | 116 | Newton & Deutscher, Phage Peptide Display in Handbook of Experimental Pharmacology, pages 145-163, Springer-Verlag, Berlin (2008) |
| SGKGPRQITAL | 117 | Newton & Deutscher, Phage Peptide Display in Handbook of Experimental Pharmacology, pages 145-163, Springer-Verlag, Berlin (2008) |
| A(A/Q)(N/A)(L/Y)(T/V/M/R)(R/K) | 118 | Newton & Deutscher, Phage Peptide Display in Handbook of Experimental Pharmacology, pages 145-163, Springer-Verlag, Berlin (2008) |
| VYMSPF | 119 | Newton & Deutscher, Phage Peptide Display in Handbook of Experimental Pharmacology, pages 145-163, Springer-Verlag, Berlin (2008) |
| MQLPLAT | 120 | Newton & Deutscher, Phage Peptide Display in Handbook of Experimental Pharmacology, pages 145-163, Springer-Verlag, Berlin (2008) |
| ATWLPPR | 121 | Newton & Deutscher, Phage Peptide Display in Handbook of Experimental Pharmacology, pages 145-163, Springer-Verlag, Berlin (2008) |
| HTMYYHHYQHHL | 122 | Newton & Deutscher, Phage Peptide Display in Handbook of Experimental Pharmacology, pages 145-163, Springer-Verlag, Berlin (2008) |

TABLE 7-continued

TARGETING SEQUENCES

| Sequence | SEQ ID NO | Reference |
|---|---|---|
| SEVGCRAGPLQWLCEKYFG | 123 | Newton & Deutscher, Phage Peptide Display in Handbook of Experimental Pharmacology, pages 145-163, Springer-Verlag, Berlin (2008) |
| CGLLPVGRPDRNVWRWLC | 124 | Newton & Deutscher, Phage Peptide Display in Handbook of Experimental Pharmacology, pages 145-163, Springer-Verlag, Berlin (2008) |
| CKGQCDRFKGLPWEC | 125 | Newton & Deutscher, Phage Peptide Display in Handbook of Experimental Pharmacology, pages 145-163, Springer-Verlag, Berlin (2008) |
| SGRSA | 126 | Newton & Deutscher, Phage Peptide Display in Handbook of Experimental Pharmacology, pages 145-163, Springer-Verlag, Berlin (2008) |
| WGFP | 127 | Newton & Deutscher, Phage Peptide Display in Handbook of Experimental Pharmacology, pages 145-163, Springer-Verlag, Berlin (2008) |
| LWXXAr | 128 | Newton & Deutscher, Phage Peptide Display in Handbook of Experimental Pharmacology, pages 145-163, Springer-Verlag, Berlin (2008) |
| XFXXYLW | 129 | Newton & Deutscher, Phage Peptide Display in Handbook of Experimental Pharmacology, pages 145-163, Springer-Verlag, Berlin (2008) |
| AEPMPHSLNFSQYLWYT | 130 | Newton & Deutscher, Phage Peptide Display in Handbook of Experimental Pharmacology, pages 145-163, Springer-Verlag, Berlin (2008) |
| WAY(W/F)SP | 131 | Newton & Deutscher, Phage Peptide Display in Handbook of Experimental Pharmacology, pages 145-163, Springer-Verlag, Berlin (2008) |
| IELLQAR | 132 | Newton & Deutscher, Phage Peptide Display in Handbook of Experimental Pharmacology, pages 145-163, Springer-Verlag, Berlin (2008) |
| DITWDQLWDLMK | 133 | Newton & Deutscher, Phage Peptide Display in Handbook of Experimental Pharmacology, pages 145-163, Springer-Verlag, Berlin (2008) |
| AYTKCSRQWRTCMTTH | 134 | Newton & Deutscher, Phage Peptide Display in Handbook of Experimental Pharmacology, pages 145-163, Springer-Verlag, Berlin (2008) |
| PQNSKIPGPTFLDPH | 135 | Newton & Deutscher, Phage Peptide Display in Handbook of Experimental Pharmacology, pages 145-163, Springer-Verlag, Berlin (2008) |
| SMEPALPDWWKMFK | 136 | Newton & Deutscher, Phage Peptide Display in Handbook of Experimental Pharmacology, pages 145-163, Springer-Verlag, Berlin (2008) |
| ANTPCGPYTHDCPVKR | 137 | Newton & Deutscher, Phage Peptide Display in Handbook of Experimental Pharmacology, pages 145-163, Springer-Verlag, Berlin (2008) |
| TACHQHVRMVRP | 138 | Newton & Deutscher, Phage Peptide Display in Handbook of Experimental Pharmacology, pages 145-163, Springer-Verlag, Berlin (2008) |
| VPWMEPAYQRFL | 139 | Newton & Deutscher, Phage Peptide Display in Handbook of Experimental Pharmacology, pages 145-163, Springer-Verlag, Berlin (2008) |
| DPRATPGS | 140 | Newton & Deutscher, Phage Peptide Display in Handbook of Experimental Pharmacology, pages 145-163, Springer-Verlag, Berlin (2008) |

TABLE 7-continued

TARGETING SEQUENCES

| Sequence | SEQ ID NO | Reference |
|---|---|---|
| FRPNRAQDYNTN | 141 | Newton & Deutscher, Phage Peptide Display in Handbook of Experimental Pharmacology, pages 145-163, Springer-Verlag, Berlin (2008) |
| CTKNSYLMC | 142 | Newton & Deutscher, Phage Peptide Display in Handbook of Experimental Pharmacology, pages 145-163, Springer-Verlag, Berlin (2008) |
| C(R/Q)L/RT(G/N)XX G(A/V)GC | 143 | Newton & Deutscher, Phage Peptide Display in Handbook of Experimental Pharmacology, pages 145-163, Springer-Verlag, Berlin (2008) |
| CPIEDRPMC | 144 | Newton & Deutscher, Phage Peptide Display in Handbook of Experimental Pharmacology, pages 145-163, Springer-Verlag, Berlin (2008) |
| HEWSYLAPYPWF | 145 | Newton & Deutscher, Phage Peptide Display in Handbook of Experimental Pharmacology, pages 145-163, Springer-Verlag, Berlin (2008) |
| MCPKHPLGC | 146 | Newton & Deutscher, Phage Peptide Display in Handbook of Experimental Pharmacology, pages 145-163, Springer-Verlag, Berlin (2008) |
| RMWPSSTVNLSAGRR | 147 | Newton & Deutscher, Phage Peptide Display in Handbook of Experimental Pharmacology, pages 145-163, Springer-Verlag, Berlin (2008) |
| SAKTAVSQRVWLPSHRGGEP | 148 | Newton & Deutscher, Phage Peptide Display in Handbook of Experimental Pharmacology, pages 145-163, Springer-Verlag, Berlin (2008) |
| KSREHVNNSACPSKRITAAL | 149 | Newton & Deutscher, Phage Peptide Display in Handbook of Experimental Pharmacology, pages 145-163, Springer-Verlag, Berlin (2008) |
| EGFR | 150 | Newton & Deutscher, Phage Peptide Display in Handbook of Experimental Pharmacology, pages 145-163, Springer-Verlag, Berlin (2008) |
| AGLGVR | 151 | Newton & Deutscher, Phage Peptide Display in Handbook of Experimental Pharmacology, pages 145-163, Springer-Verlag, Berlin (2008) |
| GTRQGHTMRLGVSDG | 152 | Newton & Deutscher, Phage Peptide Display in Handbook of Experimental Pharmacology, pages 145-163, Springer-Verlag, Berlin (2008) |
| IAGLATPGWSHWLAL | 153 | Newton & Deutscher, Phage Peptide Display in Handbook of Experimental Pharmacology, pages 145-163, Springer-Verlag, Berlin (2008) |
| SMSIARL | 154 | Newton & Deutscher, Phage Peptide Display in Handbook of Experimental Pharmacology, pages 145-163, Springer-Verlag, Berlin (2008) |
| HTFEPGV | 155 | Newton & Deutscher, Phage Peptide Display in Handbook of Experimental Pharmacology, pages 145-163, Springer-Verlag, Berlin (2008) |
| NTSLKRISNKR1RRK | 156 | Newton & Deutscher, Phage Peptide Display in Handbook of Experimental Pharmacology, pages 145-163, Springer-Verlag, Berlin (2008) |
| LRIKRKRRKRKKTRK | 157 | Newton & Deutscher, Phage Peptide Display in Handbook of Experimental Pharmacology, pages 145-163, Springer-Verlag, Berlin (2008) |

Y* is phospho-Tyr

In some embodiments, the targeting sequence may be a peptide that can be used for chemical coupling (e.g., can comprise arginine and/or lysine residues that can be chemically coupled through their R groups) to another molecule that targets entry into a cell.

In some embodiments, the AAV capsid protein or virus capsid can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV serotype.

Additionally, or alternatively, in some embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.).

Furthermore, in some embodiments, the capsid protein, virus capsid or vector can comprise amino acid modifications such as described in PCT Publication No. WO 2010/093784 (e.g., 2i8) and/or in PCT Publication No. WO 2014/144229 (e.g., dual glycan).

In some embodiments, the capsid protein, virus capsid or vector can have equivalent or enhanced transduction efficiency relative to the transduction efficiency of the AAV serotype from which the capsid protein, virus capsid or vector originated. In some embodiments, the capsid protein, virus capsid or vector can have reduced transduction efficiency relative to the transduction efficiency of the AAV serotype from which the capsid protein, virus capsid or vector originated. In some embodiments, the capsid protein, virus capsid or vector can have equivalent or enhanced tropism relative to the tropism of the AAV serotype from which the capsid protein, virus capsid or vector originated. In some embodiments, the capsid protein, virus capsid or vector can have an altered or different tropism relative to the tropism of the AAV serotype from which the capsid protein, virus capsid or vector originated. In some embodiments, the capsid protein, virus capsid or vector can have or be engineered to have tropism for brain tissue. In some embodiments, the capsid protein, virus capsid or vector can have or be engineered to have tropism for liver tissue.

The AAV vectors described herein can be used to deliver a heterologous nucleic acid to a cell or subject. For example, the modified vector can be used to treat a lysosomal storage disorder such as a mucopolysaccharidosis disorder (e.g., Sly syndrome [3-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome (A [heparan sulfamidase], B [N-acetylglucosaminidase], C [acetyl-CoA:alpha-glucosaminide acetyltransferase], D [N-acetylglucosamine 6-sulfatase]), Morquio Syndrome (A [galactose-6-sulfate sulfatase], B [3-galactosidase]), Maroteaux-Lamy Syndrome [N-acetylgalactosamine-4-sulfatase], etc.), Fabry disease (a-galactosidase), Gaucher's disease (glucocerebrosidase), or a glycogen storage disorder (e.g., Pompe disease; lysosomal acid alpha-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent.

In some embodiments, virus vectors comprise the modified capsid proteins and capsids described herein. In some embodiments, the virus vector is a parvovirus vector (e.g., comprising a parvovirus capsid and/or vector genome), for example, an AAV vector (e.g., comprising an AAV capsid and/or vector genome). In some embodiments, the virus vector comprises a modified AAV capsid comprising a modified capsid as described herein and a vector genome.

For example, in some embodiments, the virus vector comprises: (a) a modified virus capsid (e.g., a modified AAV capsid) comprising a modified capsid protein described herein; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In some embodiments, the virus vector is a recombinant virus vector comprising a heterologous nucleic acid encoding a polypeptide or functional RNA of interest. Recombinant virus vectors are described in more detail below.

In some embodiments, the virus vectors (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), (v) exhibit a selective enhancement in transduction of liver tissue, and/or (vi) reduced transduction of brain tissues (e.g., neurons) as compared with the level of transduction by a virus vector without the modified capsid protein. In some embodiments, the virus vector has systemic transduction toward liver.

It will be understood by those skilled in the art that the modified capsid proteins, virus capsids and virus vectors described herein exclude those capsid proteins, capsids and virus vectors that have the indicated amino acids at the specified positions in their native state (i.e., are not mutants).

Methods of Producing Virus Vectors

Also provided herein are methods of producing virus vectors. In some embodiments, a method of producing an AAV vector that evades neutralizing antibodies, comprises: a) identifying contact amino acid residues that form a three dimensional antigenic footprint on an AAV capsid protein; b) generating a library of AAV capsid proteins comprising amino acid substitutions of the contact amino acid residues identified in (a); c) producing AAV particles comprising capsid proteins from the library of AAV capsid proteins of (b); d) contacting the AAV particles of (c) with cells under conditions whereby infection and replication can occur; e) selecting AAV particles that can complete at least one infectious cycle and replicate to titers similar to control AAV particles: 1) contacting the AAV particles selected in (e) with neutralizing antibodies and cells under conditions whereby infection and replication can occur; and g) selecting AAV particles that are not neutralized by the neutralizing antibodies of (f). Nonlimiting examples of methods for identifying contact amino acid residues include peptide epitope mapping and/or cryo-electron microscopy.

Resolution and identification of the antibody contact residues within the three dimensional antigenic footprint allows for their subsequent modification through random, rational and/or degenerate mutagenesis to generate antibody-evading AAV capsids that can be identified through further selection and/or screening.

Thus, in some embodiments, a method of producing an AAV vector that evades neutralizing antibodies comprises: a) identifying contact amino acid residues that form a three dimensional antigenic footprint on an AAV capsid protein; b) generating AAV capsid proteins comprising amino acid substitutions of the contact amino acid residues identified in (a) by random, rational and/or degenerate mutagenesis; c) producing AAV particles comprising capsid proteins from the AAV capsid proteins of (b); d) contacting the AAV particles of (c) with cells under conditions whereby infection and replication can occur; e) selecting AAV particles that can complete at least one infectious cycle and replicate to titers similar to control AAV particles; f) contacting the AAV particles selected in (e) with neutralizing antibodies and cells under conditions whereby infection and replication can occur; and g) selecting AAV particles that are not neutralized by the neutralizing antibodies of (f).

Nonlimiting examples of methods for identifying contact amino acid residues include peptide epitope mapping and/or cryo-electron microscopy. Methods of generating AAV capsid proteins comprising amino acid substitutions of contact amino acid residues by random, rational and/or degenerate mutagenesis are known in the art.

This comprehensive approach presents a platform technology that can be applied to modifying any AAV capsid. Application of this platform technology yields AAV antigenic variants derived from the original AAV capsid template without loss of transduction efficiency. As one advantage and benefit, application of this technology will expand the cohort of patients eligible for gene therapy with AAV vectors.

In some embodiments, a method of producing a virus vector comprises providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids). Optionally, the nucleic acid template further comprises at least one heterologous nucleic acid sequence. In some embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In some embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid.

The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In some embodiments, the nucleic acid template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In some embodiments, the nucleic acid template is provided by a replicating rAAV virus. In some embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a noninfectious adenovirus miniplasmid that carries all of the helper genes that promote efficient AAV production as described by Ferrari et al., (1997) Nature Med. 3: 1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In some embodiments, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the Ela or E3 regions) of the adenovirus.

In some embodiments, the AAV rep/cap sequences and the adenovirus helper sequences are supplied by a single adenovirus helper vector. According to this embodiment, the rAAV template can be provided as a plasmid template.

In some embodiments, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In some embodiments, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions. Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) Gene Therapy 6:986 and WO 00/17377.

As a further alternative, virus vectors can be produced in insect cells using baculovirus vectors to deliver the rep/cap genes and rAAV template as described, for example, by Urabe et al., (2002) Human Gene Therapy 13: 1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The virus vectors described herein are useful for the delivery of nucleic acids to cells in vitro, ex vivo, and in vivo. In particular, the virus vectors can be advantageously employed to deliver or transfer nucleic acids to animal, including mammalian, cells. Thus, in some embodiments, a nucleic acid may be encapsidated by a capsid protein described herein. In some embodiments, the nucleic acid is a cargo nucleic acid. In some embodiments, the cargo nucleic acid comprises a vector genome (e.g., 5' ITR, transgene, and 3' ITR).

The cargo nucleic acid sequence delivered by the virus vectors may be any heterologous nucleic acid sequence(s) of interest. Nucleic acids of interest include nucleic acids encoding polypeptides, including therapeutic (e.g., for medical or veterinary uses) or immunogenic (e.g., for vaccines) polypeptides or RNAs. In some embodiments, the cargo nucleic acid comprises a 5' ITR and a 3' ITR. In some embodiments, the cargo nucleic acid comprises a 5' ITR, a transgene, and a 3'ITR. In some embodiments, the transgene encodes a therapeutic protein or RNA.

Therapeutic polypeptides include, but are not limited to, cystic fibrosis transmembrane regulator protein (CFTR), dystrophin (including mini- and micro-dystrophins, see, e.g., Vincent et al, (1993) Nature Genetics 5: 130; U.S. Patent Publication No. 2003/017131; International publication WO/2008/088895, Wang et al., Proc. Natl. Acad. Sci. USA 97: 1 3714-13719 (2000); and Gregorevic et al., Mol. Ther. 16:657-64 (2008)), myostatin propeptide, follistatin, activin type 11 soluble receptor, IGF-1, apolipoproteins such as apoA (apoA1, apoA2, apoA4, apoA-V), apoB (apoB100, ApoB48), apoC (apoCI, apoCII, apoCIII, apoCIV), apoD, apoE, apoH, apoL, apo(a), anti-inflammatory polypeptides such as the Ikappa B dominant mutant, amyloid beta, tau, sarcospan, utrophin (Tinsley et al, (1996) Nature 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, progranulin, ornithine transcarbamylase, β-globin, α-globin, spectrin, alpha-1-antitrypsin, adenosine deaminase, hypoxanthine guanine phosphoribosyl transferase, β-glucocerebrosidase, battenin, sphingomyelinase, lysosomal hexosaminidase A, branched-chain keto acid dehydrogenase, frataxin, RP65 protein, cytokines (e.g., alpha-interferon, beta-interferon, gamma-interferon, interleukin-2, interleukin-4, alpha synuclein, parkin, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), huntingin, lysosomal acid alpha-glucosidase, iduronate-2-sulfatase, N-sulfoglucosamine sulfohydrolase, alpha-galactosidase A, receptors (e.g., the tumor necrosis growth factor soluble receptor), S100A1, ubiquitin protein ligase E3, parvalbumin, adenylyl cyclase type 6, a molecule that modulates calcium handling (e.g., SERCA2A, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172)), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins that enhance or inhibit transcription of host factors (e.g., nuclease-dead Cas9 linked to a transcription enhancer or inhibitor element, zinc-finger proteins linked to a transcription enhancer or inhibitor element, transcription activator-like (TAL) effectors linked to a transcription enhancer or inhibitor element), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., Nature Biotechnology 23:584-590 (2005)). Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in some embodiments, the heterologous nucleic acid may encode an antisense nucleic acid, a ribozyme (e.g., as described in U.S. Pat. No. 5,877,022), RNAs that effect spliceosome-mediated/ram-splicing (see, Puttaraju et al, (1999) Nature Biotech. 17:246; U.S. Pat. Nos. 6,013,487, 6,083,702), interfering RNAs (RNAi) including siRNA, shRNA or miRNA that mediate gene silencing (see, Sharp et al, (2000) Science 287:2431), and other non-translated RNAs, such as "guide" RNAs (Gorman et al., (1998) Proc. Nat. Acad. Sci. USA 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., J. Gene Med. 10: 132-142 (2008) and Li et al., Acta Pharmacol Sin. 26:51-55 (2005)); phospholamban inhibitory or dominant-negative molecules such as phospholamban S16E (e.g., to treat cardiovascular disease, see, e.g., Hoshijima et al. Nat. Med. 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid.

In some embodiments, a nucleic acid sequence that directs gene editing can be delivered. For example, the nucleic acid may encode a guide RNA. In some embodiments, the guide RNA is a single guide RNA (sgRNA) comprising a crRNA sequence and a tracrRNA sequence. In some embodiments, the nucleic acid may encode a nuclease. In some embodiments, the nuclease is a zinc-finger nuclease, a homing endonuclease, a TALEN (transcription activator-like effector nuclease), a NgAgo (agronaute endonuclease), a SGN (structure-guided endonuclease), a RGN (RNA-guided nuclease), or modified or truncated variants thereof. In some embodiments, the RNA-guided nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, or modified or truncated variants thereof. In some embodiments, the Cas9 nuclease is isolated or derived from *S. pyogenes* or *S. aureus*.

In some embodiments, a nucleic acid sequence that directs gene knockdown can be delivered. For example, the nucleic acid sequence may encode a siRNA, an shRNA, a microRNA, or an antisense nucleic acid. The virus vector may also comprise a heterologous nucleic acid that shares homology with and recombines with a locus on a host chromosome. This approach can be utilized, for example, to correct a genetic defect in the host cell.

Also provided are virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura el al, (1994) Proc. Nat. Acad. Sci USA 91:8507; U.S. Pat. No. 5,916,563 to Young et al, U.S. Pat. No. 5,905,040 to Mazzara et al, U.S. Pat. No. 5,882,652, 5,863,541 to Samulski et al). The antigen may be presented in the parvovirus capsid.

Alternatively, the antigen may be expressed from a heterologous nucleic acid introduced into a recombinant vector genome. In some embodiments, any immunogen of interest as described herein and/or as is known in the art can be provided by the virus vectors described herein.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP 160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus, such as the vaccinia LI or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens), a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell.

Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, FRAME, p15, melanoma tumor antigens (Kawakami et al., (1994) Proc. Natl. Acad. Sci. USA 91:3515; Kawakami et al., (1994) J. Exp. Med., 180:347; Kawakami et al., (1994) Cancer Res. 54:3124), MART-1, gp100, MAGE-1, MAGE-2, MAGE-3, CEA, TRP-1, TRP-2, P-15, tyrosinase (Brichard et al., (1993) J Exp. Med. 178:489); HER-2/neu gene product (U.S. Pat. No. 4,968,603), CA 125, LK26, FB5 (endosialin), TAG 72, AFP, CA 19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) Ann. Rev. Biochem. 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition or metastasis thereof now known or later identified (see, e.g., Rosenberg, (1996) Ann. Rev. Med. 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In some embodiments, the promoter/enhancer elements can be native to the target cell or subject to be treated. In some embodiments, the promoters/enhancer element can be native to the heterologous nucleic acid sequence. The promoter/enhancer element is generally chosen so that it functions in the target cell(s) of interest. Further, in some embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In some embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors described herein provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the described herein can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders. Alzheimer's disease (GDF; neprilysin), multiple sclerosis (β-interferon), Parkinson's disease (glial-cell line derived neurotrophic factor [GDNF]), Huntington's disease (RNAi to remove repeats), Canavan's disease, amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatic myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Myotonic dystrophy 1 or 2, facioscapulohumeral muscular dystrophy (FSHD), Gaucher disease (glucocerebrosidase), Hurler's disease (a-L-iduronidase), adenosine deaminase deficiency (adenosine deaminase), glycogen storage diseases (e.g., Fabry disease [a-galactosidase] and Pompe disease [lysosomal acid alpha-glucosidase]) and other metabolic disorders, congenital emphysema (alpha-1-antitrypsin), Lesch-Nyhan Syndrome (hypoxan thine guanine phosphoribosyl transferase), Niemann-Pick disease (sphingomyelinase), Tay-Sachs disease (lysosomal hexosaminidase A), frontotemporal dementia, Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor 1 (1-1) and fragments thereof (e.g., IIC), serca2a, zinc finger proteins that regulate the phospholamban gene, Barkct, [32-adrenergic receptor, 2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as I RAP and TNFa soluble receptor), hepatitis (a-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The compositions and methods disclosed herein can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

In some embodiments, the virus vectors described herein can be employed to deliver a heterologous nucleic acid encoding a polypeptide or functional RNA to treat and/or prevent a liver disease or disorder. The liver disease or disorder may be, for example, primary biliary cirrhosis, nonalcoholic fatty liver disease (NAFLD), non-alcoholic steatohepatitis (NASH), autoimmune hepatitis, hepatitis B, hepatitis C, alcoholic liver disease, fibrosis, jaundice, primary sclerosing cholangitis (PSC), Budd-Chiari syndrome, hemochromatosis, Wilson's disease, alcoholic fibrosis, non-alcoholic fibrosis, liver steatosis, Gilbert's syndrome, biliary atresia, alpha-1-antitrypsin deficiency, alagille syndrome, progressive familial intrahepatic cholestasis, Hemophilia B, Hereditary Angioedema (HAE), Homozygous Familial Hypercholesterolemia (HoFH), Heterozygous Familial Hypercholesterolemia (HeFH), Von Gierke's Disease (GSD 1), Hemophilia A, Methylmalonic Acidemia, Propionic Acidemia, Homocystinuria, Phenylketonuria (PKU), Tyrosinemia Type 1, Arginase 1 Deficiency, Argininosuccinate Lyase Deficiency, Carbamoyl-phosphate synthetase 1 deficiency, Citrullinemia Type 1, Citrin Deficiency, Crigler-Najjar Syndrome Type 1, Cystinosis, Fabry Disease, Glycogen Storage Disease 1b, LPL Deficiency, N-Acetylglutamate Synthetase Deficiency, Ornithine Transcarbamylase Deficiency, Ornithine Translocase Deficiency, Primary Hyperoxaluria Type 1, or ADA SCID.

The compositions and methods described herein can also be used to produce induced pluripotent stem cells (iPS). For example, a virus vector described herein can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like.

Nucleic acids encoding factors associated with stem cells are known in the art. Nonlimiting examples of such factors associated with stem cells and pluripotency include Oct-3/4, the SOX family (e.g., SOX 1, SOX2, SOX3 and/or SOX 15), the KIf family (e.g., KIf1, KHZ KIf4 and/or KIf5), the Myc family (e.g., C-myc, L-myc and/or N-myc), NANOG and/or LIN28.

The methods described herein can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome A [heparan sulfamidase], B [N-acetylglucosaminidase], C [acetyl-CoA:alpha-glucosaminide acetyltransferase], D [N-acetylglucosamine 6-sulfatase], Morquio Syndrome A [galactoses-sulfate sulfatase], B [3-galactosidase], Maroteaux-Lamy Syndrome [N-acetylgalactosamine-4-sulfatase], etc.), Fabry disease (alpha-galactosidase), Gaucher's disease (glucocerebrosidase), or a glycogen storage disorder (e.g., Pompe disease; lysosomal acid alpha-glucosidase).

Gene transfer has substantial use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors as described herein permit the treatment and/or prevention of genetic diseases.

The virus vectors described herein may also be employed to provide a functional RNA to a cell in vitro or in vivo. The functional RNA may be, for example, a non-coding RNA. In some embodiments, expression of the functional RNA in the cell can diminish expression of a particular target protein by the cell. Accordingly, functional RNA can be administered to decrease expression of a particular protein in a subject in need thereof. In some embodiments, expression of the functional RNA in the cell can increase expression of a particular target protein by the cell. Accordingly, functional RNA can be administered to increase expression of a particular protein in a subject in need thereof. In some embodiments, expression of the functional RNA can regulate splicing of a particular target RNA in a cell. Accordingly, functional RNA can be administered to regulate splicing a particular RNA in a subject in need thereof. In some embodiments, expression of the functional RNA in the cell can regulate the function of a particular target protein by the cell. Accordingly, functional RNA can be administered to regulate the function of a particular protein in a subject in need thereof. Functional RNA can also be administered to cells in vitro to regulate gene expression and/or cell physiology, e.g., to optimize cell or tissue culture systems or in screening methods.

In addition, virus vectors as described herein find use in diagnostic and screening methods, whereby a nucleic acid of interest is transiently or stably expressed in a cell culture system, or alternatively, a transgenic animal model.

The virus vectors can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

In some embodiments, the virus vectors may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In some embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the transfer of preformed substances (antibody, transfer factor, thymic graft, interleukin-2) from an actively immunized host to a non-immune host.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In some embodiments, the virus vector or cell comprising the heterologous nucleic acid can be administered in an immunogenically effective amount, as described below.

In some embodiments, the virus vectors can be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein.

Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In some embodiments, a method of treating and/or preventing tumor-forming cancers is provided.

The term "tumor" is also understood in the art, for example, as an abnormal mass of undifferentiated cells within a multicellular organism. Tumors can be malignant or benign. In some embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In some embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In some embodiments, cells may be removed from a subject with cancer and contacted with a virus vector expressing a cancer cell antigen as described herein. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., alpha-interferon, beta-interferon, gamma-interferon, omega-interferon, tau-interferon, interleukin-1-alpha, interleukin-1p, interleukin-2, interleukin-3, interleukin-4, interleukin 5, interleukin-6, interleukin-7, interleukin-8, interleukin-9, interleukin-10, interleukin-11, interleukin-12, interleukin-13, interleukin-14, interleukin-18, B cell Growth factor, CD40 Ligand, tumor necrosis factor-alpha, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector. Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids as described herein find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammals" as used herein includes, but is not limited to, humans, non-human primates, bovines, ovines, caprines, equines, felines, canines, lagomorphs, etc. Human subjects include neonates, infants, juveniles, adults and geriatric subjects.

In some embodiments, the subject is "in need" of the methods described herein.

In some embodiments, a pharmaceutical composition provided comprising a virus vector and/or capsid and/or capsid protein and/or virus particle in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

Also provided herein are method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In some embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In some embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In some embodiments, the cells have been removed from a subject, the virus vector is introduced therein, and the cells are then administered back into the subject. Methods of removing cells from the subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In some embodiments, the cells transduced with the virus vector are administered to the subject in a therapeutically effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In some embodiments, the dosage is sufficient to produce a protective immune response (as defined above). The degree of protection conferred need not be complete or permanent, as long as the benefits of administering the immunogenic polypeptide outweigh any disadvantages thereof.

Thus, in some embodiments, a method of administering a nucleic acid to a cell comprises contacting the cell with the virus vector, virus particle and/or composition as described herein.

Also provided herein is a method of administering the virus vector, virus particle and/or virus capsid as described herein to a subject. In some embodiments, a method of delivering a nucleic acid to a subject comprises administering to the subject a virus particle, virus vector and/or composition as described herein. Administration of the virus vectors, virus particles and/or capsids to a human subject or an animal in need thereof can be by any means known in the art. Optionally, the virus vector, virus particle and/or capsid is delivered in a therapeutically effective dose in a pharmaceutically acceptable carrier. In some embodiments, a therapeutically effective amount of the virus vector, virus particle and/or capsid is delivered.

The virus vectors and/or capsids described herein can further be administered to elicit an immunogenic response (e.g., as a vaccine). Typically, immunogenic compositions comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, about $10^6$, about $10^7$, about $10^8$, about $10^9$, about $10^{10}$, about $10^{11}$, about $10^{12}$, about $10^{13}$, about $10^{14}$, or about $10^{15}$ transducing units, optionally about $10^8$-$10^{13}$ transducing units. In some embodiments, the dose of AAV may be from about $2.0\times10^{13}$ vg/kg body weight of the subject to about $4.0\times10^{13}$ vg/kg body weight of the subject, such as about $2.0\times10^{13}$ vg/kg, about $2.1\times10^{13}$ vg/kg, about $2.2\times10^{13}$ vg/kg, about $2.3\times10^{13}$ vg/kg, about $2.4\times10^{13}$ vg/kg, about $2.5\times10^{13}$ vg/kg, about $2.6\times10^{13}$ vg/kg, about $2.7\times10^{13}$ vg/kg, about $2.8\times10^{13}$ vg/kg, about $2.9\times10^{13}$ vg/kg, about $3.0\times10^{13}$ vg/kg, about $3.1\times10^{13}$ vg/kg, about $3.2\times10^{13}$ vg/kg, about $3.3\times10^{13}$ vg/kg, about $3.4\times10^{13}$ vg/kg, about $3.5\times10^{13}$ vg/kg, about $3.6\times10^{13}$ vg/kg, about $3.7\times10^{13}$ vg/kg, about $3.8\times10^{13}$ vg/kg, about $3.9\times10^{13}$ vg/kg, or about $4.0\times10^{13}$ vg/kg. In some embodiments, the dose of AAV may be from about $2\times10^{13}$ vg to about $4.0\times10^{13}$ vg, such as about $2.0\times10^{13}$ vg, about $2.1\times10^{13}$ vg, about $2.2\times10^{13}$ vg, about $2.3\times10^{13}$ vg, about $2.4\times10^{13}$ vg, about $2.5\times10^{13}$ vg, about $2.6\times10^{13}$ vg, about $2.7\times10^{13}$ vg, about $2.8\times10^{13}$ vg, about $2.9\times10^{13}$ vg, about $3.0\times10^{13}$ vg, about $3.1\times10^{13}$ vg, about $3.2\times10^{13}$ vg, about $3.3\times10^{13}$ vg, about $3.4\times10^{13}$ vg, about $3.5\times10^{13}$ vg, about $3.6\times10^{13}$ vg, about $3.7\times10^{13}$ vg, about $3.8\times10^{13}$ vg, about $3.9\times10^{13}$ vg, or about $4.0\times10^{13}$ vg.

In some embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficial is, flexor hallucis brevis, flexor hallucis longus, flexor pollicis brevis. flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g. Arruda et al., (2005) Blood 105: 3458-3464), and/or direct intramuscular injection. In some embodiments, the virus vector and/or capsid is administered to a limb (arm and/or leg) of a subject (e.g., a subject with muscular dystrophy such as Duchenne muscular dystrophy (DMD) or limb-girdle muscular dystrophy (LGMD)) by limb perfusion, optionally isolated limb perfusion (e.g., by intravenous or intra-articular administration). In some embodiments, the virus vectors and/or capsids can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In some embodiments, the viral vectors and/or capsids can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome. Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In some embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In some embodiments, a virus vector and/or virus capsid according is administered to skeletal muscle, diaphragm muscle and/or cardiac muscle (e.g., to treat and/or prevent muscular dystrophy, heart disease [for example, PAD or congestive heart failure]).

In some embodiments, the compositions and methods described herein are used to treat and/or prevent diseases or disorders of skeletal, cardiac and/or diaphragm muscle. The diseases or disorders of the muscle may be, for example, muscular dystrophy, myopathy, motor neuron disease, and cardiomyopathy. The diseases or disorders of the muscle may be, for example, dystrophinopathies, Duchenne muscular dystrophy, Becker muscular dystrophy, myotonic dystrophies (e.g., myotonic dystrophy 1 and 2), facioscapulohumeral muscular dystrophy (FDHD), Eimery-Dreifuss muscular dystrophy, limb-girdle disease, facioscapulohumeral muscular dystrophy, oculopharyngeal muscular dystrophy, distal muscular dystrophy, congenital muscular dystrophy, juvenile macular dystrophy, centronuclear myopathy, central core myopathy, and inclusion body myositis.

In some embodiments, a method of treating and/or preventing muscular dystrophy in a subject in need thereof is provided, the method comprising: administering a treatment or prevention effective amount of a virus vector to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-a2, alpha-sarcoglycan, beta-sarcoglycan, gamma-sarcoglycan, delta-sarcoglycan, IGF-1, an antibody or antibody fragment against myostatin or myostatin propeptide, and/or RNAi against myostatin. In some embodiments, the virus vector can be administered to skeletal, diaphragm and/or cardiac muscle as described elsewhere herein.

Alternatively, methods described herein can be practiced to deliver a nucleic acid to skeletal, cardiac or diaphragm muscle, which is used as a platform for production of a polypeptide (e.g., an enzyme) or functional RNA (e.g., RNAi, micro RNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [a-galactosidase A] or a glycogen storage disorder such as Pompe disease [lysosomal acid alpha glucosidase]). Other suitable proteins for treating and/or preventing metabolic disorders are described herein. The use of muscle as a platform to express a nucleic acid of interest is described in U.S. Patent publication US 2002/0192189.

In some embodiments, a method of treating and/or preventing a metabolic disorder in a subject in need thereof comprises administering a treatment or prevention effective amount of a virus vector to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory, according to this embodiment, administration to the skeletal muscle can result in secretion of the polypeptide into the systemic circulation and delivery to target tissue(s). Methods of delivering virus vectors to skeletal muscle is described in more detail herein.

The methods described herein can also be practiced to produce noncoding RNA, such as antisense RNA, RNAi or other functional RNA (e.g., a ribozyme) for systemic delivery.

In some embodiments, a method of treating and/or preventing congenital heart failure or PAD in a subject in need thereof comprises administering a treatment or prevention effective amount of a virus vector to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., 11C), RNAi against phospholamban; a phospholamban inhibitory or dominant-negative molecule such as phospholamban S16E, a zinc finger protein that regulates the phospholamban gene, beta-2-adrenergic receptor, beta-2-adrenergic receptor kinase (BARK), PI3 kinase, calsarcan, a β-adrenergic receptor kinase inhibitor (PARKct), inhibitor 1 of protein phosphatase 1 and fragments thereof (e.g., I1 C), S100A1, parvalbumin, adenylyl cyclase type 6, a molecule that effects G-protein coupled receptor kinase type 2 knockdown such as a truncated constitutively active bARKct, Pim-1, PGC-I α, SOD-1, SOD-2, EC-SOD, kallikrein, HIF, thymosin-p4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the compositions and methods described herein.

In some embodiments, the delivery vectors described herein may be administered to treat diseases of the CNS, including genetic disorders, neurodegenerative disorders, psychiatric disorders and tumors. Illustrative diseases of the CNS include, but are not limited to Adrenomyeloneuropathy (AMN), Alzheimer's disease, Angelman Syndrome, Frontotemporal Dementia, Parkinson's disease, Huntington's disease, Fragile X syndrome, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease (GM2 Gangliosidosis), Lesch-Nyhan disease, MC4R Obesity, Metachromatic Leukodystrophy (MLD), MPS I (Hurler/Scheie), MPS IIIA (Sanfilippo A), Niemann Pick C1, Rett Syndrome, Spinal Muscular Atrophy (SMA), AADC Deficiency, Monogenic Amyotropic Lateral Sclerosis (ALS), Alpha mannosidosis, Aspartylglucosaminuria, Dravet Syndrome, Giant Axonal Neuropathy, Globoid Cell Leukodystrophy (Krabbe), Glut 1 Deficiency, GM1 Gangliosidosis, Infantile Neuronal Ceroid Lipfuscinosis (INCL, Batten), Juvenile Neuronal Ceroid Lipfuscinosis (JNCL, Batten), Late Infantile Neuronal Ceroid Lipfuscinosis (LINCL, Batten), MPS II (Hunter), MPS IIIB (Sanfilippo B), MPS IIIC (Sanfilippo C), MPS IVA (Morquio Syndrome), MPS VI (Maroteaux-Lamy), Peroxisome Biogenesis Disorders (Zellweger Syndrome Spectrum), Sandhoff Disease (GM2 Gangliosidosis), epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The viral vectors described herein can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector.

Retinitis pigmentosa, by comparison, is characterized by retinal degeneration. In some embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In some embodiments, the compositions and methods described herein may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, epilepsy, which is marked by multiple seizures over time, may also be treated.

In some embodiments, a method of treating a subject in need thereof comprises administering to the subject an AAV vector comprising a capsid protein, wherein the capsid protein comprises the amino acid sequence of any one of SEQ ID NO: 165-187. In some embodiments, the AAV vector comprises a capsid protein comprising the amino acid sequence of SEQ ID NO: 175, or a sequence at least 95% identical thereto. In some embodiments, the AAV vector comprises a capsid protein comprising the amino acid sequence of SEQ ID NO: 175, or a sequence at least 95% identical thereto. In some embodiments, the subject has Dravet syndrome. In some embodiments, the subject has Rett syndrome. In some embodiments, the subject has Angelman syndrome. In some embodiments, the subject has Niemann-Pick disease. In some embodiments, the subject has Fragile X syndrome. In some embodiments, the subject has Alzheimer's disease. In some embodiments, the subject has Gaucher's disease. In some embodiments, the subject has Huntington's disease. In some embodiments, the subject has Parkinson's disease. In some embodiments, the subject has Friedrich's ataxia. In some embodiments, the AAV vector is administered to the subject by intracerebroventricular (ICV) injection. In some embodiments, the AAV vector is administered to the subject by intrathecal (IT) injection. In some embodiments, the AAV vector is administered to the subject by intravenous (IV) injection.

In some embodiments, a method of treating a subject in need thereof comprises administering to the subject an AAV vector comprising a capsid protein, wherein the capsid protein comprises the amino acid sequence of SEQ ID NO: 175 or 180, wherein the subject has Dravet syndrome, Rett syndrome, Angelman syndrome, Niemann-Pick disease, or Fragile X syndrome, and wherein the AAV vector is administered to the subject by ICV or IT injection.

In some embodiments, a method of treating a subject in need thereof comprises administering to the subject an AAV vector comprising a capsid protein, wherein the capsid protein comprises the amino acid sequence of SEQ ID NO: 175 or 180, wherein the subject has Gaucher's disease, Huntington's disease, Parkinson's disease, or Friedrich's ataxia, and wherein the AAV vector is administered to the subject by ICV or IT injection.

In some embodiments, somatostatin (or an active fragment thereof) is administered to the brain using a delivery vector to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In some embodiments, the vector can comprise a secretory signal as described in U.S. Pat. No. 7,071,172.

In some embodiments, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons. In some embodiments, the virus vector and/or capsid is administered in a liquid formulation by direct injection (e.g., stereotactic injection) to the desired region or compartment in the CNS. In some embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In some embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Numbered Embodiments

Notwithstanding the appended claims, the disclosure sets forth the following numbered embodiments:

1. An adeno-associated virus (AAV) vector comprising (i) a recombinant capsid protein and (ii) a cargo nucleic acid encapsidated by the capsid protein, wherein the capsid protein comprises a peptide having the sequence of any one of SEQ ID NO: 12-20.

2. The AAV vector of embodiment 1, wherein the cargo nucleic acid comprises 5' and 3' AAV inverted terminal repeats.

3. The AAV vector of embodiment 1 or 2, wherein the cargo nucleic acid comprises a transgene.

4. The AAV vector of embodiment 3, wherein the transgene encodes a therapeutic protein or RNA.

5. The AAV vector of any one of embodiments 1-4, wherein the recombinant capsid protein has at least 90%, at least 95%, at least 96%, at least 97%, at least 98%, or at least 99% sequence identity to the native sequence of the AAV1, AAV2, AAV3, AAV4, AAV5, AAV6, AAV7, AAV8, AAV9, AAV10, AAV11, AAV12, AAVrh.8, AAVrh.10, AAVrh32.33, AAVrh74, bovine AAV or avian AAV capsid.

6. The AAV vector of embodiment 5, wherein the recombinant capsid protein has at least 90% sequence identity to the native sequence of the AAV9 capsid.

7. The AAV vector of any one of embodiments 1-6, wherein the peptide is located at the amino acid positions corresponding to amino acids 451-458 of the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and wherein the peptide is selected from any one of SEQ ID NO: 12-18.

8. The AAV vector of any one of embodiments 1-6, wherein the peptide is located at the amino acid positions corresponding to amino acids 587-594 of the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and wherein the peptide is selected from SEQ ID NO: 19 or 20.

9. The AAV vector of embodiment 1, wherein the recombinant capsid protein comprises: a) a first peptide having a sequence of any one of SEQ ID NO: 12-18; and b) a second peptide having a sequence of any one of SEQ ID NO: 19-20.

10. The AAV vector of embodiment 9, wherein the first peptide is at amino acid positions 451-458, and the second peptide is at amino acids 587-594, wherein the amino acid numbering is based on the native AAV9 capsid, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV.

11. The AAV vector of any one of embodiments 1-10, wherein the peptide inhibits binding of at least one antibody to the capsid protein.

12. The AAV vector of embodiment 11, wherein the peptide inhibits neutralization of infectivity of the AAV vector by the antibody.

13. The AAV vector of any one of embodiments 1-12, wherein the peptide selectively binds to a receptor expressed on the surface of a cell in the central nervous system (CNS).

14. The AAV vector of embodiment 13, wherein the cell is in the premotor cortex, the thalamus, the cerebellar cortex, the dentate nucleus, the spinal cord, or the dorsal root ganglion.

15. The AAV vector of any one of embodiments 1-14, wherein the peptide selectively binds to a receptor expressed on the surface of a cell in the heart.

16. The AAV vector of any one of embodiments 1-15, wherein the capsid protein further comprises a peptide that modifies the HI loop of the capsid.

17. An adeno-associated virus (AAV) vector comprising (i) a mutant AAV9 capsid protein and (ii) a cargo nucleic acid encapsidated by the capsid protein, wherein the capsid protein comprises a peptide having the sequence $X^1$-$X^2$-$X^3$-$X^4$-$X^5$-$X^6$-$X^7$-$X^8$ (SEQ ID NO: 158) at amino acids 451-458 of the native AAV9 capsid protein sequence, wherein the peptide does not occur in the native AAV9 capsid protein sequence.

18. The AAV vector of embodiment 17, wherein $X^1$ is not I, $X^2$ is not N, $X^3$ is not G, $X^4$ is not S, $X^5$ is not G, $X^6$ is not Q, $X^7$ is not N, and/or $X^8$ is not Q.

19. The AAV vector of embodiment 18, wherein $X^1$ is S, F, Q, G, K, or R.

20. The AAV vector of embodiment 18 or 19, wherein $X^2$ is C, G, R, D, T, or Q.

21. The AAV vector of any one of embodiments 18-20, wherein $X^3$ is Q, V, G, Y, R, F, or D.

22. The AAV vector of any one of embodiments 18-21, wherein $X^4$ is P, Q, A, or R.

23. The AAV vector of any one of embodiments 18-22, wherein $X^5$ is T, N, A, P, or I.

24. The AAV vector of anyone of embodiments 18-23, wherein $X^6$ is V, Q, A, or I.

25. The AAV vector of any one of embodiments 18-24, wherein $X^7$ is M, P, R, Q, or N.

26. The AAV vector of any one of embodiments 18-25, wherein $X^8$ is N, L, F, E, H, or A.

27. The AAV vector of embodiment 17, wherein $X^1$ is S, $X^2$ is C, $X^3$ is Q, $X^4$ is P, $X^5$ is T, $X^6$ is V, $X^7$ is M, and $X^8$ is N.

28. The AAV vector of embodiment 17, wherein $X^1$ is F, $X^2$ is G, $X^3$ is V, $X^4$ is P, $X^5$ is N, $X^6$ is Q, $X^7$ is P, and $X^8$ is L.

29. The AAV vector of embodiment 17, wherein $X^1$ is Q, $X^2$ is R, $X^3$ is G, $X^4$ is Q, $X^5$ is A, $X^6$ is A, $X^7$ is P, and $X^8$ is F.

30. The AAV vector of embodiment 17, wherein $X^1$ is G, $X^2$ is D, $X^3$ is Y, $X^4$ is A, $X^5$ is P, $X^6$ is I, $X^7$ is R, and $X^8$ is E.

31. The AAV vector of embodiment 17, wherein $X^1$ is K, $X^2$ is T, $X^3$ is R, $X^4$ is R, $X^5$ is I, $X^6$ is V, $X^7$ is Q, and $X^8$ is H.

32. The AAV vector of embodiment 17, wherein $X^1$ is F, $X^2$ is G, $X^3$ is F, $X^4$ is P, $X^5$ is N, $X^6$ is Q, $X^7$ is P, and $X^8$ is L.

33. The AAV vector of embodiment 17, wherein $X^1$ is R, $X^2$ is Q, $X^3$ is D, $X^4$ is Q, $X^5$ is P, $X^6$ is I, $X^7$ is N, and $X^8$ is A.

34. An adeno-associated virus (AAV) vector comprising (i) a mutant AAV9 capsid protein and (ii) a cargo nucleic acid encapsidated by the capsid protein, wherein the capsid protein comprises a peptide having the sequence $X^1$-$X^2$-$X^3$-$X^4$-$X^5$-$X^6$-$X^7$-$X^8$ (SEQ ID NO: 158) at amino acids 587-594 of the native AAV9 capsid protein sequence, wherein the peptide does not occur in the native AAV9 capsid protein sequence.

35. The AAV vector of embodiment 34, wherein $X^1$ is not A, $X^2$ is not Q, $X^3$ is not A, $X^4$ is not Q, $X^5$ is not A, $X^6$ is not Q, $X^7$ is not T, and/or $X^8$ is not G.

36. The AAV vector of embodiment 35, wherein $X^1$ is S.

37. The AAV vector of embodiment 35 or 36, wherein $X^2$ is K or T.

38. The AAV vector of any one of embodiments 35-37, wherein $X^3$ is V.

39. The AAV vector of any one of embodiments 35-38, wherein $X^4$ is E or D.

40. The AAV vector of any one of embodiments 35-39, wherein $X^5$ is S.

41. The AAV vector of any one of embodiments 35-40, wherein $X^6$ is W or I.

42. The AAV vector of any one of embodiments 35-41, wherein $X^7$ is T or A.

43. The AAV vector of any one of embodiments 35-42, wherein $X^8$ is E or I.

44. The AAV vector of embodiment 34, wherein $X^1$ is S, $X^2$ is K, $X^3$ is V, $X^4$ is E, $X^5$ is S, $X^6$ is W, $X^7$ is T, and $X^8$ is E.

45. The AAV vector of embodiment 34, wherein $X^1$ is S, $X^2$ is T, $X^3$ is V, $X^4$ is D, $X^5$ is S, $X^6$ is I, $X^7$ is A, and $X^8$ is I.

46. An adeno-associated virus (AAV) vector comprising (i) a recombinant capsid protein and (ii) a cargo nucleic acid encapsidated by the capsid protein, wherein the capsid protein comprises an amino acid sequence that is at least 95%, at least 96%, at least 97%, at least 98%, or at least 99% identical to any one of SEQ ID NO: 165-187.

47. The AAV vector of embodiment 46, wherein the capsid protein comprises the amino acid sequence of any one of SEQ ID NO: 165-187.

48. The AAV vector of embodiment 47, wherein the capsid protein comprises the amino acid sequence of SEQ ID NO: 175.

49. The AAV vector of embodiment 47, wherein the capsid protein comprises the amino acid sequence of SEQ ID NO: 180.

50. The AAV vector of any one of embodiments 46-49, wherein the AAV vector selectively delivers the cargo nucleic acid to a cell or tissue of the central nervous system.

51. The AAV vector of embodiment 50, wherein the tissue of the central nervous system is the premotor cortex, the thalamus, the cerebellar cortex, the dentate nucleus, the spinal cord, or the dorsal root ganglion.

52. The AAV vector of any one of embodiments 46-49, wherein the AAV vector delivers the cargo nucleic acid to the brain, but does not deliver the AAV vector to the heart.

53. The AAV vector of any one of embodiments 46-49, wherein the AAV vector delivers the cargo nucleic acid to the brain and to the heart.

54. The AAV vector of embodiment 53, wherein delivery of the cargo nucleic acid is greater to the brain than to the heart.

55. The AAV vector of embodiment 53, wherein delivery of the cargo nucleic acid is approximately equal in the brain in the heart.

56. A nucleic acid sequence encoding the recombinant capsid protein of the AAV vector of any one of embodiments 1 to 55.

57. The nucleic acid sequence of embodiment 56, wherein the nucleic acid sequence is a DNA sequence.

58. The nucleic acid sequence of embodiment 56, wherein the nucleic acid sequence is an RNA sequence.

59. An expression vector comprising the nucleic acid sequence of any one of embodiments 56-58.

60. A cell comprising the nucleic acid sequence of any one of embodiments 56-58.

61. A cell comprising the expression vector of embodiment 59.

62. A pharmaceutical composition comprising the AAV vector of any one of embodiments 1-55.

63. The pharmaceutical composition of embodiment 62, wherein the composition further comprises a pharmaceutically acceptable carrier.

64. A pharmaceutical composition comprising the cell of embodiment 60 or 61.

65. The pharmaceutical composition of embodiment 64, wherein the composition further comprises a pharmaceutically acceptable carrier.

66. A method of treating a subject in need thereof comprising administering to the subject a therapeutically effective amount of the AAV vector of any one of embodiments 1-55.

67. The method of embodiment 66, wherein the subject has a disease or disorder of the central nervous system.

68. The method of embodiment 67, wherein the disease or disorder of the central nervous system is Dravet syndrome.

69. The method of embodiment 67, wherein the disease or disorder of the central nervous system is Rett syndrome.

70. The method of embodiment 67, wherein the disease or disorder of the central nervous system is Angelman syndrome.

71. The method of embodiment 67, wherein the disease or disorder of the central nervous system is Niemann-Pick disease.

72. The method of embodiment 67, wherein the disease or disorder of the central nervous system is Fragile X syndrome.

73. The method of embodiment 67, wherein the disease or disorder of the central nervous system is Gaucher's disease.

74. The method of embodiment 67, wherein the disease or disorder of the central nervous system is Huntington's disease.

75. The method of embodiment 67, wherein the disease or disorder of the central nervous system is Parkinson's disease.

76. The method of embodiment 67, wherein the disease or disorder of the central nervous system is Friedrich's ataxia.

77. The method of any one of embodiments 66-76, wherein AAV vector comprises a capsid protein, wherein the capsid protein comprises the amino acid sequence of any one of SEQ ID NO: 165-187.

78. The method of any one of embodiments 66-76, wherein AAV vector comprises a capsid protein, wherein the capsid protein comprises the amino acid sequence of SEQ ID NO: 175.

79. The method of any one of embodiments 66-76, wherein AAV vector comprises a capsid protein, wherein the capsid protein comprises the amino acid sequence of SEQ ID NO: 180.

80. The method of any one of embodiments 66-79, wherein the AAV vector is administered to the subject by intracerebroventricular (ICV) injection.

81. The method of any one of embodiments 66-79, wherein the AAV vector is administered to the subject by intrathecal (IT) injection.

82. The method of any one of embodiments 66-79, wherein the AAV vector is administered to the subject by intravenous (IV) injection.

83. The method of any one of embodiments 66-82, wherein the subject is a mammal.

84. The method of embodiment 83, wherein the subject is a human.

85. An in vitro method of introducing a nucleic acid molecule into a cell, comprising contacting the cell with the AAV vector of any one of embodiments 1-55.

86. An AAV vector of any one of embodiments 1-55 for use as a medicament.

87. An AAV vector of any one of embodiments 1-55 for use in a method of treatment of a subject in need thereof.

88. An AAV vector of any one of embodiments 1-55 for use in a method of treating or preventing a disease or disorder of the CNS in a subject in need thereof.

EXAMPLES

The following examples, which are included herein for illustration purposes only, are not intended to be limiting. As used herein, the terms STRD.101 and STRD.102 are used to describe capsid protein sequences, and AAV-STRD.101 and AAV-STRD.102 are used to describe AAV vectors comprising the capsid proteins. However, the terms STRD.101 and STRD.102 may be used in some contexts to describe AAV vectors comprising the named capsids, as will be apparent to the skilled artisan.

Example 1. Combinatorial Engineering and Selection of Antibody-Evading AAV Vectors The method for generating antibody evading AAV mutants is as follows. The first step involves identification of conformational 3D antigenic epitopes on the AAV capsid surface, for example using cryo-electron microscopy. Selected residues within antigenic motifs are then subjected to mutagenesis using degenerate primers with each codon substituted by nucleotides NNK and gene fragments combined together by Gibson assembly and/or multistep PCR. Capsid-encoding genes containing a degenerate library of mutated antigenic motifs are cloned into a wild type AAV genome to replace the original Cap encoding DNA sequence, yielding a plasmid library. Plasmid libraries are then transfected into 293 producer cell lines with an adenoviral helper plasmid to generate AAV capsid libraries, which can then be subjected to selection. Successful generation of AAV libraries is confirmed via DNA sequencing.

In order to select for new AAV strains that can escape neutralizing antibodies (NAbs) and/or target the central nervous system (CNS), AAV libraries are subjected to multiple rounds of infection in non-human primates. At each stage, tissues of interest are isolated from animal subjects. Cell lysates harvested from the tissues of interest are sequenced to identify AAV isolates escaping antibody neutralization. After multiple rounds of infection in non-human primates, the isolated sequences from each mutagenized region are combined in all permutations and combinations.

Figure 5:
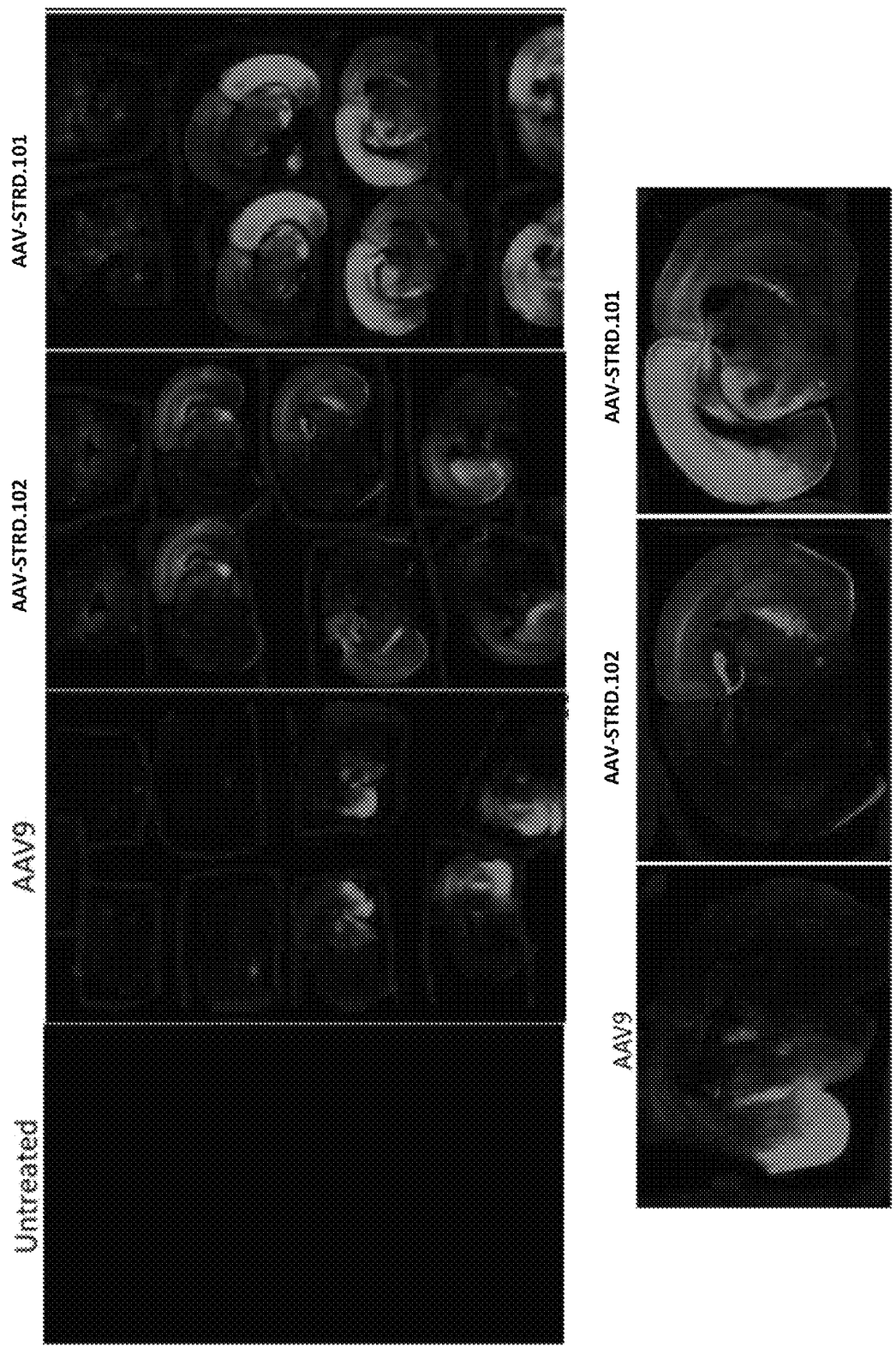
FIG. 5. Representative fluorescent microscopy images showing tdTomato expression in coronal vibratome sections 24 hours post-fixation with 4% PFA. Each section is 25 μm thick. Top panel shows images obtained using a 4× objective lens with native tdTomato fluorescence. The bottom panel shows images obtained using a 10× objective lens with native tdTomato fluorescence.
Figure 6:
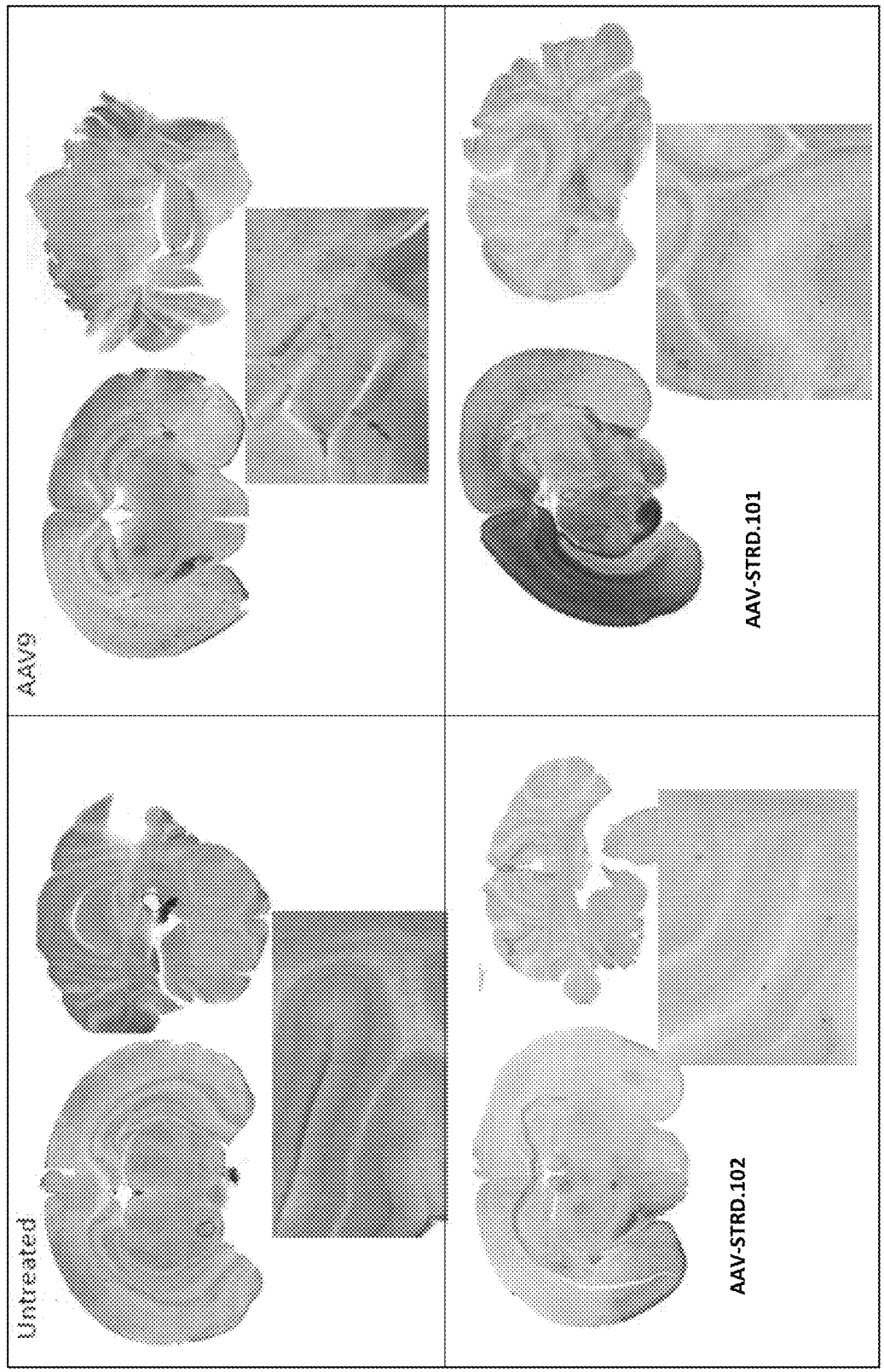
FIG. 6. Representative immunohistochemistry images showing tdTomato expression in coronal vibratome sections 24 hours post-fixation with 4% PFA. Each section is 25 μm thick.

As a specific example, a common antigenic motif on an AAV capsid protein (VP1) was subjected to mutagenesis as described above. The degenerate libraries (FIG. 1A) were then subjected to a first round of infection in a non-human primate (intravenous injection). Tissues were harvested at day 7 post-infection and sequenced to identify single AAV isolates.

Various recombinant AAV isolates were identified in tissue samples, including the spinal cord, dorsal root ganglion, frontal lobe, temporal lobe, occipital lobe, putamen, globus pallidus, thalamus, amygdala, hippocampus, substantia nigra, pons, cerebellum, medulla. Results from this first round of evolution are shown in FIG. 1B.

The recombinant AAVs isolated during the first round of evolution (FIG. 1B) were then reintroduced into a second non-human primate. Tissues were harvested at day 7 post-infection and sequenced to identify single AAV isolates. The results from this second round of evolution are shown in FIG. 1C.

Recombinant AAVs with the highest frequency were sequenced. Substitutions present in these AAVs are shown in Tables 6.1 and 6.2. These data demonstrate that recombinant AAV virions having capsid proteins comprising the substitutions listed in Tables 6.1 and 6.2 evade neutralizing antibodies in vivo in non-human primates and have a tropism for the desired target tissues.

Example 2: Manufacturability of Recombinant AAV Vectors

To determine whether various recombinant AAVs identified in Example 1 may be manufactured in large-scale systems, the AAVs were produced according to standard methods, and yield was compared to that of wildtype AAV vectors.

AAVs were produced in HEK293 cells according to a standard triple transfection protocol. Briefly, the cells were transfected with (i) a plasmid comprising either the wildtype AAV9 capsid sequence, the STRD.101 capsid variant sequence (SEQ ID NO: 180), or the STRD.102 capsid variant sequence (SEQ ID NO: 175), (ii) a plasmid comprising a 5'ITR, a transgene, and a 3' ITR sequence, and (ii) a plasmid comprising helper genes necessary for AAV production. Two different transgenes were used with each capsid, in self-complementary constructs. The cells were subsequently lysed and the virions were purified using an affinity column, CsCl density ultracentrifugation, and dialysis. Subsequently, yield of each AAV was measured using a PCR-based quantification approach.

As shown in FIG. 2, recombinant AAV vectors comprising the STRD.101 and STRD.102 capsids had a yield that was similar to the yield of wildtype AAV9. This data confirms that recombinant AAVs comprising the recombinant capsid proteins are suitable for commercial manufacturing.

Example 3: In Vitro Transduction Using Recombinant AAV Viral Vectors

To confirm whether the recombinant AAV vectors of Example 1 are generally infective and able to transduce cells in culture, various AAV vectors were prepared according to a standard protocol.

The infectivity of the recombinant AAVs was tested using a standard TCID50 assay. Briefly, HeLaRC32 cells were infected with recombinant AAV particles in the presence of Adenovirus (Ad5) at doses spanning 5 orders of magnitude. After 72 hours, DNA was extracted and vector genome replication was quantified by qPCR.

The particle to infectivity ratio was calculated to determine infectivity. As shown in FIG. 3, the infectivity ratio of an AAV-STRD.101 vector was lower compared to that of wildtype AAV9. Because a lower infectivity ratio translates to a higher potency, AAV-STRD.101 is more infectious than wildtype AAV9.

Separately, infectivity was also determined in various cell lines. Recombinant AAVs packaging a luciferase transgene were generated and contacted with the cells in culture at a dose of 10,000 vector genomes (vg) per cell. 48-hours post infection, cells were lysed. The lysate was contacted with a bioluminescent substrate, and relative fluorescence units (RFUs) were measured. As shown in FIG. 4A-4D, AAV-STRD.101 vectors infected U87 cells (human glioblastoma cell line, FIG. 4A), N2A cells (mouse neural crest-derived cell line, FIG. 4B), SY5Y cells (human neuroblastoma cell line, FIG. 4C), and U2OS cells (human osteosarcoma cell line, FIG. 4D) at levels comparable to wildtype AAV9.

Accordingly, this data demonstrates that the recombinant AAV vectors of Example 1 can effectively transduce cells in culture.

Example 4: In Vivo Characterization of Recombinant AAVs Targeting the Central Nervous System Two recombinant capsid proteins, STRD.101 and STRD.102 were selected for in vivo characterization. Recombinant AAVs comprising these capsid proteins and packaging a native tdTomato fluorescent transgene were generated. The recombinant AAVs were administered to neonatal mice by intracerebroventricular injection at day 0. At three weeks post-injection, brain tissues were harvested and fixed to evaluate the expression by visual assessment of the tdTomato fluorescence. FIG. 5 provides representative images showing tdTomato expression in coronal vibratome sections after 24 hours post-fixation with 4% PFA. These same sections were also visualized using immunohistochemistry (FIG. 6). As shown in the images of FIG. 5 and FIG. 6, AAV9, AAV-STRD.102 and AAV-STRD.101 vectors each had different distribution in the brain tissues, with the highest transgene expression localized near the site of injection. Taken together, this data shows that the recombinant AAVs tested successfully deliver a transgene to target cells in vivo after intracerbroventricular injection.

The AAV-STRD.101 and AAV-STRD.102 vectors packaging tdTomato were also administered to four adult mice by intravenous injection at a dose of $5.5 \times 10^{13}$ vg/kg. Three weeks post-injection, liver and heart were harvested and fixed to evaluate the expression profile by visual assessment of tdTomato fluorescence.

Figure 7:
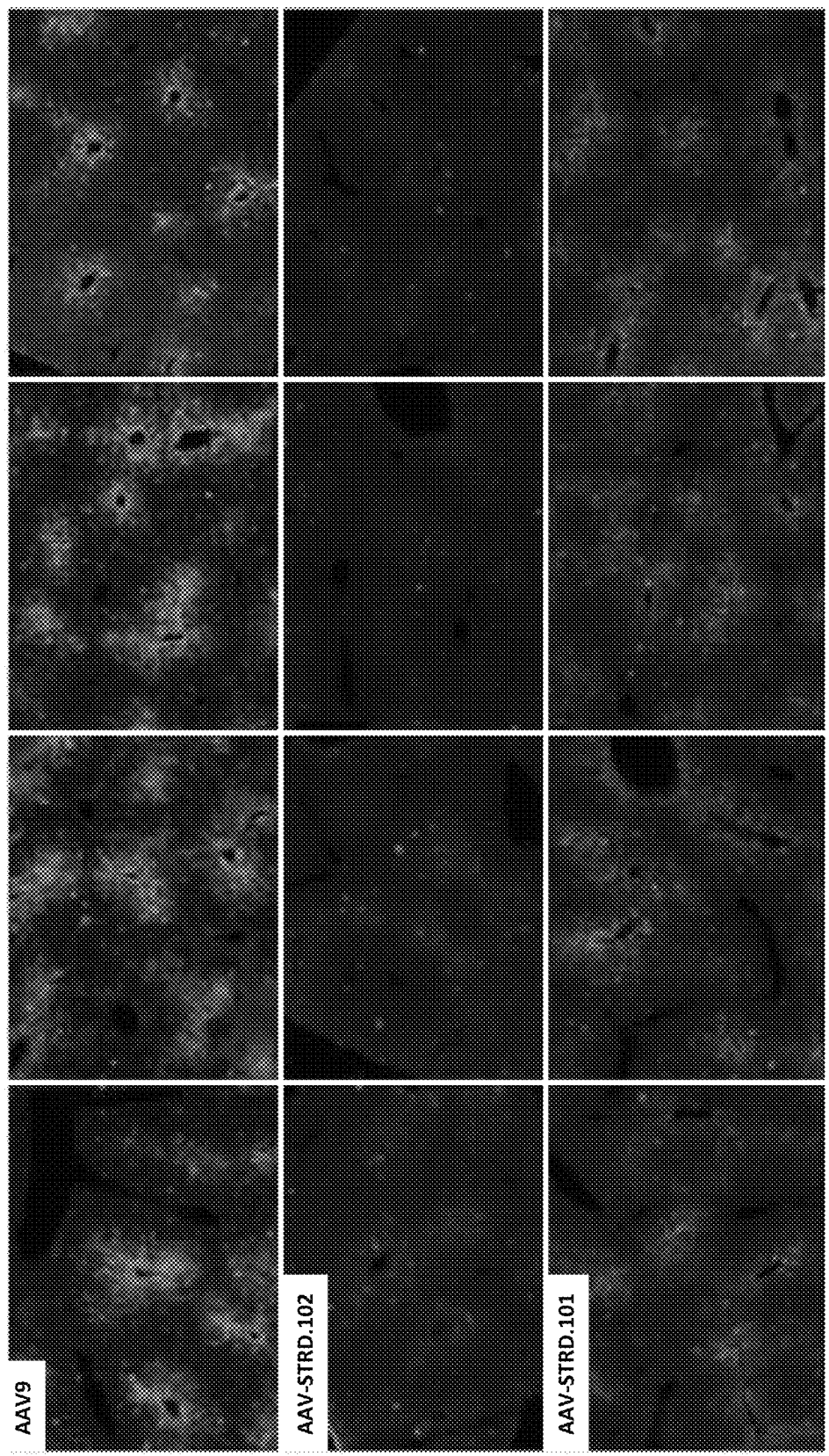
FIG. 7. Representative fluorescent microscopy images showing TdTomato expression in vibratrome liver sections 24 hours post-fixation with 4% PFA. Each section is 25 μm in thick. Panels show native tdTomato fluorescence with DAPI counterstain.

Representative images from one mouse showing TdTomato expression in vibratrome liver sections after 24 hours post-fixation with 4% PFA are provided in FIG. 7. Notably, the AAV-STRD.102 and AAV-STRD.101 vectors were detargeted to the liver compared to wildtype AAV9. This desirable property was unexpected, as no counter screen in the liver was performed during evolution.

Figure 8:
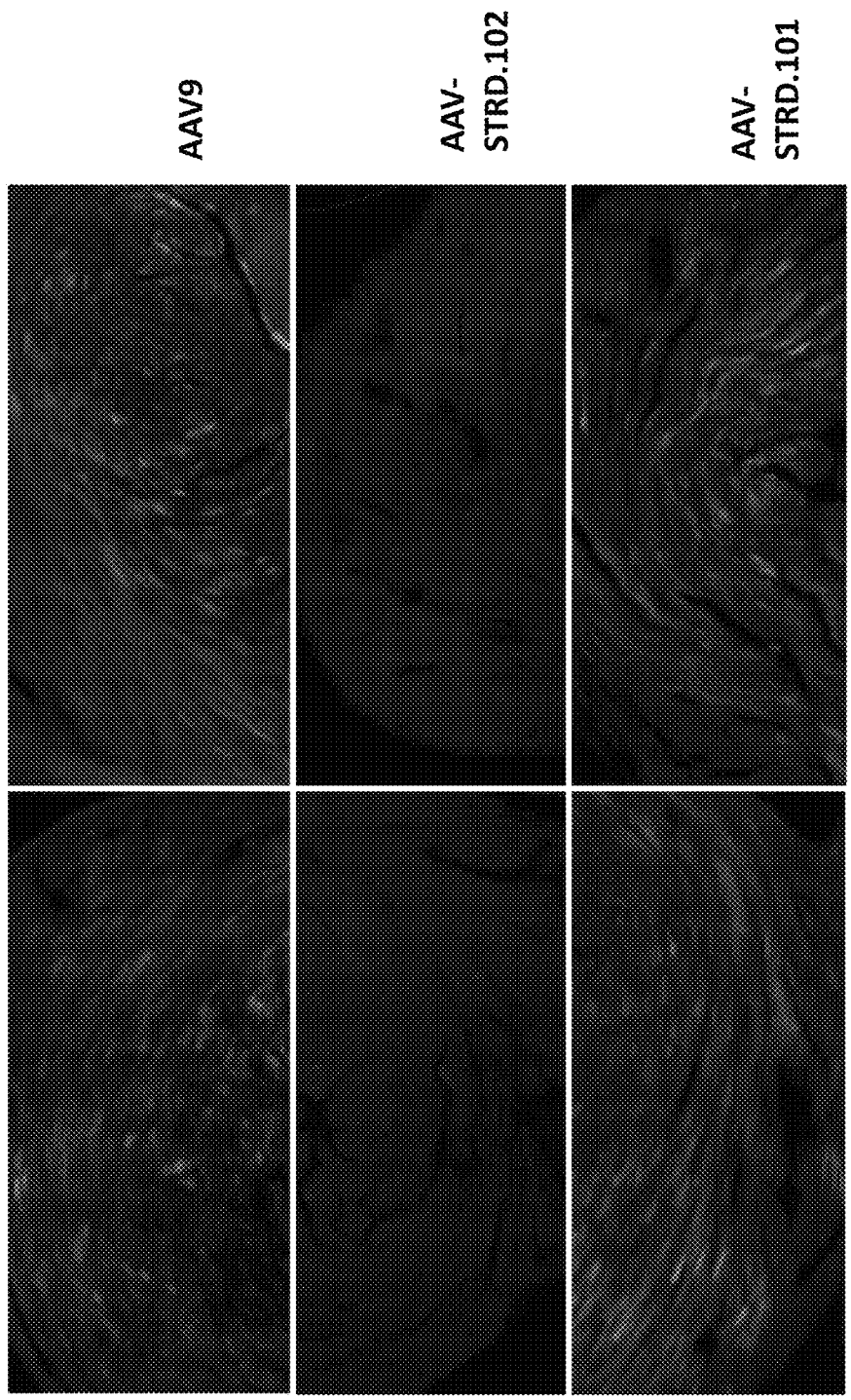
FIG. 8. Representative fluorescent microscopy images showing TdTomato expression in vibratrome heart sections 24 hours post-fixation with 4% PFA. Each section is 50 μm in thick. Panels show native tdTomato fluorescence with DAPI counterstain.

Representative images from one mouse showing TdTomato expression in vibratrome heart sections after 24 hours post-fixation with 4% PFA are provided in FIG. 8. Notably, the vectors tested had different tropism for the heart. Specifically, the AAV-STRD.102 vector was less infective in heart compared to AAV-STRD.101. Because no heart screen was performed during evolution, this differential transduction was wholly unexpected.

Taken together, this data indicates that the AAV-STRD.102 and AAV-STRD.101 vectors can be successfully used to target CNS tissues in vivo, avoid clearance by the liver, and are powerful tools for gene therapy. Given their different tropisms (i.e., AAV-STRD.101 was more infective in the heart than AAV-STRD.102), these vectors will be powerful tools for targeting gene therapy treatments to specifically desired tissues.

Example 5: Biodistribution of Recombinant AAVs in Non-Human Primates

Figure 9:
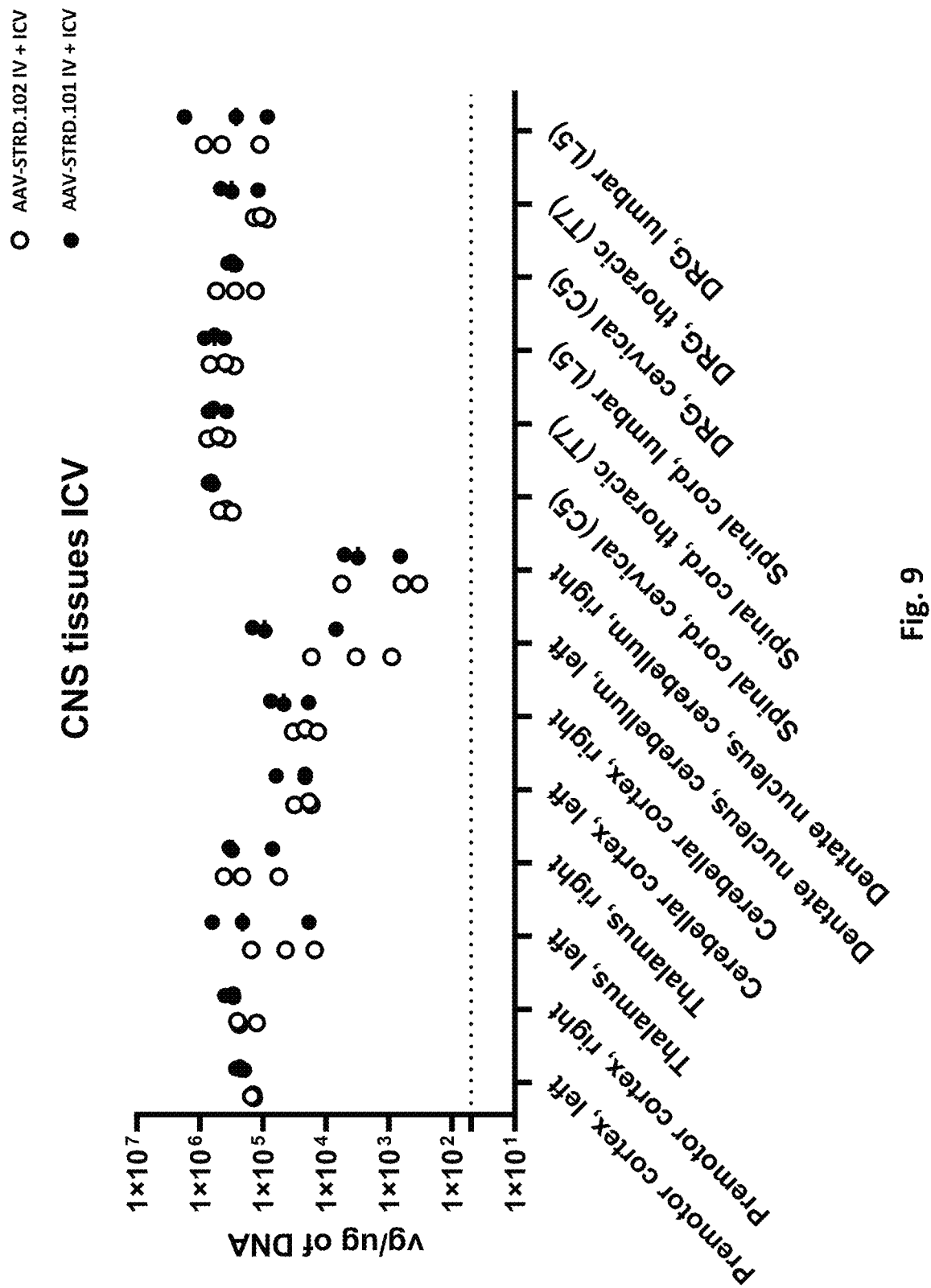
FIG. 9. Biodistribution of recombinant AAVs in non-human primates. Horizontal line shows limit of detection.

Recombinant AAVs were administered to non-human primates, in order to determine biodistribution. Recombinant AAVs were administered by intravenous (IV) and intracerebrovascular (ICV) injection (FIG. 9). AAV-STRD.101 was administered at a dose of $2.9 \times 10^{13}$ vg/kg by IV injection, and $2.1 \times 10^{13}$ vg by ICV injection (black dots). AAV-STRD.102 was administered at a dose of $2.8 \times 10^{13}$ vg/kg by IV injection, and $3.0 \times 10^{13}$ vg by ICV injection (white dots). After 30 days, the animals were sacrificed, and viral load in various CNS tissues was measured by qPCR.

As shown in FIG. 9, both AAV-STRD.102 and AAV-STRD.101 infected various CNS tissues. Additionally, because the AAVs showed high levels of transduction, this data suggest that these AAVs are likely to avoid neutralizing AAVs in vivo.

Example 6: Cell Therapy Method for Treating a Subject in Need Thereof

Cells are transduced using an AAV vector ex vivo. For some purposes, the cells may be autologous (i.e., derived from the subject to be treated) or allogenic (i.e., derived from a different subject/donor). After transduction of the cells using an AAV, and after expression of a transgene has been verified, the cells are administered to the subject using standard clinical methods.

Cells may be administered to the subject once, or administration may be repeated multiple times at therapeutically effective intervals. The number of cells administered varies depending on, for example, the disease or condition to be treated, the severity of the subject's disease/condition, and the subject's height and weight.

Example 7: Gene Therapy Method for Treating a Subject in Need Thereof

An AAV vector described herein (e.g., an AAV vector comprising a capsid having the sequence of SEQ ID NO: 175 or 180) is administered to a subject in need thereof, wherein the subject has a disease or disorder of the CNS. The AAV vector is administered to the subject once, or administration may be repeated multiple times at therapeutically effective intervals. The administration is by one or more therapeutically effective routes, such as intravenous (IV), intracerebroventricular (ICV), or intrathecal (IT) injection. The dose of AAV vector varies depending on, for example, the disease or condition to be treated, the severity of the subject's disease/condition, and the subject's height and weight. For example, the dose of AAV administered to the subject may be $2.8 \times 10^{13}$ vg/kg or $2.9 \times 10^{13}$ vg/kg when the AAV vector is administered by IV injection. When the AAV vector is administered by ICV injection, the dose may be $2.1 \times 10^{13}$ vg or $3.0 \times 10^{13}$ vg. In some protocols, the AAV vector may be administered to the subject by both IV and ICV injection.

The foregoing is illustrative of the present invention, and is not to be construed as limiting thereof. The invention is defined by the following claims, with equivalents of the claims to be included therein.

SEQUENCE LISTING

```
Sequence total quantity: 2760
SEQ ID NO: 1            moltype = AA  length = 736
FEATURE                 Location/Qualifiers
source                  1..736
                        mol_type = protein
                        note = Dependovirus adeno-associated virus 1
                        organism = unidentified
SEQUENCE: 1
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
```

```
AKKRVLEPLG LVEEGAKTAP GKKRPVEQSP QEPDSSSGIG KTGQQPAKKR LNFGQTGDSE     180
SVPDPQPLGE PPATPAAVGP TTMASGGGAP MADNNEGADG VGNASGNWHC DSTWLGDRVI     240
TTSTRTWALP TYNNHLYKQI SSASTGASND NHYFGYSTPW GYFDFNRFHC HFSPRDWQRL     300
INNNWGFRPK RLNFKLFNIQ VKEVTTNDGV TTIANNLTST VQVFSDSEYQ LPYVLGSAHQ     360
GCLPPFPADV FMIPQYGYLT LNNGSQAVGR SSFYCLEYFP SQMLRTGNNF TFSYTFEEVP     420
FHSSYAHSQS LDRLMNPLID QYLYYLNRTQ NQSGSAQNKD LLFSRGSPAG MSVQPKNWLP     480
GPCYRQQRVS KTKTDNNNSN FTWTGASKYN LNGRESIINP GTAMASHKDD EDKFFPMSGV     540
MIFGKESAGA SNTALDNVMI TDEEEIKATN PVATERFGTV AVNFQSSSTD PATGDVHAMG     600
ALPGMVWQDR DVYLQGPIWA KIPHTDGHFH PSPLMGGFGL KNPPPQILIK NTPVPANPPA     660
EFSATKFASF ITQYSTGQVS VEIEWELQKE NSKRWNPEVQ YTSNYAKSAN VDFTVDNNGL     720
YTEPRPIGTR YLTRPL                                                    736

SEQ ID NO: 2           moltype = AA  length = 735
FEATURE                Location/Qualifiers
source                 1..735
                       mol_type = protein
                       note = Dependovirus adeno-associated virus 2
                       organism = unidentified
SEQUENCE: 2
MAADGYLPDW LEDTLSEGIR QWWKLKPGPP PPKAERHKD DSRGLVLPGY KYLGPFNGLD      60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDSE    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNRQA ATADVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEIQY TSNYNKSVNV DFTVDTNGVY    720
SEPRPIGTRY LTRNL                                                    735

SEQ ID NO: 3           moltype = AA  length = 736
FEATURE                Location/Qualifiers
source                 1..736
                       mol_type = protein
                       note = Dependovirus adeno-associated virus 3
                       organism = unidentified
SEQUENCE: 3
MAADGYLPDW LEDNLSEGIR EWWALKPGVP QPKANQQHQD NRRGLVLPGY KYLGPGNGLD     60
KGEPVNEADA AALEHDKAYD QQLKAGDNPY LKYNHADAEF QERLQEDTSF GGNLGRAVFQ    120
AKKRILEPLG LVEEAAKTAP GKKRPVDQSP QEPDSSSGIG KSGKQPARKR LNFGQTGDAD    180
SVPDPQPLGE PPAAPTSLGS NTMASGGGAP MADNNEGADG VGNSSGNWHC DSQWLGDRVI    240
TTSTRTWALP TYNNHLYKQI SSQSGASNDN HYFGYSTPWG YFDFNRFHCH FSPRDWQRLI    300
NNNWGFRPKK LSFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFQ FSYTFEDVPF    420
HSSYAHSQSL DRLMNPLIDQ YLYYLNRTQT TSGTTNQSR LLFSQAGPQS MSLQARNWLP     480
GPCYRQQRLS KTANDNNSN FPWTAASKYH LNGRDSLVNP GPAMASHKDD EEKFFPMHGN     540
LIFGKEGTTA SNAELDNVMI TDEEEIRTTN PVATEQYGTV ANNLQSSNTA PTTRTVNDQG    600
ALPGMVWQDR DVYLQGPIWA KIPHTDGHFH PSPLMGGFGL KHPPPQIMIK NTPVPANPPT    660
TFSPAKFASF ITQYSTGQVS VEIEWELQKE NSKRWNPEIQ YTSNYNKSVN VDFTVDTNGV    720
YSEPRPIGTR YLTRNL                                                   736

SEQ ID NO: 4           moltype = AA  length = 734
FEATURE                Location/Qualifiers
source                 1..734
                       mol_type = protein
                       note = Dependovirus adeno-associated virus 4
                       organism = unidentified
SEQUENCE: 4
MTDGYLPDWL EDNLSEGVRE WWALQPGAPK PKANQQHQDN ARGLVLPGYK YLGPGNGLDK     60
GEPVNAADAA ALEHDKAYDQ QLKAGDNPYL KYNHADAEFQ QRLQGDTSFG GNLGRAVFQA    120
KKRVLEPLGL VEQAGETAPG KKRPLIESPQ QPDSSTGIGK KGKQPAKKKL VFEDETGAGD    180
GPPEGSTSGA MSDDSEMRAA AGGAAVEGGQ GADGVGNASG DWHCDSTWSE GHVTTTSTRT    240
WVLPTYNNHL YKRLGESLQS NTYNGFSTPW GYFDFNRFHC HFSPRDWQRL INNNWGMRPK    300
AMRVKIFNIQ VKEVTTSNGE TTVANNLTST VQIFADSSYE LPYVMDAGQE GSLPPFPNDV    360
FMVPQYGYCG LVTGNTSQQQ TDRNAFYCLE YFPSQMLRTG NNFEITYSFE KVPFHSMYAH    420
SQSLDRLMNP LIDQYLWGLQ STTTGTTLNA GTATTNFTKL RPTNFSNFKK NWLPGPSIKQ    480
QGFSKTANQN YKIPATGSDS LIKYETHSTL DGRWSALTPG PPMATAGPAD SKFSNSQLIF    540
AGPKQNGNTA TVPGTLIFTS EEELAATNAT DTDMWGNLPG GDQSNSNLPT VDRLTALGAV    600
PGMVWQNRDI YYQGPIWAKI PHTDGHFHPS PLIGGFGLKH PPPQIFIKNT PVPANPATTF    660
SSTPVNSFIT QYSTGQVSVQ IDWEIQKERS KRWNPEVQFT SNYGQQNSLL WAPDAAGKYT    720
EPRAIGTRYL THHL                                                     734

SEQ ID NO: 5           moltype = AA  length = 724
FEATURE                Location/Qualifiers
source                 1..724
                       mol_type = protein
```

```
                        note = Dependovirus adeno-associated virus 5
                        organism = unidentified
SEQUENCE: 5
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                              724

SEQ ID NO: 6            moltype = AA  length = 736
FEATURE                 Location/Qualifiers
source                  1..736
                        mol_type = protein
                        note = Dependovirus adeno-associated virus 6
                        organism = unidentified
SEQUENCE: 6
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 7            moltype = AA  length = 737
FEATURE                 Location/Qualifiers
source                  1..737
                        mol_type = protein
                        note = Dependovirus adeno-associated virus 7
                        organism = unidentified
SEQUENCE: 7
MAADGYLPDW LEDNLSEGIR EWWDLKPGAP KPKANQQKQD NGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP AKKRPVEPSP QRSPDSSTGI GKKGQQPARK RLNFGQTGDS  180
ESVPDPQPLG EPPAAPSSVG SGTVAAGGGA PMADNNEGAD GVGNASGNWH CDSTWLGDRV  240
ITTSTRTWAL PTYNNHLYKQ ISSETAGSTN DNTYFGYSTP WGYFDFNRFH CHFSPRDWQR  300
LINNNWGFRP KKLRFKLFNI QVKEVTTNDG VTTIANNLTS TIQVFSDSEY QLPYVLGSAH  360
QGCLPPFPAD VFMIPQYGYL TLNNGSQSVG RSSFYCLEYF PSQMLRTGNN FEFSYSFEDV  420
PPFHSSYAHS QSLDRLMNPL IDQYLYYLAR TQSNPGGTAG NRELQFYQGP STMAEQAKNW  480
LPGPCFRQQR VSKTLDQNNN SNFAWTGATK YHLNGRNSLV NPGVAMATHK DDEDRFFPSS  540
GVLIFGKTGA TNKTTLENVL MTNEEEIRPT NPVATEEYGI VSSNLQAANT AAQTQVVRNQ  600
GALPGMVWQN RDVYLQGPIW AKIPHTDGNF HPSPLMGGFG LKHPPPQILI KNTPVPANPP  660
EVFTPAKFAS FITQYSTGQV SVEIEWELQK ENSKRWNPEI QYTSNFEKQT GVDFAVDSQG  720
VYSEPRPIGT RYLTRNL                                                737

SEQ ID NO: 8            moltype = AA  length = 738
FEATURE                 Location/Qualifiers
source                  1..738
                        mol_type = protein
                        note = Dependovirus adeno-associated virus 8
                        organism = unidentified
SEQUENCE: 8
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738
```

```
SEQ ID NO: 9                moltype = AA   length = 736
FEATURE                     Location/Qualifiers
source                      1..736
                            mol_type = protein
                            note = Dependovirus adeno-associated virus 9
                            organism = unidentified
SEQUENCE: 9
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEDSSAGIG KSGAQPAKKR LNFGQTGDTE    180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 10               moltype = AA   length = 738
FEATURE                     Location/Qualifiers
source                      1..738
                            mol_type = protein
                            note = Dependovirus adeno-associated virus rh.10
                            organism = unidentified
SEQUENCE: 10
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYQFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFSQAKLA SFITQYSTGQ VSVEIEWELQ KENSKRWNPE IQYTSNYYKS TNVDFAVNTD   720
GTYSEPRPIG TRYLTRNL                                                738

SEQ ID NO: 11               moltype = AA   length = 733
FEATURE                     Location/Qualifiers
source                      1..733
                            mol_type = protein
                            note = Dependovirus adeno-associated virus 11
                            organism = unidentified
SEQUENCE: 11
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPLESPQ EPDSSSGIGK KGKQPARKRL NFEEDTGAGD   180
GPPEGSDTSA MSSDIEMRAA PGGNAVDAGQ GSDGVGNASG DWHCDSTWSE GKVTTTSTRT   240
WVLPTYNNHL YLRLGTTSSS NTYNGFSTPW GYFDFNRPHC HFSPRDWQRL INNNWGLRPK   300
AMRVKIFNIQ VKEVTTSNGE TTVANNLTST VQIFADSSYE LPYVMDAGQE GSLPPFPNDV   360
FMVPQYGYCG IVTGENQNQT DRNAFYCLEY FPSQMLRTGN NFEMAYNFEK VPFHSMYAHS   420
QSLDRLMNPL IDQYLWHLQS TTSGETLNQG NAATTFGKIR SGDFAFYRKN WLPGPCVKQQ   480
RFSKTASQNY KIPASGGNAL LKYDTHYTLN NRWSNIAPGP PMATAGPSDG DFSNAQLIFP   540
GPSVTGNTTT SANNLLFTSE EEIAATNPRD TDMFGQIADN NQNATTAPIT GNVTAMGVLP   600
GMVWQNRDIY YQGPIWAKIP HADGHFHPSP LIGGFGLKHP PPQIFIKNTP VPANPATTFT   660
AARVDSFITQ YSTGQVAVQI EWEIEKERSK RWNPEVQFTS NYGNQSSMLW APDTTGKYTE   720
PRVIGSRYLT NHL                                                     733

SEQ ID NO: 12               moltype = AA   length = 8
FEATURE                     Location/Qualifiers
REGION                      1..8
                            note = Amino acid substitution
source                      1..8
                            mol_type = protein
                            organism = synthetic construct
SEQUENCE: 12
SCQPTVMN                                                             8

SEQ ID NO: 13               moltype = AA   length = 8
FEATURE                     Location/Qualifiers
REGION                      1..8
                            note = Amino acid substitution
source                      1..8
```

```
                           mol_type = protein
                           organism = synthetic construct
SEQUENCE: 13
FGVPNQPL                                                                   8

SEQ ID NO: 14              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 14
QRGQAAPF                                                                   8

SEQ ID NO: 15              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 15
GDYAPIRE                                                                   8

SEQ ID NO: 16              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 16
KTRRIVQH                                                                   8

SEQ ID NO: 17              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 17
FGFPNQPL                                                                   8

SEQ ID NO: 18              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 18
RQDQPINA                                                                   8

SEQ ID NO: 19              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 19
SKVESWTE                                                                   8

SEQ ID NO: 20              moltype = AA   length = 8
FEATURE                    Location/Qualifiers
REGION                     1..8
                           note = Amino acid substitution
source                     1..8
                           mol_type = protein
                           organism = synthetic construct
SEQUENCE: 20
STVDSIAI                                                                   8

SEQ ID NO: 21              moltype =    length =
SEQUENCE: 21
000
```

```
SEQ ID NO: 22        moltype = AA  length = 5
FEATURE              Location/Qualifiers
REGION               1..5
                     note = peptide motif
source               1..5
                     mol_type = protein
                     organism = synthetic construct
SEQUENCE: 22
FVFLP                                                                    5

SEQ ID NO: 23        moltype =     length =
SEQUENCE: 23
000

SEQ ID NO: 24        moltype = AA  length = 4
FEATURE              Location/Qualifiers
REGION               1..4
                     note = peptide motif
source               1..4
                     mol_type = protein
                     organism = synthetic construct
SEQUENCE: 24
RGNR                                                                     4

SEQ ID NO: 25        moltype = AA  length = 7
FEATURE              Location/Qualifiers
REGION               1..7
                     note = targeting sequence
source               1..7
                     mol_type = protein
                     organism = synthetic construct
VARIANT              7
                     note = X can be G or S
SEQUENCE: 25
NSVRDLX                                                                  7

SEQ ID NO: 26        moltype = AA  length = 7
FEATURE              Location/Qualifiers
REGION               1..7
                     note = targeting sequence
source               1..7
                     mol_type = protein
                     organism = synthetic construct
SEQUENCE: 26
PRSVTVP                                                                  7

SEQ ID NO: 27        moltype = AA  length = 7
FEATURE              Location/Qualifiers
REGION               1..7
                     note = targeting sequence
source               1..7
                     mol_type = protein
                     organism = synthetic construct
VARIANT              6
                     note = X can be any amino acid
VARIANT              7
                     note = X can be S or A
SEQUENCE: 27
NSVSSXX                                                                  7

SEQ ID NO: 28        moltype = AA  length = 6
FEATURE              Location/Qualifiers
REGION               1..6
                     note = targeting sequence
source               1..6
                     mol_type = protein
                     organism = synthetic construct
SEQUENCE: 28
NGRAHA                                                                   6

SEQ ID NO: 29        moltype = AA  length = 7
FEATURE              Location/Qualifiers
REGION               1..7
                     note = targeting sequence
source               1..7
                     mol_type = protein
                     organism = synthetic construct
SEQUENCE: 29
QPEHSST                                                                  7
```

```
SEQ ID NO: 30           moltype = AA   length = 7
FEATURE                 Location/Qualifiers
REGION                  1..7
                        note = targeting sequence
source                  1..7
                        mol_type = protein
                        organism = synthetic construct
SEQUENCE: 30
VNTANST                                                                  7

SEQ ID NO: 31           moltype = AA   length = 6
FEATURE                 Location/Qualifiers
REGION                  1..6
                        note = targeting sequence
source                  1..6
                        mol_type = protein
                        organism = synthetic construct
SEQUENCE: 31
HGPMQS                                                                   6

SEQ ID NO: 32           moltype = AA   length = 7
FEATURE                 Location/Qualifiers
REGION                  1..7
                        note = targeting sequence
source                  1..7
                        mol_type = protein
                        organism = synthetic construct
SEQUENCE: 32
PHKPPLA                                                                  7

SEQ ID NO: 33           moltype = AA   length = 7
FEATURE                 Location/Qualifiers
REGION                  1..7
                        note = targeting sequence
source                  1..7
                        mol_type = protein
                        organism = synthetic construct
SEQUENCE: 33
IKNNEMW                                                                  7

SEQ ID NO: 34           moltype = AA   length = 7
FEATURE                 Location/Qualifiers
REGION                  1..7
                        note = targeting sequence
source                  1..7
                        mol_type = protein
                        organism = synthetic construct
SEQUENCE: 34
RNLDTPM                                                                  7

SEQ ID NO: 35           moltype = AA   length = 7
FEATURE                 Location/Qualifiers
REGION                  1..7
                        note = targeting sequence
source                  1..7
                        mol_type = protein
                        organism = synthetic construct
SEQUENCE: 35
VDSHRQS                                                                  7

SEQ ID NO: 36           moltype = AA   length = 7
FEATURE                 Location/Qualifiers
REGION                  1..7
                        note = targeting sequence
source                  1..7
                        mol_type = protein
                        organism = synthetic construct
SEQUENCE: 36
YDSKTKT                                                                  7

SEQ ID NO: 37           moltype = AA   length = 7
FEATURE                 Location/Qualifiers
REGION                  1..7
                        note = targeting sequence
source                  1..7
                        mol_type = protein
                        organism = synthetic construct
SEQUENCE: 37
```

SQLPHQK                                                                         7

SEQ ID NO: 38          moltype = AA   length = 7
FEATURE                Location/Qualifiers
REGION                 1..7
                       note = targeting sequence
source                 1..7
                       mol_type = protein
                       organism = synthetic construct
SEQUENCE: 38
STMQQNT                                                                         7

SEQ ID NO: 39          moltype = AA   length = 7
FEATURE                Location/Qualifiers
REGION                 1..7
                       note = targeting sequence
source                 1..7
                       mol_type = protein
                       organism = synthetic construct
SEQUENCE: 39
TERYMTQ                                                                         7

SEQ ID NO: 40          moltype = AA   length = 7
FEATURE                Location/Qualifiers
REGION                 1..7
                       note = targeting sequence
source                 1..7
                       mol_type = protein
                       organism = synthetic construct
SEQUENCE: 40
QPEHSST                                                                         7

SEQ ID NO: 41          moltype = AA   length = 7
FEATURE                Location/Qualifiers
REGION                 1..7
                       note = targeting sequence
source                 1..7
                       mol_type = protein
                       organism = synthetic construct
SEQUENCE: 41
DASLSTS                                                                         7

SEQ ID NO: 42          moltype = AA   length = 6
FEATURE                Location/Qualifiers
REGION                 1..6
                       note = targeting sequence
source                 1..6
                       mol_type = protein
                       organism = synthetic construct
SEQUENCE: 42
DLPNKT                                                                          6

SEQ ID NO: 43          moltype = AA   length = 7
FEATURE                Location/Qualifiers
REGION                 1..7
                       note = targeting sequence
source                 1..7
                       mol_type = protein
                       organism = synthetic construct
SEQUENCE: 43
DLTAARL                                                                         7

SEQ ID NO: 44          moltype = AA   length = 7
FEATURE                Location/Qualifiers
REGION                 1..7
                       note = targeting sequence
source                 1..7
                       mol_type = protein
                       organism = synthetic construct
SEQUENCE: 44
EPHQFNY                                                                         7

SEQ ID NO: 45          moltype = AA   length = 7
FEATURE                Location/Qualifiers
REGION                 1..7
                       note = targeting sequence
source                 1..7
                       mol_type = protein
                       organism = synthetic construct

```
SEQUENCE: 45
EPQSNHT                                                                                7

SEQ ID NO: 46           moltype = AA  length = 7
FEATURE                 Location/Qualifiers
REGION                  1..7
                        note = targeting sequence
source                  1..7
                        mol_type = protein
                        organism = synthetic construct
SEQUENCE: 46
MSSWPSQ                                                                                7

SEQ ID NO: 47           moltype = AA  length = 7
FEATURE                 Location/Qualifiers
REGION                  1..7
                        note = targeting sequence
source                  1..7
                        mol_type = protein
                        organism = synthetic construct
SEQUENCE: 47
NPKHNAT                                                                                7

SEQ ID NO: 48           moltype = AA  length = 7
FEATURE                 Location/Qualifiers
REGION                  1..7
                        note = targeting sequence
source                  1..7
                        mol_type = protein
                        organism = synthetic construct
SEQUENCE: 48
PDGMRTT                                                                                7

SEQ ID NO: 49           moltype = AA  length = 7
FEATURE                 Location/Qualifiers
REGION                  1..7
                        note = targeting sequence
source                  1..7
                        mol_type = protein
                        organism = synthetic construct
SEQUENCE: 49
PNNNKTT                                                                                7

SEQ ID NO: 50           moltype = AA  length = 7
FEATURE                 Location/Qualifiers
REGION                  1..7
                        note = targeting sequence
source                  1..7
                        mol_type = protein
                        organism = synthetic construct
SEQUENCE: 50
QSTTHDS                                                                                7

SEQ ID NO: 51           moltype = AA  length = 7
FEATURE                 Location/Qualifiers
REGION                  1..7
                        note = targeting sequence
source                  1..7
                        mol_type = protein
                        organism = synthetic construct
SEQUENCE: 51
TGSKQKQ                                                                                7

SEQ ID NO: 52           moltype = AA  length = 7
FEATURE                 Location/Qualifiers
REGION                  1..7
                        note = targeting sequence
source                  1..7
                        mol_type = protein
                        organism = synthetic construct
SEQUENCE: 52
SLKHQAL                                                                                7

SEQ ID NO: 53           moltype = AA  length = 7
FEATURE                 Location/Qualifiers
REGION                  1..7
                        note = targeting sequence
source                  1..7
                        mol_type = protein
```

```
                             organism = synthetic construct
SEQUENCE: 53
SPIDGEQ                                                                       7

SEQ ID NO: 54               moltype = AA  length = 8
FEATURE                     Location/Qualifiers
REGION                      1..8
                            note = targeting sequence
source                      1..8
                            mol_type = protein
                            organism = synthetic construct
SEQUENCE: 54
WIFPWIQL                                                                      8

SEQ ID NO: 55               moltype = AA  length = 9
FEATURE                     Location/Qualifiers
REGION                      1..9
                            note = targeting sequence
source                      1..9
                            mol_type = protein
                            organism = synthetic construct
SEQUENCE: 55
CDCRGDCFC                                                                     9

SEQ ID NO: 56               moltype = AA  length = 5
FEATURE                     Location/Qualifiers
REGION                      1..5
                            note = targeting sequence
source                      1..5
                            mol_type = protein
                            organism = synthetic construct
SEQUENCE: 56
CNGRC                                                                         5

SEQ ID NO: 57               moltype = AA  length = 7
FEATURE                     Location/Qualifiers
REGION                      1..7
                            note = targeting sequence
source                      1..7
                            mol_type = protein
                            organism = synthetic construct
SEQUENCE: 57
CPRECES                                                                       7

SEQ ID NO: 58               moltype = AA  length = 10
FEATURE                     Location/Qualifiers
REGION                      1..10
                            note = targeting sequence
source                      1..10
                            mol_type = protein
                            organism = synthetic construct
SEQUENCE: 58
CTTHWGFTLC                                                                   10

SEQ ID NO: 59               moltype = AA  length = 9
FEATURE                     Location/Qualifiers
REGION                      1..9
                            note = targeting sequence
source                      1..9
                            mol_type = protein
                            organism = synthetic construct
SEQUENCE: 59
CGRRAGGSC                                                                     9

SEQ ID NO: 60               moltype = AA  length = 9
FEATURE                     Location/Qualifiers
REGION                      1..9
                            note = targeting sequence
source                      1..9
                            mol_type = protein
                            organism = synthetic construct
SEQUENCE: 60
CKGGRAKDC                                                                     9

SEQ ID NO: 61               moltype = AA  length = 9
FEATURE                     Location/Qualifiers
REGION                      1..9
                            note = targeting sequence
source                      1..9
```

```
                           mol_type = protein
                           organism = synthetic construct
SEQUENCE: 61
CVPELGHEC                                                              9

SEQ ID NO: 62              moltype = AA   length = 9
FEATURE                    Location/Qualifiers
REGION                     1..9
                           note = targeting sequence
source                     1..9
                           mol_type = protein
                           organism = synthetic construct
SEQUENCE: 62
CRRETAWAK                                                              9

SEQ ID NO: 63              moltype = AA   length = 14
FEATURE                    Location/Qualifiers
REGION                     1..14
                           note = targeting sequence
source                     1..14
                           mol_type = protein
                           organism = synthetic construct
SEQUENCE: 63
VSWFSHRYSP FAVS                                                       14

SEQ ID NO: 64              moltype = AA   length = 13
FEATURE                    Location/Qualifiers
REGION                     1..13
                           note = targeting sequence
source                     1..13
                           mol_type = protein
                           organism = synthetic construct
SEQUENCE: 64
GYRDGYAGPI LYN                                                        13

SEQ ID NO: 65              moltype =     length =
SEQUENCE: 65
000

SEQ ID NO: 66              moltype =     length =
SEQUENCE: 66
000

SEQ ID NO: 67              moltype = AA   length = 7
FEATURE                    Location/Qualifiers
REGION                     1..7
                           note = targeting sequence
source                     1..7
                           mol_type = protein
                           organism = synthetic construct
SEQUENCE: 67
RPLPPLP                                                                7

SEQ ID NO: 68              moltype = AA   length = 7
FEATURE                    Location/Qualifiers
REGION                     1..7
                           note = targeting sequence
source                     1..7
                           mol_type = protein
                           organism = synthetic construct
SEQUENCE: 68
APPLPPR                                                                7

SEQ ID NO: 69              moltype = AA   length = 12
FEATURE                    Location/Qualifiers
REGION                     1..12
                           note = targeting sequence
source                     1..12
                           mol_type = protein
                           organism = synthetic construct
SEQUENCE: 69
DVFYPYPYAS GS                                                         12

SEQ ID NO: 70              moltype = AA   length = 6
FEATURE                    Location/Qualifiers
REGION                     1..6
                           note = targeting sequence
source                     1..6
                           mol_type = protein
```

```
                        organism = synthetic construct
SEQUENCE: 70
MYWYPY                                                                     6

SEQ ID NO: 71           moltype = AA  length = 12
FEATURE                 Location/Qualifiers
REGION                  1..12
                        note = targeting sequence
source                  1..12
                        mol_type = protein
                        organism = synthetic construct
SEQUENCE: 71
DITWDQLWDL MK                                                              12

SEQ ID NO: 72           moltype = AA  length = 8
FEATURE                 Location/Qualifiers
REGION                  1..8
                        note = targeting sequence
source                  1..8
                        mol_type = protein
                        organism = synthetic construct
VARIANT                 5
                        note = X can be G or L
SEQUENCE: 72
CWDDXWLC                                                                   8

SEQ ID NO: 73           moltype = AA  length = 14
FEATURE                 Location/Qualifiers
REGION                  1..14
                        note = targeting sequence
source                  1..14
                        mol_type = protein
                        organism = synthetic construct
SEQUENCE: 73
EWCEYLGGYL RCYA                                                            14

SEQ ID NO: 74           moltype = AA  length = 14
FEATURE                 Location/Qualifiers
REGION                  1..14
                        note = targeting sequence
source                  1..14
                        mol_type = protein
                        organism = synthetic construct
VARIANT                 2
                        note = X can be any amino acid
VARIANT                 4..5
                        note = X can be any amino acid
VARIANT                 8
                        note = X can be any amino acid
VARIANT                 11
                        note = X can be any amino acid
VARIANT                 13
                        note = X can be any amino acid
SEQUENCE: 74
YXCXXGPXTW XCXP                                                            14

SEQ ID NO: 75           moltype = AA  length = 14
FEATURE                 Location/Qualifiers
REGION                  1..14
                        note = targeting sequence
source                  1..14
                        mol_type = protein
                        organism = synthetic construct
SEQUENCE: 75
IEGPTLRQWL AARA                                                            14

SEQ ID NO: 76           moltype =    length =
SEQUENCE: 76
000

SEQ ID NO: 77           moltype = AA  length = 7
FEATURE                 Location/Qualifiers
REGION                  1..7
                        note = targeting sequence
source                  1..7
                        mol_type = protein
                        organism = synthetic construct
VARIANT                 1
                        note = X can be any amino acid
```

```
VARIANT                  3..4
                         note = X can be any amino acid
SEQUENCE: 77
XFXXYLW                                                                 7

SEQ ID NO: 78            moltype = AA  length = 6
FEATURE                  Location/Qualifiers
REGION                   1..6
                         note = targeting sequence
source                   1..6
                         mol_type = protein
                         organism = synthetic construct
SEQUENCE: 78
RWGLCD                                                                  6

SEQ ID NO: 79            moltype = AA  length = 13
FEATURE                  Location/Qualifiers
REGION                   1..13
                         note = targeting sequence
source                   1..13
                         mol_type = protein
                         organism = synthetic construct
SEQUENCE: 79
MSRPACPPND KYE                                                         13

SEQ ID NO: 80            moltype = AA  length = 8
FEATURE                  Location/Qualifiers
REGION                   1..8
                         note = targeting sequence
source                   1..8
                         mol_type = protein
                         organism = synthetic construct
SEQUENCE: 80
CLRSGRGC                                                                8

SEQ ID NO: 81            moltype = AA  length = 9
FEATURE                  Location/Qualifiers
REGION                   1..9
                         note = targeting sequence
source                   1..9
                         mol_type = protein
                         organism = synthetic construct
SEQUENCE: 81
CHWMFSPWC                                                               9

SEQ ID NO: 82            moltype =   length =
SEQUENCE: 82
000

SEQ ID NO: 83            moltype = AA  length = 8
FEATURE                  Location/Qualifiers
REGION                   1..8
                         note = targeting sequence
source                   1..8
                         mol_type = protein
                         organism = synthetic construct
SEQUENCE: 83
CSSRLDAC                                                                8

SEQ ID NO: 84            moltype = AA  length = 7
FEATURE                  Location/Qualifiers
REGION                   1..7
                         note = targeting sequence
source                   1..7
                         mol_type = protein
                         organism = synthetic construct
SEQUENCE: 84
CLPVASC                                                                 7

SEQ ID NO: 85            moltype = AA  length = 13
FEATURE                  Location/Qualifiers
REGION                   1..13
                         note = targeting sequence
source                   1..13
                         mol_type = protein
                         organism = synthetic construct
SEQUENCE: 85
CGFECVRQCP ERC                                                         13
```

```
SEQ ID NO: 86            moltype = AA   length = 13
FEATURE                  Location/Qualifiers
REGION                   1..13
                         note = targeting sequence
source                   1..13
                         mol_type = protein
                         organism = synthetic construct
SEQUENCE: 86
CVALCREACG EGC                                                             13

SEQ ID NO: 87            moltype = AA   length = 9
FEATURE                  Location/Qualifiers
REGION                   1..9
                         note = targeting sequence
source                   1..9
                         mol_type = protein
                         organism = synthetic construct
SEQUENCE: 87
SWCEPGWCR                                                                   9

SEQ ID NO: 88            moltype = AA   length = 6
FEATURE                  Location/Qualifiers
REGION                   1..6
                         note = targeting sequence
source                   1..6
                         mol_type = protein
                         organism = synthetic construct
SEQUENCE: 88
YSGWGW                                                                      6

SEQ ID NO: 89            moltype = AA   length = 7
FEATURE                  Location/Qualifiers
REGION                   1..7
                         note = targeting sequence
source                   1..7
                         mol_type = protein
                         organism = synthetic construct
SEQUENCE: 89
GLSGGRS                                                                     7

SEQ ID NO: 90            moltype = AA   length = 7
FEATURE                  Location/Qualifiers
REGION                   1..7
                         note = targeting sequence
source                   1..7
                         mol_type = protein
                         organism = synthetic construct
SEQUENCE: 90
LMLPRAD                                                                     7

SEQ ID NO: 91            moltype = AA   length = 9
FEATURE                  Location/Qualifiers
REGION                   1..9
                         note = targeting sequence
source                   1..9
                         mol_type = protein
                         organism = synthetic construct
SEQUENCE: 91
CSCFRDVCC                                                                   9

SEQ ID NO: 92            moltype = AA   length = 9
FEATURE                  Location/Qualifiers
REGION                   1..9
                         note = targeting sequence
source                   1..9
                         mol_type = protein
                         organism = synthetic construct
SEQUENCE: 92
CRDVVSVIC                                                                   9

SEQ ID NO: 93            moltype = AA   length = 5
FEATURE                  Location/Qualifiers
REGION                   1..5
                         note = targeting sequence
source                   1..5
                         mol_type = protein
                         organism = synthetic construct
SEQUENCE: 93
CNGRC                                                                       5
```

```
SEQ ID NO: 94           moltype = AA   length = 6
FEATURE                 Location/Qualifiers
REGION                  1..6
                        note = targeting sequence
source                  1..6
                        mol_type = protein
                        organism = synthetic construct
SEQUENCE: 94
MARSGL                                                                    6

SEQ ID NO: 95           moltype = AA   length = 6
FEATURE                 Location/Qualifiers
REGION                  1..6
                        note = targeting sequence
source                  1..6
                        mol_type = protein
                        organism = synthetic construct
SEQUENCE: 95
MARAKE                                                                    6

SEQ ID NO: 96           moltype = AA   length = 6
FEATURE                 Location/Qualifiers
REGION                  1..6
                        note = targeting sequence
source                  1..6
                        mol_type = protein
                        organism = synthetic construct
SEQUENCE: 96
MSRTMS                                                                    6

SEQ ID NO: 97           moltype = AA   length = 6
FEATURE                 Location/Qualifiers
REGION                  1..6
                        note = targeting sequence
source                  1..6
                        mol_type = protein
                        organism = synthetic construct
SEQUENCE: 97
KCCYSL                                                                    6

SEQ ID NO: 98           moltype = AA   length = 14
FEATURE                 Location/Qualifiers
REGION                  1..14
                        note = targeting sequence
source                  1..14
                        mol_type = protein
                        organism = synthetic construct
SEQUENCE: 98
MYWGDSHWLQ YWYE                                                          14

SEQ ID NO: 99           moltype = AA   length = 7
FEATURE                 Location/Qualifiers
REGION                  1..7
                        note = targeting sequence
source                  1..7
                        mol_type = protein
                        organism = synthetic construct
SEQUENCE: 99
MQLPLAT                                                                   7

SEQ ID NO: 100          moltype = AA   length = 4
FEATURE                 Location/Qualifiers
REGION                  1..4
                        note = targeting sequence
source                  1..4
                        mol_type = protein
                        organism = synthetic construct
SEQUENCE: 100
EWLS                                                                      4

SEQ ID NO: 101          moltype = AA   length = 4
FEATURE                 Location/Qualifiers
REGION                  1..4
                        note = targeting sequence
source                  1..4
                        mol_type = protein
                        organism = synthetic construct
SEQUENCE: 101
```

```
SNEW                                                                              4

SEQ ID NO: 102           moltype = AA  length = 4
FEATURE                  Location/Qualifiers
REGION                   1..4
                         note = targeting sequence
source                   1..4
                         mol_type = protein
                         organism = synthetic construct
SEQUENCE: 102
TNYL                                                                              4

SEQ ID NO: 103           moltype = AA  length = 8
FEATURE                  Location/Qualifiers
REGION                   1..8
                         note = targeting sequence
source                   1..8
                         mol_type = protein
                         organism = synthetic construct
SEQUENCE: 103
WIFPWIQL                                                                          8

SEQ ID NO: 104           moltype = AA  length = 12
FEATURE                  Location/Qualifiers
REGION                   1..12
                         note = targeting sequence
source                   1..12
                         mol_type = protein
                         organism = synthetic construct
SEQUENCE: 104
WDLAWMFRLP VG                                                                    12

SEQ ID NO: 105           moltype = AA  length = 13
FEATURE                  Location/Qualifiers
REGION                   1..13
                         note = targeting sequence
source                   1..13
                         mol_type = protein
                         organism = synthetic construct
SEQUENCE: 105
CTVALPGGYV RVC                                                                   13

SEQ ID NO: 106           moltype = AA  length = 9
FEATURE                  Location/Qualifiers
REGION                   1..9
                         note = targeting sequence
source                   1..9
                         mol_type = protein
                         organism = synthetic construct
SEQUENCE: 106
CVPELGHEC                                                                         9

SEQ ID NO: 107           moltype = AA  length = 9
FEATURE                  Location/Qualifiers
REGION                   1..9
                         note = targeting sequence
source                   1..9
                         mol_type = protein
                         organism = synthetic construct
SEQUENCE: 107
CGRRAGGSC                                                                         9

SEQ ID NO: 108           moltype = AA  length = 13
FEATURE                  Location/Qualifiers
REGION                   1..13
                         note = targeting sequence
source                   1..13
                         mol_type = protein
                         organism = synthetic construct
SEQUENCE: 108
CVAYCIEHHC WTC                                                                   13

SEQ ID NO: 109           moltype = AA  length = 12
FEATURE                  Location/Qualifiers
REGION                   1..12
                         note = targeting sequence
source                   1..12
                         mol_type = protein
                         organism = synthetic construct
```

```
SEQUENCE: 109
CVFAHNYDYL VC                                                       12

SEQ ID NO: 110          moltype = AA  length = 10
FEATURE                 Location/Qualifiers
REGION                  1..10
                        note = targeting sequence
source                  1..10
                        mol_type = protein
                        organism = synthetic construct
SEQUENCE: 110
CVFTSNYAFC                                                          10

SEQ ID NO: 111          moltype = AA  length = 7
FEATURE                 Location/Qualifiers
REGION                  1..7
                        note = targeting sequence
source                  1..7
                        mol_type = protein
                        organism = synthetic construct
SEQUENCE: 111
VHSPNKK                                                             7

SEQ ID NO: 112          moltype = AA  length = 9
FEATURE                 Location/Qualifiers
REGION                  1..9
                        note = targeting sequence
source                  1..9
                        mol_type = protein
                        organism = synthetic construct
SEQUENCE: 112
CDCRGDCFC                                                           9

SEQ ID NO: 113          moltype = AA  length = 7
FEATURE                 Location/Qualifiers
REGION                  1..7
                        note = targeting sequence
source                  1..7
                        mol_type = protein
                        organism = synthetic construct
SEQUENCE: 113
CRGDGWC                                                             7

SEQ ID NO: 114          moltype = AA  length = 6
FEATURE                 Location/Qualifiers
REGION                  1..6
                        note = targeting sequence
source                  1..6
                        mol_type = protein
                        organism = synthetic construct
VARIANT                 1
                        note = X can be any amino acid
VARIANT                 6
                        note = X can be any amino acid
SEQUENCE: 114
XRGCDX                                                              6

SEQ ID NO: 115          moltype =   length =
SEQUENCE: 115
000

SEQ ID NO: 116          moltype = AA  length = 10
FEATURE                 Location/Qualifiers
REGION                  1..10
                        note = targeting sequence
source                  1..10
                        mol_type = protein
                        organism = synthetic construct
SEQUENCE: 116
CTTHWGFTLC                                                          10

SEQ ID NO: 117          moltype = AA  length = 11
FEATURE                 Location/Qualifiers
REGION                  1..11
                        note = targeting sequence
source                  1..11
                        mol_type = protein
                        organism = synthetic construct
SEQUENCE: 117
```

```
SGKGPRQITA L                                                           11

SEQ ID NO: 119          moltype = AA  length = 6
FEATURE                 Location/Qualifiers
REGION                  1..6
                        note = targeting sequence
source                  1..6
                        mol_type = protein
                        organism = synthetic construct
SEQUENCE: 119
VYMSPF                                                                 6

SEQ ID NO: 120          moltype = AA  length = 7
FEATURE                 Location/Qualifiers
REGION                  1..7
                        note = targeting sequence
source                  1..7
                        mol_type = protein
                        organism = synthetic construct
SEQUENCE: 120
MQLPLAT                                                                7

SEQ ID NO: 121          moltype = AA  length = 7
FEATURE                 Location/Qualifiers
REGION                  1..7
                        note = targeting sequence
source                  1..7
                        mol_type = protein
                        organism = synthetic construct
SEQUENCE: 121
ATWLPPR                                                                7

SEQ ID NO: 122          moltype = AA  length = 12
FEATURE                 Location/Qualifiers
REGION                  1..12
                        note = targeting sequence
source                  1..12
                        mol_type = protein
                        organism = synthetic construct
SEQUENCE: 122
HTMYYHHYQH HL                                                          12

SEQ ID NO: 123          moltype = AA  length = 19
FEATURE                 Location/Qualifiers
REGION                  1..19
                        note = targeting sequence
source                  1..19
                        mol_type = protein
                        organism = synthetic construct
SEQUENCE: 123
SEVGCRAGPL QWLCEKYFG                                                   19

SEQ ID NO: 124          moltype = AA  length = 18
FEATURE                 Location/Qualifiers
REGION                  1..18
                        note = targeting sequence
source                  1..18
                        mol_type = protein
                        organism = synthetic construct
SEQUENCE: 124
CGLLPVGRPD RNVWRWLC                                                    18

SEQ ID NO: 125          moltype = AA  length = 15
FEATURE                 Location/Qualifiers
REGION                  1..15
                        note = targeting sequence
source                  1..15
                        mol_type = protein
                        organism = synthetic construct
SEQUENCE: 125
CKGQCDRFKG LPWEC                                                       15

SEQ ID NO: 126          moltype = AA  length = 5
FEATURE                 Location/Qualifiers
REGION                  1..5
```

```
                        note = targeting sequence
source                  1..5
                        mol_type = protein
                        organism = synthetic construct
SEQUENCE: 126
SGRSA                                                                    5

SEQ ID NO: 127          moltype = AA   length = 4
FEATURE                 Location/Qualifiers
REGION                  1..4
                        note = targeting sequence
source                  1..4
                        mol_type = protein
                        organism = synthetic construct
SEQUENCE: 127
WGFP                                                                     4

SEQ ID NO: 128          moltype = AA   length = 6
FEATURE                 Location/Qualifiers
REGION                  1..6
                        note = targeting sequence
source                  1..6
                        mol_type = protein
                        organism = synthetic construct
VARIANT                 3..4
                        note = X can be any amino acid
SEQUENCE: 128
LWXXAR                                                                   6

SEQ ID NO: 129          moltype = AA   length = 7
FEATURE                 Location/Qualifiers
REGION                  1..7
                        note = targeting sequence
source                  1..7
                        mol_type = protein
                        organism = synthetic construct
VARIANT                 1
                        note = X can be any amino acid
VARIANT                 3..4
                        note = X can be any amino acid
SEQUENCE: 129
XFXXYLW                                                                  7

SEQ ID NO: 130          moltype = AA   length = 17
FEATURE                 Location/Qualifiers
REGION                  1..17
                        note = targeting sequence
source                  1..17
                        mol_type = protein
                        organism = synthetic construct
SEQUENCE: 130
AEPMPHSLNF SQYLWYT                                                      17

SEQ ID NO: 131          moltype = AA   length = 6
FEATURE                 Location/Qualifiers
REGION                  1..6
                        note = targeting sequence
source                  1..6
                        mol_type = protein
                        organism = synthetic construct
VARIANT                 4
                        note = X can be W or F
SEQUENCE: 131
WAYXSP                                                                   6

SEQ ID NO: 132          moltype = AA   length = 7
FEATURE                 Location/Qualifiers
REGION                  1..7
                        note = targeting sequence
source                  1..7
                        mol_type = protein
                        organism = synthetic construct
SEQUENCE: 132
IELLQAR                                                                  7

SEQ ID NO: 133          moltype = AA   length = 12
FEATURE                 Location/Qualifiers
REGION                  1..12
                        note = targeting sequence
```

```
source                      1..12
                            mol_type = protein
                            organism = synthetic construct
SEQUENCE: 133
DITWDQLWDL MK                                                           12

SEQ ID NO: 134              moltype = AA  length = 16
FEATURE                     Location/Qualifiers
REGION                      1..16
                            note = targeting sequence
source                      1..16
                            mol_type = protein
                            organism = synthetic construct
SEQUENCE: 134
AYTKCSRQWR TCMTTH                                                       16

SEQ ID NO: 135              moltype = AA  length = 15
FEATURE                     Location/Qualifiers
REGION                      1..15
                            note = targeting sequence
source                      1..15
                            mol_type = protein
                            organism = synthetic construct
SEQUENCE: 135
PQNSKIPGPT FLDPH                                                        15

SEQ ID NO: 136              moltype = AA  length = 15
FEATURE                     Location/Qualifiers
REGION                      1..15
                            note = targeting sequence
source                      1..15
                            mol_type = protein
                            organism = synthetic construct
SEQUENCE: 136
SMEPALPDWW KMFK                                                         15

SEQ ID NO: 137              moltype = AA  length = 16
FEATURE                     Location/Qualifiers
REGION                      1..16
                            note = targeting sequence
source                      1..16
                            mol_type = protein
                            organism = synthetic construct
SEQUENCE: 137
ANTPCGPYTH DCPVKR                                                       16

SEQ ID NO: 138              moltype = AA  length = 12
FEATURE                     Location/Qualifiers
REGION                      1..12
                            note = targeting sequence
source                      1..12
                            mol_type = protein
                            organism = synthetic construct
SEQUENCE: 138
TACHQHVRMV RP                                                           12

SEQ ID NO: 139              moltype = AA  length = 12
FEATURE                     Location/Qualifiers
REGION                      1..12
                            note = targeting sequence
source                      1..12
                            mol_type = protein
                            organism = synthetic construct
SEQUENCE: 139
VPWMEPAYQR FL                                                           12

SEQ ID NO: 140              moltype = AA  length = 8
FEATURE                     Location/Qualifiers
REGION                      1..8
                            note = targeting sequence
source                      1..8
                            mol_type = protein
                            organism = synthetic construct
SEQUENCE: 140
DPRATPGS                                                                8

SEQ ID NO: 141              moltype = AA  length = 12
FEATURE                     Location/Qualifiers
REGION                      1..12
```

```
                        note = targeting sequence
source                  1..12
                        mol_type = protein
                        organism = synthetic construct
SEQUENCE: 141
FRPNRAQDYN TN                                                           12

SEQ ID NO: 142          moltype = AA  length = 9
FEATURE                 Location/Qualifiers
REGION                  1..9
                        note = targeting sequence
source                  1..9
                        mol_type = protein
                        organism = synthetic construct
SEQUENCE: 142
CTKNSYLMC                                                               9

SEQ ID NO: 143          moltype = AA  length = 11
FEATURE                 Location/Qualifiers
REGION                  1..11
                        note = targeting sequence
source                  1..11
                        mol_type = protein
                        organism = synthetic construct
VARIANT                 2
                        note = X can be R or Q
VARIANT                 3
                        note = X can be L or R
VARIANT                 5
                        note = X can be G or N
VARIANT                 6..7
                        note = X can be any amino acid
VARIANT                 9
                        note = X can be A or V
SEQUENCE: 143
CXXTXXXGXG C                                                            11

SEQ ID NO: 144          moltype = AA  length = 9
FEATURE                 Location/Qualifiers
REGION                  1..9
                        note = targeting sequence
source                  1..9
                        mol_type = protein
                        organism = synthetic construct
SEQUENCE: 144
CPIEDRPMC                                                               9

SEQ ID NO: 145          moltype = AA  length = 12
FEATURE                 Location/Qualifiers
REGION                  1..12
                        note = targeting sequence
source                  1..12
                        mol_type = protein
                        organism = synthetic construct
SEQUENCE: 145
HEWSYLAPYP WF                                                           12

SEQ ID NO: 146          moltype = AA  length = 9
FEATURE                 Location/Qualifiers
REGION                  1..9
                        note = targeting sequence
source                  1..9
                        mol_type = protein
                        organism = synthetic construct
SEQUENCE: 146
MCPKHPLGC                                                               9

SEQ ID NO: 147          moltype = AA  length = 15
FEATURE                 Location/Qualifiers
REGION                  1..15
                        note = targeting sequence
source                  1..15
                        mol_type = protein
                        organism = synthetic construct
SEQUENCE: 147
RMWPSSTVNL SAGRR                                                        15

SEQ ID NO: 148          moltype = AA  length = 20
FEATURE                 Location/Qualifiers
```

```
REGION                    1..20
                          note = targeting sequence
source                    1..20
                          mol_type = protein
                          organism = synthetic construct
SEQUENCE: 148
SAKTAVSQRV WLPSHRGGEP                                                   20

SEQ ID NO: 149            moltype = AA   length = 20
FEATURE                   Location/Qualifiers
REGION                    1..20
                          note = targeting sequence
source                    1..20
                          mol_type = protein
                          organism = synthetic construct
SEQUENCE: 149
KSREHVNNSA CPSKRITAAL                                                   20

SEQ ID NO: 150            moltype = AA   length = 4
FEATURE                   Location/Qualifiers
REGION                    1..4
                          note = targeting sequence
source                    1..4
                          mol_type = protein
                          organism = synthetic construct
SEQUENCE: 150
EGFR                                                                     4

SEQ ID NO: 151            moltype = AA   length = 6
FEATURE                   Location/Qualifiers
REGION                    1..6
                          note = targeting sequence
source                    1..6
                          mol_type = protein
                          organism = synthetic construct
SEQUENCE: 151
AGLGVR                                                                   6

SEQ ID NO: 152            moltype = AA   length = 15
FEATURE                   Location/Qualifiers
REGION                    1..15
                          note = targeting sequence
source                    1..15
                          mol_type = protein
                          organism = synthetic construct
SEQUENCE: 152
GTRQGHTMRL GVSDG                                                        15

SEQ ID NO: 153            moltype = AA   length = 15
FEATURE                   Location/Qualifiers
REGION                    1..15
                          note = targeting sequence
source                    1..15
                          mol_type = protein
                          organism = synthetic construct
SEQUENCE: 153
IAGLATPGWS HWLAL                                                        15

SEQ ID NO: 154            moltype = AA   length = 7
FEATURE                   Location/Qualifiers
REGION                    1..7
                          note = targeting sequence
source                    1..7
                          mol_type = protein
                          organism = synthetic construct
SEQUENCE: 154
SMSIARL                                                                  7

SEQ ID NO: 155            moltype = AA   length = 7
FEATURE                   Location/Qualifiers
REGION                    1..7
                          note = targeting sequence
source                    1..7
                          mol_type = protein
                          organism = synthetic construct
SEQUENCE: 155
HTFEPGV                                                                  7

SEQ ID NO: 156            moltype = AA   length = 14
```

```
FEATURE                 Location/Qualifiers
REGION                  1..14
                        note = targeting sequence
source                  1..14
                        mol_type = protein
                        organism = synthetic construct
SEQUENCE: 156
NTSLKRISNK RRRK                                                     14

SEQ ID NO: 157          moltype = AA  length = 15
FEATURE                 Location/Qualifiers
REGION                  1..15
                        note = targeting sequence
source                  1..15
                        mol_type = protein
                        organism = synthetic construct
SEQUENCE: 157
LRIKRKRRKR KKTRK                                                    15

SEQ ID NO: 158          moltype =   length =
SEQUENCE: 158
000

SEQ ID NO: 159          moltype =   length =
SEQUENCE: 159
000

SEQ ID NO: 160          moltype =   length =
SEQUENCE: 160
000

SEQ ID NO: 161          moltype =   length =
SEQUENCE: 161
000

SEQ ID NO: 162          moltype =   length =
SEQUENCE: 162
000

SEQ ID NO: 163          moltype =   length =
SEQUENCE: 163
000

SEQ ID NO: 164          moltype =   length =
SEQUENCE: 164
000

SEQ ID NO: 165          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 165
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT SCQPTVMNQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 166          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 166
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
```

```
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT FGVPNQPLQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 167          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 167
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT QRGQAAPFQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 168          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 168
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT GDYAPIREQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 169          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 169
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT KTRRIVQHQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 170          moltype = AA  length = 736
```

```
FEATURE                 Location/Qualifiers
REGION                  1..736
                        note = AAV capsid variant
source                  1..736
                        mol_type = protein
                        organism = synthetic construct
SEQUENCE: 170
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT FGFPNQPLQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 171          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 171
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT RQDQPINAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 172          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 172
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSSKVE SWTEWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 173          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 173
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
```

```
EGCLPPFPAD VFMIPQYGYL TLNDGSQAVG RSSFYCLEYF PSQMLRTGNN FQFSYEFENV     420
PFHSSYAHSQ SLDRLMNPLI DQYLYYLSKT INGSGQNQQT LKFSVAGPSN MAVQGRNYIP     480
GPSYRQQRVS TTVTQNNNSE FAWPGASSWA LNGRNSLMNP GPAMASHKEG EDRFFPLSGS     540
LIFGKQGTGR DNVDADKVMI TNEEEIKTTN PVATESYGQV ATNHQSSTVD SIAIWVQNQG     600
ILPGMVWQDR DVYLQGPIWA KIPHTDGNFH PSPLMGGFGM KHPPPQILIK NTPVPADPPT     660
AFNKDKLNSF ITQYSTGQVS VEIEWELQKE NSKRWNPEIQ YTSNYYKSNN VEFAVNTEGV     720
YSEPRPIGTR YLTRNL                                                    736

SEQ ID NO: 174           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 174
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDTE     180
SVPDPQPIGE PPAAPSGVGS LTMASGGGAP VADNNEGADG VGSSSGNWHC DSQWLGDRVI     240
TTSTRTWALP TYNNHLYKQI SNSTSGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH     360
EGCLPPFPAD VFMIPQYGYL TLNDGSQAVG RSSFYCLEYF PSQMLRTGNN FQFSYEFENV     420
PFHSSYAHSQ SLDRLMNPLI DQYLYYLSKT SCQPTVMNQT LKFSVAGPSN MAVQGRNYIP     480
GPSYRQQRVS TTVTQNNNSE FAWPGASSWA LNGRNSLMNP GPAMASHKEG EDRFFPLSGS     540
LIFGKQGTGR DNVDADKVMI TNEEEIKTTN PVATESYGQV ATNHQSSKVE SWTEWVQNQG     600
ILPGMVWQDR DVYLQGPIWA KIPHTDGNFH PSPLMGGFGM KHPPPQILIK NTPVPADPPT     660
AFNKDKLNSF ITQYSTGQVS VEIEWELQKE NSKRWNPEIQ YTSNYYKSNN VEFAVNTEGV     720
YSEPRPIGTR YLTRNL                                                    736

SEQ ID NO: 175           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 175
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDTE     180
SVPDPQPIGE PPAAPSGVGS LTMASGGGAP VADNNEGADG VGSSSGNWHC DSQWLGDRVI     240
TTSTRTWALP TYNNHLYKQI SNSTSGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH     360
EGCLPPFPAD VFMIPQYGYL TLNDGSQAVG RSSFYCLEYF PSQMLRTGNN FQFSYEFENV     420
PFHSSYAHSQ SLDRLMNPLI DQYLYYLSKT FGVPNQPLQT LKFSVAGPSN MAVQGRNYIP     480
GPSYRQQRVS TTVTQNNNSE FAWPGASSWA LNGRNSLMNP GPAMASHKEG EDRFFPLSGS     540
LIFGKQGTGR DNVDADKVMI TNEEEIKTTN PVATESYGQV ATNHQSSKVE SWTEWVQNQG     600
ILPGMVWQDR DVYLQGPIWA KIPHTDGNFH PSPLMGGFGM KHPPPQILIK NTPVPADPPT     660
AFNKDKLNSF ITQYSTGQVS VEIEWELQKE NSKRWNPEIQ YTSNYYKSNN VEFAVNTEGV     720
YSEPRPIGTR YLTRNL                                                    736

SEQ ID NO: 176           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 176
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDTE     180
SVPDPQPIGE PPAAPSGVGS LTMASGGGAP VADNNEGADG VGSSSGNWHC DSQWLGDRVI     240
TTSTRTWALP TYNNHLYKQI SNSTSGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH     360
EGCLPPFPAD VFMIPQYGYL TLNDGSQAVG RSSFYCLEYF PSQMLRTGNN FQFSYEFENV     420
PFHSSYAHSQ SLDRLMNPLI DQYLYYLSKT QRGQAAPFQT LKFSVAGPSN MAVQGRNYIP     480
GPSYRQQRVS TTVTQNNNSE FAWPGASSWA LNGRNSLMNP GPAMASHKEG EDRFFPLSGS     540
LIFGKQGTGR DNVDADKVMI TNEEEIKTTN PVATESYGQV ATNHQSSKVE SWTEWVQNQG     600
ILPGMVWQDR DVYLQGPIWA KIPHTDGNFH PSPLMGGFGM KHPPPQILIK NTPVPADPPT     660
AFNKDKLNSF ITQYSTGQVS VEIEWELQKE NSKRWNPEIQ YTSNYYKSNN VEFAVNTEGV     720
YSEPRPIGTR YLTRNL                                                    736

SEQ ID NO: 177           moltype = AA  length = 736
FEATURE                  Location/Qualifiers
REGION                   1..736
                         note = AAV capsid variant
source                   1..736
```

```
                        mol_type = protein
                        organism = synthetic construct
SEQUENCE: 177
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT GDYAPIREQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSSKVE SWTEWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 178         moltype = AA   length = 736
FEATURE                Location/Qualifiers
REGION                 1..736
                       note = AAV capsid variant
source                 1..736
                       mol_type = protein
                       organism = synthetic construct
SEQUENCE: 178
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT KTRRIVQHQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSSKVE SWTEWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 179         moltype = AA   length = 736
FEATURE                Location/Qualifiers
REGION                 1..736
                       note = AAV capsid variant
source                 1..736
                       mol_type = protein
                       organism = synthetic construct
SEQUENCE: 179
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT FGFPNQPLQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSSKVE SWTEWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 180         moltype = AA   length = 736
FEATURE                Location/Qualifiers
REGION                 1..736
                       note = AAV capsid variant
source                 1..736
                       mol_type = protein
                       organism = synthetic construct
SEQUENCE: 180
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT RQDQPINAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSSKVE SWTEWVQNQG  600
```

```
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 181          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 181
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT SCQPTVMNQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 182          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 182
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT FGVPNQPLQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 183          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 183
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT QRGQAAPFQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 184          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 184
MAADGYLPDW LEDNLSEGIR EWWALKPGAP QPKANQQHQD NARGLVLPGY KYLGPGNGLD     60
```

```
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT GDYAPIREQT LKFSVAGPSN MAVQGRNYIP    480
GPSYRQQRVS TTVTQNNSE FAWPGASSWA LNGRNSLMNP GPAMASHKEG EDRFFPLSGS     540
LIFGKQGTGR DNVDADKVMI TNEEEIKTTN PVATESYGQV ATNHQSSTVD SIAIWVQNDG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 185         moltype = AA  length = 736
FEATURE                Location/Qualifiers
REGION                 1..736
                       note = AAV capsid variant
source                 1..736
                       mol_type = protein
                       organism = synthetic construct
SEQUENCE: 185
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT KTRRIVQHQT LKFSVAGPSN MAVQGRNYIP    480
GPSYRQQRVS TTVTQNNSE FAWPGASSWA LNGRNSLMNP GPAMASHKEG EDRFFPLSGS     540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 186         moltype = AA  length = 736
FEATURE                Location/Qualifiers
REGION                 1..736
                       note = AAV capsid variant
source                 1..736
                       mol_type = protein
                       organism = synthetic construct
SEQUENCE: 186
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT FGFPNQPLQT LKFSVAGPSN MAVQGRNYIP    480
GPSYRQQRVS TTVTQNNSE FAWPGASSWA LNGRNSLMNP GPAMASHKEG EDRFFPLSGS     540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 187         moltype = AA  length = 736
FEATURE                Location/Qualifiers
REGION                 1..736
                       note = AAV capsid variant
source                 1..736
                       mol_type = protein
                       organism = synthetic construct
SEQUENCE: 187
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT RQDQPINAQT LKFSVAGPSN MAVQGRNYIP    480
GPSYRQQRVS TTVTQNNSE FAWPGASSWA LNGRNSLMNP GPAMASHKEG EDRFFPLSGS     540
LIFGKQGTGR DNVDADKVMI TNEEEIKTTN PVATESYGQV ATNHQSSTVD SIAIWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736
```

| | | |
|---|---|---|
| SEQ ID NO: 188 SEQUENCE: 188 | moltype = | length = 000 |
| SEQ ID NO: 189 SEQUENCE: 189 | moltype = | length = 000 |
| SEQ ID NO: 190 SEQUENCE: 190 | moltype = | length = 000 |
| SEQ ID NO: 191 SEQUENCE: 191 | moltype = | length = 000 |
| SEQ ID NO: 192 SEQUENCE: 192 | moltype = | length = 000 |
| SEQ ID NO: 193 SEQUENCE: 193 | moltype = | length = 000 |
| SEQ ID NO: 194 SEQUENCE: 194 | moltype = | length = 000 |
| SEQ ID NO: 195 SEQUENCE: 195 | moltype = | length = 000 |
| SEQ ID NO: 196 SEQUENCE: 196 | moltype = | length = 000 |
| SEQ ID NO: 197 SEQUENCE: 197 | moltype = | length = 000 |
| SEQ ID NO: 198 SEQUENCE: 198 | moltype = | length = 000 |
| SEQ ID NO: 199 SEQUENCE: 199 | moltype = | length = 000 |
| SEQ ID NO: 200 SEQUENCE: 200 | moltype = | length = 000 |
| SEQ ID NO: 201 SEQUENCE: 201 | moltype = | length = 000 |
| SEQ ID NO: 202 SEQUENCE: 202 | moltype = | length = 000 |
| SEQ ID NO: 203 SEQUENCE: 203 | moltype = | length = 000 |
| SEQ ID NO: 204 SEQUENCE: 204 | moltype = | length = 000 |
| SEQ ID NO: 205 SEQUENCE: 205 | moltype = | length = 000 |
| SEQ ID NO: 206 SEQUENCE: 206 | moltype = | length = 000 |
| SEQ ID NO: 207 SEQUENCE: 207 | moltype = | length = 000 |

| | | |
|---|---|---|
| SEQ ID NO: 208 SEQUENCE: 208 000 | moltype = | length = |
| SEQ ID NO: 209 SEQUENCE: 209 000 | moltype = | length = |
| SEQ ID NO: 210 SEQUENCE: 210 000 | moltype = | length = |
| SEQ ID NO: 211 SEQUENCE: 211 000 | moltype = | length = |
| SEQ ID NO: 212 SEQUENCE: 212 000 | moltype = | length = |
| SEQ ID NO: 213 SEQUENCE: 213 000 | moltype = | length = |
| SEQ ID NO: 214 SEQUENCE: 214 000 | moltype = | length = |
| SEQ ID NO: 215 SEQUENCE: 215 000 | moltype = | length = |
| SEQ ID NO: 216 SEQUENCE: 216 000 | moltype = | length = |
| SEQ ID NO: 217 SEQUENCE: 217 000 | moltype = | length = |
| SEQ ID NO: 218 SEQUENCE: 218 000 | moltype = | length = |
| SEQ ID NO: 219 SEQUENCE: 219 000 | moltype = | length = |
| SEQ ID NO: 220 SEQUENCE: 220 000 | moltype = | length = |
| SEQ ID NO: 221 SEQUENCE: 221 000 | moltype = | length = |
| SEQ ID NO: 222 SEQUENCE: 222 000 | moltype = | length = |
| SEQ ID NO: 223 SEQUENCE: 223 000 | moltype = | length = |
| SEQ ID NO: 224 SEQUENCE: 224 000 | moltype = | length = |
| SEQ ID NO: 225 SEQUENCE: 225 000 | moltype = | length = |
| SEQ ID NO: 226 SEQUENCE: 226 000 | moltype = | length = |
| SEQ ID NO: 227 SEQUENCE: 227 | moltype = | length = |

```
000

SEQ ID NO: 228          moltype =     length =
SEQUENCE: 228
000

SEQ ID NO: 229          moltype =     length =
SEQUENCE: 229
000

SEQ ID NO: 230          moltype =     length =
SEQUENCE: 230
000

SEQ ID NO: 231          moltype =     length =
SEQUENCE: 231
000

SEQ ID NO: 232          moltype =     length =
SEQUENCE: 232
000

SEQ ID NO: 233          moltype =     length =
SEQUENCE: 233
000

SEQ ID NO: 234          moltype =     length =
SEQUENCE: 234
000

SEQ ID NO: 235          moltype =     length =
SEQUENCE: 235
000

SEQ ID NO: 236          moltype =     length =
SEQUENCE: 236
000

SEQ ID NO: 237          moltype =     length =
SEQUENCE: 237
000

SEQ ID NO: 238          moltype =     length =
SEQUENCE: 238
000

SEQ ID NO: 239          moltype =     length =
SEQUENCE: 239
000

SEQ ID NO: 240          moltype =     length =
SEQUENCE: 240
000

SEQ ID NO: 241          moltype =     length =
SEQUENCE: 241
000

SEQ ID NO: 242          moltype =     length =
SEQUENCE: 242
000

SEQ ID NO: 243          moltype =     length =
SEQUENCE: 243
000

SEQ ID NO: 244          moltype =     length =
SEQUENCE: 244
000

SEQ ID NO: 245          moltype =     length =
SEQUENCE: 245
000

SEQ ID NO: 246          moltype =     length =
SEQUENCE: 246
000

SEQ ID NO: 247          moltype =     length =
```

| | | |
|---|---|---|
| SEQUENCE: 247 000 | | |
| SEQ ID NO: 248 SEQUENCE: 248 000 | moltype = | length = |
| SEQ ID NO: 249 SEQUENCE: 249 000 | moltype = | length = |
| SEQ ID NO: 250 SEQUENCE: 250 000 | moltype = | length = |
| SEQ ID NO: 251 SEQUENCE: 251 000 | moltype = | length = |
| SEQ ID NO: 252 SEQUENCE: 252 000 | moltype = | length = |
| SEQ ID NO: 253 SEQUENCE: 253 000 | moltype = | length = |
| SEQ ID NO: 254 SEQUENCE: 254 000 | moltype = | length = |
| SEQ ID NO: 255 SEQUENCE: 255 000 | moltype = | length = |
| SEQ ID NO: 256 SEQUENCE: 256 000 | moltype = | length = |
| SEQ ID NO: 257 SEQUENCE: 257 000 | moltype = | length = |
| SEQ ID NO: 258 SEQUENCE: 258 000 | moltype = | length = |
| SEQ ID NO: 259 SEQUENCE: 259 000 | moltype = | length = |
| SEQ ID NO: 260 SEQUENCE: 260 000 | moltype = | length = |
| SEQ ID NO: 261 SEQUENCE: 261 000 | moltype = | length = |
| SEQ ID NO: 262 SEQUENCE: 262 000 | moltype = | length = |
| SEQ ID NO: 263 SEQUENCE: 263 000 | moltype = | length = |
| SEQ ID NO: 264 SEQUENCE: 264 000 | moltype = | length = |
| SEQ ID NO: 265 SEQUENCE: 265 000 | moltype = | length = |
| SEQ ID NO: 266 SEQUENCE: 266 000 | moltype = | length = |

```
SEQ ID NO: 267       moltype =    length =
SEQUENCE: 267
000

SEQ ID NO: 268       moltype =    length =
SEQUENCE: 268
000

SEQ ID NO: 269       moltype =    length =
SEQUENCE: 269
000

SEQ ID NO: 270       moltype =    length =
SEQUENCE: 270
000

SEQ ID NO: 271       moltype =    length =
SEQUENCE: 271
000

SEQ ID NO: 272       moltype =    length =
SEQUENCE: 272
000

SEQ ID NO: 273       moltype =    length =
SEQUENCE: 273
000

SEQ ID NO: 274       moltype =    length =
SEQUENCE: 274
000

SEQ ID NO: 275       moltype =    length =
SEQUENCE: 275
000

SEQ ID NO: 276       moltype =    length =
SEQUENCE: 276
000

SEQ ID NO: 277       moltype =    length =
SEQUENCE: 277
000

SEQ ID NO: 278       moltype =    length =
SEQUENCE: 278
000

SEQ ID NO: 279       moltype =    length =
SEQUENCE: 279
000

SEQ ID NO: 280       moltype =    length =
SEQUENCE: 280
000

SEQ ID NO: 281       moltype =    length =
SEQUENCE: 281
000

SEQ ID NO: 282       moltype =    length =
SEQUENCE: 282
000

SEQ ID NO: 283       moltype =    length =
SEQUENCE: 283
000

SEQ ID NO: 284       moltype =    length =
SEQUENCE: 284
000

SEQ ID NO: 285       moltype =    length =
SEQUENCE: 285
000

SEQ ID NO: 286       moltype =    length =
SEQUENCE: 286
000
```

| | | |
|---|---|---|
| SEQ ID NO: 287 SEQUENCE: 287 000 | moltype = | length = |
| SEQ ID NO: 288 SEQUENCE: 288 000 | moltype = | length = |
| SEQ ID NO: 289 SEQUENCE: 289 000 | moltype = | length = |
| SEQ ID NO: 290 SEQUENCE: 290 000 | moltype = | length = |
| SEQ ID NO: 291 SEQUENCE: 291 000 | moltype = | length = |
| SEQ ID NO: 292 SEQUENCE: 292 000 | moltype = | length = |
| SEQ ID NO: 293 SEQUENCE: 293 000 | moltype = | length = |
| SEQ ID NO: 294 SEQUENCE: 294 000 | moltype = | length = |
| SEQ ID NO: 295 SEQUENCE: 295 000 | moltype = | length = |
| SEQ ID NO: 296 SEQUENCE: 296 000 | moltype = | length = |
| SEQ ID NO: 297 SEQUENCE: 297 000 | moltype = | length = |
| SEQ ID NO: 298 SEQUENCE: 298 000 | moltype = | length = |
| SEQ ID NO: 299 SEQUENCE: 299 000 | moltype = | length = |
| SEQ ID NO: 300 SEQUENCE: 300 000 | moltype = | length = |
| SEQ ID NO: 301 SEQUENCE: 301 000 | moltype = | length = |
| SEQ ID NO: 302 SEQUENCE: 302 000 | moltype = | length = |
| SEQ ID NO: 303 SEQUENCE: 303 000 | moltype = | length = |
| SEQ ID NO: 304 SEQUENCE: 304 000 | moltype = | length = |
| SEQ ID NO: 305 SEQUENCE: 305 000 | moltype = | length = |
| SEQ ID NO: 306 SEQUENCE: 306 | moltype = | length = |

000

SEQ ID NO: 307          moltype =    length =
SEQUENCE: 307
000

SEQ ID NO: 308          moltype =    length =
SEQUENCE: 308
000

SEQ ID NO: 309          moltype =    length =
SEQUENCE: 309
000

SEQ ID NO: 310          moltype =    length =
SEQUENCE: 310
000

SEQ ID NO: 311          moltype =    length =
SEQUENCE: 311
000

SEQ ID NO: 312          moltype =    length =
SEQUENCE: 312
000

SEQ ID NO: 313          moltype =    length =
SEQUENCE: 313
000

SEQ ID NO: 314          moltype =    length =
SEQUENCE: 314
000

SEQ ID NO: 315          moltype =    length =
SEQUENCE: 315
000

SEQ ID NO: 316          moltype =    length =
SEQUENCE: 316
000

SEQ ID NO: 317          moltype =    length =
SEQUENCE: 317
000

SEQ ID NO: 318          moltype =    length =
SEQUENCE: 318
000

SEQ ID NO: 319          moltype =    length =
SEQUENCE: 319
000

SEQ ID NO: 320          moltype =    length =
SEQUENCE: 320
000

SEQ ID NO: 321          moltype =    length =
SEQUENCE: 321
000

SEQ ID NO: 322          moltype =    length =
SEQUENCE: 322
000

SEQ ID NO: 323          moltype =    length =
SEQUENCE: 323
000

SEQ ID NO: 324          moltype =    length =
SEQUENCE: 324
000

SEQ ID NO: 325          moltype =    length =
SEQUENCE: 325
000

SEQ ID NO: 326          moltype =    length =

```
SEQUENCE: 326
000

SEQ ID NO: 327         moltype =    length =
SEQUENCE: 327
000

SEQ ID NO: 328         moltype =    length =
SEQUENCE: 328
000

SEQ ID NO: 329         moltype =    length =
SEQUENCE: 329
000

SEQ ID NO: 330         moltype =    length =
SEQUENCE: 330
000

SEQ ID NO: 331         moltype =    length =
SEQUENCE: 331
000

SEQ ID NO: 332         moltype =    length =
SEQUENCE: 332
000

SEQ ID NO: 333         moltype =    length =
SEQUENCE: 333
000

SEQ ID NO: 334         moltype =    length =
SEQUENCE: 334
000

SEQ ID NO: 335         moltype =    length =
SEQUENCE: 335
000

SEQ ID NO: 336         moltype =    length =
SEQUENCE: 336
000

SEQ ID NO: 337         moltype =    length =
SEQUENCE: 337
000

SEQ ID NO: 338         moltype =    length =
SEQUENCE: 338
000

SEQ ID NO: 339         moltype =    length =
SEQUENCE: 339
000

SEQ ID NO: 340         moltype =    length =
SEQUENCE: 340
000

SEQ ID NO: 341         moltype =    length =
SEQUENCE: 341
000

SEQ ID NO: 342         moltype =    length =
SEQUENCE: 342
000

SEQ ID NO: 343         moltype =    length =
SEQUENCE: 343
000

SEQ ID NO: 344         moltype =    length =
SEQUENCE: 344
000

SEQ ID NO: 345         moltype =    length =
SEQUENCE: 345
000
```

| | | |
|---|---|---|
| SEQ ID NO: 346<br>SEQUENCE: 346<br>000 | moltype = | length = |
| SEQ ID NO: 347<br>SEQUENCE: 347<br>000 | moltype = | length = |
| SEQ ID NO: 348<br>SEQUENCE: 348<br>000 | moltype = | length = |
| SEQ ID NO: 349<br>SEQUENCE: 349<br>000 | moltype = | length = |
| SEQ ID NO: 350<br>SEQUENCE: 350<br>000 | moltype = | length = |
| SEQ ID NO: 351<br>SEQUENCE: 351<br>000 | moltype = | length = |
| SEQ ID NO: 352<br>SEQUENCE: 352<br>000 | moltype = | length = |
| SEQ ID NO: 353<br>SEQUENCE: 353<br>000 | moltype = | length = |
| SEQ ID NO: 354<br>SEQUENCE: 354<br>000 | moltype = | length = |
| SEQ ID NO: 355<br>SEQUENCE: 355<br>000 | moltype = | length = |
| SEQ ID NO: 356<br>SEQUENCE: 356<br>000 | moltype = | length = |
| SEQ ID NO: 357<br>SEQUENCE: 357<br>000 | moltype = | length = |
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360<br>000 | moltype = | length = |
| SEQ ID NO: 361<br>SEQUENCE: 361<br>000 | moltype = | length = |
| SEQ ID NO: 362<br>SEQUENCE: 362<br>000 | moltype = | length = |
| SEQ ID NO: 363<br>SEQUENCE: 363<br>000 | moltype = | length = |
| SEQ ID NO: 364<br>SEQUENCE: 364<br>000 | moltype = | length = |
| SEQ ID NO: 365<br>SEQUENCE: 365<br>000 | moltype = | length = |

| | | |
|---|---|---|
| SEQ ID NO: 366
SEQUENCE: 366
000 | moltype = | length = |
| SEQ ID NO: 367
SEQUENCE: 367
000 | moltype = | length = |
| SEQ ID NO: 368
SEQUENCE: 368
000 | moltype = | length = |
| SEQ ID NO: 369
SEQUENCE: 369
000 | moltype = | length = |
| SEQ ID NO: 370
SEQUENCE: 370
000 | moltype = | length = |
| SEQ ID NO: 371
SEQUENCE: 371
000 | moltype = | length = |
| SEQ ID NO: 372
SEQUENCE: 372
000 | moltype = | length = |
| SEQ ID NO: 373
SEQUENCE: 373
000 | moltype = | length = |
| SEQ ID NO: 374
SEQUENCE: 374
000 | moltype = | length = |
| SEQ ID NO: 375
SEQUENCE: 375
000 | moltype = | length = |
| SEQ ID NO: 376
SEQUENCE: 376
000 | moltype = | length = |
| SEQ ID NO: 377
SEQUENCE: 377
000 | moltype = | length = |
| SEQ ID NO: 378
SEQUENCE: 378
000 | moltype = | length = |
| SEQ ID NO: 379
SEQUENCE: 379
000 | moltype = | length = |
| SEQ ID NO: 380
SEQUENCE: 380
000 | moltype = | length = |
| SEQ ID NO: 381
SEQUENCE: 381
000 | moltype = | length = |
| SEQ ID NO: 382
SEQUENCE: 382
000 | moltype = | length = |
| SEQ ID NO: 383
SEQUENCE: 383
000 | moltype = | length = |
| SEQ ID NO: 384
SEQUENCE: 384
000 | moltype = | length = |
| SEQ ID NO: 385
SEQUENCE: 385 | moltype = | length = |

000

SEQ ID NO: 386          moltype =    length =
SEQUENCE: 386
000

SEQ ID NO: 387          moltype =    length =
SEQUENCE: 387
000

SEQ ID NO: 388          moltype =    length =
SEQUENCE: 388
000

SEQ ID NO: 389          moltype =    length =
SEQUENCE: 389
000

SEQ ID NO: 390          moltype =    length =
SEQUENCE: 390
000

SEQ ID NO: 391          moltype =    length =
SEQUENCE: 391
000

SEQ ID NO: 392          moltype =    length =
SEQUENCE: 392
000

SEQ ID NO: 393          moltype =    length =
SEQUENCE: 393
000

SEQ ID NO: 394          moltype =    length =
SEQUENCE: 394
000

SEQ ID NO: 395          moltype =    length =
SEQUENCE: 395
000

SEQ ID NO: 396          moltype =    length =
SEQUENCE: 396
000

SEQ ID NO: 397          moltype =    length =
SEQUENCE: 397
000

SEQ ID NO: 398          moltype =    length =
SEQUENCE: 398
000

SEQ ID NO: 399          moltype =    length =
SEQUENCE: 399
000

SEQ ID NO: 400          moltype =    length =
SEQUENCE: 400
000

SEQ ID NO: 401          moltype =    length =
SEQUENCE: 401
000

SEQ ID NO: 402          moltype =    length =
SEQUENCE: 402
000

SEQ ID NO: 403          moltype =    length =
SEQUENCE: 403
000

SEQ ID NO: 404          moltype =    length =
SEQUENCE: 404
000

SEQ ID NO: 405          moltype =    length =

```
SEQUENCE: 405
000

SEQ ID NO: 406          moltype =     length =
SEQUENCE: 406
000

SEQ ID NO: 407          moltype =     length =
SEQUENCE: 407
000

SEQ ID NO: 408          moltype =     length =
SEQUENCE: 408
000

SEQ ID NO: 409          moltype =     length =
SEQUENCE: 409
000

SEQ ID NO: 410          moltype =     length =
SEQUENCE: 410
000

SEQ ID NO: 411          moltype =     length =
SEQUENCE: 411
000

SEQ ID NO: 412          moltype =     length =
SEQUENCE: 412
000

SEQ ID NO: 413          moltype =     length =
SEQUENCE: 413
000

SEQ ID NO: 414          moltype =     length =
SEQUENCE: 414
000

SEQ ID NO: 415          moltype =     length =
SEQUENCE: 415
000

SEQ ID NO: 416          moltype =     length =
SEQUENCE: 416
000

SEQ ID NO: 417          moltype =     length =
SEQUENCE: 417
000

SEQ ID NO: 418          moltype =     length =
SEQUENCE: 418
000

SEQ ID NO: 419          moltype =     length =
SEQUENCE: 419
000

SEQ ID NO: 420          moltype =     length =
SEQUENCE: 420
000

SEQ ID NO: 421          moltype =     length =
SEQUENCE: 421
000

SEQ ID NO: 422          moltype =     length =
SEQUENCE: 422
000

SEQ ID NO: 423          moltype =     length =
SEQUENCE: 423
000

SEQ ID NO: 424          moltype =     length =
SEQUENCE: 424
000
```

-continued

```
SEQ ID NO: 425         moltype =    length =
SEQUENCE: 425
000

SEQ ID NO: 426         moltype =    length =
SEQUENCE: 426
000

SEQ ID NO: 427         moltype =    length =
SEQUENCE: 427
000

SEQ ID NO: 428         moltype =    length =
SEQUENCE: 428
000

SEQ ID NO: 429         moltype =    length =
SEQUENCE: 429
000

SEQ ID NO: 430         moltype =    length =
SEQUENCE: 430
000

SEQ ID NO: 431         moltype =    length =
SEQUENCE: 431
000

SEQ ID NO: 432         moltype =    length =
SEQUENCE: 432
000

SEQ ID NO: 433         moltype =    length =
SEQUENCE: 433
000

SEQ ID NO: 434         moltype =    length =
SEQUENCE: 434
000

SEQ ID NO: 435         moltype =    length =
SEQUENCE: 435
000

SEQ ID NO: 436         moltype =    length =
SEQUENCE: 436
000

SEQ ID NO: 437         moltype =    length =
SEQUENCE: 437
000

SEQ ID NO: 438         moltype =    length =
SEQUENCE: 438
000

SEQ ID NO: 439         moltype =    length =
SEQUENCE: 439
000

SEQ ID NO: 440         moltype =    length =
SEQUENCE: 440
000

SEQ ID NO: 441         moltype =    length =
SEQUENCE: 441
000

SEQ ID NO: 442         moltype =    length =
SEQUENCE: 442
000

SEQ ID NO: 443         moltype =    length =
SEQUENCE: 443
000

SEQ ID NO: 444         moltype =    length =
SEQUENCE: 444
000
```

```
SEQ ID NO: 445        moltype =     length =
SEQUENCE: 445
000

SEQ ID NO: 446        moltype =     length =
SEQUENCE: 446
000

SEQ ID NO: 447        moltype =     length =
SEQUENCE: 447
000

SEQ ID NO: 448        moltype =     length =
SEQUENCE: 448
000

SEQ ID NO: 449        moltype =     length =
SEQUENCE: 449
000

SEQ ID NO: 450        moltype =     length =
SEQUENCE: 450
000

SEQ ID NO: 451        moltype =     length =
SEQUENCE: 451
000

SEQ ID NO: 452        moltype =     length =
SEQUENCE: 452
000

SEQ ID NO: 453        moltype =     length =
SEQUENCE: 453
000

SEQ ID NO: 454        moltype =     length =
SEQUENCE: 454
000

SEQ ID NO: 455        moltype =     length =
SEQUENCE: 455
000

SEQ ID NO: 456        moltype =     length =
SEQUENCE: 456
000

SEQ ID NO: 457        moltype =     length =
SEQUENCE: 457
000

SEQ ID NO: 458        moltype =     length =
SEQUENCE: 458
000

SEQ ID NO: 459        moltype =     length =
SEQUENCE: 459
000

SEQ ID NO: 460        moltype =     length =
SEQUENCE: 460
000

SEQ ID NO: 461        moltype =     length =
SEQUENCE: 461
000

SEQ ID NO: 462        moltype =     length =
SEQUENCE: 462
000

SEQ ID NO: 463        moltype =     length =
SEQUENCE: 463
000

SEQ ID NO: 464        moltype =     length =
SEQUENCE: 464
```

000

SEQ ID NO: 465         moltype =    length =
SEQUENCE: 465
000

SEQ ID NO: 466         moltype =    length =
SEQUENCE: 466
000

SEQ ID NO: 467         moltype =    length =
SEQUENCE: 467
000

SEQ ID NO: 468         moltype =    length =
SEQUENCE: 468
000

SEQ ID NO: 469         moltype =    length =
SEQUENCE: 469
000

SEQ ID NO: 470         moltype =    length =
SEQUENCE: 470
000

SEQ ID NO: 471         moltype =    length =
SEQUENCE: 471
000

SEQ ID NO: 472         moltype =    length =
SEQUENCE: 472
000

SEQ ID NO: 473         moltype =    length =
SEQUENCE: 473
000

SEQ ID NO: 474         moltype =    length =
SEQUENCE: 474
000

SEQ ID NO: 475         moltype =    length =
SEQUENCE: 475
000

SEQ ID NO: 476         moltype =    length =
SEQUENCE: 476
000

SEQ ID NO: 477         moltype =    length =
SEQUENCE: 477
000

SEQ ID NO: 478         moltype =    length =
SEQUENCE: 478
000

SEQ ID NO: 479         moltype =    length =
SEQUENCE: 479
000

SEQ ID NO: 480         moltype =    length =
SEQUENCE: 480
000

SEQ ID NO: 481         moltype =    length =
SEQUENCE: 481
000

SEQ ID NO: 482         moltype =    length =
SEQUENCE: 482
000

SEQ ID NO: 483         moltype =    length =
SEQUENCE: 483
000

SEQ ID NO: 484         moltype =    length =

| | | |
|---|---|---|
| SEQUENCE: 484 000 | | |
| SEQ ID NO: 485 SEQUENCE: 485 000 | moltype = | length = |
| SEQ ID NO: 486 SEQUENCE: 486 000 | moltype = | length = |
| SEQ ID NO: 487 SEQUENCE: 487 000 | moltype = | length = |
| SEQ ID NO: 488 SEQUENCE: 488 000 | moltype = | length = |
| SEQ ID NO: 489 SEQUENCE: 489 000 | moltype = | length = |
| SEQ ID NO: 490 SEQUENCE: 490 000 | moltype = | length = |
| SEQ ID NO: 491 SEQUENCE: 491 000 | moltype = | length = |
| SEQ ID NO: 492 SEQUENCE: 492 000 | moltype = | length = |
| SEQ ID NO: 493 SEQUENCE: 493 000 | moltype = | length = |
| SEQ ID NO: 494 SEQUENCE: 494 000 | moltype = | length = |
| SEQ ID NO: 495 SEQUENCE: 495 000 | moltype = | length = |
| SEQ ID NO: 496 SEQUENCE: 496 000 | moltype = | length = |
| SEQ ID NO: 497 SEQUENCE: 497 000 | moltype = | length = |
| SEQ ID NO: 498 SEQUENCE: 498 000 | moltype = | length = |
| SEQ ID NO: 499 SEQUENCE: 499 000 | moltype = | length = |
| SEQ ID NO: 500 SEQUENCE: 500 000 | moltype = | length = |
| SEQ ID NO: 501 SEQUENCE: 501 000 | moltype = | length = |
| SEQ ID NO: 502 SEQUENCE: 502 000 | moltype = | length = |
| SEQ ID NO: 503 SEQUENCE: 503 000 | moltype = | length = |

-continued

| | | |
|---|---|---|
| SEQ ID NO: 504<br>SEQUENCE: 504<br>000 | moltype = | length = |
| SEQ ID NO: 505<br>SEQUENCE: 505<br>000 | moltype = | length = |
| SEQ ID NO: 506<br>SEQUENCE: 506<br>000 | moltype = | length = |
| SEQ ID NO: 507<br>SEQUENCE: 507<br>000 | moltype = | length = |
| SEQ ID NO: 508<br>SEQUENCE: 508<br>000 | moltype = | length = |
| SEQ ID NO: 509<br>SEQUENCE: 509<br>000 | moltype = | length = |
| SEQ ID NO: 510<br>SEQUENCE: 510<br>000 | moltype = | length = |
| SEQ ID NO: 511<br>SEQUENCE: 511<br>000 | moltype = | length = |
| SEQ ID NO: 512<br>SEQUENCE: 512<br>000 | moltype = | length = |
| SEQ ID NO: 513<br>SEQUENCE: 513<br>000 | moltype = | length = |
| SEQ ID NO: 514<br>SEQUENCE: 514<br>000 | moltype = | length = |
| SEQ ID NO: 515<br>SEQUENCE: 515<br>000 | moltype = | length = |
| SEQ ID NO: 516<br>SEQUENCE: 516<br>000 | moltype = | length = |
| SEQ ID NO: 517<br>SEQUENCE: 517<br>000 | moltype = | length = |
| SEQ ID NO: 518<br>SEQUENCE: 518<br>000 | moltype = | length = |
| SEQ ID NO: 519<br>SEQUENCE: 519<br>000 | moltype = | length = |
| SEQ ID NO: 520<br>SEQUENCE: 520<br>000 | moltype = | length = |
| SEQ ID NO: 521<br>SEQUENCE: 521<br>000 | moltype = | length = |
| SEQ ID NO: 522<br>SEQUENCE: 522<br>000 | moltype = | length = |
| SEQ ID NO: 523<br>SEQUENCE: 523<br>000 | moltype = | length = |

| | | |
|---|---|---|
| SEQ ID NO: 524<br>SEQUENCE: 524<br>000 | moltype = | length = |
| SEQ ID NO: 525<br>SEQUENCE: 525<br>000 | moltype = | length = |
| SEQ ID NO: 526<br>SEQUENCE: 526<br>000 | moltype = | length = |
| SEQ ID NO: 527<br>SEQUENCE: 527<br>000 | moltype = | length = |
| SEQ ID NO: 528<br>SEQUENCE: 528<br>000 | moltype = | length = |
| SEQ ID NO: 529<br>SEQUENCE: 529<br>000 | moltype = | length = |
| SEQ ID NO: 530<br>SEQUENCE: 530<br>000 | moltype = | length = |
| SEQ ID NO: 531<br>SEQUENCE: 531<br>000 | moltype = | length = |
| SEQ ID NO: 532<br>SEQUENCE: 532<br>000 | moltype = | length = |
| SEQ ID NO: 533<br>SEQUENCE: 533<br>000 | moltype = | length = |
| SEQ ID NO: 534<br>SEQUENCE: 534<br>000 | moltype = | length = |
| SEQ ID NO: 535<br>SEQUENCE: 535<br>000 | moltype = | length = |
| SEQ ID NO: 536<br>SEQUENCE: 536<br>000 | moltype = | length = |
| SEQ ID NO: 537<br>SEQUENCE: 537<br>000 | moltype = | length = |
| SEQ ID NO: 538<br>SEQUENCE: 538<br>000 | moltype = | length = |
| SEQ ID NO: 539<br>SEQUENCE: 539<br>000 | moltype = | length = |
| SEQ ID NO: 540<br>SEQUENCE: 540<br>000 | moltype = | length = |
| SEQ ID NO: 541<br>SEQUENCE: 541<br>000 | moltype = | length = |
| SEQ ID NO: 542<br>SEQUENCE: 542<br>000 | moltype = | length = |
| SEQ ID NO: 543<br>SEQUENCE: 543 | moltype = | length = |

```
000

SEQ ID NO: 544          moltype =    length =
SEQUENCE: 544
000

SEQ ID NO: 545          moltype =    length =
SEQUENCE: 545
000

SEQ ID NO: 546          moltype =    length =
SEQUENCE: 546
000

SEQ ID NO: 547          moltype =    length =
SEQUENCE: 547
000

SEQ ID NO: 548          moltype =    length =
SEQUENCE: 548
000

SEQ ID NO: 549          moltype =    length =
SEQUENCE: 549
000

SEQ ID NO: 550          moltype =    length =
SEQUENCE: 550
000

SEQ ID NO: 551          moltype =    length =
SEQUENCE: 551
000

SEQ ID NO: 552          moltype =    length =
SEQUENCE: 552
000

SEQ ID NO: 553          moltype =    length =
SEQUENCE: 553
000

SEQ ID NO: 554          moltype =    length =
SEQUENCE: 554
000

SEQ ID NO: 555          moltype =    length =
SEQUENCE: 555
000

SEQ ID NO: 556          moltype =    length =
SEQUENCE: 556
000

SEQ ID NO: 557          moltype =    length =
SEQUENCE: 557
000

SEQ ID NO: 558          moltype =    length =
SEQUENCE: 558
000

SEQ ID NO: 559          moltype =    length =
SEQUENCE: 559
000

SEQ ID NO: 560          moltype =    length =
SEQUENCE: 560
000

SEQ ID NO: 561          moltype =    length =
SEQUENCE: 561
000

SEQ ID NO: 562          moltype =    length =
SEQUENCE: 562
000

SEQ ID NO: 563          moltype =    length =
```

```
SEQUENCE: 563
000

SEQ ID NO: 564          moltype =     length =
SEQUENCE: 564
000

SEQ ID NO: 565          moltype =     length =
SEQUENCE: 565
000

SEQ ID NO: 566          moltype =     length =
SEQUENCE: 566
000

SEQ ID NO: 567          moltype =     length =
SEQUENCE: 567
000

SEQ ID NO: 568          moltype =     length =
SEQUENCE: 568
000

SEQ ID NO: 569          moltype =     length =
SEQUENCE: 569
000

SEQ ID NO: 570          moltype =     length =
SEQUENCE: 570
000

SEQ ID NO: 571          moltype =     length =
SEQUENCE: 571
000

SEQ ID NO: 572          moltype =     length =
SEQUENCE: 572
000

SEQ ID NO: 573          moltype =     length =
SEQUENCE: 573
000

SEQ ID NO: 574          moltype =     length =
SEQUENCE: 574
000

SEQ ID NO: 575          moltype =     length =
SEQUENCE: 575
000

SEQ ID NO: 576          moltype =     length =
SEQUENCE: 576
000

SEQ ID NO: 577          moltype =     length =
SEQUENCE: 577
000

SEQ ID NO: 578          moltype =     length =
SEQUENCE: 578
000

SEQ ID NO: 579          moltype =     length =
SEQUENCE: 579
000

SEQ ID NO: 580          moltype =     length =
SEQUENCE: 580
000

SEQ ID NO: 581          moltype =     length =
SEQUENCE: 581
000

SEQ ID NO: 582          moltype =     length =
SEQUENCE: 582
000
```

| | | |
|---|---|---|
| SEQ ID NO: 583<br>SEQUENCE: 583<br>000 | moltype = | length = |
| SEQ ID NO: 584<br>SEQUENCE: 584<br>000 | moltype = | length = |
| SEQ ID NO: 585<br>SEQUENCE: 585<br>000 | moltype = | length = |
| SEQ ID NO: 586<br>SEQUENCE: 586<br>000 | moltype = | length = |
| SEQ ID NO: 587<br>SEQUENCE: 587<br>000 | moltype = | length = |
| SEQ ID NO: 588<br>SEQUENCE: 588<br>000 | moltype = | length = |
| SEQ ID NO: 589<br>SEQUENCE: 589<br>000 | moltype = | length = |
| SEQ ID NO: 590<br>SEQUENCE: 590<br>000 | moltype = | length = |
| SEQ ID NO: 591<br>SEQUENCE: 591<br>000 | moltype = | length = |
| SEQ ID NO: 592<br>SEQUENCE: 592<br>000 | moltype = | length = |
| SEQ ID NO: 593<br>SEQUENCE: 593<br>000 | moltype = | length = |
| SEQ ID NO: 594<br>SEQUENCE: 594<br>000 | moltype = | length = |
| SEQ ID NO: 595<br>SEQUENCE: 595<br>000 | moltype = | length = |
| SEQ ID NO: 596<br>SEQUENCE: 596<br>000 | moltype = | length = |
| SEQ ID NO: 597<br>SEQUENCE: 597<br>000 | moltype = | length = |
| SEQ ID NO: 598<br>SEQUENCE: 598<br>000 | moltype = | length = |
| SEQ ID NO: 599<br>SEQUENCE: 599<br>000 | moltype = | length = |
| SEQ ID NO: 600<br>SEQUENCE: 600<br>000 | moltype = | length = |
| SEQ ID NO: 601<br>SEQUENCE: 601<br>000 | moltype = | length = |
| SEQ ID NO: 602<br>SEQUENCE: 602<br>000 | moltype = | length = |

| | | |
|---|---|---|
| SEQ ID NO: 603<br>SEQUENCE: 603<br>000 | moltype = | length = |
| SEQ ID NO: 604<br>SEQUENCE: 604<br>000 | moltype = | length = |
| SEQ ID NO: 605<br>SEQUENCE: 605<br>000 | moltype = | length = |
| SEQ ID NO: 606<br>SEQUENCE: 606<br>000 | moltype = | length = |
| SEQ ID NO: 607<br>SEQUENCE: 607<br>000 | moltype = | length = |
| SEQ ID NO: 608<br>SEQUENCE: 608<br>000 | moltype = | length = |
| SEQ ID NO: 609<br>SEQUENCE: 609<br>000 | moltype = | length = |
| SEQ ID NO: 610<br>SEQUENCE: 610<br>000 | moltype = | length = |
| SEQ ID NO: 611<br>SEQUENCE: 611<br>000 | moltype = | length = |
| SEQ ID NO: 612<br>SEQUENCE: 612<br>000 | moltype = | length = |
| SEQ ID NO: 613<br>SEQUENCE: 613<br>000 | moltype = | length = |
| SEQ ID NO: 614<br>SEQUENCE: 614<br>000 | moltype = | length = |
| SEQ ID NO: 615<br>SEQUENCE: 615<br>000 | moltype = | length = |
| SEQ ID NO: 616<br>SEQUENCE: 616<br>000 | moltype = | length = |
| SEQ ID NO: 617<br>SEQUENCE: 617<br>000 | moltype = | length = |
| SEQ ID NO: 618<br>SEQUENCE: 618<br>000 | moltype = | length = |
| SEQ ID NO: 619<br>SEQUENCE: 619<br>000 | moltype = | length = |
| SEQ ID NO: 620<br>SEQUENCE: 620<br>000 | moltype = | length = |
| SEQ ID NO: 621<br>SEQUENCE: 621<br>000 | moltype = | length = |
| SEQ ID NO: 622<br>SEQUENCE: 622 | moltype = | length = |

-continued

000

SEQ ID NO: 623    moltype =    length =
SEQUENCE: 623
000

SEQ ID NO: 624    moltype =    length =
SEQUENCE: 624
000

SEQ ID NO: 625    moltype =    length =
SEQUENCE: 625
000

SEQ ID NO: 626    moltype =    length =
SEQUENCE: 626
000

SEQ ID NO: 627    moltype =    length =
SEQUENCE: 627
000

SEQ ID NO: 628    moltype =    length =
SEQUENCE: 628
000

SEQ ID NO: 629    moltype =    length =
SEQUENCE: 629
000

SEQ ID NO: 630    moltype =    length =
SEQUENCE: 630
000

SEQ ID NO: 631    moltype =    length =
SEQUENCE: 631
000

SEQ ID NO: 632    moltype =    length =
SEQUENCE: 632
000

SEQ ID NO: 633    moltype =    length =
SEQUENCE: 633
000

SEQ ID NO: 634    moltype =    length =
SEQUENCE: 634
000

SEQ ID NO: 635    moltype =    length =
SEQUENCE: 635
000

SEQ ID NO: 636    moltype =    length =
SEQUENCE: 636
000

SEQ ID NO: 637    moltype =    length =
SEQUENCE: 637
000

SEQ ID NO: 638    moltype =    length =
SEQUENCE: 638
000

SEQ ID NO: 639    moltype =    length =
SEQUENCE: 639
000

SEQ ID NO: 640    moltype =    length =
SEQUENCE: 640
000

SEQ ID NO: 641    moltype =    length =
SEQUENCE: 641
000

SEQ ID NO: 642    moltype =    length =

| | | |
|---|---|---|
| SEQUENCE: 642 000 | | |
| SEQ ID NO: 643 SEQUENCE: 643 000 | moltype = | length = |
| SEQ ID NO: 644 SEQUENCE: 644 000 | moltype = | length = |
| SEQ ID NO: 645 SEQUENCE: 645 000 | moltype = | length = |
| SEQ ID NO: 646 SEQUENCE: 646 000 | moltype = | length = |
| SEQ ID NO: 647 SEQUENCE: 647 000 | moltype = | length = |
| SEQ ID NO: 648 SEQUENCE: 648 000 | moltype = | length = |
| SEQ ID NO: 649 SEQUENCE: 649 000 | moltype = | length = |
| SEQ ID NO: 650 SEQUENCE: 650 000 | moltype = | length = |
| SEQ ID NO: 651 SEQUENCE: 651 000 | moltype = | length = |
| SEQ ID NO: 652 SEQUENCE: 652 000 | moltype = | length = |
| SEQ ID NO: 653 SEQUENCE: 653 000 | moltype = | length = |
| SEQ ID NO: 654 SEQUENCE: 654 000 | moltype = | length = |
| SEQ ID NO: 655 SEQUENCE: 655 000 | moltype = | length = |
| SEQ ID NO: 656 SEQUENCE: 656 000 | moltype = | length = |
| SEQ ID NO: 657 SEQUENCE: 657 000 | moltype = | length = |
| SEQ ID NO: 658 SEQUENCE: 658 000 | moltype = | length = |
| SEQ ID NO: 659 SEQUENCE: 659 000 | moltype = | length = |
| SEQ ID NO: 660 SEQUENCE: 660 000 | moltype = | length = |
| SEQ ID NO: 661 SEQUENCE: 661 000 | moltype = | length = |

-continued

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

| | | |
|---|---|---|
| SEQ ID NO: 682<br>SEQUENCE: 682<br>000 | moltype = | length = |
| SEQ ID NO: 683<br>SEQUENCE: 683<br>000 | moltype = | length = |
| SEQ ID NO: 684<br>SEQUENCE: 684<br>000 | moltype = | length = |
| SEQ ID NO: 685<br>SEQUENCE: 685<br>000 | moltype = | length = |
| SEQ ID NO: 686<br>SEQUENCE: 686<br>000 | moltype = | length = |
| SEQ ID NO: 687<br>SEQUENCE: 687<br>000 | moltype = | length = |
| SEQ ID NO: 688<br>SEQUENCE: 688<br>000 | moltype = | length = |
| SEQ ID NO: 689<br>SEQUENCE: 689<br>000 | moltype = | length = |
| SEQ ID NO: 690<br>SEQUENCE: 690<br>000 | moltype = | length = |
| SEQ ID NO: 691<br>SEQUENCE: 691<br>000 | moltype = | length = |
| SEQ ID NO: 692<br>SEQUENCE: 692<br>000 | moltype = | length = |
| SEQ ID NO: 693<br>SEQUENCE: 693<br>000 | moltype = | length = |
| SEQ ID NO: 694<br>SEQUENCE: 694<br>000 | moltype = | length = |
| SEQ ID NO: 695<br>SEQUENCE: 695<br>000 | moltype = | length = |
| SEQ ID NO: 696<br>SEQUENCE: 696<br>000 | moltype = | length = |
| SEQ ID NO: 697<br>SEQUENCE: 697<br>000 | moltype = | length = |
| SEQ ID NO: 698<br>SEQUENCE: 698<br>000 | moltype = | length = |
| SEQ ID NO: 699<br>SEQUENCE: 699<br>000 | moltype = | length = |
| SEQ ID NO: 700<br>SEQUENCE: 700<br>000 | moltype = | length = |
| SEQ ID NO: 701<br>SEQUENCE: 701 | moltype = | length = |

```
000

SEQ ID NO: 702          moltype =    length =
SEQUENCE: 702
000

SEQ ID NO: 703          moltype =    length =
SEQUENCE: 703
000

SEQ ID NO: 704          moltype =    length =
SEQUENCE: 704
000

SEQ ID NO: 705          moltype =    length =
SEQUENCE: 705
000

SEQ ID NO: 706          moltype =    length =
SEQUENCE: 706
000

SEQ ID NO: 707          moltype =    length =
SEQUENCE: 707
000

SEQ ID NO: 708          moltype =    length =
SEQUENCE: 708
000

SEQ ID NO: 709          moltype =    length =
SEQUENCE: 709
000

SEQ ID NO: 710          moltype =    length =
SEQUENCE: 710
000

SEQ ID NO: 711          moltype =    length =
SEQUENCE: 711
000

SEQ ID NO: 712          moltype =    length =
SEQUENCE: 712
000

SEQ ID NO: 713          moltype =    length =
SEQUENCE: 713
000

SEQ ID NO: 714          moltype =    length =
SEQUENCE: 714
000

SEQ ID NO: 715          moltype =    length =
SEQUENCE: 715
000

SEQ ID NO: 716          moltype =    length =
SEQUENCE: 716
000

SEQ ID NO: 717          moltype =    length =
SEQUENCE: 717
000

SEQ ID NO: 718          moltype =    length =
SEQUENCE: 718
000

SEQ ID NO: 719          moltype =    length =
SEQUENCE: 719
000

SEQ ID NO: 720          moltype =    length =
SEQUENCE: 720
000

SEQ ID NO: 721          moltype =    length =
```

```
SEQUENCE: 721
000

SEQ ID NO: 722        moltype =    length =
SEQUENCE: 722
000

SEQ ID NO: 723        moltype =    length =
SEQUENCE: 723
000

SEQ ID NO: 724        moltype =    length =
SEQUENCE: 724
000

SEQ ID NO: 725        moltype =    length =
SEQUENCE: 725
000

SEQ ID NO: 726        moltype =    length =
SEQUENCE: 726
000

SEQ ID NO: 727        moltype =    length =
SEQUENCE: 727
000

SEQ ID NO: 728        moltype =    length =
SEQUENCE: 728
000

SEQ ID NO: 729        moltype =    length =
SEQUENCE: 729
000

SEQ ID NO: 730        moltype =    length =
SEQUENCE: 730
000

SEQ ID NO: 731        moltype =    length =
SEQUENCE: 731
000

SEQ ID NO: 732        moltype =    length =
SEQUENCE: 732
000

SEQ ID NO: 733        moltype =    length =
SEQUENCE: 733
000

SEQ ID NO: 734        moltype =    length =
SEQUENCE: 734
000

SEQ ID NO: 735        moltype =    length =
SEQUENCE: 735
000

SEQ ID NO: 736        moltype =    length =
SEQUENCE: 736
000

SEQ ID NO: 737        moltype =    length =
SEQUENCE: 737
000

SEQ ID NO: 738        moltype =    length =
SEQUENCE: 738
000

SEQ ID NO: 739        moltype =    length =
SEQUENCE: 739
000

SEQ ID NO: 740        moltype =    length =
SEQUENCE: 740
000
```

| | | |
|---|---|---|
| SEQ ID NO: 741<br>SEQUENCE: 741<br>000 | moltype = | length = |
| SEQ ID NO: 742<br>SEQUENCE: 742<br>000 | moltype = | length = |
| SEQ ID NO: 743<br>SEQUENCE: 743<br>000 | moltype = | length = |
| SEQ ID NO: 744<br>SEQUENCE: 744<br>000 | moltype = | length = |
| SEQ ID NO: 745<br>SEQUENCE: 745<br>000 | moltype = | length = |
| SEQ ID NO: 746<br>SEQUENCE: 746<br>000 | moltype = | length = |
| SEQ ID NO: 747<br>SEQUENCE: 747<br>000 | moltype = | length = |
| SEQ ID NO: 748<br>SEQUENCE: 748<br>000 | moltype = | length = |
| SEQ ID NO: 749<br>SEQUENCE: 749<br>000 | moltype = | length = |
| SEQ ID NO: 750<br>SEQUENCE: 750<br>000 | moltype = | length = |
| SEQ ID NO: 751<br>SEQUENCE: 751<br>000 | moltype = | length = |
| SEQ ID NO: 752<br>SEQUENCE: 752<br>000 | moltype = | length = |
| SEQ ID NO: 753<br>SEQUENCE: 753<br>000 | moltype = | length = |
| SEQ ID NO: 754<br>SEQUENCE: 754<br>000 | moltype = | length = |
| SEQ ID NO: 755<br>SEQUENCE: 755<br>000 | moltype = | length = |
| SEQ ID NO: 756<br>SEQUENCE: 756<br>000 | moltype = | length = |
| SEQ ID NO: 757<br>SEQUENCE: 757<br>000 | moltype = | length = |
| SEQ ID NO: 758<br>SEQUENCE: 758<br>000 | moltype = | length = |
| SEQ ID NO: 759<br>SEQUENCE: 759<br>000 | moltype = | length = |
| SEQ ID NO: 760<br>SEQUENCE: 760<br>000 | moltype = | length = |

| | | |
|---|---|---|
| SEQ ID NO: 761 SEQUENCE: 761 000 | moltype = | length = |
| SEQ ID NO: 762 SEQUENCE: 762 000 | moltype = | length = |
| SEQ ID NO: 763 SEQUENCE: 763 000 | moltype = | length = |
| SEQ ID NO: 764 SEQUENCE: 764 000 | moltype = | length = |
| SEQ ID NO: 765 SEQUENCE: 765 000 | moltype = | length = |
| SEQ ID NO: 766 SEQUENCE: 766 000 | moltype = | length = |
| SEQ ID NO: 767 SEQUENCE: 767 000 | moltype = | length = |
| SEQ ID NO: 768 SEQUENCE: 768 000 | moltype = | length = |
| SEQ ID NO: 769 SEQUENCE: 769 000 | moltype = | length = |
| SEQ ID NO: 770 SEQUENCE: 770 000 | moltype = | length = |
| SEQ ID NO: 771 SEQUENCE: 771 000 | moltype = | length = |
| SEQ ID NO: 772 SEQUENCE: 772 000 | moltype = | length = |
| SEQ ID NO: 773 SEQUENCE: 773 000 | moltype = | length = |
| SEQ ID NO: 774 SEQUENCE: 774 000 | moltype = | length = |
| SEQ ID NO: 775 SEQUENCE: 775 000 | moltype = | length = |
| SEQ ID NO: 776 SEQUENCE: 776 000 | moltype = | length = |
| SEQ ID NO: 777 SEQUENCE: 777 000 | moltype = | length = |
| SEQ ID NO: 778 SEQUENCE: 778 000 | moltype = | length = |
| SEQ ID NO: 779 SEQUENCE: 779 000 | moltype = | length = |
| SEQ ID NO: 780 SEQUENCE: 780 | moltype = | length = |

000

SEQ ID NO: 781          moltype =     length =
SEQUENCE: 781
000

SEQ ID NO: 782          moltype =     length =
SEQUENCE: 782
000

SEQ ID NO: 783          moltype =     length =
SEQUENCE: 783
000

SEQ ID NO: 784          moltype =     length =
SEQUENCE: 784
000

SEQ ID NO: 785          moltype =     length =
SEQUENCE: 785
000

SEQ ID NO: 786          moltype =     length =
SEQUENCE: 786
000

SEQ ID NO: 787          moltype =     length =
SEQUENCE: 787
000

SEQ ID NO: 788          moltype =     length =
SEQUENCE: 788
000

SEQ ID NO: 789          moltype =     length =
SEQUENCE: 789
000

SEQ ID NO: 790          moltype =     length =
SEQUENCE: 790
000

SEQ ID NO: 791          moltype =     length =
SEQUENCE: 791
000

SEQ ID NO: 792          moltype =     length =
SEQUENCE: 792
000

SEQ ID NO: 793          moltype =     length =
SEQUENCE: 793
000

SEQ ID NO: 794          moltype =     length =
SEQUENCE: 794
000

SEQ ID NO: 795          moltype =     length =
SEQUENCE: 795
000

SEQ ID NO: 796          moltype =     length =
SEQUENCE: 796
000

SEQ ID NO: 797          moltype =     length =
SEQUENCE: 797
000

SEQ ID NO: 798          moltype =     length =
SEQUENCE: 798
000

SEQ ID NO: 799          moltype =     length =
SEQUENCE: 799
000

SEQ ID NO: 800          moltype =     length =

| | | |
|---|---|---|
| SEQUENCE: 800 000 | | |
| SEQ ID NO: 801 SEQUENCE: 801 000 | moltype = | length = |
| SEQ ID NO: 802 SEQUENCE: 802 000 | moltype = | length = |
| SEQ ID NO: 803 SEQUENCE: 803 000 | moltype = | length = |
| SEQ ID NO: 804 SEQUENCE: 804 000 | moltype = | length = |
| SEQ ID NO: 805 SEQUENCE: 805 000 | moltype = | length = |
| SEQ ID NO: 806 SEQUENCE: 806 000 | moltype = | length = |
| SEQ ID NO: 807 SEQUENCE: 807 000 | moltype = | length = |
| SEQ ID NO: 808 SEQUENCE: 808 000 | moltype = | length = |
| SEQ ID NO: 809 SEQUENCE: 809 000 | moltype = | length = |
| SEQ ID NO: 810 SEQUENCE: 810 000 | moltype = | length = |
| SEQ ID NO: 811 SEQUENCE: 811 000 | moltype = | length = |
| SEQ ID NO: 812 SEQUENCE: 812 000 | moltype = | length = |
| SEQ ID NO: 813 SEQUENCE: 813 000 | moltype = | length = |
| SEQ ID NO: 814 SEQUENCE: 814 000 | moltype = | length = |
| SEQ ID NO: 815 SEQUENCE: 815 000 | moltype = | length = |
| SEQ ID NO: 816 SEQUENCE: 816 000 | moltype = | length = |
| SEQ ID NO: 817 SEQUENCE: 817 000 | moltype = | length = |
| SEQ ID NO: 818 SEQUENCE: 818 000 | moltype = | length = |
| SEQ ID NO: 819 SEQUENCE: 819 000 | moltype = | length = |

| | | |
|---|---|---|
| SEQ ID NO: 820
SEQUENCE: 820
000 | moltype = | length = |
| SEQ ID NO: 821
SEQUENCE: 821
000 | moltype = | length = |
| SEQ ID NO: 822
SEQUENCE: 822
000 | moltype = | length = |
| SEQ ID NO: 823
SEQUENCE: 823
000 | moltype = | length = |
| SEQ ID NO: 824
SEQUENCE: 824
000 | moltype = | length = |
| SEQ ID NO: 825
SEQUENCE: 825
000 | moltype = | length = |
| SEQ ID NO: 826
SEQUENCE: 826
000 | moltype = | length = |
| SEQ ID NO: 827
SEQUENCE: 827
000 | moltype = | length = |
| SEQ ID NO: 828
SEQUENCE: 828
000 | moltype = | length = |
| SEQ ID NO: 829
SEQUENCE: 829
000 | moltype = | length = |
| SEQ ID NO: 830
SEQUENCE: 830
000 | moltype = | length = |
| SEQ ID NO: 831
SEQUENCE: 831
000 | moltype = | length = |
| SEQ ID NO: 832
SEQUENCE: 832
000 | moltype = | length = |
| SEQ ID NO: 833
SEQUENCE: 833
000 | moltype = | length = |
| SEQ ID NO: 834
SEQUENCE: 834
000 | moltype = | length = |
| SEQ ID NO: 835
SEQUENCE: 835
000 | moltype = | length = |
| SEQ ID NO: 836
SEQUENCE: 836
000 | moltype = | length = |
| SEQ ID NO: 837
SEQUENCE: 837
000 | moltype = | length = |
| SEQ ID NO: 838
SEQUENCE: 838
000 | moltype = | length = |
| SEQ ID NO: 839
SEQUENCE: 839
000 | moltype = | length = |

| | | |
|---|---|---|
| SEQ ID NO: 840<br>SEQUENCE: 840<br>000 | moltype = | length = |
| SEQ ID NO: 841<br>SEQUENCE: 841<br>000 | moltype = | length = |
| SEQ ID NO: 842<br>SEQUENCE: 842<br>000 | moltype = | length = |
| SEQ ID NO: 843<br>SEQUENCE: 843<br>000 | moltype = | length = |
| SEQ ID NO: 844<br>SEQUENCE: 844<br>000 | moltype = | length = |
| SEQ ID NO: 845<br>SEQUENCE: 845<br>000 | moltype = | length = |
| SEQ ID NO: 846<br>SEQUENCE: 846<br>000 | moltype = | length = |
| SEQ ID NO: 847<br>SEQUENCE: 847<br>000 | moltype = | length = |
| SEQ ID NO: 848<br>SEQUENCE: 848<br>000 | moltype = | length = |
| SEQ ID NO: 849<br>SEQUENCE: 849<br>000 | moltype = | length = |
| SEQ ID NO: 850<br>SEQUENCE: 850<br>000 | moltype = | length = |
| SEQ ID NO: 851<br>SEQUENCE: 851<br>000 | moltype = | length = |
| SEQ ID NO: 852<br>SEQUENCE: 852<br>000 | moltype = | length = |
| SEQ ID NO: 853<br>SEQUENCE: 853<br>000 | moltype = | length = |
| SEQ ID NO: 854<br>SEQUENCE: 854<br>000 | moltype = | length = |
| SEQ ID NO: 855<br>SEQUENCE: 855<br>000 | moltype = | length = |
| SEQ ID NO: 856<br>SEQUENCE: 856<br>000 | moltype = | length = |
| SEQ ID NO: 857<br>SEQUENCE: 857<br>000 | moltype = | length = |
| SEQ ID NO: 858<br>SEQUENCE: 858<br>000 | moltype = | length = |
| SEQ ID NO: 859<br>SEQUENCE: 859 | moltype = | length = |

000

SEQ ID NO: 860           moltype =   length =
SEQUENCE: 860
000

SEQ ID NO: 861           moltype =   length =
SEQUENCE: 861
000

SEQ ID NO: 862           moltype =   length =
SEQUENCE: 862
000

SEQ ID NO: 863           moltype =   length =
SEQUENCE: 863
000

SEQ ID NO: 864           moltype =   length =
SEQUENCE: 864
000

SEQ ID NO: 865           moltype =   length =
SEQUENCE: 865
000

SEQ ID NO: 866           moltype =   length =
SEQUENCE: 866
000

SEQ ID NO: 867           moltype =   length =
SEQUENCE: 867
000

SEQ ID NO: 868           moltype =   length =
SEQUENCE: 868
000

SEQ ID NO: 869           moltype =   length =
SEQUENCE: 869
000

SEQ ID NO: 870           moltype =   length =
SEQUENCE: 870
000

SEQ ID NO: 871           moltype =   length =
SEQUENCE: 871
000

SEQ ID NO: 872           moltype =   length =
SEQUENCE: 872
000

SEQ ID NO: 873           moltype =   length =
SEQUENCE: 873
000

SEQ ID NO: 874           moltype =   length =
SEQUENCE: 874
000

SEQ ID NO: 875           moltype =   length =
SEQUENCE: 875
000

SEQ ID NO: 876           moltype =   length =
SEQUENCE: 876
000

SEQ ID NO: 877           moltype =   length =
SEQUENCE: 877
000

SEQ ID NO: 878           moltype =   length =
SEQUENCE: 878
000

SEQ ID NO: 879           moltype =   length =

| | | |
|---|---|---|
| SEQUENCE: 879 000 | | |
| SEQ ID NO: 880 SEQUENCE: 880 000 | moltype = | length = |
| SEQ ID NO: 881 SEQUENCE: 881 000 | moltype = | length = |
| SEQ ID NO: 882 SEQUENCE: 882 000 | moltype = | length = |
| SEQ ID NO: 883 SEQUENCE: 883 000 | moltype = | length = |
| SEQ ID NO: 884 SEQUENCE: 884 000 | moltype = | length = |
| SEQ ID NO: 885 SEQUENCE: 885 000 | moltype = | length = |
| SEQ ID NO: 886 SEQUENCE: 886 000 | moltype = | length = |
| SEQ ID NO: 887 SEQUENCE: 887 000 | moltype = | length = |
| SEQ ID NO: 888 SEQUENCE: 888 000 | moltype = | length = |
| SEQ ID NO: 889 SEQUENCE: 889 000 | moltype = | length = |
| SEQ ID NO: 890 SEQUENCE: 890 000 | moltype = | length = |
| SEQ ID NO: 891 SEQUENCE: 891 000 | moltype = | length = |
| SEQ ID NO: 892 SEQUENCE: 892 000 | moltype = | length = |
| SEQ ID NO: 893 SEQUENCE: 893 000 | moltype = | length = |
| SEQ ID NO: 894 SEQUENCE: 894 000 | moltype = | length = |
| SEQ ID NO: 895 SEQUENCE: 895 000 | moltype = | length = |
| SEQ ID NO: 896 SEQUENCE: 896 000 | moltype = | length = |
| SEQ ID NO: 897 SEQUENCE: 897 000 | moltype = | length = |
| SEQ ID NO: 898 SEQUENCE: 898 000 | moltype = | length = |

| | | |
|---|---|---|
| SEQ ID NO: 899<br>SEQUENCE: 899<br>000 | moltype = | length = |
| SEQ ID NO: 900<br>SEQUENCE: 900<br>000 | moltype = | length = |
| SEQ ID NO: 901<br>SEQUENCE: 901<br>000 | moltype = | length = |
| SEQ ID NO: 902<br>SEQUENCE: 902<br>000 | moltype = | length = |
| SEQ ID NO: 903<br>SEQUENCE: 903<br>000 | moltype = | length = |
| SEQ ID NO: 904<br>SEQUENCE: 904<br>000 | moltype = | length = |
| SEQ ID NO: 905<br>SEQUENCE: 905<br>000 | moltype = | length = |
| SEQ ID NO: 906<br>SEQUENCE: 906<br>000 | moltype = | length = |
| SEQ ID NO: 907<br>SEQUENCE: 907<br>000 | moltype = | length = |
| SEQ ID NO: 908<br>SEQUENCE: 908<br>000 | moltype = | length = |
| SEQ ID NO: 909<br>SEQUENCE: 909<br>000 | moltype = | length = |
| SEQ ID NO: 910<br>SEQUENCE: 910<br>000 | moltype = | length = |
| SEQ ID NO: 911<br>SEQUENCE: 911<br>000 | moltype = | length = |
| SEQ ID NO: 912<br>SEQUENCE: 912<br>000 | moltype = | length = |
| SEQ ID NO: 913<br>SEQUENCE: 913<br>000 | moltype = | length = |
| SEQ ID NO: 914<br>SEQUENCE: 914<br>000 | moltype = | length = |
| SEQ ID NO: 915<br>SEQUENCE: 915<br>000 | moltype = | length = |
| SEQ ID NO: 916<br>SEQUENCE: 916<br>000 | moltype = | length = |
| SEQ ID NO: 917<br>SEQUENCE: 917<br>000 | moltype = | length = |
| SEQ ID NO: 918<br>SEQUENCE: 918<br>000 | moltype = | length = |

| | | |
|---|---|---|
| SEQ ID NO: 919<br>SEQUENCE: 919<br>000 | moltype = | length = |
| SEQ ID NO: 920<br>SEQUENCE: 920<br>000 | moltype = | length = |
| SEQ ID NO: 921<br>SEQUENCE: 921<br>000 | moltype = | length = |
| SEQ ID NO: 922<br>SEQUENCE: 922<br>000 | moltype = | length = |
| SEQ ID NO: 923<br>SEQUENCE: 923<br>000 | moltype = | length = |
| SEQ ID NO: 924<br>SEQUENCE: 924<br>000 | moltype = | length = |
| SEQ ID NO: 925<br>SEQUENCE: 925<br>000 | moltype = | length = |
| SEQ ID NO: 926<br>SEQUENCE: 926<br>000 | moltype = | length = |
| SEQ ID NO: 927<br>SEQUENCE: 927<br>000 | moltype = | length = |
| SEQ ID NO: 928<br>SEQUENCE: 928<br>000 | moltype = | length = |
| SEQ ID NO: 929<br>SEQUENCE: 929<br>000 | moltype = | length = |
| SEQ ID NO: 930<br>SEQUENCE: 930<br>000 | moltype = | length = |
| SEQ ID NO: 931<br>SEQUENCE: 931<br>000 | moltype = | length = |
| SEQ ID NO: 932<br>SEQUENCE: 932<br>000 | moltype = | length = |
| SEQ ID NO: 933<br>SEQUENCE: 933<br>000 | moltype = | length = |
| SEQ ID NO: 934<br>SEQUENCE: 934<br>000 | moltype = | length = |
| SEQ ID NO: 935<br>SEQUENCE: 935<br>000 | moltype = | length = |
| SEQ ID NO: 936<br>SEQUENCE: 936<br>000 | moltype = | length = |
| SEQ ID NO: 937<br>SEQUENCE: 937<br>000 | moltype = | length = |
| SEQ ID NO: 938<br>SEQUENCE: 938 | moltype = | length = |

-continued

SEQ ID NO: 939    moltype =    length =
SEQUENCE: 939
000

SEQ ID NO: 940    moltype =    length =
SEQUENCE: 940
000

SEQ ID NO: 941    moltype =    length =
SEQUENCE: 941
000

SEQ ID NO: 942    moltype =    length =
SEQUENCE: 942
000

SEQ ID NO: 943    moltype =    length =
SEQUENCE: 943
000

SEQ ID NO: 944    moltype =    length =
SEQUENCE: 944
000

SEQ ID NO: 945    moltype =    length =
SEQUENCE: 945
000

SEQ ID NO: 946    moltype =    length =
SEQUENCE: 946
000

SEQ ID NO: 947    moltype =    length =
SEQUENCE: 947
000

SEQ ID NO: 948    moltype =    length =
SEQUENCE: 948
000

SEQ ID NO: 949    moltype =    length =
SEQUENCE: 949
000

SEQ ID NO: 950    moltype =    length =
SEQUENCE: 950
000

SEQ ID NO: 951    moltype =    length =
SEQUENCE: 951
000

SEQ ID NO: 952    moltype =    length =
SEQUENCE: 952
000

SEQ ID NO: 953    moltype =    length =
SEQUENCE: 953
000

SEQ ID NO: 954    moltype =    length =
SEQUENCE: 954
000

SEQ ID NO: 955    moltype =    length =
SEQUENCE: 955
000

SEQ ID NO: 956    moltype =    length =
SEQUENCE: 956
000

SEQ ID NO: 957    moltype =    length =
SEQUENCE: 957
000

SEQ ID NO: 958    moltype =    length =

-continued

| | | |
|---|---|---|
| SEQUENCE: 958 000 | | |
| SEQ ID NO: 959 SEQUENCE: 959 000 | moltype = | length = |
| SEQ ID NO: 960 SEQUENCE: 960 000 | moltype = | length = |
| SEQ ID NO: 961 SEQUENCE: 961 000 | moltype = | length = |
| SEQ ID NO: 962 SEQUENCE: 962 000 | moltype = | length = |
| SEQ ID NO: 963 SEQUENCE: 963 000 | moltype = | length = |
| SEQ ID NO: 964 SEQUENCE: 964 000 | moltype = | length = |
| SEQ ID NO: 965 SEQUENCE: 965 000 | moltype = | length = |
| SEQ ID NO: 966 SEQUENCE: 966 000 | moltype = | length = |
| SEQ ID NO: 967 SEQUENCE: 967 000 | moltype = | length = |
| SEQ ID NO: 968 SEQUENCE: 968 000 | moltype = | length = |
| SEQ ID NO: 969 SEQUENCE: 969 000 | moltype = | length = |
| SEQ ID NO: 970 SEQUENCE: 970 000 | moltype = | length = |
| SEQ ID NO: 971 SEQUENCE: 971 000 | moltype = | length = |
| SEQ ID NO: 972 SEQUENCE: 972 000 | moltype = | length = |
| SEQ ID NO: 973 SEQUENCE: 973 000 | moltype = | length = |
| SEQ ID NO: 974 SEQUENCE: 974 000 | moltype = | length = |
| SEQ ID NO: 975 SEQUENCE: 975 000 | moltype = | length = |
| SEQ ID NO: 976 SEQUENCE: 976 000 | moltype = | length = |
| SEQ ID NO: 977 SEQUENCE: 977 000 | moltype = | length = |

-continued

| | | |
|---|---|---|
| SEQ ID NO: 978<br>SEQUENCE: 978<br>000 | moltype = | length = |
| SEQ ID NO: 979<br>SEQUENCE: 979<br>000 | moltype = | length = |
| SEQ ID NO: 980<br>SEQUENCE: 980<br>000 | moltype = | length = |
| SEQ ID NO: 981<br>SEQUENCE: 981<br>000 | moltype = | length = |
| SEQ ID NO: 982<br>SEQUENCE: 982<br>000 | moltype = | length = |
| SEQ ID NO: 983<br>SEQUENCE: 983<br>000 | moltype = | length = |
| SEQ ID NO: 984<br>SEQUENCE: 984<br>000 | moltype = | length = |
| SEQ ID NO: 985<br>SEQUENCE: 985<br>000 | moltype = | length = |
| SEQ ID NO: 986<br>SEQUENCE: 986<br>000 | moltype = | length = |
| SEQ ID NO: 987<br>SEQUENCE: 987<br>000 | moltype = | length = |
| SEQ ID NO: 988<br>SEQUENCE: 988<br>000 | moltype = | length = |
| SEQ ID NO: 989<br>SEQUENCE: 989<br>000 | moltype = | length = |
| SEQ ID NO: 990<br>SEQUENCE: 990<br>000 | moltype = | length = |
| SEQ ID NO: 991<br>SEQUENCE: 991<br>000 | moltype = | length = |
| SEQ ID NO: 992<br>SEQUENCE: 992<br>000 | moltype = | length = |
| SEQ ID NO: 993<br>SEQUENCE: 993<br>000 | moltype = | length = |
| SEQ ID NO: 994<br>SEQUENCE: 994<br>000 | moltype = | length = |
| SEQ ID NO: 995<br>SEQUENCE: 995<br>000 | moltype = | length = |
| SEQ ID NO: 996<br>SEQUENCE: 996<br>000 | moltype = | length = |
| SEQ ID NO: 997<br>SEQUENCE: 997<br>000 | moltype = | length = |

| | | |
|---|---|---|
| SEQ ID NO: 998
SEQUENCE: 998
000 | moltype = | length = |
| SEQ ID NO: 999
SEQUENCE: 999
000 | moltype = | length = |
| SEQ ID NO: 1000
SEQUENCE: 1000
000 | moltype = | length = |
| SEQ ID NO: 1001
SEQUENCE: 1001
000 | moltype = | length = |
| SEQ ID NO: 1002
SEQUENCE: 1002
000 | moltype = | length = |
| SEQ ID NO: 1003
SEQUENCE: 1003
000 | moltype = | length = |
| SEQ ID NO: 1004
SEQUENCE: 1004
000 | moltype = | length = |
| SEQ ID NO: 1005
SEQUENCE: 1005
000 | moltype = | length = |
| SEQ ID NO: 1006
SEQUENCE: 1006
000 | moltype = | length = |
| SEQ ID NO: 1007
SEQUENCE: 1007
000 | moltype = | length = |
| SEQ ID NO: 1008
SEQUENCE: 1008
000 | moltype = | length = |
| SEQ ID NO: 1009
SEQUENCE: 1009
000 | moltype = | length = |
| SEQ ID NO: 1010
SEQUENCE: 1010
000 | moltype = | length = |
| SEQ ID NO: 1011
SEQUENCE: 1011
000 | moltype = | length = |
| SEQ ID NO: 1012
SEQUENCE: 1012
000 | moltype = | length = |
| SEQ ID NO: 1013
SEQUENCE: 1013
000 | moltype = | length = |
| SEQ ID NO: 1014
SEQUENCE: 1014
000 | moltype = | length = |
| SEQ ID NO: 1015
SEQUENCE: 1015
000 | moltype = | length = |
| SEQ ID NO: 1016
SEQUENCE: 1016
000 | moltype = | length = |
| SEQ ID NO: 1017
SEQUENCE: 1017 | moltype = | length = |

000

SEQ ID NO: 1018      moltype =    length =
SEQUENCE: 1018
000

SEQ ID NO: 1019      moltype =    length =
SEQUENCE: 1019
000

SEQ ID NO: 1020      moltype =    length =
SEQUENCE: 1020
000

SEQ ID NO: 1021      moltype =    length =
SEQUENCE: 1021
000

SEQ ID NO: 1022      moltype =    length =
SEQUENCE: 1022
000

SEQ ID NO: 1023      moltype =    length =
SEQUENCE: 1023
000

SEQ ID NO: 1024      moltype =    length =
SEQUENCE: 1024
000

SEQ ID NO: 1025      moltype =    length =
SEQUENCE: 1025
000

SEQ ID NO: 1026      moltype =    length =
SEQUENCE: 1026
000

SEQ ID NO: 1027      moltype =    length =
SEQUENCE: 1027
000

SEQ ID NO: 1028      moltype =    length =
SEQUENCE: 1028
000

SEQ ID NO: 1029      moltype =    length =
SEQUENCE: 1029
000

SEQ ID NO: 1030      moltype =    length =
SEQUENCE: 1030
000

SEQ ID NO: 1031      moltype =    length =
SEQUENCE: 1031
000

SEQ ID NO: 1032      moltype =    length =
SEQUENCE: 1032
000

SEQ ID NO: 1033      moltype =    length =
SEQUENCE: 1033
000

SEQ ID NO: 1034      moltype =    length =
SEQUENCE: 1034
000

SEQ ID NO: 1035      moltype =    length =
SEQUENCE: 1035
000

SEQ ID NO: 1036      moltype =    length =
SEQUENCE: 1036
000

SEQ ID NO: 1037      moltype =    length =

| | | |
|---|---|---|
| SEQUENCE: 1037<br>000 | | |
| SEQ ID NO: 1038<br>SEQUENCE: 1038<br>000 | moltype = | length = |
| SEQ ID NO: 1039<br>SEQUENCE: 1039<br>000 | moltype = | length = |
| SEQ ID NO: 1040<br>SEQUENCE: 1040<br>000 | moltype = | length = |
| SEQ ID NO: 1041<br>SEQUENCE: 1041<br>000 | moltype = | length = |
| SEQ ID NO: 1042<br>SEQUENCE: 1042<br>000 | moltype = | length = |
| SEQ ID NO: 1043<br>SEQUENCE: 1043<br>000 | moltype = | length = |
| SEQ ID NO: 1044<br>SEQUENCE: 1044<br>000 | moltype = | length = |
| SEQ ID NO: 1045<br>SEQUENCE: 1045<br>000 | moltype = | length = |
| SEQ ID NO: 1046<br>SEQUENCE: 1046<br>000 | moltype = | length = |
| SEQ ID NO: 1047<br>SEQUENCE: 1047<br>000 | moltype = | length = |
| SEQ ID NO: 1048<br>SEQUENCE: 1048<br>000 | moltype = | length = |
| SEQ ID NO: 1049<br>SEQUENCE: 1049<br>000 | moltype = | length = |
| SEQ ID NO: 1050<br>SEQUENCE: 1050<br>000 | moltype = | length = |
| SEQ ID NO: 1051<br>SEQUENCE: 1051<br>000 | moltype = | length = |
| SEQ ID NO: 1052<br>SEQUENCE: 1052<br>000 | moltype = | length = |
| SEQ ID NO: 1053<br>SEQUENCE: 1053<br>000 | moltype = | length = |
| SEQ ID NO: 1054<br>SEQUENCE: 1054<br>000 | moltype = | length = |
| SEQ ID NO: 1055<br>SEQUENCE: 1055<br>000 | moltype = | length = |
| SEQ ID NO: 1056<br>SEQUENCE: 1056<br>000 | moltype = | length = |

-continued

| | | |
|---|---|---|
| SEQ ID NO: 1057 SEQUENCE: 1057 | moltype = | length = 000 |
| SEQ ID NO: 1058 SEQUENCE: 1058 | moltype = | length = 000 |
| SEQ ID NO: 1059 SEQUENCE: 1059 | moltype = | length = 000 |
| SEQ ID NO: 1060 SEQUENCE: 1060 | moltype = | length = 000 |
| SEQ ID NO: 1061 SEQUENCE: 1061 | moltype = | length = 000 |
| SEQ ID NO: 1062 SEQUENCE: 1062 | moltype = | length = 000 |
| SEQ ID NO: 1063 SEQUENCE: 1063 | moltype = | length = 000 |
| SEQ ID NO: 1064 SEQUENCE: 1064 | moltype = | length = 000 |
| SEQ ID NO: 1065 SEQUENCE: 1065 | moltype = | length = 000 |
| SEQ ID NO: 1066 SEQUENCE: 1066 | moltype = | length = 000 |
| SEQ ID NO: 1067 SEQUENCE: 1067 | moltype = | length = 000 |
| SEQ ID NO: 1068 SEQUENCE: 1068 | moltype = | length = 000 |
| SEQ ID NO: 1069 SEQUENCE: 1069 | moltype = | length = 000 |
| SEQ ID NO: 1070 SEQUENCE: 1070 | moltype = | length = 000 |
| SEQ ID NO: 1071 SEQUENCE: 1071 | moltype = | length = 000 |
| SEQ ID NO: 1072 SEQUENCE: 1072 | moltype = | length = 000 |
| SEQ ID NO: 1073 SEQUENCE: 1073 | moltype = | length = 000 |
| SEQ ID NO: 1074 SEQUENCE: 1074 | moltype = | length = 000 |
| SEQ ID NO: 1075 SEQUENCE: 1075 | moltype = | length = 000 |
| SEQ ID NO: 1076 SEQUENCE: 1076 | moltype = | length = 000 |

| | | |
|---|---|---|
| SEQ ID NO: 1077 SEQUENCE: 1077 | moltype = 000 | length = |
| SEQ ID NO: 1078 SEQUENCE: 1078 | moltype = 000 | length = |
| SEQ ID NO: 1079 SEQUENCE: 1079 | moltype = 000 | length = |
| SEQ ID NO: 1080 SEQUENCE: 1080 | moltype = 000 | length = |
| SEQ ID NO: 1081 SEQUENCE: 1081 | moltype = 000 | length = |
| SEQ ID NO: 1082 SEQUENCE: 1082 | moltype = 000 | length = |
| SEQ ID NO: 1083 SEQUENCE: 1083 | moltype = 000 | length = |
| SEQ ID NO: 1084 SEQUENCE: 1084 | moltype = 000 | length = |
| SEQ ID NO: 1085 SEQUENCE: 1085 | moltype = 000 | length = |
| SEQ ID NO: 1086 SEQUENCE: 1086 | moltype = 000 | length = |
| SEQ ID NO: 1087 SEQUENCE: 1087 | moltype = 000 | length = |
| SEQ ID NO: 1088 SEQUENCE: 1088 | moltype = 000 | length = |
| SEQ ID NO: 1089 SEQUENCE: 1089 | moltype = 000 | length = |
| SEQ ID NO: 1090 SEQUENCE: 1090 | moltype = 000 | length = |
| SEQ ID NO: 1091 SEQUENCE: 1091 | moltype = 000 | length = |
| SEQ ID NO: 1092 SEQUENCE: 1092 | moltype = 000 | length = |
| SEQ ID NO: 1093 SEQUENCE: 1093 | moltype = 000 | length = |
| SEQ ID NO: 1094 SEQUENCE: 1094 | moltype = 000 | length = |
| SEQ ID NO: 1095 SEQUENCE: 1095 | moltype = 000 | length = |
| SEQ ID NO: 1096 SEQUENCE: 1096 | moltype = | length = |

000

SEQ ID NO: 1097         moltype =     length =
SEQUENCE: 1097
000

SEQ ID NO: 1098         moltype =     length =
SEQUENCE: 1098
000

SEQ ID NO: 1099         moltype =     length =
SEQUENCE: 1099
000

SEQ ID NO: 1100         moltype =     length =
SEQUENCE: 1100
000

SEQ ID NO: 1101         moltype =     length =
SEQUENCE: 1101
000

SEQ ID NO: 1102         moltype =     length =
SEQUENCE: 1102
000

SEQ ID NO: 1103         moltype =     length =
SEQUENCE: 1103
000

SEQ ID NO: 1104         moltype =     length =
SEQUENCE: 1104
000

SEQ ID NO: 1105         moltype =     length =
SEQUENCE: 1105
000

SEQ ID NO: 1106         moltype =     length =
SEQUENCE: 1106
000

SEQ ID NO: 1107         moltype =     length =
SEQUENCE: 1107
000

SEQ ID NO: 1108         moltype =     length =
SEQUENCE: 1108
000

SEQ ID NO: 1109         moltype =     length =
SEQUENCE: 1109
000

SEQ ID NO: 1110         moltype =     length =
SEQUENCE: 1110
000

SEQ ID NO: 1111         moltype =     length =
SEQUENCE: 1111
000

SEQ ID NO: 1112         moltype =     length =
SEQUENCE: 1112
000

SEQ ID NO: 1113         moltype =     length =
SEQUENCE: 1113
000

SEQ ID NO: 1114         moltype =     length =
SEQUENCE: 1114
000

SEQ ID NO: 1115         moltype =     length =
SEQUENCE: 1115
000

SEQ ID NO: 1116         moltype =     length =

```
SEQUENCE: 1116
000

SEQ ID NO: 1117          moltype =    length =
SEQUENCE: 1117
000

SEQ ID NO: 1118          moltype =    length =
SEQUENCE: 1118
000

SEQ ID NO: 1119          moltype =    length =
SEQUENCE: 1119
000

SEQ ID NO: 1120          moltype =    length =
SEQUENCE: 1120
000

SEQ ID NO: 1121          moltype =    length =
SEQUENCE: 1121
000

SEQ ID NO: 1122          moltype =    length =
SEQUENCE: 1122
000

SEQ ID NO: 1123          moltype =    length =
SEQUENCE: 1123
000

SEQ ID NO: 1124          moltype =    length =
SEQUENCE: 1124
000

SEQ ID NO: 1125          moltype =    length =
SEQUENCE: 1125
000

SEQ ID NO: 1126          moltype =    length =
SEQUENCE: 1126
000

SEQ ID NO: 1127          moltype =    length =
SEQUENCE: 1127
000

SEQ ID NO: 1128          moltype =    length =
SEQUENCE: 1128
000

SEQ ID NO: 1129          moltype =    length =
SEQUENCE: 1129
000

SEQ ID NO: 1130          moltype =    length =
SEQUENCE: 1130
000

SEQ ID NO: 1131          moltype =    length =
SEQUENCE: 1131
000

SEQ ID NO: 1132          moltype =    length =
SEQUENCE: 1132
000

SEQ ID NO: 1133          moltype =    length =
SEQUENCE: 1133
000

SEQ ID NO: 1134          moltype =    length =
SEQUENCE: 1134
000

SEQ ID NO: 1135          moltype =    length =
SEQUENCE: 1135
000
```

-continued

| | | |
|---|---|---|
| SEQ ID NO: 1136<br>SEQUENCE: 1136<br>000 | moltype = | length = |
| SEQ ID NO: 1137<br>SEQUENCE: 1137<br>000 | moltype = | length = |
| SEQ ID NO: 1138<br>SEQUENCE: 1138<br>000 | moltype = | length = |
| SEQ ID NO: 1139<br>SEQUENCE: 1139<br>000 | moltype = | length = |
| SEQ ID NO: 1140<br>SEQUENCE: 1140<br>000 | moltype = | length = |
| SEQ ID NO: 1141<br>SEQUENCE: 1141<br>000 | moltype = | length = |
| SEQ ID NO: 1142<br>SEQUENCE: 1142<br>000 | moltype = | length = |
| SEQ ID NO: 1143<br>SEQUENCE: 1143<br>000 | moltype = | length = |
| SEQ ID NO: 1144<br>SEQUENCE: 1144<br>000 | moltype = | length = |
| SEQ ID NO: 1145<br>SEQUENCE: 1145<br>000 | moltype = | length = |
| SEQ ID NO: 1146<br>SEQUENCE: 1146<br>000 | moltype = | length = |
| SEQ ID NO: 1147<br>SEQUENCE: 1147<br>000 | moltype = | length = |
| SEQ ID NO: 1148<br>SEQUENCE: 1148<br>000 | moltype = | length = |
| SEQ ID NO: 1149<br>SEQUENCE: 1149<br>000 | moltype = | length = |
| SEQ ID NO: 1150<br>SEQUENCE: 1150<br>000 | moltype = | length = |
| SEQ ID NO: 1151<br>SEQUENCE: 1151<br>000 | moltype = | length = |
| SEQ ID NO: 1152<br>SEQUENCE: 1152<br>000 | moltype = | length = |
| SEQ ID NO: 1153<br>SEQUENCE: 1153<br>000 | moltype = | length = |
| SEQ ID NO: 1154<br>SEQUENCE: 1154<br>000 | moltype = | length = |
| SEQ ID NO: 1155<br>SEQUENCE: 1155<br>000 | moltype = | length = |

```
SEQ ID NO: 1156         moltype =    length =
SEQUENCE: 1156
000

SEQ ID NO: 1157         moltype =    length =
SEQUENCE: 1157
000

SEQ ID NO: 1158         moltype =    length =
SEQUENCE: 1158
000

SEQ ID NO: 1159         moltype =    length =
SEQUENCE: 1159
000

SEQ ID NO: 1160         moltype =    length =
SEQUENCE: 1160
000

SEQ ID NO: 1161         moltype =    length =
SEQUENCE: 1161
000

SEQ ID NO: 1162         moltype =    length =
SEQUENCE: 1162
000

SEQ ID NO: 1163         moltype =    length =
SEQUENCE: 1163
000

SEQ ID NO: 1164         moltype =    length =
SEQUENCE: 1164
000

SEQ ID NO: 1165         moltype =    length =
SEQUENCE: 1165
000

SEQ ID NO: 1166         moltype =    length =
SEQUENCE: 1166
000

SEQ ID NO: 1167         moltype =    length =
SEQUENCE: 1167
000

SEQ ID NO: 1168         moltype =    length =
SEQUENCE: 1168
000

SEQ ID NO: 1169         moltype =    length =
SEQUENCE: 1169
000

SEQ ID NO: 1170         moltype =    length =
SEQUENCE: 1170
000

SEQ ID NO: 1171         moltype =    length =
SEQUENCE: 1171
000

SEQ ID NO: 1172         moltype =    length =
SEQUENCE: 1172
000

SEQ ID NO: 1173         moltype =    length =
SEQUENCE: 1173
000

SEQ ID NO: 1174         moltype =    length =
SEQUENCE: 1174
000

SEQ ID NO: 1175         moltype =    length =
SEQUENCE: 1175
```

000

SEQ ID NO: 1176         moltype =    length =
SEQUENCE: 1176
000

SEQ ID NO: 1177         moltype =    length =
SEQUENCE: 1177
000

SEQ ID NO: 1178         moltype =    length =
SEQUENCE: 1178
000

SEQ ID NO: 1179         moltype =    length =
SEQUENCE: 1179
000

SEQ ID NO: 1180         moltype =    length =
SEQUENCE: 1180
000

SEQ ID NO: 1181         moltype =    length =
SEQUENCE: 1181
000

SEQ ID NO: 1182         moltype =    length =
SEQUENCE: 1182
000

SEQ ID NO: 1183         moltype =    length =
SEQUENCE: 1183
000

SEQ ID NO: 1184         moltype =    length =
SEQUENCE: 1184
000

SEQ ID NO: 1185         moltype =    length =
SEQUENCE: 1185
000

SEQ ID NO: 1186         moltype =    length =
SEQUENCE: 1186
000

SEQ ID NO: 1187         moltype =    length =
SEQUENCE: 1187
000

SEQ ID NO: 1188         moltype =    length =
SEQUENCE: 1188
000

SEQ ID NO: 1189         moltype =    length =
SEQUENCE: 1189
000

SEQ ID NO: 1190         moltype =    length =
SEQUENCE: 1190
000

SEQ ID NO: 1191         moltype =    length =
SEQUENCE: 1191
000

SEQ ID NO: 1192         moltype =    length =
SEQUENCE: 1192
000

SEQ ID NO: 1193         moltype =    length =
SEQUENCE: 1193
000

SEQ ID NO: 1194         moltype =    length =
SEQUENCE: 1194
000

SEQ ID NO: 1195         moltype =    length =

-continued

| | | |
|---|---|---|
| SEQ ID NO: 1195 SEQUENCE: 1195 000 | | |
| SEQ ID NO: 1196 SEQUENCE: 1196 000 | moltype = | length = |
| SEQ ID NO: 1197 SEQUENCE: 1197 000 | moltype = | length = |
| SEQ ID NO: 1198 SEQUENCE: 1198 000 | moltype = | length = |
| SEQ ID NO: 1199 SEQUENCE: 1199 000 | moltype = | length = |
| SEQ ID NO: 1200 SEQUENCE: 1200 000 | moltype = | length = |
| SEQ ID NO: 1201 SEQUENCE: 1201 000 | moltype = | length = |
| SEQ ID NO: 1202 SEQUENCE: 1202 000 | moltype = | length = |
| SEQ ID NO: 1203 SEQUENCE: 1203 000 | moltype = | length = |
| SEQ ID NO: 1204 SEQUENCE: 1204 000 | moltype = | length = |
| SEQ ID NO: 1205 SEQUENCE: 1205 000 | moltype = | length = |
| SEQ ID NO: 1206 SEQUENCE: 1206 000 | moltype = | length = |
| SEQ ID NO: 1207 SEQUENCE: 1207 000 | moltype = | length = |
| SEQ ID NO: 1208 SEQUENCE: 1208 000 | moltype = | length = |
| SEQ ID NO: 1209 SEQUENCE: 1209 000 | moltype = | length = |
| SEQ ID NO: 1210 SEQUENCE: 1210 000 | moltype = | length = |
| SEQ ID NO: 1211 SEQUENCE: 1211 000 | moltype = | length = |
| SEQ ID NO: 1212 SEQUENCE: 1212 000 | moltype = | length = |
| SEQ ID NO: 1213 SEQUENCE: 1213 000 | moltype = | length = |
| SEQ ID NO: 1214 SEQUENCE: 1214 000 | moltype = | length = |

-continued

| SEQ ID NO: 1215 SEQUENCE: 1215 | moltype = | length = 000 |
| SEQ ID NO: 1216 SEQUENCE: 1216 | moltype = | length = 000 |
| SEQ ID NO: 1217 SEQUENCE: 1217 | moltype = | length = 000 |
| SEQ ID NO: 1218 SEQUENCE: 1218 | moltype = | length = 000 |
| SEQ ID NO: 1219 SEQUENCE: 1219 | moltype = | length = 000 |
| SEQ ID NO: 1220 SEQUENCE: 1220 | moltype = | length = 000 |
| SEQ ID NO: 1221 SEQUENCE: 1221 | moltype = | length = 000 |
| SEQ ID NO: 1222 SEQUENCE: 1222 | moltype = | length = 000 |
| SEQ ID NO: 1223 SEQUENCE: 1223 | moltype = | length = 000 |
| SEQ ID NO: 1224 SEQUENCE: 1224 | moltype = | length = 000 |
| SEQ ID NO: 1225 SEQUENCE: 1225 | moltype = | length = 000 |
| SEQ ID NO: 1226 SEQUENCE: 1226 | moltype = | length = 000 |
| SEQ ID NO: 1227 SEQUENCE: 1227 | moltype = | length = 000 |
| SEQ ID NO: 1228 SEQUENCE: 1228 | moltype = | length = 000 |
| SEQ ID NO: 1229 SEQUENCE: 1229 | moltype = | length = 000 |
| SEQ ID NO: 1230 SEQUENCE: 1230 | moltype = | length = 000 |
| SEQ ID NO: 1231 SEQUENCE: 1231 | moltype = | length = 000 |
| SEQ ID NO: 1232 SEQUENCE: 1232 | moltype = | length = 000 |
| SEQ ID NO: 1233 SEQUENCE: 1233 | moltype = | length = 000 |
| SEQ ID NO: 1234 SEQUENCE: 1234 | moltype = | length = 000 |

| SEQ ID NO: 1235 | moltype = | length = |
|---|---|---|
| SEQUENCE: 1235 | | |
| 000 | | |

| SEQ ID NO: 1236 | moltype = | length = |
|---|---|---|
| SEQUENCE: 1236 | | |
| 000 | | |

| SEQ ID NO: 1237 | moltype = | length = |
|---|---|---|
| SEQUENCE: 1237 | | |
| 000 | | |

| SEQ ID NO: 1238 | moltype = | length = |
|---|---|---|
| SEQUENCE: 1238 | | |
| 000 | | |

| SEQ ID NO: 1239 | moltype = | length = |
|---|---|---|
| SEQUENCE: 1239 | | |
| 000 | | |

| SEQ ID NO: 1240 | moltype = | length = |
|---|---|---|
| SEQUENCE: 1240 | | |
| 000 | | |

| SEQ ID NO: 1241 | moltype = | length = |
|---|---|---|
| SEQUENCE: 1241 | | |
| 000 | | |

| SEQ ID NO: 1242 | moltype = | length = |
|---|---|---|
| SEQUENCE: 1242 | | |
| 000 | | |

| SEQ ID NO: 1243 | moltype = | length = |
|---|---|---|
| SEQUENCE: 1243 | | |
| 000 | | |

| SEQ ID NO: 1244 | moltype = | length = |
|---|---|---|
| SEQUENCE: 1244 | | |
| 000 | | |

| SEQ ID NO: 1245 | moltype = | length = |
|---|---|---|
| SEQUENCE: 1245 | | |
| 000 | | |

| SEQ ID NO: 1246 | moltype = | length = |
|---|---|---|
| SEQUENCE: 1246 | | |
| 000 | | |

| SEQ ID NO: 1247 | moltype = | length = |
|---|---|---|
| SEQUENCE: 1247 | | |
| 000 | | |

| SEQ ID NO: 1248 | moltype = | length = |
|---|---|---|
| SEQUENCE: 1248 | | |
| 000 | | |

| SEQ ID NO: 1249 | moltype = | length = |
|---|---|---|
| SEQUENCE: 1249 | | |
| 000 | | |

| SEQ ID NO: 1250 | moltype = | length = |
|---|---|---|
| SEQUENCE: 1250 | | |
| 000 | | |

| SEQ ID NO: 1251 | moltype = | length = |
|---|---|---|
| SEQUENCE: 1251 | | |
| 000 | | |

| SEQ ID NO: 1252 | moltype = | length = |
|---|---|---|
| SEQUENCE: 1252 | | |
| 000 | | |

| SEQ ID NO: 1253 | moltype = | length = |
|---|---|---|
| SEQUENCE: 1253 | | |
| 000 | | |

| SEQ ID NO: 1254 | moltype = | length = |
|---|---|---|
| SEQUENCE: 1254 | | |

-continued

000

SEQ ID NO: 1255        moltype =    length =
SEQUENCE: 1255
000

SEQ ID NO: 1256        moltype =    length =
SEQUENCE: 1256
000

SEQ ID NO: 1257        moltype =    length =
SEQUENCE: 1257
000

SEQ ID NO: 1258        moltype =    length =
SEQUENCE: 1258
000

SEQ ID NO: 1259        moltype =    length =
SEQUENCE: 1259
000

SEQ ID NO: 1260        moltype =    length =
SEQUENCE: 1260
000

SEQ ID NO: 1261        moltype =    length =
SEQUENCE: 1261
000

SEQ ID NO: 1262        moltype =    length =
SEQUENCE: 1262
000

SEQ ID NO: 1263        moltype =    length =
SEQUENCE: 1263
000

SEQ ID NO: 1264        moltype =    length =
SEQUENCE: 1264
000

SEQ ID NO: 1265        moltype =    length =
SEQUENCE: 1265
000

SEQ ID NO: 1266        moltype =    length =
SEQUENCE: 1266
000

SEQ ID NO: 1267        moltype =    length =
SEQUENCE: 1267
000

SEQ ID NO: 1268        moltype =    length =
SEQUENCE: 1268
000

SEQ ID NO: 1269        moltype =    length =
SEQUENCE: 1269
000

SEQ ID NO: 1270        moltype =    length =
SEQUENCE: 1270
000

SEQ ID NO: 1271        moltype =    length =
SEQUENCE: 1271
000

SEQ ID NO: 1272        moltype =    length =
SEQUENCE: 1272
000

SEQ ID NO: 1273        moltype =    length =
SEQUENCE: 1273
000

SEQ ID NO: 1274        moltype =    length =

```
SEQUENCE: 1274
000

SEQ ID NO: 1275         moltype =   length =
SEQUENCE: 1275
000

SEQ ID NO: 1276         moltype =   length =
SEQUENCE: 1276
000

SEQ ID NO: 1277         moltype =   length =
SEQUENCE: 1277
000

SEQ ID NO: 1278         moltype =   length =
SEQUENCE: 1278
000

SEQ ID NO: 1279         moltype =   length =
SEQUENCE: 1279
000

SEQ ID NO: 1280         moltype =   length =
SEQUENCE: 1280
000

SEQ ID NO: 1281         moltype =   length =
SEQUENCE: 1281
000

SEQ ID NO: 1282         moltype =   length =
SEQUENCE: 1282
000

SEQ ID NO: 1283         moltype =   length =
SEQUENCE: 1283
000

SEQ ID NO: 1284         moltype =   length =
SEQUENCE: 1284
000

SEQ ID NO: 1285         moltype =   length =
SEQUENCE: 1285
000

SEQ ID NO: 1286         moltype =   length =
SEQUENCE: 1286
000

SEQ ID NO: 1287         moltype =   length =
SEQUENCE: 1287
000

SEQ ID NO: 1288         moltype =   length =
SEQUENCE: 1288
000

SEQ ID NO: 1289         moltype =   length =
SEQUENCE: 1289
000

SEQ ID NO: 1290         moltype =   length =
SEQUENCE: 1290
000

SEQ ID NO: 1291         moltype =   length =
SEQUENCE: 1291
000

SEQ ID NO: 1292         moltype =   length =
SEQUENCE: 1292
000

SEQ ID NO: 1293         moltype =   length =
SEQUENCE: 1293
000
```

| | | |
|---|---|---|
| SEQ ID NO: 1294<br>SEQUENCE: 1294<br>000 | moltype = | length = |
| SEQ ID NO: 1295<br>SEQUENCE: 1295<br>000 | moltype = | length = |
| SEQ ID NO: 1296<br>SEQUENCE: 1296<br>000 | moltype = | length = |
| SEQ ID NO: 1297<br>SEQUENCE: 1297<br>000 | moltype = | length = |
| SEQ ID NO: 1298<br>SEQUENCE: 1298<br>000 | moltype = | length = |
| SEQ ID NO: 1299<br>SEQUENCE: 1299<br>000 | moltype = | length = |
| SEQ ID NO: 1300<br>SEQUENCE: 1300<br>000 | moltype = | length = |
| SEQ ID NO: 1301<br>SEQUENCE: 1301<br>000 | moltype = | length = |
| SEQ ID NO: 1302<br>SEQUENCE: 1302<br>000 | moltype = | length = |
| SEQ ID NO: 1303<br>SEQUENCE: 1303<br>000 | moltype = | length = |
| SEQ ID NO: 1304<br>SEQUENCE: 1304<br>000 | moltype = | length = |
| SEQ ID NO: 1305<br>SEQUENCE: 1305<br>000 | moltype = | length = |
| SEQ ID NO: 1306<br>SEQUENCE: 1306<br>000 | moltype = | length = |
| SEQ ID NO: 1307<br>SEQUENCE: 1307<br>000 | moltype = | length = |
| SEQ ID NO: 1308<br>SEQUENCE: 1308<br>000 | moltype = | length = |
| SEQ ID NO: 1309<br>SEQUENCE: 1309<br>000 | moltype = | length = |
| SEQ ID NO: 1310<br>SEQUENCE: 1310<br>000 | moltype = | length = |
| SEQ ID NO: 1311<br>SEQUENCE: 1311<br>000 | moltype = | length = |
| SEQ ID NO: 1312<br>SEQUENCE: 1312<br>000 | moltype = | length = |
| SEQ ID NO: 1313<br>SEQUENCE: 1313<br>000 | moltype = | length = |

| SEQ ID NO: 1314 | moltype = | length = |
| --- | --- | --- |
| SEQUENCE: 1314 | | |
| 000 | | |

| SEQ ID NO: 1315 | moltype = | length = |
| --- | --- | --- |
| SEQUENCE: 1315 | | |
| 000 | | |

| SEQ ID NO: 1316 | moltype = | length = |
| --- | --- | --- |
| SEQUENCE: 1316 | | |
| 000 | | |

| SEQ ID NO: 1317 | moltype = | length = |
| --- | --- | --- |
| SEQUENCE: 1317 | | |
| 000 | | |

| SEQ ID NO: 1318 | moltype = | length = |
| --- | --- | --- |
| SEQUENCE: 1318 | | |
| 000 | | |

| SEQ ID NO: 1319 | moltype = | length = |
| --- | --- | --- |
| SEQUENCE: 1319 | | |
| 000 | | |

| SEQ ID NO: 1320 | moltype = | length = |
| --- | --- | --- |
| SEQUENCE: 1320 | | |
| 000 | | |

| SEQ ID NO: 1321 | moltype = | length = |
| --- | --- | --- |
| SEQUENCE: 1321 | | |
| 000 | | |

| SEQ ID NO: 1322 | moltype = | length = |
| --- | --- | --- |
| SEQUENCE: 1322 | | |
| 000 | | |

| SEQ ID NO: 1323 | moltype = | length = |
| --- | --- | --- |
| SEQUENCE: 1323 | | |
| 000 | | |

| SEQ ID NO: 1324 | moltype = | length = |
| --- | --- | --- |
| SEQUENCE: 1324 | | |
| 000 | | |

| SEQ ID NO: 1325 | moltype = | length = |
| --- | --- | --- |
| SEQUENCE: 1325 | | |
| 000 | | |

| SEQ ID NO: 1326 | moltype = | length = |
| --- | --- | --- |
| SEQUENCE: 1326 | | |
| 000 | | |

| SEQ ID NO: 1327 | moltype = | length = |
| --- | --- | --- |
| SEQUENCE: 1327 | | |
| 000 | | |

| SEQ ID NO: 1328 | moltype = | length = |
| --- | --- | --- |
| SEQUENCE: 1328 | | |
| 000 | | |

| SEQ ID NO: 1329 | moltype = | length = |
| --- | --- | --- |
| SEQUENCE: 1329 | | |
| 000 | | |

| SEQ ID NO: 1330 | moltype = | length = |
| --- | --- | --- |
| SEQUENCE: 1330 | | |
| 000 | | |

| SEQ ID NO: 1331 | moltype = | length = |
| --- | --- | --- |
| SEQUENCE: 1331 | | |
| 000 | | |

| SEQ ID NO: 1332 | moltype = | length = |
| --- | --- | --- |
| SEQUENCE: 1332 | | |
| 000 | | |

| SEQ ID NO: 1333 | moltype = | length = |
| --- | --- | --- |
| SEQUENCE: 1333 | | |

000

SEQ ID NO: 1334         moltype =    length =
SEQUENCE: 1334
000

SEQ ID NO: 1335         moltype =    length =
SEQUENCE: 1335
000

SEQ ID NO: 1336         moltype =    length =
SEQUENCE: 1336
000

SEQ ID NO: 1337         moltype =    length =
SEQUENCE: 1337
000

SEQ ID NO: 1338         moltype =    length =
SEQUENCE: 1338
000

SEQ ID NO: 1339         moltype =    length =
SEQUENCE: 1339
000

SEQ ID NO: 1340         moltype =    length =
SEQUENCE: 1340
000

SEQ ID NO: 1341         moltype =    length =
SEQUENCE: 1341
000

SEQ ID NO: 1342         moltype =    length =
SEQUENCE: 1342
000

SEQ ID NO: 1343         moltype =    length =
SEQUENCE: 1343
000

SEQ ID NO: 1344         moltype =    length =
SEQUENCE: 1344
000

SEQ ID NO: 1345         moltype =    length =
SEQUENCE: 1345
000

SEQ ID NO: 1346         moltype =    length =
SEQUENCE: 1346
000

SEQ ID NO: 1347         moltype =    length =
SEQUENCE: 1347
000

SEQ ID NO: 1348         moltype =    length =
SEQUENCE: 1348
000

SEQ ID NO: 1349         moltype =    length =
SEQUENCE: 1349
000

SEQ ID NO: 1350         moltype =    length =
SEQUENCE: 1350
000

SEQ ID NO: 1351         moltype =    length =
SEQUENCE: 1351
000

SEQ ID NO: 1352         moltype =    length =
SEQUENCE: 1352
000

SEQ ID NO: 1353         moltype =    length =

| | | |
|---|---|---|
| SEQUENCE: 1353 000 | | |
| SEQ ID NO: 1354 SEQUENCE: 1354 000 | moltype = | length = |
| SEQ ID NO: 1355 SEQUENCE: 1355 000 | moltype = | length = |
| SEQ ID NO: 1356 SEQUENCE: 1356 000 | moltype = | length = |
| SEQ ID NO: 1357 SEQUENCE: 1357 000 | moltype = | length = |
| SEQ ID NO: 1358 SEQUENCE: 1358 000 | moltype = | length = |
| SEQ ID NO: 1359 SEQUENCE: 1359 000 | moltype = | length = |
| SEQ ID NO: 1360 SEQUENCE: 1360 000 | moltype = | length = |
| SEQ ID NO: 1361 SEQUENCE: 1361 000 | moltype = | length = |
| SEQ ID NO: 1362 SEQUENCE: 1362 000 | moltype = | length = |
| SEQ ID NO: 1363 SEQUENCE: 1363 000 | moltype = | length = |
| SEQ ID NO: 1364 SEQUENCE: 1364 000 | moltype = | length = |
| SEQ ID NO: 1365 SEQUENCE: 1365 000 | moltype = | length = |
| SEQ ID NO: 1366 SEQUENCE: 1366 000 | moltype = | length = |
| SEQ ID NO: 1367 SEQUENCE: 1367 000 | moltype = | length = |
| SEQ ID NO: 1368 SEQUENCE: 1368 000 | moltype = | length = |
| SEQ ID NO: 1369 SEQUENCE: 1369 000 | moltype = | length = |
| SEQ ID NO: 1370 SEQUENCE: 1370 000 | moltype = | length = |
| SEQ ID NO: 1371 SEQUENCE: 1371 000 | moltype = | length = |
| SEQ ID NO: 1372 SEQUENCE: 1372 000 | moltype = | length = |

| | | |
|---|---|---|
| SEQ ID NO: 1373 SEQUENCE: 1373 | moltype = length = | |
| 000 | | |
| SEQ ID NO: 1374 FEATURE REGION source | moltype = AA  length = 8 Location/Qualifiers 1..8 note = AAV peptide sequence 1..8 mol_type = protein organism = synthetic construct | |
| SEQUENCE: 1374 LSKTQTLK | | 8 |
| SEQ ID NO: 1375 FEATURE REGION source | moltype = AA  length = 10 Location/Qualifiers 1..10 note = AAV peptide sequence 1..10 mol_type = protein organism = synthetic construct | |
| SEQUENCE: 1375 LSKTDPQTLK | | 10 |
| SEQ ID NO: 1376 SEQUENCE: 1376 000 | moltype = length = | |
| SEQ ID NO: 1377 SEQUENCE: 1377 000 | moltype = length = | |
| SEQ ID NO: 1378 SEQUENCE: 1378 000 | moltype = length = | |
| SEQ ID NO: 1379 SEQUENCE: 1379 000 | moltype = length = | |
| SEQ ID NO: 1380 SEQUENCE: 1380 000 | moltype = length = | |
| SEQ ID NO: 1381 SEQUENCE: 1381 000 | moltype = length = | |
| SEQ ID NO: 1382 SEQUENCE: 1382 000 | moltype = length = | |
| SEQ ID NO: 1383 SEQUENCE: 1383 000 | moltype = length = | |
| SEQ ID NO: 1384 SEQUENCE: 1384 000 | moltype = length = | |
| SEQ ID NO: 1385 SEQUENCE: 1385 000 | moltype = length = | |
| SEQ ID NO: 1386 SEQUENCE: 1386 000 | moltype = length = | |
| SEQ ID NO: 1387 SEQUENCE: 1387 000 | moltype = length = | |
| SEQ ID NO: 1388 SEQUENCE: 1388 000 | moltype = length = | |
| SEQ ID NO: 1389 SEQUENCE: 1389 000 | moltype = length = | |

| | | |
|---|---|---|
| SEQ ID NO: 1390 SEQUENCE: 1390 000 | moltype = | length = |
| SEQ ID NO: 1391 SEQUENCE: 1391 000 | moltype = | length = |
| SEQ ID NO: 1392 SEQUENCE: 1392 000 | moltype = | length = |
| SEQ ID NO: 1393 SEQUENCE: 1393 000 | moltype = | length = |
| SEQ ID NO: 1394 SEQUENCE: 1394 000 | moltype = | length = |
| SEQ ID NO: 1395 SEQUENCE: 1395 000 | moltype = | length = |
| SEQ ID NO: 1396 SEQUENCE: 1396 000 | moltype = | length = |
| SEQ ID NO: 1397 SEQUENCE: 1397 000 | moltype = | length = |
| SEQ ID NO: 1398 SEQUENCE: 1398 000 | moltype = | length = |
| SEQ ID NO: 1399 SEQUENCE: 1399 000 | moltype = | length = |
| SEQ ID NO: 1400 SEQUENCE: 1400 000 | moltype = | length = |
| SEQ ID NO: 1401 SEQUENCE: 1401 000 | moltype = | length = |
| SEQ ID NO: 1402 SEQUENCE: 1402 000 | moltype = | length = |
| SEQ ID NO: 1403 SEQUENCE: 1403 000 | moltype = | length = |
| SEQ ID NO: 1404 SEQUENCE: 1404 000 | moltype = | length = |
| SEQ ID NO: 1405 SEQUENCE: 1405 000 | moltype = | length = |
| SEQ ID NO: 1406 SEQUENCE: 1406 000 | moltype = | length = |
| SEQ ID NO: 1407 SEQUENCE: 1407 000 | moltype = | length = |
| SEQ ID NO: 1408 SEQUENCE: 1408 000 | moltype = | length = |
| SEQ ID NO: 1409 SEQUENCE: 1409 | moltype = | length = |

-continued

000

SEQ ID NO: 1410    moltype =    length =
SEQUENCE: 1410
000

SEQ ID NO: 1411    moltype =    length =
SEQUENCE: 1411
000

SEQ ID NO: 1412    moltype =    length =
SEQUENCE: 1412
000

SEQ ID NO: 1413    moltype =    length =
SEQUENCE: 1413
000

SEQ ID NO: 1414    moltype =    length =
SEQUENCE: 1414
000

SEQ ID NO: 1415    moltype =    length =
SEQUENCE: 1415
000

SEQ ID NO: 1416    moltype =    length =
SEQUENCE: 1416
000

SEQ ID NO: 1417    moltype =    length =
SEQUENCE: 1417
000

SEQ ID NO: 1418    moltype =    length =
SEQUENCE: 1418
000

SEQ ID NO: 1419    moltype =    length =
SEQUENCE: 1419
000

SEQ ID NO: 1420    moltype =    length =
SEQUENCE: 1420
000

SEQ ID NO: 1421    moltype =    length =
SEQUENCE: 1421
000

SEQ ID NO: 1422    moltype =    length =
SEQUENCE: 1422
000

SEQ ID NO: 1423    moltype =    length =
SEQUENCE: 1423
000

SEQ ID NO: 1424    moltype =    length =
SEQUENCE: 1424
000

SEQ ID NO: 1425    moltype =    length =
SEQUENCE: 1425
000

SEQ ID NO: 1426    moltype =    length =
SEQUENCE: 1426
000

SEQ ID NO: 1427    moltype =    length =
SEQUENCE: 1427
000

SEQ ID NO: 1428    moltype =    length =
SEQUENCE: 1428
000

SEQ ID NO: 1429    moltype =    length =

```
SEQUENCE: 1429
000

SEQ ID NO: 1430        moltype =    length =
SEQUENCE: 1430
000

SEQ ID NO: 1431        moltype =    length =
SEQUENCE: 1431
000

SEQ ID NO: 1432        moltype =    length =
SEQUENCE: 1432
000

SEQ ID NO: 1433        moltype =    length =
SEQUENCE: 1433
000

SEQ ID NO: 1434        moltype =    length =
SEQUENCE: 1434
000

SEQ ID NO: 1435        moltype =    length =
SEQUENCE: 1435
000

SEQ ID NO: 1436        moltype =    length =
SEQUENCE: 1436
000

SEQ ID NO: 1437        moltype =    length =
SEQUENCE: 1437
000

SEQ ID NO: 1438        moltype =    length =
SEQUENCE: 1438
000

SEQ ID NO: 1439        moltype =    length =
SEQUENCE: 1439
000

SEQ ID NO: 1440        moltype =    length =
SEQUENCE: 1440
000

SEQ ID NO: 1441        moltype =    length =
SEQUENCE: 1441
000

SEQ ID NO: 1442        moltype =    length =
SEQUENCE: 1442
000

SEQ ID NO: 1443        moltype =    length =
SEQUENCE: 1443
000

SEQ ID NO: 1444        moltype =    length =
SEQUENCE: 1444
000

SEQ ID NO: 1445        moltype =    length =
SEQUENCE: 1445
000

SEQ ID NO: 1446        moltype =    length =
SEQUENCE: 1446
000

SEQ ID NO: 1447        moltype =    length =
SEQUENCE: 1447
000

SEQ ID NO: 1448        moltype =    length =
SEQUENCE: 1448
000
```

-continued

| | | |
|---|---|---|
| SEQ ID NO: 1449<br>SEQUENCE: 1449<br>000 | moltype = | length = |
| SEQ ID NO: 1450<br>SEQUENCE: 1450<br>000 | moltype = | length = |
| SEQ ID NO: 1451<br>SEQUENCE: 1451<br>000 | moltype = | length = |
| SEQ ID NO: 1452<br>SEQUENCE: 1452<br>000 | moltype = | length = |
| SEQ ID NO: 1453<br>SEQUENCE: 1453<br>000 | moltype = | length = |
| SEQ ID NO: 1454<br>SEQUENCE: 1454<br>000 | moltype = | length = |
| SEQ ID NO: 1455<br>SEQUENCE: 1455<br>000 | moltype = | length = |
| SEQ ID NO: 1456<br>SEQUENCE: 1456<br>000 | moltype = | length = |
| SEQ ID NO: 1457<br>SEQUENCE: 1457<br>000 | moltype = | length = |
| SEQ ID NO: 1458<br>SEQUENCE: 1458<br>000 | moltype = | length = |
| SEQ ID NO: 1459<br>SEQUENCE: 1459<br>000 | moltype = | length = |
| SEQ ID NO: 1460<br>SEQUENCE: 1460<br>000 | moltype = | length = |
| SEQ ID NO: 1461<br>SEQUENCE: 1461<br>000 | moltype = | length = |
| SEQ ID NO: 1462<br>SEQUENCE: 1462<br>000 | moltype = | length = |
| SEQ ID NO: 1463<br>SEQUENCE: 1463<br>000 | moltype = | length = |
| SEQ ID NO: 1464<br>SEQUENCE: 1464<br>000 | moltype = | length = |
| SEQ ID NO: 1465<br>SEQUENCE: 1465<br>000 | moltype = | length = |
| SEQ ID NO: 1466<br>SEQUENCE: 1466<br>000 | moltype = | length = |
| SEQ ID NO: 1467<br>SEQUENCE: 1467<br>000 | moltype = | length = |
| SEQ ID NO: 1468<br>SEQUENCE: 1468<br>000 | moltype = | length = |

SEQ ID NO: 1469        moltype =     length =
SEQUENCE: 1469
000

SEQ ID NO: 1470        moltype =     length =
SEQUENCE: 1470
000

SEQ ID NO: 1471        moltype =     length =
SEQUENCE: 1471
000

SEQ ID NO: 1472        moltype =     length =
SEQUENCE: 1472
000

SEQ ID NO: 1473        moltype =     length =
SEQUENCE: 1473
000

SEQ ID NO: 1474        moltype =     length =
SEQUENCE: 1474
000

SEQ ID NO: 1475        moltype =     length =
SEQUENCE: 1475
000

SEQ ID NO: 1476        moltype =     length =
SEQUENCE: 1476
000

SEQ ID NO: 1477        moltype =     length =
SEQUENCE: 1477
000

SEQ ID NO: 1478        moltype =     length =
SEQUENCE: 1478
000

SEQ ID NO: 1479        moltype =     length =
SEQUENCE: 1479
000

SEQ ID NO: 1480        moltype =     length =
SEQUENCE: 1480
000

SEQ ID NO: 1481        moltype =     length =
SEQUENCE: 1481
000

SEQ ID NO: 1482        moltype =     length =
SEQUENCE: 1482
000

SEQ ID NO: 1483        moltype =     length =
SEQUENCE: 1483
000

SEQ ID NO: 1484        moltype =     length =
SEQUENCE: 1484
000

SEQ ID NO: 1485        moltype =     length =
SEQUENCE: 1485
000

SEQ ID NO: 1486        moltype =     length =
SEQUENCE: 1486
000

SEQ ID NO: 1487        moltype =     length =
SEQUENCE: 1487
000

SEQ ID NO: 1488        moltype =     length =
SEQUENCE: 1488

000

SEQ ID NO: 1489　　　moltype =　　length =
SEQUENCE: 1489
000

SEQ ID NO: 1490　　　moltype =　　length =
SEQUENCE: 1490
000

SEQ ID NO: 1491　　　moltype =　　length =
SEQUENCE: 1491
000

SEQ ID NO: 1492　　　moltype =　　length =
SEQUENCE: 1492
000

SEQ ID NO: 1493　　　moltype =　　length =
SEQUENCE: 1493
000

SEQ ID NO: 1494　　　moltype =　　length =
SEQUENCE: 1494
000

SEQ ID NO: 1495　　　moltype =　　length =
SEQUENCE: 1495
000

SEQ ID NO: 1496　　　moltype =　　length =
SEQUENCE: 1496
000

SEQ ID NO: 1497　　　moltype =　　length =
SEQUENCE: 1497
000

SEQ ID NO: 1498　　　moltype =　　length =
SEQUENCE: 1498
000

SEQ ID NO: 1499　　　moltype =　　length =
SEQUENCE: 1499
000

SEQ ID NO: 1500　　　moltype =　　length =
SEQUENCE: 1500
000

SEQ ID NO: 1501　　　moltype =　　length =
SEQUENCE: 1501
000

SEQ ID NO: 1502　　　moltype =　　length =
SEQUENCE: 1502
000

SEQ ID NO: 1503　　　moltype =　　length =
SEQUENCE: 1503
000

SEQ ID NO: 1504　　　moltype =　　length =
SEQUENCE: 1504
000

SEQ ID NO: 1505　　　moltype =　　length =
SEQUENCE: 1505
000

SEQ ID NO: 1506　　　moltype =　　length =
SEQUENCE: 1506
000

SEQ ID NO: 1507　　　moltype =　　length =
SEQUENCE: 1507
000

SEQ ID NO: 1508　　　moltype =　　length =

| | | |
|---|---|---|
| SEQUENCE: 1508 000 | | |
| SEQ ID NO: 1509 SEQUENCE: 1509 000 | moltype = | length = |
| SEQ ID NO: 1510 SEQUENCE: 1510 000 | moltype = | length = |
| SEQ ID NO: 1511 SEQUENCE: 1511 000 | moltype = | length = |
| SEQ ID NO: 1512 SEQUENCE: 1512 000 | moltype = | length = |
| SEQ ID NO: 1513 SEQUENCE: 1513 000 | moltype = | length = |
| SEQ ID NO: 1514 SEQUENCE: 1514 000 | moltype = | length = |
| SEQ ID NO: 1515 SEQUENCE: 1515 000 | moltype = | length = |
| SEQ ID NO: 1516 SEQUENCE: 1516 000 | moltype = | length = |
| SEQ ID NO: 1517 SEQUENCE: 1517 000 | moltype = | length = |
| SEQ ID NO: 1518 SEQUENCE: 1518 000 | moltype = | length = |
| SEQ ID NO: 1519 SEQUENCE: 1519 000 | moltype = | length = |
| SEQ ID NO: 1520 SEQUENCE: 1520 000 | moltype = | length = |
| SEQ ID NO: 1521 SEQUENCE: 1521 000 | moltype = | length = |
| SEQ ID NO: 1522 SEQUENCE: 1522 000 | moltype = | length = |
| SEQ ID NO: 1523 SEQUENCE: 1523 000 | moltype = | length = |
| SEQ ID NO: 1524 SEQUENCE: 1524 000 | moltype = | length = |
| SEQ ID NO: 1525 SEQUENCE: 1525 000 | moltype = | length = |
| SEQ ID NO: 1526 SEQUENCE: 1526 000 | moltype = | length = |
| SEQ ID NO: 1527 SEQUENCE: 1527 000 | moltype = | length = |

| | | |
|---|---|---|
| SEQ ID NO: 1528 SEQUENCE: 1528 | moltype = | length = 000 |
| SEQ ID NO: 1529 SEQUENCE: 1529 | moltype = | length = 000 |
| SEQ ID NO: 1530 SEQUENCE: 1530 | moltype = | length = 000 |
| SEQ ID NO: 1531 SEQUENCE: 1531 | moltype = | length = 000 |
| SEQ ID NO: 1532 SEQUENCE: 1532 | moltype = | length = 000 |
| SEQ ID NO: 1533 SEQUENCE: 1533 | moltype = | length = 000 |
| SEQ ID NO: 1534 SEQUENCE: 1534 | moltype = | length = 000 |
| SEQ ID NO: 1535 SEQUENCE: 1535 | moltype = | length = 000 |
| SEQ ID NO: 1536 SEQUENCE: 1536 | moltype = | length = 000 |
| SEQ ID NO: 1537 SEQUENCE: 1537 | moltype = | length = 000 |
| SEQ ID NO: 1538 SEQUENCE: 1538 | moltype = | length = 000 |
| SEQ ID NO: 1539 SEQUENCE: 1539 | moltype = | length = 000 |
| SEQ ID NO: 1540 SEQUENCE: 1540 | moltype = | length = 000 |
| SEQ ID NO: 1541 SEQUENCE: 1541 | moltype = | length = 000 |
| SEQ ID NO: 1542 SEQUENCE: 1542 | moltype = | length = 000 |
| SEQ ID NO: 1543 SEQUENCE: 1543 | moltype = | length = 000 |
| SEQ ID NO: 1544 SEQUENCE: 1544 | moltype = | length = 000 |
| SEQ ID NO: 1545 SEQUENCE: 1545 | moltype = | length = 000 |
| SEQ ID NO: 1546 SEQUENCE: 1546 | moltype = | length = 000 |
| SEQ ID NO: 1547 SEQUENCE: 1547 | moltype = | length = 000 |

```
SEQ ID NO: 1548         moltype =    length =
SEQUENCE: 1548
000

SEQ ID NO: 1549         moltype =    length =
SEQUENCE: 1549
000

SEQ ID NO: 1550         moltype =    length =
SEQUENCE: 1550
000

SEQ ID NO: 1551         moltype =    length =
SEQUENCE: 1551
000

SEQ ID NO: 1552         moltype =    length =
SEQUENCE: 1552
000

SEQ ID NO: 1553         moltype =    length =
SEQUENCE: 1553
000

SEQ ID NO: 1554         moltype =    length =
SEQUENCE: 1554
000

SEQ ID NO: 1555         moltype =    length =
SEQUENCE: 1555
000

SEQ ID NO: 1556         moltype =    length =
SEQUENCE: 1556
000

SEQ ID NO: 1557         moltype =    length =
SEQUENCE: 1557
000

SEQ ID NO: 1558         moltype =    length =
SEQUENCE: 1558
000

SEQ ID NO: 1559         moltype =    length =
SEQUENCE: 1559
000

SEQ ID NO: 1560         moltype =    length =
SEQUENCE: 1560
000

SEQ ID NO: 1561         moltype =    length =
SEQUENCE: 1561
000

SEQ ID NO: 1562         moltype =    length =
SEQUENCE: 1562
000

SEQ ID NO: 1563         moltype =    length =
SEQUENCE: 1563
000

SEQ ID NO: 1564         moltype =    length =
SEQUENCE: 1564
000

SEQ ID NO: 1565         moltype =    length =
SEQUENCE: 1565
000

SEQ ID NO: 1566         moltype =    length =
SEQUENCE: 1566
000

SEQ ID NO: 1567         moltype =    length =
SEQUENCE: 1567
```

-continued

000

SEQ ID NO: 1568    moltype =    length =
SEQUENCE: 1568
000

SEQ ID NO: 1569    moltype =    length =
SEQUENCE: 1569
000

SEQ ID NO: 1570    moltype =    length =
SEQUENCE: 1570
000

SEQ ID NO: 1571    moltype =    length =
SEQUENCE: 1571
000

SEQ ID NO: 1572    moltype =    length =
SEQUENCE: 1572
000

SEQ ID NO: 1573    moltype =    length =
SEQUENCE: 1573
000

SEQ ID NO: 1574    moltype =    length =
SEQUENCE: 1574
000

SEQ ID NO: 1575    moltype =    length =
SEQUENCE: 1575
000

SEQ ID NO: 1576    moltype =    length =
SEQUENCE: 1576
000

SEQ ID NO: 1577    moltype =    length =
SEQUENCE: 1577
000

SEQ ID NO: 1578    moltype =    length =
SEQUENCE: 1578
000

SEQ ID NO: 1579    moltype =    length =
SEQUENCE: 1579
000

SEQ ID NO: 1580    moltype =    length =
SEQUENCE: 1580
000

SEQ ID NO: 1581    moltype =    length =
SEQUENCE: 1581
000

SEQ ID NO: 1582    moltype =    length =
SEQUENCE: 1582
000

SEQ ID NO: 1583    moltype =    length =
SEQUENCE: 1583
000

SEQ ID NO: 1584    moltype =    length =
SEQUENCE: 1584
000

SEQ ID NO: 1585    moltype =    length =
SEQUENCE: 1585
000

SEQ ID NO: 1586    moltype =    length =
SEQUENCE: 1586
000

SEQ ID NO: 1587    moltype =    length =

| | | |
|---|---|---|
| SEQUENCE: 1587 000 | | |
| SEQ ID NO: 1588 SEQUENCE: 1588 000 | moltype = | length = |
| SEQ ID NO: 1589 SEQUENCE: 1589 000 | moltype = | length = |
| SEQ ID NO: 1590 SEQUENCE: 1590 000 | moltype = | length = |
| SEQ ID NO: 1591 SEQUENCE: 1591 000 | moltype = | length = |
| SEQ ID NO: 1592 SEQUENCE: 1592 000 | moltype = | length = |
| SEQ ID NO: 1593 SEQUENCE: 1593 000 | moltype = | length = |
| SEQ ID NO: 1594 SEQUENCE: 1594 000 | moltype = | length = |
| SEQ ID NO: 1595 SEQUENCE: 1595 000 | moltype = | length = |
| SEQ ID NO: 1596 SEQUENCE: 1596 000 | moltype = | length = |
| SEQ ID NO: 1597 SEQUENCE: 1597 000 | moltype = | length = |
| SEQ ID NO: 1598 SEQUENCE: 1598 000 | moltype = | length = |
| SEQ ID NO: 1599 SEQUENCE: 1599 000 | moltype = | length = |
| SEQ ID NO: 1600 SEQUENCE: 1600 000 | moltype = | length = |
| SEQ ID NO: 1601 SEQUENCE: 1601 000 | moltype = | length = |
| SEQ ID NO: 1602 SEQUENCE: 1602 000 | moltype = | length = |
| SEQ ID NO: 1603 SEQUENCE: 1603 000 | moltype = | length = |
| SEQ ID NO: 1604 SEQUENCE: 1604 000 | moltype = | length = |
| SEQ ID NO: 1605 SEQUENCE: 1605 000 | moltype = | length = |
| SEQ ID NO: 1606 SEQUENCE: 1606 000 | moltype = | length = |

-continued

| SEQ ID NO: 1607 SEQUENCE: 1607 | moltype = | length = 000 |
| SEQ ID NO: 1608 SEQUENCE: 1608 | moltype = | length = 000 |
| SEQ ID NO: 1609 SEQUENCE: 1609 | moltype = | length = 000 |
| SEQ ID NO: 1610 SEQUENCE: 1610 | moltype = | length = 000 |
| SEQ ID NO: 1611 SEQUENCE: 1611 | moltype = | length = 000 |
| SEQ ID NO: 1612 SEQUENCE: 1612 | moltype = | length = 000 |
| SEQ ID NO: 1613 SEQUENCE: 1613 | moltype = | length = 000 |
| SEQ ID NO: 1614 SEQUENCE: 1614 | moltype = | length = 000 |
| SEQ ID NO: 1615 SEQUENCE: 1615 | moltype = | length = 000 |
| SEQ ID NO: 1616 SEQUENCE: 1616 | moltype = | length = 000 |
| SEQ ID NO: 1617 SEQUENCE: 1617 | moltype = | length = 000 |
| SEQ ID NO: 1618 SEQUENCE: 1618 | moltype = | length = 000 |
| SEQ ID NO: 1619 SEQUENCE: 1619 | moltype = | length = 000 |
| SEQ ID NO: 1620 SEQUENCE: 1620 | moltype = | length = 000 |
| SEQ ID NO: 1621 SEQUENCE: 1621 | moltype = | length = 000 |
| SEQ ID NO: 1622 SEQUENCE: 1622 | moltype = | length = 000 |
| SEQ ID NO: 1623 SEQUENCE: 1623 | moltype = | length = 000 |
| SEQ ID NO: 1624 SEQUENCE: 1624 | moltype = | length = 000 |
| SEQ ID NO: 1625 SEQUENCE: 1625 | moltype = | length = 000 |
| SEQ ID NO: 1626 SEQUENCE: 1626 | moltype = | length = 000 |

| | | |
|---|---|---|
| SEQ ID NO: 1627<br>SEQUENCE: 1627<br>000 | moltype = | length = |
| SEQ ID NO: 1628<br>SEQUENCE: 1628<br>000 | moltype = | length = |
| SEQ ID NO: 1629<br>SEQUENCE: 1629<br>000 | moltype = | length = |
| SEQ ID NO: 1630<br>SEQUENCE: 1630<br>000 | moltype = | length = |
| SEQ ID NO: 1631<br>SEQUENCE: 1631<br>000 | moltype = | length = |
| SEQ ID NO: 1632<br>SEQUENCE: 1632<br>000 | moltype = | length = |
| SEQ ID NO: 1633<br>SEQUENCE: 1633<br>000 | moltype = | length = |
| SEQ ID NO: 1634<br>SEQUENCE: 1634<br>000 | moltype = | length = |
| SEQ ID NO: 1635<br>SEQUENCE: 1635<br>000 | moltype = | length = |
| SEQ ID NO: 1636<br>SEQUENCE: 1636<br>000 | moltype = | length = |
| SEQ ID NO: 1637<br>SEQUENCE: 1637<br>000 | moltype = | length = |
| SEQ ID NO: 1638<br>SEQUENCE: 1638<br>000 | moltype = | length = |
| SEQ ID NO: 1639<br>SEQUENCE: 1639<br>000 | moltype = | length = |
| SEQ ID NO: 1640<br>SEQUENCE: 1640<br>000 | moltype = | length = |
| SEQ ID NO: 1641<br>SEQUENCE: 1641<br>000 | moltype = | length = |
| SEQ ID NO: 1642<br>SEQUENCE: 1642<br>000 | moltype = | length = |
| SEQ ID NO: 1643<br>SEQUENCE: 1643<br>000 | moltype = | length = |
| SEQ ID NO: 1644<br>SEQUENCE: 1644<br>000 | moltype = | length = |
| SEQ ID NO: 1645<br>SEQUENCE: 1645<br>000 | moltype = | length = |
| SEQ ID NO: 1646<br>SEQUENCE: 1646 | moltype = | length = |

-continued

000

SEQ ID NO: 1647          moltype =          length =
SEQUENCE: 1647
000

SEQ ID NO: 1648          moltype =          length =
SEQUENCE: 1648
000

SEQ ID NO: 1649          moltype =          length =
SEQUENCE: 1649
000

SEQ ID NO: 1650          moltype =          length =
SEQUENCE: 1650
000

SEQ ID NO: 1651          moltype =          length =
SEQUENCE: 1651
000

SEQ ID NO: 1652          moltype =          length =
SEQUENCE: 1652
000

SEQ ID NO: 1653          moltype =          length =
SEQUENCE: 1653
000

SEQ ID NO: 1654          moltype =          length =
SEQUENCE: 1654
000

SEQ ID NO: 1655          moltype =          length =
SEQUENCE: 1655
000

SEQ ID NO: 1656          moltype =          length =
SEQUENCE: 1656
000

SEQ ID NO: 1657          moltype =          length =
SEQUENCE: 1657
000

SEQ ID NO: 1658          moltype =          length =
SEQUENCE: 1658
000

SEQ ID NO: 1659          moltype =          length =
SEQUENCE: 1659
000

SEQ ID NO: 1660          moltype =          length =
SEQUENCE: 1660
000

SEQ ID NO: 1661          moltype =          length =
SEQUENCE: 1661
000

SEQ ID NO: 1662          moltype =          length =
SEQUENCE: 1662
000

SEQ ID NO: 1663          moltype =          length =
SEQUENCE: 1663
000

SEQ ID NO: 1664          moltype =          length =
SEQUENCE: 1664
000

SEQ ID NO: 1665          moltype =          length =
SEQUENCE: 1665
000

SEQ ID NO: 1666          moltype =          length =

```
SEQUENCE: 1666
000

SEQ ID NO: 1667        moltype =    length =
SEQUENCE: 1667
000

SEQ ID NO: 1668        moltype =    length =
SEQUENCE: 1668
000

SEQ ID NO: 1669        moltype =    length =
SEQUENCE: 1669
000

SEQ ID NO: 1670        moltype =    length =
SEQUENCE: 1670
000

SEQ ID NO: 1671        moltype =    length =
SEQUENCE: 1671
000

SEQ ID NO: 1672        moltype =    length =
SEQUENCE: 1672
000

SEQ ID NO: 1673        moltype =    length =
SEQUENCE: 1673
000

SEQ ID NO: 1674        moltype =    length =
SEQUENCE: 1674
000

SEQ ID NO: 1675        moltype =    length =
SEQUENCE: 1675
000

SEQ ID NO: 1676        moltype =    length =
SEQUENCE: 1676
000

SEQ ID NO: 1677        moltype =    length =
SEQUENCE: 1677
000

SEQ ID NO: 1678        moltype =    length =
SEQUENCE: 1678
000

SEQ ID NO: 1679        moltype =    length =
SEQUENCE: 1679
000

SEQ ID NO: 1680        moltype =    length =
SEQUENCE: 1680
000

SEQ ID NO: 1681        moltype =    length =
SEQUENCE: 1681
000

SEQ ID NO: 1682        moltype =    length =
SEQUENCE: 1682
000

SEQ ID NO: 1683        moltype =    length =
SEQUENCE: 1683
000

SEQ ID NO: 1684        moltype =    length =
SEQUENCE: 1684
000

SEQ ID NO: 1685        moltype =    length =
SEQUENCE: 1685
000
```

| | | |
|---|---|---|
| SEQ ID NO: 1686<br>SEQUENCE: 1686 | moltype =<br>000 | length = |
| SEQ ID NO: 1687<br>SEQUENCE: 1687 | moltype =<br>000 | length = |
| SEQ ID NO: 1688<br>SEQUENCE: 1688 | moltype =<br>000 | length = |
| SEQ ID NO: 1689<br>SEQUENCE: 1689 | moltype =<br>000 | length = |
| SEQ ID NO: 1690<br>SEQUENCE: 1690 | moltype =<br>000 | length = |
| SEQ ID NO: 1691<br>SEQUENCE: 1691 | moltype =<br>000 | length = |
| SEQ ID NO: 1692<br>SEQUENCE: 1692 | moltype =<br>000 | length = |
| SEQ ID NO: 1693<br>SEQUENCE: 1693 | moltype =<br>000 | length = |
| SEQ ID NO: 1694<br>SEQUENCE: 1694 | moltype =<br>000 | length = |
| SEQ ID NO: 1695<br>SEQUENCE: 1695 | moltype =<br>000 | length = |
| SEQ ID NO: 1696<br>SEQUENCE: 1696 | moltype =<br>000 | length = |
| SEQ ID NO: 1697<br>SEQUENCE: 1697 | moltype =<br>000 | length = |
| SEQ ID NO: 1698<br>SEQUENCE: 1698 | moltype =<br>000 | length = |
| SEQ ID NO: 1699<br>SEQUENCE: 1699 | moltype =<br>000 | length = |
| SEQ ID NO: 1700<br>SEQUENCE: 1700 | moltype =<br>000 | length = |
| SEQ ID NO: 1701<br>SEQUENCE: 1701 | moltype =<br>000 | length = |
| SEQ ID NO: 1702<br>SEQUENCE: 1702 | moltype =<br>000 | length = |
| SEQ ID NO: 1703<br>SEQUENCE: 1703 | moltype =<br>000 | length = |
| SEQ ID NO: 1704<br>SEQUENCE: 1704 | moltype =<br>000 | length = |
| SEQ ID NO: 1705<br>SEQUENCE: 1705 | moltype =<br>000 | length = |

-continued

SEQ ID NO: 1706  moltype =  length =
SEQUENCE: 1706
000

SEQ ID NO: 1707  moltype =  length =
SEQUENCE: 1707
000

SEQ ID NO: 1708  moltype =  length =
SEQUENCE: 1708
000

SEQ ID NO: 1709  moltype =  length =
SEQUENCE: 1709
000

SEQ ID NO: 1710  moltype =  length =
SEQUENCE: 1710
000

SEQ ID NO: 1711  moltype =  length =
SEQUENCE: 1711
000

SEQ ID NO: 1712  moltype =  length =
SEQUENCE: 1712
000

SEQ ID NO: 1713  moltype =  length =
SEQUENCE: 1713
000

SEQ ID NO: 1714  moltype =  length =
SEQUENCE: 1714
000

SEQ ID NO: 1715  moltype =  length =
SEQUENCE: 1715
000

SEQ ID NO: 1716  moltype =  length =
SEQUENCE: 1716
000

SEQ ID NO: 1717  moltype =  length =
SEQUENCE: 1717
000

SEQ ID NO: 1718  moltype =  length =
SEQUENCE: 1718
000

SEQ ID NO: 1719  moltype =  length =
SEQUENCE: 1719
000

SEQ ID NO: 1720  moltype =  length =
SEQUENCE: 1720
000

SEQ ID NO: 1721  moltype =  length =
SEQUENCE: 1721
000

SEQ ID NO: 1722  moltype =  length =
SEQUENCE: 1722
000

SEQ ID NO: 1723  moltype =  length =
SEQUENCE: 1723
000

SEQ ID NO: 1724  moltype =  length =
SEQUENCE: 1724
000

SEQ ID NO: 1725  moltype =  length =
SEQUENCE: 1725

000

SEQ ID NO: 1726        moltype =    length =
SEQUENCE: 1726
000

SEQ ID NO: 1727        moltype =    length =
SEQUENCE: 1727
000

SEQ ID NO: 1728        moltype =    length =
SEQUENCE: 1728
000

SEQ ID NO: 1729        moltype =    length =
SEQUENCE: 1729
000

SEQ ID NO: 1730        moltype =    length =
SEQUENCE: 1730
000

SEQ ID NO: 1731        moltype =    length =
SEQUENCE: 1731
000

SEQ ID NO: 1732        moltype =    length =
SEQUENCE: 1732
000

SEQ ID NO: 1733        moltype =    length =
SEQUENCE: 1733
000

SEQ ID NO: 1734        moltype =    length =
SEQUENCE: 1734
000

SEQ ID NO: 1735        moltype =    length =
SEQUENCE: 1735
000

SEQ ID NO: 1736        moltype =    length =
SEQUENCE: 1736
000

SEQ ID NO: 1737        moltype =    length =
SEQUENCE: 1737
000

SEQ ID NO: 1738        moltype =    length =
SEQUENCE: 1738
000

SEQ ID NO: 1739        moltype =    length =
SEQUENCE: 1739
000

SEQ ID NO: 1740        moltype =    length =
SEQUENCE: 1740
000

SEQ ID NO: 1741        moltype =    length =
SEQUENCE: 1741
000

SEQ ID NO: 1742        moltype =    length =
SEQUENCE: 1742
000

SEQ ID NO: 1743        moltype =    length =
SEQUENCE: 1743
000

SEQ ID NO: 1744        moltype =    length =
SEQUENCE: 1744
000

SEQ ID NO: 1745        moltype =    length =

| | | |
|---|---|---|
| SEQ ID NO: 1745 SEQUENCE: 1745 000 | moltype = | length = |
| SEQ ID NO: 1746 SEQUENCE: 1746 000 | moltype = | length = |
| SEQ ID NO: 1747 SEQUENCE: 1747 000 | moltype = | length = |
| SEQ ID NO: 1748 SEQUENCE: 1748 000 | moltype = | length = |
| SEQ ID NO: 1749 SEQUENCE: 1749 000 | moltype = | length = |
| SEQ ID NO: 1750 SEQUENCE: 1750 000 | moltype = | length = |
| SEQ ID NO: 1751 SEQUENCE: 1751 000 | moltype = | length = |
| SEQ ID NO: 1752 SEQUENCE: 1752 000 | moltype = | length = |
| SEQ ID NO: 1753 SEQUENCE: 1753 000 | moltype = | length = |
| SEQ ID NO: 1754 SEQUENCE: 1754 000 | moltype = | length = |
| SEQ ID NO: 1755 SEQUENCE: 1755 000 | moltype = | length = |
| SEQ ID NO: 1756 SEQUENCE: 1756 000 | moltype = | length = |
| SEQ ID NO: 1757 SEQUENCE: 1757 000 | moltype = | length = |
| SEQ ID NO: 1758 SEQUENCE: 1758 000 | moltype = | length = |
| SEQ ID NO: 1759 SEQUENCE: 1759 000 | moltype = | length = |
| SEQ ID NO: 1760 SEQUENCE: 1760 000 | moltype = | length = |
| SEQ ID NO: 1761 SEQUENCE: 1761 000 | moltype = | length = |
| SEQ ID NO: 1762 SEQUENCE: 1762 000 | moltype = | length = |
| SEQ ID NO: 1763 SEQUENCE: 1763 000 | moltype = | length = |
| SEQ ID NO: 1764 SEQUENCE: 1764 000 | moltype = | length = |

| | | |
|---|---|---|
| SEQ ID NO: 1765<br>SEQUENCE: 1765 | moltype = | length = 000 |
| SEQ ID NO: 1766<br>SEQUENCE: 1766 | moltype = | length = 000 |
| SEQ ID NO: 1767<br>SEQUENCE: 1767 | moltype = | length = 000 |
| SEQ ID NO: 1768<br>SEQUENCE: 1768 | moltype = | length = 000 |
| SEQ ID NO: 1769<br>SEQUENCE: 1769 | moltype = | length = 000 |
| SEQ ID NO: 1770<br>SEQUENCE: 1770 | moltype = | length = 000 |
| SEQ ID NO: 1771<br>SEQUENCE: 1771 | moltype = | length = 000 |
| SEQ ID NO: 1772<br>SEQUENCE: 1772 | moltype = | length = 000 |
| SEQ ID NO: 1773<br>SEQUENCE: 1773 | moltype = | length = 000 |
| SEQ ID NO: 1774<br>SEQUENCE: 1774 | moltype = | length = 000 |
| SEQ ID NO: 1775<br>SEQUENCE: 1775 | moltype = | length = 000 |
| SEQ ID NO: 1776<br>SEQUENCE: 1776 | moltype = | length = 000 |
| SEQ ID NO: 1777<br>SEQUENCE: 1777 | moltype = | length = 000 |
| SEQ ID NO: 1778<br>SEQUENCE: 1778 | moltype = | length = 000 |
| SEQ ID NO: 1779<br>SEQUENCE: 1779 | moltype = | length = 000 |
| SEQ ID NO: 1780<br>SEQUENCE: 1780 | moltype = | length = 000 |
| SEQ ID NO: 1781<br>SEQUENCE: 1781 | moltype = | length = 000 |
| SEQ ID NO: 1782<br>SEQUENCE: 1782 | moltype = | length = 000 |
| SEQ ID NO: 1783<br>SEQUENCE: 1783 | moltype = | length = 000 |
| SEQ ID NO: 1784<br>SEQUENCE: 1784 | moltype = | length = 000 |

SEQ ID NO: 1785    moltype =    length =
SEQUENCE: 1785
000

SEQ ID NO: 1786    moltype =    length =
SEQUENCE: 1786
000

SEQ ID NO: 1787    moltype =    length =
SEQUENCE: 1787
000

SEQ ID NO: 1788    moltype =    length =
SEQUENCE: 1788
000

SEQ ID NO: 1789    moltype =    length =
SEQUENCE: 1789
000

SEQ ID NO: 1790    moltype =    length =
SEQUENCE: 1790
000

SEQ ID NO: 1791    moltype =    length =
SEQUENCE: 1791
000

SEQ ID NO: 1792    moltype =    length =
SEQUENCE: 1792
000

SEQ ID NO: 1793    moltype =    length =
SEQUENCE: 1793
000

SEQ ID NO: 1794    moltype =    length =
SEQUENCE: 1794
000

SEQ ID NO: 1795    moltype =    length =
SEQUENCE: 1795
000

SEQ ID NO: 1796    moltype =    length =
SEQUENCE: 1796
000

SEQ ID NO: 1797    moltype =    length =
SEQUENCE: 1797
000

SEQ ID NO: 1798    moltype =    length =
SEQUENCE: 1798
000

SEQ ID NO: 1799    moltype =    length =
SEQUENCE: 1799
000

SEQ ID NO: 1800    moltype =    length =
SEQUENCE: 1800
000

SEQ ID NO: 1801    moltype =    length =
SEQUENCE: 1801
000

SEQ ID NO: 1802    moltype =    length =
SEQUENCE: 1802
000

SEQ ID NO: 1803    moltype =    length =
SEQUENCE: 1803
000

SEQ ID NO: 1804    moltype =    length =
SEQUENCE: 1804

000

SEQ ID NO: 1805          moltype =     length =
SEQUENCE: 1805
000

SEQ ID NO: 1806          moltype =     length =
SEQUENCE: 1806
000

SEQ ID NO: 1807          moltype =     length =
SEQUENCE: 1807
000

SEQ ID NO: 1808          moltype =     length =
SEQUENCE: 1808
000

SEQ ID NO: 1809          moltype =     length =
SEQUENCE: 1809
000

SEQ ID NO: 1810          moltype =     length =
SEQUENCE: 1810
000

SEQ ID NO: 1811          moltype =     length =
SEQUENCE: 1811
000

SEQ ID NO: 1812          moltype =     length =
SEQUENCE: 1812
000

SEQ ID NO: 1813          moltype =     length =
SEQUENCE: 1813
000

SEQ ID NO: 1814          moltype =     length =
SEQUENCE: 1814
000

SEQ ID NO: 1815          moltype =     length =
SEQUENCE: 1815
000

SEQ ID NO: 1816          moltype =     length =
SEQUENCE: 1816
000

SEQ ID NO: 1817          moltype =     length =
SEQUENCE: 1817
000

SEQ ID NO: 1818          moltype =     length =
SEQUENCE: 1818
000

SEQ ID NO: 1819          moltype =     length =
SEQUENCE: 1819
000

SEQ ID NO: 1820          moltype =     length =
SEQUENCE: 1820
000

SEQ ID NO: 1821          moltype =     length =
SEQUENCE: 1821
000

SEQ ID NO: 1822          moltype =     length =
SEQUENCE: 1822
000

SEQ ID NO: 1823          moltype =     length =
SEQUENCE: 1823
000

SEQ ID NO: 1824          moltype =     length =

SEQUENCE: 1824
000

SEQ ID NO: 1825          moltype =      length =
SEQUENCE: 1825
000

SEQ ID NO: 1826          moltype =      length =
SEQUENCE: 1826
000

SEQ ID NO: 1827          moltype =      length =
SEQUENCE: 1827
000

SEQ ID NO: 1828          moltype =      length =
SEQUENCE: 1828
000

SEQ ID NO: 1829          moltype =      length =
SEQUENCE: 1829
000

SEQ ID NO: 1830          moltype =      length =
SEQUENCE: 1830
000

SEQ ID NO: 1831          moltype =      length =
SEQUENCE: 1831
000

SEQ ID NO: 1832          moltype =      length =
SEQUENCE: 1832
000

SEQ ID NO: 1833          moltype =      length =
SEQUENCE: 1833
000

SEQ ID NO: 1834          moltype =      length =
SEQUENCE: 1834
000

SEQ ID NO: 1835          moltype =      length =
SEQUENCE: 1835
000

SEQ ID NO: 1836          moltype =      length =
SEQUENCE: 1836
000

SEQ ID NO: 1837          moltype =      length =
SEQUENCE: 1837
000

SEQ ID NO: 1838          moltype =      length =
SEQUENCE: 1838
000

SEQ ID NO: 1839          moltype =      length =
SEQUENCE: 1839
000

SEQ ID NO: 1840          moltype =      length =
SEQUENCE: 1840
000

SEQ ID NO: 1841          moltype =      length =
SEQUENCE: 1841
000

SEQ ID NO: 1842          moltype =      length =
SEQUENCE: 1842
000

SEQ ID NO: 1843          moltype =      length =
SEQUENCE: 1843
000

| | | |
|---|---|---|
| SEQ ID NO: 1844<br>SEQUENCE: 1844<br>000 | moltype = | length = |
| SEQ ID NO: 1845<br>SEQUENCE: 1845<br>000 | moltype = | length = |
| SEQ ID NO: 1846<br>SEQUENCE: 1846<br>000 | moltype = | length = |
| SEQ ID NO: 1847<br>SEQUENCE: 1847<br>000 | moltype = | length = |
| SEQ ID NO: 1848<br>SEQUENCE: 1848<br>000 | moltype = | length = |
| SEQ ID NO: 1849<br>SEQUENCE: 1849<br>000 | moltype = | length = |
| SEQ ID NO: 1850<br>SEQUENCE: 1850<br>000 | moltype = | length = |
| SEQ ID NO: 1851<br>SEQUENCE: 1851<br>000 | moltype = | length = |
| SEQ ID NO: 1852<br>SEQUENCE: 1852<br>000 | moltype = | length = |
| SEQ ID NO: 1853<br>SEQUENCE: 1853<br>000 | moltype = | length = |
| SEQ ID NO: 1854<br>SEQUENCE: 1854<br>000 | moltype = | length = |
| SEQ ID NO: 1855<br>SEQUENCE: 1855<br>000 | moltype = | length = |
| SEQ ID NO: 1856<br>SEQUENCE: 1856<br>000 | moltype = | length = |
| SEQ ID NO: 1857<br>SEQUENCE: 1857<br>000 | moltype = | length = |
| SEQ ID NO: 1858<br>SEQUENCE: 1858<br>000 | moltype = | length = |
| SEQ ID NO: 1859<br>SEQUENCE: 1859<br>000 | moltype = | length = |
| SEQ ID NO: 1860<br>SEQUENCE: 1860<br>000 | moltype = | length = |
| SEQ ID NO: 1861<br>SEQUENCE: 1861<br>000 | moltype = | length = |
| SEQ ID NO: 1862<br>SEQUENCE: 1862<br>000 | moltype = | length = |
| SEQ ID NO: 1863<br>SEQUENCE: 1863<br>000 | moltype = | length = |

SEQ ID NO: 1864         moltype =      length =
SEQUENCE: 1864
000

SEQ ID NO: 1865         moltype =      length =
SEQUENCE: 1865
000

SEQ ID NO: 1866         moltype =      length =
SEQUENCE: 1866
000

SEQ ID NO: 1867         moltype =      length =
SEQUENCE: 1867
000

SEQ ID NO: 1868         moltype =      length =
SEQUENCE: 1868
000

SEQ ID NO: 1869         moltype =      length =
SEQUENCE: 1869
000

SEQ ID NO: 1870         moltype =      length =
SEQUENCE: 1870
000

SEQ ID NO: 1871         moltype =      length =
SEQUENCE: 1871
000

SEQ ID NO: 1872         moltype =      length =
SEQUENCE: 1872
000

SEQ ID NO: 1873         moltype =      length =
SEQUENCE: 1873
000

SEQ ID NO: 1874         moltype =      length =
SEQUENCE: 1874
000

SEQ ID NO: 1875         moltype =      length =
SEQUENCE: 1875
000

SEQ ID NO: 1876         moltype =      length =
SEQUENCE: 1876
000

SEQ ID NO: 1877         moltype =      length =
SEQUENCE: 1877
000

SEQ ID NO: 1878         moltype =      length =
SEQUENCE: 1878
000

SEQ ID NO: 1879         moltype =      length =
SEQUENCE: 1879
000

SEQ ID NO: 1880         moltype =      length =
SEQUENCE: 1880
000

SEQ ID NO: 1881         moltype =      length =
SEQUENCE: 1881
000

SEQ ID NO: 1882         moltype =      length =
SEQUENCE: 1882
000

SEQ ID NO: 1883         moltype =      length =
SEQUENCE: 1883

000

SEQ ID NO: 1884        moltype =      length =
SEQUENCE: 1884
000

SEQ ID NO: 1885        moltype =      length =
SEQUENCE: 1885
000

SEQ ID NO: 1886        moltype =      length =
SEQUENCE: 1886
000

SEQ ID NO: 1887        moltype =      length =
SEQUENCE: 1887
000

SEQ ID NO: 1888        moltype =      length =
SEQUENCE: 1888
000

SEQ ID NO: 1889        moltype =      length =
SEQUENCE: 1889
000

SEQ ID NO: 1890        moltype =      length =
SEQUENCE: 1890
000

SEQ ID NO: 1891        moltype =      length =
SEQUENCE: 1891
000

SEQ ID NO: 1892        moltype =      length =
SEQUENCE: 1892
000

SEQ ID NO: 1893        moltype =      length =
SEQUENCE: 1893
000

SEQ ID NO: 1894        moltype =      length =
SEQUENCE: 1894
000

SEQ ID NO: 1895        moltype =      length =
SEQUENCE: 1895
000

SEQ ID NO: 1896        moltype =      length =
SEQUENCE: 1896
000

SEQ ID NO: 1897        moltype =      length =
SEQUENCE: 1897
000

SEQ ID NO: 1898        moltype =      length =
SEQUENCE: 1898
000

SEQ ID NO: 1899        moltype =      length =
SEQUENCE: 1899
000

SEQ ID NO: 1900        moltype =      length =
SEQUENCE: 1900
000

SEQ ID NO: 1901        moltype =      length =
SEQUENCE: 1901
000

SEQ ID NO: 1902        moltype =      length =
SEQUENCE: 1902
000

SEQ ID NO: 1903        moltype =      length =

| | | |
|---|---|---|
| SEQUENCE: 1903 000 | | |
| SEQ ID NO: 1904 SEQUENCE: 1904 000 | moltype = | length = |
| SEQ ID NO: 1905 SEQUENCE: 1905 000 | moltype = | length = |
| SEQ ID NO: 1906 SEQUENCE: 1906 000 | moltype = | length = |
| SEQ ID NO: 1907 SEQUENCE: 1907 000 | moltype = | length = |
| SEQ ID NO: 1908 SEQUENCE: 1908 000 | moltype = | length = |
| SEQ ID NO: 1909 SEQUENCE: 1909 000 | moltype = | length = |
| SEQ ID NO: 1910 SEQUENCE: 1910 000 | moltype = | length = |
| SEQ ID NO: 1911 SEQUENCE: 1911 000 | moltype = | length = |
| SEQ ID NO: 1912 SEQUENCE: 1912 000 | moltype = | length = |
| SEQ ID NO: 1913 SEQUENCE: 1913 000 | moltype = | length = |
| SEQ ID NO: 1914 SEQUENCE: 1914 000 | moltype = | length = |
| SEQ ID NO: 1915 SEQUENCE: 1915 000 | moltype = | length = |
| SEQ ID NO: 1916 SEQUENCE: 1916 000 | moltype = | length = |
| SEQ ID NO: 1917 SEQUENCE: 1917 000 | moltype = | length = |
| SEQ ID NO: 1918 SEQUENCE: 1918 000 | moltype = | length = |
| SEQ ID NO: 1919 SEQUENCE: 1919 000 | moltype = | length = |
| SEQ ID NO: 1920 SEQUENCE: 1920 000 | moltype = | length = |
| SEQ ID NO: 1921 SEQUENCE: 1921 000 | moltype = | length = |
| SEQ ID NO: 1922 SEQUENCE: 1922 000 | moltype = | length = |

-continued

| | | |
|---|---|---|
| SEQ ID NO: 1923<br>SEQUENCE: 1923<br>000 | moltype = | length = |
| SEQ ID NO: 1924<br>SEQUENCE: 1924<br>000 | moltype = | length = |
| SEQ ID NO: 1925<br>SEQUENCE: 1925<br>000 | moltype = | length = |
| SEQ ID NO: 1926<br>SEQUENCE: 1926<br>000 | moltype = | length = |
| SEQ ID NO: 1927<br>SEQUENCE: 1927<br>000 | moltype = | length = |
| SEQ ID NO: 1928<br>SEQUENCE: 1928<br>000 | moltype = | length = |
| SEQ ID NO: 1929<br>SEQUENCE: 1929<br>000 | moltype = | length = |
| SEQ ID NO: 1930<br>SEQUENCE: 1930<br>000 | moltype = | length = |
| SEQ ID NO: 1931<br>SEQUENCE: 1931<br>000 | moltype = | length = |
| SEQ ID NO: 1932<br>SEQUENCE: 1932<br>000 | moltype = | length = |
| SEQ ID NO: 1933<br>SEQUENCE: 1933<br>000 | moltype = | length = |
| SEQ ID NO: 1934<br>SEQUENCE: 1934<br>000 | moltype = | length = |
| SEQ ID NO: 1935<br>SEQUENCE: 1935<br>000 | moltype = | length = |
| SEQ ID NO: 1936<br>SEQUENCE: 1936<br>000 | moltype = | length = |
| SEQ ID NO: 1937<br>SEQUENCE: 1937<br>000 | moltype = | length = |
| SEQ ID NO: 1938<br>SEQUENCE: 1938<br>000 | moltype = | length = |
| SEQ ID NO: 1939<br>SEQUENCE: 1939<br>000 | moltype = | length = |
| SEQ ID NO: 1940<br>SEQUENCE: 1940<br>000 | moltype = | length = |
| SEQ ID NO: 1941<br>SEQUENCE: 1941<br>000 | moltype = | length = |
| SEQ ID NO: 1942<br>SEQUENCE: 1942<br>000 | moltype = | length = |

SEQ ID NO: 1943      moltype =     length =
SEQUENCE: 1943
000

SEQ ID NO: 1944      moltype =     length =
SEQUENCE: 1944
000

SEQ ID NO: 1945      moltype =     length =
SEQUENCE: 1945
000

SEQ ID NO: 1946      moltype =     length =
SEQUENCE: 1946
000

SEQ ID NO: 1947      moltype =     length =
SEQUENCE: 1947
000

SEQ ID NO: 1948      moltype =     length =
SEQUENCE: 1948
000

SEQ ID NO: 1949      moltype =     length =
SEQUENCE: 1949
000

SEQ ID NO: 1950      moltype =     length =
SEQUENCE: 1950
000

SEQ ID NO: 1951      moltype =     length =
SEQUENCE: 1951
000

SEQ ID NO: 1952      moltype =     length =
SEQUENCE: 1952
000

SEQ ID NO: 1953      moltype =     length =
SEQUENCE: 1953
000

SEQ ID NO: 1954      moltype =     length =
SEQUENCE: 1954
000

SEQ ID NO: 1955      moltype =     length =
SEQUENCE: 1955
000

SEQ ID NO: 1956      moltype =     length =
SEQUENCE: 1956
000

SEQ ID NO: 1957      moltype =     length =
SEQUENCE: 1957
000

SEQ ID NO: 1958      moltype =     length =
SEQUENCE: 1958
000

SEQ ID NO: 1959      moltype =     length =
SEQUENCE: 1959
000

SEQ ID NO: 1960      moltype =     length =
SEQUENCE: 1960
000

SEQ ID NO: 1961      moltype =     length =
SEQUENCE: 1961
000

SEQ ID NO: 1962      moltype =     length =
SEQUENCE: 1962

```
000

SEQ ID NO: 1963          moltype =    length =
SEQUENCE: 1963
000

SEQ ID NO: 1964          moltype =    length =
SEQUENCE: 1964
000

SEQ ID NO: 1965          moltype =    length =
SEQUENCE: 1965
000

SEQ ID NO: 1966          moltype =    length =
SEQUENCE: 1966
000

SEQ ID NO: 1967          moltype =    length =
SEQUENCE: 1967
000

SEQ ID NO: 1968          moltype =    length =
SEQUENCE: 1968
000

SEQ ID NO: 1969          moltype =    length =
SEQUENCE: 1969
000

SEQ ID NO: 1970          moltype =    length =
SEQUENCE: 1970
000

SEQ ID NO: 1971          moltype =    length =
SEQUENCE: 1971
000

SEQ ID NO: 1972          moltype =    length =
SEQUENCE: 1972
000

SEQ ID NO: 1973          moltype =    length =
SEQUENCE: 1973
000

SEQ ID NO: 1974          moltype =    length =
SEQUENCE: 1974
000

SEQ ID NO: 1975          moltype =    length =
SEQUENCE: 1975
000

SEQ ID NO: 1976          moltype =    length =
SEQUENCE: 1976
000

SEQ ID NO: 1977          moltype =    length =
SEQUENCE: 1977
000

SEQ ID NO: 1978          moltype =    length =
SEQUENCE: 1978
000

SEQ ID NO: 1979          moltype =    length =
SEQUENCE: 1979
000

SEQ ID NO: 1980          moltype =    length =
SEQUENCE: 1980
000

SEQ ID NO: 1981          moltype =    length =
SEQUENCE: 1981
000

SEQ ID NO: 1982          moltype =    length =
```

-continued

| | | |
|---|---|---|
| SEQUENCE: 1982 000 | | |
| SEQ ID NO: 1983 SEQUENCE: 1983 000 | moltype = | length = |
| SEQ ID NO: 1984 SEQUENCE: 1984 000 | moltype = | length = |
| SEQ ID NO: 1985 SEQUENCE: 1985 000 | moltype = | length = |
| SEQ ID NO: 1986 SEQUENCE: 1986 000 | moltype = | length = |
| SEQ ID NO: 1987 SEQUENCE: 1987 000 | moltype = | length = |
| SEQ ID NO: 1988 SEQUENCE: 1988 000 | moltype = | length = |
| SEQ ID NO: 1989 SEQUENCE: 1989 000 | moltype = | length = |
| SEQ ID NO: 1990 SEQUENCE: 1990 000 | moltype = | length = |
| SEQ ID NO: 1991 SEQUENCE: 1991 000 | moltype = | length = |
| SEQ ID NO: 1992 SEQUENCE: 1992 000 | moltype = | length = |
| SEQ ID NO: 1993 SEQUENCE: 1993 000 | moltype = | length = |
| SEQ ID NO: 1994 SEQUENCE: 1994 000 | moltype = | length = |
| SEQ ID NO: 1995 SEQUENCE: 1995 000 | moltype = | length = |
| SEQ ID NO: 1996 SEQUENCE: 1996 000 | moltype = | length = |
| SEQ ID NO: 1997 SEQUENCE: 1997 000 | moltype = | length = |
| SEQ ID NO: 1998 SEQUENCE: 1998 000 | moltype = | length = |
| SEQ ID NO: 1999 SEQUENCE: 1999 000 | moltype = | length = |
| SEQ ID NO: 2000 SEQUENCE: 2000 000 | moltype = | length = |
| SEQ ID NO: 2001 SEQUENCE: 2001 000 | moltype = | length = |

-continued

| | | |
|---|---|---|
| SEQ ID NO: 2002<br>SEQUENCE: 2002<br>000 | moltype = | length = |
| SEQ ID NO: 2003<br>SEQUENCE: 2003<br>000 | moltype = | length = |
| SEQ ID NO: 2004<br>SEQUENCE: 2004<br>000 | moltype = | length = |
| SEQ ID NO: 2005<br>SEQUENCE: 2005<br>000 | moltype = | length = |
| SEQ ID NO: 2006<br>SEQUENCE: 2006<br>000 | moltype = | length = |
| SEQ ID NO: 2007<br>SEQUENCE: 2007<br>000 | moltype = | length = |
| SEQ ID NO: 2008<br>SEQUENCE: 2008<br>000 | moltype = | length = |
| SEQ ID NO: 2009<br>SEQUENCE: 2009<br>000 | moltype = | length = |
| SEQ ID NO: 2010<br>SEQUENCE: 2010<br>000 | moltype = | length = |
| SEQ ID NO: 2011<br>SEQUENCE: 2011<br>000 | moltype = | length = |
| SEQ ID NO: 2012<br>SEQUENCE: 2012<br>000 | moltype = | length = |
| SEQ ID NO: 2013<br>SEQUENCE: 2013<br>000 | moltype = | length = |
| SEQ ID NO: 2014<br>SEQUENCE: 2014<br>000 | moltype = | length = |
| SEQ ID NO: 2015<br>SEQUENCE: 2015<br>000 | moltype = | length = |
| SEQ ID NO: 2016<br>SEQUENCE: 2016<br>000 | moltype = | length = |
| SEQ ID NO: 2017<br>SEQUENCE: 2017<br>000 | moltype = | length = |
| SEQ ID NO: 2018<br>SEQUENCE: 2018<br>000 | moltype = | length = |
| SEQ ID NO: 2019<br>SEQUENCE: 2019<br>000 | moltype = | length = |
| SEQ ID NO: 2020<br>SEQUENCE: 2020<br>000 | moltype = | length = |
| SEQ ID NO: 2021<br>SEQUENCE: 2021<br>000 | moltype = | length = |

| | | |
|---|---|---|
| SEQ ID NO: 2022<br>SEQUENCE: 2022<br>000 | moltype = | length = |
| SEQ ID NO: 2023<br>SEQUENCE: 2023<br>000 | moltype = | length = |
| SEQ ID NO: 2024<br>SEQUENCE: 2024<br>000 | moltype = | length = |
| SEQ ID NO: 2025<br>SEQUENCE: 2025<br>000 | moltype = | length = |
| SEQ ID NO: 2026<br>SEQUENCE: 2026<br>000 | moltype = | length = |
| SEQ ID NO: 2027<br>SEQUENCE: 2027<br>000 | moltype = | length = |
| SEQ ID NO: 2028<br>SEQUENCE: 2028<br>000 | moltype = | length = |
| SEQ ID NO: 2029<br>SEQUENCE: 2029<br>000 | moltype = | length = |
| SEQ ID NO: 2030<br>SEQUENCE: 2030<br>000 | moltype = | length = |
| SEQ ID NO: 2031<br>SEQUENCE: 2031<br>000 | moltype = | length = |
| SEQ ID NO: 2032<br>SEQUENCE: 2032<br>000 | moltype = | length = |
| SEQ ID NO: 2033<br>SEQUENCE: 2033<br>000 | moltype = | length = |
| SEQ ID NO: 2034<br>SEQUENCE: 2034<br>000 | moltype = | length = |
| SEQ ID NO: 2035<br>SEQUENCE: 2035<br>000 | moltype = | length = |
| SEQ ID NO: 2036<br>SEQUENCE: 2036<br>000 | moltype = | length = |
| SEQ ID NO: 2037<br>SEQUENCE: 2037<br>000 | moltype = | length = |
| SEQ ID NO: 2038<br>SEQUENCE: 2038<br>000 | moltype = | length = |
| SEQ ID NO: 2039<br>SEQUENCE: 2039<br>000 | moltype = | length = |
| SEQ ID NO: 2040<br>SEQUENCE: 2040<br>000 | moltype = | length = |
| SEQ ID NO: 2041<br>SEQUENCE: 2041 | moltype = | length = |

-continued

000

SEQ ID NO: 2042        moltype =    length =
SEQUENCE: 2042
000

SEQ ID NO: 2043        moltype =    length =
SEQUENCE: 2043
000

SEQ ID NO: 2044        moltype =    length =
SEQUENCE: 2044
000

SEQ ID NO: 2045        moltype =    length =
SEQUENCE: 2045
000

SEQ ID NO: 2046        moltype =    length =
SEQUENCE: 2046
000

SEQ ID NO: 2047        moltype =    length =
SEQUENCE: 2047
000

SEQ ID NO: 2048        moltype =    length =
SEQUENCE: 2048
000

SEQ ID NO: 2049        moltype =    length =
SEQUENCE: 2049
000

SEQ ID NO: 2050        moltype =    length =
SEQUENCE: 2050
000

SEQ ID NO: 2051        moltype =    length =
SEQUENCE: 2051
000

SEQ ID NO: 2052        moltype =    length =
SEQUENCE: 2052
000

SEQ ID NO: 2053        moltype =    length =
SEQUENCE: 2053
000

SEQ ID NO: 2054        moltype =    length =
SEQUENCE: 2054
000

SEQ ID NO: 2055        moltype =    length =
SEQUENCE: 2055
000

SEQ ID NO: 2056        moltype =    length =
SEQUENCE: 2056
000

SEQ ID NO: 2057        moltype =    length =
SEQUENCE: 2057
000

SEQ ID NO: 2058        moltype =    length =
SEQUENCE: 2058
000

SEQ ID NO: 2059        moltype =    length =
SEQUENCE: 2059
000

SEQ ID NO: 2060        moltype =    length =
SEQUENCE: 2060
000

SEQ ID NO: 2061        moltype =    length =

| | | |
|---|---|---|
| SEQUENCE: 2061 000 | | |
| SEQ ID NO: 2062 SEQUENCE: 2062 000 | moltype = | length = |
| SEQ ID NO: 2063 SEQUENCE: 2063 000 | moltype = | length = |
| SEQ ID NO: 2064 SEQUENCE: 2064 000 | moltype = | length = |
| SEQ ID NO: 2065 SEQUENCE: 2065 000 | moltype = | length = |
| SEQ ID NO: 2066 SEQUENCE: 2066 000 | moltype = | length = |
| SEQ ID NO: 2067 SEQUENCE: 2067 000 | moltype = | length = |
| SEQ ID NO: 2068 SEQUENCE: 2068 000 | moltype = | length = |
| SEQ ID NO: 2069 SEQUENCE: 2069 000 | moltype = | length = |
| SEQ ID NO: 2070 SEQUENCE: 2070 000 | moltype = | length = |
| SEQ ID NO: 2071 SEQUENCE: 2071 000 | moltype = | length = |
| SEQ ID NO: 2072 SEQUENCE: 2072 000 | moltype = | length = |
| SEQ ID NO: 2073 SEQUENCE: 2073 000 | moltype = | length = |
| SEQ ID NO: 2074 SEQUENCE: 2074 000 | moltype = | length = |
| SEQ ID NO: 2075 SEQUENCE: 2075 000 | moltype = | length = |
| SEQ ID NO: 2076 SEQUENCE: 2076 000 | moltype = | length = |
| SEQ ID NO: 2077 SEQUENCE: 2077 000 | moltype = | length = |
| SEQ ID NO: 2078 SEQUENCE: 2078 000 | moltype = | length = |
| SEQ ID NO: 2079 SEQUENCE: 2079 000 | moltype = | length = |
| SEQ ID NO: 2080 SEQUENCE: 2080 000 | moltype = | length = |

-continued

| | | |
|---|---|---|
| SEQ ID NO: 2081<br>SEQUENCE: 2081<br>000 | moltype = | length = |
| SEQ ID NO: 2082<br>SEQUENCE: 2082<br>000 | moltype = | length = |
| SEQ ID NO: 2083<br>SEQUENCE: 2083<br>000 | moltype = | length = |
| SEQ ID NO: 2084<br>SEQUENCE: 2084<br>000 | moltype = | length = |
| SEQ ID NO: 2085<br>SEQUENCE: 2085<br>000 | moltype = | length = |
| SEQ ID NO: 2086<br>SEQUENCE: 2086<br>000 | moltype = | length = |
| SEQ ID NO: 2087<br>SEQUENCE: 2087<br>000 | moltype = | length = |
| SEQ ID NO: 2088<br>SEQUENCE: 2088<br>000 | moltype = | length = |
| SEQ ID NO: 2089<br>SEQUENCE: 2089<br>000 | moltype = | length = |
| SEQ ID NO: 2090<br>SEQUENCE: 2090<br>000 | moltype = | length = |
| SEQ ID NO: 2091<br>SEQUENCE: 2091<br>000 | moltype = | length = |
| SEQ ID NO: 2092<br>SEQUENCE: 2092<br>000 | moltype = | length = |
| SEQ ID NO: 2093<br>SEQUENCE: 2093<br>000 | moltype = | length = |
| SEQ ID NO: 2094<br>SEQUENCE: 2094<br>000 | moltype = | length = |
| SEQ ID NO: 2095<br>SEQUENCE: 2095<br>000 | moltype = | length = |
| SEQ ID NO: 2096<br>SEQUENCE: 2096<br>000 | moltype = | length = |
| SEQ ID NO: 2097<br>SEQUENCE: 2097<br>000 | moltype = | length = |
| SEQ ID NO: 2098<br>SEQUENCE: 2098<br>000 | moltype = | length = |
| SEQ ID NO: 2099<br>SEQUENCE: 2099<br>000 | moltype = | length = |
| SEQ ID NO: 2100<br>SEQUENCE: 2100<br>000 | moltype = | length = |

| | | |
|---|---|---|
| SEQ ID NO: 2101 SEQUENCE: 2101 000 | moltype = | length = |
| SEQ ID NO: 2102 SEQUENCE: 2102 000 | moltype = | length = |
| SEQ ID NO: 2103 SEQUENCE: 2103 000 | moltype = | length = |
| SEQ ID NO: 2104 SEQUENCE: 2104 000 | moltype = | length = |
| SEQ ID NO: 2105 SEQUENCE: 2105 000 | moltype = | length = |
| SEQ ID NO: 2106 SEQUENCE: 2106 000 | moltype = | length = |
| SEQ ID NO: 2107 SEQUENCE: 2107 000 | moltype = | length = |
| SEQ ID NO: 2108 SEQUENCE: 2108 000 | moltype = | length = |
| SEQ ID NO: 2109 SEQUENCE: 2109 000 | moltype = | length = |
| SEQ ID NO: 2110 SEQUENCE: 2110 000 | moltype = | length = |
| SEQ ID NO: 2111 SEQUENCE: 2111 000 | moltype = | length = |
| SEQ ID NO: 2112 SEQUENCE: 2112 000 | moltype = | length = |
| SEQ ID NO: 2113 SEQUENCE: 2113 000 | moltype = | length = |
| SEQ ID NO: 2114 SEQUENCE: 2114 000 | moltype = | length = |
| SEQ ID NO: 2115 SEQUENCE: 2115 000 | moltype = | length = |
| SEQ ID NO: 2116 SEQUENCE: 2116 000 | moltype = | length = |
| SEQ ID NO: 2117 SEQUENCE: 2117 000 | moltype = | length = |
| SEQ ID NO: 2118 SEQUENCE: 2118 000 | moltype = | length = |
| SEQ ID NO: 2119 SEQUENCE: 2119 000 | moltype = | length = |
| SEQ ID NO: 2120 SEQUENCE: 2120 | moltype = | length = |

-continued

000

SEQ ID NO: 2121        moltype =    length =
SEQUENCE: 2121
000

SEQ ID NO: 2122        moltype =    length =
SEQUENCE: 2122
000

SEQ ID NO: 2123        moltype =    length =
SEQUENCE: 2123
000

SEQ ID NO: 2124        moltype =    length =
SEQUENCE: 2124
000

SEQ ID NO: 2125        moltype =    length =
SEQUENCE: 2125
000

SEQ ID NO: 2126        moltype =    length =
SEQUENCE: 2126
000

SEQ ID NO: 2127        moltype =    length =
SEQUENCE: 2127
000

SEQ ID NO: 2128        moltype =    length =
SEQUENCE: 2128
000

SEQ ID NO: 2129        moltype =    length =
SEQUENCE: 2129
000

SEQ ID NO: 2130        moltype =    length =
SEQUENCE: 2130
000

SEQ ID NO: 2131        moltype =    length =
SEQUENCE: 2131
000

SEQ ID NO: 2132        moltype =    length =
SEQUENCE: 2132
000

SEQ ID NO: 2133        moltype =    length =
SEQUENCE: 2133
000

SEQ ID NO: 2134        moltype =    length =
SEQUENCE: 2134
000

SEQ ID NO: 2135        moltype =    length =
SEQUENCE: 2135
000

SEQ ID NO: 2136        moltype =    length =
SEQUENCE: 2136
000

SEQ ID NO: 2137        moltype =    length =
SEQUENCE: 2137
000

SEQ ID NO: 2138        moltype =    length =
SEQUENCE: 2138
000

SEQ ID NO: 2139        moltype =    length =
SEQUENCE: 2139
000

SEQ ID NO: 2140        moltype =    length =

| | | |
|---|---|---|
| SEQUENCE: 2140 000 | | |
| SEQ ID NO: 2141 SEQUENCE: 2141 000 | moltype = | length = |
| SEQ ID NO: 2142 SEQUENCE: 2142 000 | moltype = | length = |
| SEQ ID NO: 2143 SEQUENCE: 2143 000 | moltype = | length = |
| SEQ ID NO: 2144 SEQUENCE: 2144 000 | moltype = | length = |
| SEQ ID NO: 2145 SEQUENCE: 2145 000 | moltype = | length = |
| SEQ ID NO: 2146 SEQUENCE: 2146 000 | moltype = | length = |
| SEQ ID NO: 2147 SEQUENCE: 2147 000 | moltype = | length = |
| SEQ ID NO: 2148 SEQUENCE: 2148 000 | moltype = | length = |
| SEQ ID NO: 2149 SEQUENCE: 2149 000 | moltype = | length = |
| SEQ ID NO: 2150 SEQUENCE: 2150 000 | moltype = | length = |
| SEQ ID NO: 2151 SEQUENCE: 2151 000 | moltype = | length = |
| SEQ ID NO: 2152 SEQUENCE: 2152 000 | moltype = | length = |
| SEQ ID NO: 2153 SEQUENCE: 2153 000 | moltype = | length = |
| SEQ ID NO: 2154 SEQUENCE: 2154 000 | moltype = | length = |
| SEQ ID NO: 2155 SEQUENCE: 2155 000 | moltype = | length = |
| SEQ ID NO: 2156 SEQUENCE: 2156 000 | moltype = | length = |
| SEQ ID NO: 2157 SEQUENCE: 2157 000 | moltype = | length = |
| SEQ ID NO: 2158 SEQUENCE: 2158 000 | moltype = | length = |
| SEQ ID NO: 2159 SEQUENCE: 2159 000 | moltype = | length = |

| | | |
|---|---|---|
| SEQ ID NO: 2160<br>SEQUENCE: 2160<br>000 | moltype = | length = |
| SEQ ID NO: 2161<br>SEQUENCE: 2161<br>000 | moltype = | length = |
| SEQ ID NO: 2162<br>SEQUENCE: 2162<br>000 | moltype = | length = |
| SEQ ID NO: 2163<br>SEQUENCE: 2163<br>000 | moltype = | length = |
| SEQ ID NO: 2164<br>SEQUENCE: 2164<br>000 | moltype = | length = |
| SEQ ID NO: 2165<br>SEQUENCE: 2165<br>000 | moltype = | length = |
| SEQ ID NO: 2166<br>SEQUENCE: 2166<br>000 | moltype = | length = |
| SEQ ID NO: 2167<br>SEQUENCE: 2167<br>000 | moltype = | length = |
| SEQ ID NO: 2168<br>SEQUENCE: 2168<br>000 | moltype = | length = |
| SEQ ID NO: 2169<br>SEQUENCE: 2169<br>000 | moltype = | length = |
| SEQ ID NO: 2170<br>SEQUENCE: 2170<br>000 | moltype = | length = |
| SEQ ID NO: 2171<br>SEQUENCE: 2171<br>000 | moltype = | length = |
| SEQ ID NO: 2172<br>SEQUENCE: 2172<br>000 | moltype = | length = |
| SEQ ID NO: 2173<br>SEQUENCE: 2173<br>000 | moltype = | length = |
| SEQ ID NO: 2174<br>SEQUENCE: 2174<br>000 | moltype = | length = |
| SEQ ID NO: 2175<br>SEQUENCE: 2175<br>000 | moltype = | length = |
| SEQ ID NO: 2176<br>SEQUENCE: 2176<br>000 | moltype = | length = |
| SEQ ID NO: 2177<br>SEQUENCE: 2177<br>000 | moltype = | length = |
| SEQ ID NO: 2178<br>SEQUENCE: 2178<br>000 | moltype = | length = |
| SEQ ID NO: 2179<br>SEQUENCE: 2179<br>000 | moltype = | length = |

SEQ ID NO: 2180        moltype =     length =
SEQUENCE: 2180
000

SEQ ID NO: 2181        moltype =     length =
SEQUENCE: 2181
000

SEQ ID NO: 2182        moltype =     length =
SEQUENCE: 2182
000

SEQ ID NO: 2183        moltype =     length =
SEQUENCE: 2183
000

SEQ ID NO: 2184        moltype =     length =
SEQUENCE: 2184
000

SEQ ID NO: 2185        moltype =     length =
SEQUENCE: 2185
000

SEQ ID NO: 2186        moltype =     length =
SEQUENCE: 2186
000

SEQ ID NO: 2187        moltype =     length =
SEQUENCE: 2187
000

SEQ ID NO: 2188        moltype =     length =
SEQUENCE: 2188
000

SEQ ID NO: 2189        moltype =     length =
SEQUENCE: 2189
000

SEQ ID NO: 2190        moltype =     length =
SEQUENCE: 2190
000

SEQ ID NO: 2191        moltype =     length =
SEQUENCE: 2191
000

SEQ ID NO: 2192        moltype =     length =
SEQUENCE: 2192
000

SEQ ID NO: 2193        moltype =     length =
SEQUENCE: 2193
000

SEQ ID NO: 2194        moltype =     length =
SEQUENCE: 2194
000

SEQ ID NO: 2195        moltype =     length =
SEQUENCE: 2195
000

SEQ ID NO: 2196        moltype =     length =
SEQUENCE: 2196
000

SEQ ID NO: 2197        moltype =     length =
SEQUENCE: 2197
000

SEQ ID NO: 2198        moltype =     length =
SEQUENCE: 2198
000

SEQ ID NO: 2199        moltype =     length =
SEQUENCE: 2199

-continued

000

SEQ ID NO: 2200          moltype =    length =
SEQUENCE: 2200
000

SEQ ID NO: 2201          moltype =    length =
SEQUENCE: 2201
000

SEQ ID NO: 2202          moltype =    length =
SEQUENCE: 2202
000

SEQ ID NO: 2203          moltype =    length =
SEQUENCE: 2203
000

SEQ ID NO: 2204          moltype =    length =
SEQUENCE: 2204
000

SEQ ID NO: 2205          moltype =    length =
SEQUENCE: 2205
000

SEQ ID NO: 2206          moltype =    length =
SEQUENCE: 2206
000

SEQ ID NO: 2207          moltype =    length =
SEQUENCE: 2207
000

SEQ ID NO: 2208          moltype =    length =
SEQUENCE: 2208
000

SEQ ID NO: 2209          moltype =    length =
SEQUENCE: 2209
000

SEQ ID NO: 2210          moltype =    length =
SEQUENCE: 2210
000

SEQ ID NO: 2211          moltype =    length =
SEQUENCE: 2211
000

SEQ ID NO: 2212          moltype =    length =
SEQUENCE: 2212
000

SEQ ID NO: 2213          moltype =    length =
SEQUENCE: 2213
000

SEQ ID NO: 2214          moltype =    length =
SEQUENCE: 2214
000

SEQ ID NO: 2215          moltype =    length =
SEQUENCE: 2215
000

SEQ ID NO: 2216          moltype =    length =
SEQUENCE: 2216
000

SEQ ID NO: 2217          moltype =    length =
SEQUENCE: 2217
000

SEQ ID NO: 2218          moltype =    length =
SEQUENCE: 2218
000

SEQ ID NO: 2219          moltype =    length =

| | | |
|---|---|---|
| SEQUENCE: 2219 000 | | |
| SEQ ID NO: 2220 SEQUENCE: 2220 000 | moltype = | length = |
| SEQ ID NO: 2221 SEQUENCE: 2221 000 | moltype = | length = |
| SEQ ID NO: 2222 SEQUENCE: 2222 000 | moltype = | length = |
| SEQ ID NO: 2223 SEQUENCE: 2223 000 | moltype = | length = |
| SEQ ID NO: 2224 SEQUENCE: 2224 000 | moltype = | length = |
| SEQ ID NO: 2225 SEQUENCE: 2225 000 | moltype = | length = |
| SEQ ID NO: 2226 SEQUENCE: 2226 000 | moltype = | length = |
| SEQ ID NO: 2227 SEQUENCE: 2227 000 | moltype = | length = |
| SEQ ID NO: 2228 SEQUENCE: 2228 000 | moltype = | length = |
| SEQ ID NO: 2229 SEQUENCE: 2229 000 | moltype = | length = |
| SEQ ID NO: 2230 SEQUENCE: 2230 000 | moltype = | length = |
| SEQ ID NO: 2231 SEQUENCE: 2231 000 | moltype = | length = |
| SEQ ID NO: 2232 SEQUENCE: 2232 000 | moltype = | length = |
| SEQ ID NO: 2233 SEQUENCE: 2233 000 | moltype = | length = |
| SEQ ID NO: 2234 SEQUENCE: 2234 000 | moltype = | length = |
| SEQ ID NO: 2235 SEQUENCE: 2235 000 | moltype = | length = |
| SEQ ID NO: 2236 SEQUENCE: 2236 000 | moltype = | length = |
| SEQ ID NO: 2237 SEQUENCE: 2237 000 | moltype = | length = |
| SEQ ID NO: 2238 SEQUENCE: 2238 000 | moltype = | length = |

| | | |
|---|---|---|
| SEQ ID NO: 2239<br>SEQUENCE: 2239<br>000 | moltype = | length = |
| SEQ ID NO: 2240<br>SEQUENCE: 2240<br>000 | moltype = | length = |
| SEQ ID NO: 2241<br>SEQUENCE: 2241<br>000 | moltype = | length = |
| SEQ ID NO: 2242<br>SEQUENCE: 2242<br>000 | moltype = | length = |
| SEQ ID NO: 2243<br>SEQUENCE: 2243<br>000 | moltype = | length = |
| SEQ ID NO: 2244<br>SEQUENCE: 2244<br>000 | moltype = | length = |
| SEQ ID NO: 2245<br>SEQUENCE: 2245<br>000 | moltype = | length = |
| SEQ ID NO: 2246<br>SEQUENCE: 2246<br>000 | moltype = | length = |
| SEQ ID NO: 2247<br>SEQUENCE: 2247<br>000 | moltype = | length = |
| SEQ ID NO: 2248<br>SEQUENCE: 2248<br>000 | moltype = | length = |
| SEQ ID NO: 2249<br>SEQUENCE: 2249<br>000 | moltype = | length = |
| SEQ ID NO: 2250<br>SEQUENCE: 2250<br>000 | moltype = | length = |
| SEQ ID NO: 2251<br>SEQUENCE: 2251<br>000 | moltype = | length = |
| SEQ ID NO: 2252<br>SEQUENCE: 2252<br>000 | moltype = | length = |
| SEQ ID NO: 2253<br>SEQUENCE: 2253<br>000 | moltype = | length = |
| SEQ ID NO: 2254<br>SEQUENCE: 2254<br>000 | moltype = | length = |
| SEQ ID NO: 2255<br>SEQUENCE: 2255<br>000 | moltype = | length = |
| SEQ ID NO: 2256<br>SEQUENCE: 2256<br>000 | moltype = | length = |
| SEQ ID NO: 2257<br>SEQUENCE: 2257<br>000 | moltype = | length = |
| SEQ ID NO: 2258<br>SEQUENCE: 2258<br>000 | moltype = | length = |

| | | |
|---|---|---|
| SEQ ID NO: 2259<br>SEQUENCE: 2259<br>000 | moltype = | length = |
| SEQ ID NO: 2260<br>SEQUENCE: 2260<br>000 | moltype = | length = |
| SEQ ID NO: 2261<br>SEQUENCE: 2261<br>000 | moltype = | length = |
| SEQ ID NO: 2262<br>SEQUENCE: 2262<br>000 | moltype = | length = |
| SEQ ID NO: 2263<br>SEQUENCE: 2263<br>000 | moltype = | length = |
| SEQ ID NO: 2264<br>SEQUENCE: 2264<br>000 | moltype = | length = |
| SEQ ID NO: 2265<br>SEQUENCE: 2265<br>000 | moltype = | length = |
| SEQ ID NO: 2266<br>SEQUENCE: 2266<br>000 | moltype = | length = |
| SEQ ID NO: 2267<br>SEQUENCE: 2267<br>000 | moltype = | length = |
| SEQ ID NO: 2268<br>SEQUENCE: 2268<br>000 | moltype = | length = |
| SEQ ID NO: 2269<br>SEQUENCE: 2269<br>000 | moltype = | length = |
| SEQ ID NO: 2270<br>SEQUENCE: 2270<br>000 | moltype = | length = |
| SEQ ID NO: 2271<br>SEQUENCE: 2271<br>000 | moltype = | length = |
| SEQ ID NO: 2272<br>SEQUENCE: 2272<br>000 | moltype = | length = |
| SEQ ID NO: 2273<br>SEQUENCE: 2273<br>000 | moltype = | length = |
| SEQ ID NO: 2274<br>SEQUENCE: 2274<br>000 | moltype = | length = |
| SEQ ID NO: 2275<br>SEQUENCE: 2275<br>000 | moltype = | length = |
| SEQ ID NO: 2276<br>SEQUENCE: 2276<br>000 | moltype = | length = |
| SEQ ID NO: 2277<br>SEQUENCE: 2277<br>000 | moltype = | length = |
| SEQ ID NO: 2278<br>SEQUENCE: 2278 | moltype = | length = |

000

SEQ ID NO: 2279        moltype =      length =
SEQUENCE: 2279
000

SEQ ID NO: 2280        moltype =      length =
SEQUENCE: 2280
000

SEQ ID NO: 2281        moltype =      length =
SEQUENCE: 2281
000

SEQ ID NO: 2282        moltype =      length =
SEQUENCE: 2282
000

SEQ ID NO: 2283        moltype =      length =
SEQUENCE: 2283
000

SEQ ID NO: 2284        moltype =      length =
SEQUENCE: 2284
000

SEQ ID NO: 2285        moltype =      length =
SEQUENCE: 2285
000

SEQ ID NO: 2286        moltype =      length =
SEQUENCE: 2286
000

SEQ ID NO: 2287        moltype =      length =
SEQUENCE: 2287
000

SEQ ID NO: 2288        moltype =      length =
SEQUENCE: 2288
000

SEQ ID NO: 2289        moltype =      length =
SEQUENCE: 2289
000

SEQ ID NO: 2290        moltype =      length =
SEQUENCE: 2290
000

SEQ ID NO: 2291        moltype =      length =
SEQUENCE: 2291
000

SEQ ID NO: 2292        moltype =      length =
SEQUENCE: 2292
000

SEQ ID NO: 2293        moltype =      length =
SEQUENCE: 2293
000

SEQ ID NO: 2294        moltype =      length =
SEQUENCE: 2294
000

SEQ ID NO: 2295        moltype =      length =
SEQUENCE: 2295
000

SEQ ID NO: 2296        moltype =      length =
SEQUENCE: 2296
000

SEQ ID NO: 2297        moltype =      length =
SEQUENCE: 2297
000

SEQ ID NO: 2298        moltype =      length =

```
SEQUENCE: 2298
000

SEQ ID NO: 2299          moltype =     length =
SEQUENCE: 2299
000

SEQ ID NO: 2300          moltype =     length =
SEQUENCE: 2300
000

SEQ ID NO: 2301          moltype =     length =
SEQUENCE: 2301
000

SEQ ID NO: 2302          moltype =     length =
SEQUENCE: 2302
000

SEQ ID NO: 2303          moltype =     length =
SEQUENCE: 2303
000

SEQ ID NO: 2304          moltype =     length =
SEQUENCE: 2304
000

SEQ ID NO: 2305          moltype =     length =
SEQUENCE: 2305
000

SEQ ID NO: 2306          moltype =     length =
SEQUENCE: 2306
000

SEQ ID NO: 2307          moltype =     length =
SEQUENCE: 2307
000

SEQ ID NO: 2308          moltype =     length =
SEQUENCE: 2308
000

SEQ ID NO: 2309          moltype =     length =
SEQUENCE: 2309
000

SEQ ID NO: 2310          moltype =     length =
SEQUENCE: 2310
000

SEQ ID NO: 2311          moltype =     length =
SEQUENCE: 2311
000

SEQ ID NO: 2312          moltype =     length =
SEQUENCE: 2312
000

SEQ ID NO: 2313          moltype =     length =
SEQUENCE: 2313
000

SEQ ID NO: 2314          moltype =     length =
SEQUENCE: 2314
000

SEQ ID NO: 2315          moltype =     length =
SEQUENCE: 2315
000

SEQ ID NO: 2316          moltype =     length =
SEQUENCE: 2316
000

SEQ ID NO: 2317          moltype =     length =
SEQUENCE: 2317
000
```

-continued

| | | |
|---|---|---|
| SEQ ID NO: 2318<br>SEQUENCE: 2318<br>000 | moltype = | length = |
| SEQ ID NO: 2319<br>SEQUENCE: 2319<br>000 | moltype = | length = |
| SEQ ID NO: 2320<br>SEQUENCE: 2320<br>000 | moltype = | length = |
| SEQ ID NO: 2321<br>SEQUENCE: 2321<br>000 | moltype = | length = |
| SEQ ID NO: 2322<br>SEQUENCE: 2322<br>000 | moltype = | length = |
| SEQ ID NO: 2323<br>SEQUENCE: 2323<br>000 | moltype = | length = |
| SEQ ID NO: 2324<br>SEQUENCE: 2324<br>000 | moltype = | length = |
| SEQ ID NO: 2325<br>SEQUENCE: 2325<br>000 | moltype = | length = |
| SEQ ID NO: 2326<br>SEQUENCE: 2326<br>000 | moltype = | length = |
| SEQ ID NO: 2327<br>SEQUENCE: 2327<br>000 | moltype = | length = |
| SEQ ID NO: 2328<br>SEQUENCE: 2328<br>000 | moltype = | length = |
| SEQ ID NO: 2329<br>SEQUENCE: 2329<br>000 | moltype = | length = |
| SEQ ID NO: 2330<br>SEQUENCE: 2330<br>000 | moltype = | length = |
| SEQ ID NO: 2331<br>SEQUENCE: 2331<br>000 | moltype = | length = |
| SEQ ID NO: 2332<br>SEQUENCE: 2332<br>000 | moltype = | length = |
| SEQ ID NO: 2333<br>SEQUENCE: 2333<br>000 | moltype = | length = |
| SEQ ID NO: 2334<br>SEQUENCE: 2334<br>000 | moltype = | length = |
| SEQ ID NO: 2335<br>SEQUENCE: 2335<br>000 | moltype = | length = |
| SEQ ID NO: 2336<br>SEQUENCE: 2336<br>000 | moltype = | length = |
| SEQ ID NO: 2337<br>SEQUENCE: 2337<br>000 | moltype = | length = |

SEQ ID NO: 2338    moltype =    length =
SEQUENCE: 2338
000

SEQ ID NO: 2339    moltype =    length =
SEQUENCE: 2339
000

SEQ ID NO: 2340    moltype =    length =
SEQUENCE: 2340
000

SEQ ID NO: 2341    moltype =    length =
SEQUENCE: 2341
000

SEQ ID NO: 2342    moltype =    length =
SEQUENCE: 2342
000

SEQ ID NO: 2343    moltype =    length =
SEQUENCE: 2343
000

SEQ ID NO: 2344    moltype =    length =
SEQUENCE: 2344
000

SEQ ID NO: 2345    moltype =    length =
SEQUENCE: 2345
000

SEQ ID NO: 2346    moltype =    length =
SEQUENCE: 2346
000

SEQ ID NO: 2347    moltype =    length =
SEQUENCE: 2347
000

SEQ ID NO: 2348    moltype =    length =
SEQUENCE: 2348
000

SEQ ID NO: 2349    moltype =    length =
SEQUENCE: 2349
000

SEQ ID NO: 2350    moltype =    length =
SEQUENCE: 2350
000

SEQ ID NO: 2351    moltype =    length =
SEQUENCE: 2351
000

SEQ ID NO: 2352    moltype =    length =
SEQUENCE: 2352
000

SEQ ID NO: 2353    moltype =    length =
SEQUENCE: 2353
000

SEQ ID NO: 2354    moltype =    length =
SEQUENCE: 2354
000

SEQ ID NO: 2355    moltype =    length =
SEQUENCE: 2355
000

SEQ ID NO: 2356    moltype =    length =
SEQUENCE: 2356
000

SEQ ID NO: 2357    moltype =    length =
SEQUENCE: 2357

000

SEQ ID NO: 2358          moltype =     length =
SEQUENCE: 2358
000

SEQ ID NO: 2359          moltype =     length =
SEQUENCE: 2359
000

SEQ ID NO: 2360          moltype =     length =
SEQUENCE: 2360
000

SEQ ID NO: 2361          moltype =     length =
SEQUENCE: 2361
000

SEQ ID NO: 2362          moltype =     length =
SEQUENCE: 2362
000

SEQ ID NO: 2363          moltype =     length =
SEQUENCE: 2363
000

SEQ ID NO: 2364          moltype =     length =
SEQUENCE: 2364
000

SEQ ID NO: 2365          moltype =     length =
SEQUENCE: 2365
000

SEQ ID NO: 2366          moltype =     length =
SEQUENCE: 2366
000

SEQ ID NO: 2367          moltype =     length =
SEQUENCE: 2367
000

SEQ ID NO: 2368          moltype =     length =
SEQUENCE: 2368
000

SEQ ID NO: 2369          moltype =     length =
SEQUENCE: 2369
000

SEQ ID NO: 2370          moltype =     length =
SEQUENCE: 2370
000

SEQ ID NO: 2371          moltype =     length =
SEQUENCE: 2371
000

SEQ ID NO: 2372          moltype =     length =
SEQUENCE: 2372
000

SEQ ID NO: 2373          moltype =     length =
SEQUENCE: 2373
000

SEQ ID NO: 2374          moltype =     length =
SEQUENCE: 2374
000

SEQ ID NO: 2375          moltype =     length =
SEQUENCE: 2375
000

SEQ ID NO: 2376          moltype =     length =
SEQUENCE: 2376
000

SEQ ID NO: 2377          moltype =     length =

-continued

| | | |
|---|---|---|
| SEQUENCE: 2377 000 | | |
| SEQ ID NO: 2378 SEQUENCE: 2378 000 | moltype = | length = |
| SEQ ID NO: 2379 SEQUENCE: 2379 000 | moltype = | length = |
| SEQ ID NO: 2380 SEQUENCE: 2380 000 | moltype = | length = |
| SEQ ID NO: 2381 SEQUENCE: 2381 000 | moltype = | length = |
| SEQ ID NO: 2382 SEQUENCE: 2382 000 | moltype = | length = |
| SEQ ID NO: 2383 SEQUENCE: 2383 000 | moltype = | length = |
| SEQ ID NO: 2384 SEQUENCE: 2384 000 | moltype = | length = |
| SEQ ID NO: 2385 SEQUENCE: 2385 000 | moltype = | length = |
| SEQ ID NO: 2386 SEQUENCE: 2386 000 | moltype = | length = |
| SEQ ID NO: 2387 SEQUENCE: 2387 000 | moltype = | length = |
| SEQ ID NO: 2388 SEQUENCE: 2388 000 | moltype = | length = |
| SEQ ID NO: 2389 SEQUENCE: 2389 000 | moltype = | length = |
| SEQ ID NO: 2390 SEQUENCE: 2390 000 | moltype = | length = |
| SEQ ID NO: 2391 SEQUENCE: 2391 000 | moltype = | length = |
| SEQ ID NO: 2392 SEQUENCE: 2392 000 | moltype = | length = |
| SEQ ID NO: 2393 SEQUENCE: 2393 000 | moltype = | length = |
| SEQ ID NO: 2394 SEQUENCE: 2394 000 | moltype = | length = |
| SEQ ID NO: 2395 SEQUENCE: 2395 000 | moltype = | length = |
| SEQ ID NO: 2396 SEQUENCE: 2396 000 | moltype = | length = |

-continued

| | | |
|---|---|---|
| SEQ ID NO: 2397 SEQUENCE: 2397 | moltype = | length = 000 |
| SEQ ID NO: 2398 SEQUENCE: 2398 | moltype = | length = 000 |
| SEQ ID NO: 2399 SEQUENCE: 2399 | moltype = | length = 000 |
| SEQ ID NO: 2400 SEQUENCE: 2400 | moltype = | length = 000 |
| SEQ ID NO: 2401 SEQUENCE: 2401 | moltype = | length = 000 |
| SEQ ID NO: 2402 SEQUENCE: 2402 | moltype = | length = 000 |
| SEQ ID NO: 2403 SEQUENCE: 2403 | moltype = | length = 000 |
| SEQ ID NO: 2404 SEQUENCE: 2404 | moltype = | length = 000 |
| SEQ ID NO: 2405 SEQUENCE: 2405 | moltype = | length = 000 |
| SEQ ID NO: 2406 SEQUENCE: 2406 | moltype = | length = 000 |
| SEQ ID NO: 2407 SEQUENCE: 2407 | moltype = | length = 000 |
| SEQ ID NO: 2408 SEQUENCE: 2408 | moltype = | length = 000 |
| SEQ ID NO: 2409 SEQUENCE: 2409 | moltype = | length = 000 |
| SEQ ID NO: 2410 SEQUENCE: 2410 | moltype = | length = 000 |
| SEQ ID NO: 2411 SEQUENCE: 2411 | moltype = | length = 000 |
| SEQ ID NO: 2412 SEQUENCE: 2412 | moltype = | length = 000 |
| SEQ ID NO: 2413 SEQUENCE: 2413 | moltype = | length = 000 |
| SEQ ID NO: 2414 SEQUENCE: 2414 | moltype = | length = 000 |
| SEQ ID NO: 2415 SEQUENCE: 2415 | moltype = | length = 000 |
| SEQ ID NO: 2416 SEQUENCE: 2416 | moltype = | length = 000 |

```
SEQ ID NO: 2417      moltype =    length =
SEQUENCE: 2417
000

SEQ ID NO: 2418      moltype =    length =
SEQUENCE: 2418
000

SEQ ID NO: 2419      moltype =    length =
SEQUENCE: 2419
000

SEQ ID NO: 2420      moltype =    length =
SEQUENCE: 2420
000

SEQ ID NO: 2421      moltype =    length =
SEQUENCE: 2421
000

SEQ ID NO: 2422      moltype =    length =
SEQUENCE: 2422
000

SEQ ID NO: 2423      moltype =    length =
SEQUENCE: 2423
000

SEQ ID NO: 2424      moltype =    length =
SEQUENCE: 2424
000

SEQ ID NO: 2425      moltype =    length =
SEQUENCE: 2425
000

SEQ ID NO: 2426      moltype =    length =
SEQUENCE: 2426
000

SEQ ID NO: 2427      moltype =    length =
SEQUENCE: 2427
000

SEQ ID NO: 2428      moltype =    length =
SEQUENCE: 2428
000

SEQ ID NO: 2429      moltype =    length =
SEQUENCE: 2429
000

SEQ ID NO: 2430      moltype =    length =
SEQUENCE: 2430
000

SEQ ID NO: 2431      moltype =    length =
SEQUENCE: 2431
000

SEQ ID NO: 2432      moltype =    length =
SEQUENCE: 2432
000

SEQ ID NO: 2433      moltype =    length =
SEQUENCE: 2433
000

SEQ ID NO: 2434      moltype =    length =
SEQUENCE: 2434
000

SEQ ID NO: 2435      moltype =    length =
SEQUENCE: 2435
000

SEQ ID NO: 2436      moltype =    length =
SEQUENCE: 2436
```

-continued

000

SEQ ID NO: 2437      moltype =    length =
SEQUENCE: 2437
000

SEQ ID NO: 2438      moltype =    length =
SEQUENCE: 2438
000

SEQ ID NO: 2439      moltype =    length =
SEQUENCE: 2439
000

SEQ ID NO: 2440      moltype =    length =
SEQUENCE: 2440
000

SEQ ID NO: 2441      moltype =    length =
SEQUENCE: 2441
000

SEQ ID NO: 2442      moltype =    length =
SEQUENCE: 2442
000

SEQ ID NO: 2443      moltype =    length =
SEQUENCE: 2443
000

SEQ ID NO: 2444      moltype =    length =
SEQUENCE: 2444
000

SEQ ID NO: 2445      moltype =    length =
SEQUENCE: 2445
000

SEQ ID NO: 2446      moltype =    length =
SEQUENCE: 2446
000

SEQ ID NO: 2447      moltype =    length =
SEQUENCE: 2447
000

SEQ ID NO: 2448      moltype =    length =
SEQUENCE: 2448
000

SEQ ID NO: 2449      moltype =    length =
SEQUENCE: 2449
000

SEQ ID NO: 2450      moltype =    length =
SEQUENCE: 2450
000

SEQ ID NO: 2451      moltype =    length =
SEQUENCE: 2451
000

SEQ ID NO: 2452      moltype =    length =
SEQUENCE: 2452
000

SEQ ID NO: 2453      moltype =    length =
SEQUENCE: 2453
000

SEQ ID NO: 2454      moltype =    length =
SEQUENCE: 2454
000

SEQ ID NO: 2455      moltype =    length =
SEQUENCE: 2455
000

SEQ ID NO: 2456      moltype =    length =

```
SEQUENCE: 2456
000

SEQ ID NO: 2457          moltype =     length =
SEQUENCE: 2457
000

SEQ ID NO: 2458          moltype =     length =
SEQUENCE: 2458
000

SEQ ID NO: 2459          moltype =     length =
SEQUENCE: 2459
000

SEQ ID NO: 2460          moltype =     length =
SEQUENCE: 2460
000

SEQ ID NO: 2461          moltype =     length =
SEQUENCE: 2461
000

SEQ ID NO: 2462          moltype =     length =
SEQUENCE: 2462
000

SEQ ID NO: 2463          moltype =     length =
SEQUENCE: 2463
000

SEQ ID NO: 2464          moltype =     length =
SEQUENCE: 2464
000

SEQ ID NO: 2465          moltype =     length =
SEQUENCE: 2465
000

SEQ ID NO: 2466          moltype =     length =
SEQUENCE: 2466
000

SEQ ID NO: 2467          moltype =     length =
SEQUENCE: 2467
000

SEQ ID NO: 2468          moltype =     length =
SEQUENCE: 2468
000

SEQ ID NO: 2469          moltype =     length =
SEQUENCE: 2469
000

SEQ ID NO: 2470          moltype =     length =
SEQUENCE: 2470
000

SEQ ID NO: 2471          moltype =     length =
SEQUENCE: 2471
000

SEQ ID NO: 2472          moltype =     length =
SEQUENCE: 2472
000

SEQ ID NO: 2473          moltype =     length =
SEQUENCE: 2473
000

SEQ ID NO: 2474          moltype =     length =
SEQUENCE: 2474
000

SEQ ID NO: 2475          moltype =     length =
SEQUENCE: 2475
000
```

| | | |
|---|---|---|
| SEQ ID NO: 2476<br>SEQUENCE: 2476<br>000 | moltype = | length = |
| SEQ ID NO: 2477<br>SEQUENCE: 2477<br>000 | moltype = | length = |
| SEQ ID NO: 2478<br>SEQUENCE: 2478<br>000 | moltype = | length = |
| SEQ ID NO: 2479<br>SEQUENCE: 2479<br>000 | moltype = | length = |
| SEQ ID NO: 2480<br>SEQUENCE: 2480<br>000 | moltype = | length = |
| SEQ ID NO: 2481<br>SEQUENCE: 2481<br>000 | moltype = | length = |
| SEQ ID NO: 2482<br>SEQUENCE: 2482<br>000 | moltype = | length = |
| SEQ ID NO: 2483<br>SEQUENCE: 2483<br>000 | moltype = | length = |
| SEQ ID NO: 2484<br>SEQUENCE: 2484<br>000 | moltype = | length = |
| SEQ ID NO: 2485<br>SEQUENCE: 2485<br>000 | moltype = | length = |
| SEQ ID NO: 2486<br>SEQUENCE: 2486<br>000 | moltype = | length = |
| SEQ ID NO: 2487<br>SEQUENCE: 2487<br>000 | moltype = | length = |
| SEQ ID NO: 2488<br>SEQUENCE: 2488<br>000 | moltype = | length = |
| SEQ ID NO: 2489<br>SEQUENCE: 2489<br>000 | moltype = | length = |
| SEQ ID NO: 2490<br>SEQUENCE: 2490<br>000 | moltype = | length = |
| SEQ ID NO: 2491<br>SEQUENCE: 2491<br>000 | moltype = | length = |
| SEQ ID NO: 2492<br>SEQUENCE: 2492<br>000 | moltype = | length = |
| SEQ ID NO: 2493<br>SEQUENCE: 2493<br>000 | moltype = | length = |
| SEQ ID NO: 2494<br>SEQUENCE: 2494<br>000 | moltype = | length = |
| SEQ ID NO: 2495<br>SEQUENCE: 2495<br>000 | moltype = | length = |

| | | |
|---|---|---|
| SEQ ID NO: 2496<br>SEQUENCE: 2496<br>000 | moltype = | length = |
| SEQ ID NO: 2497<br>SEQUENCE: 2497<br>000 | moltype = | length = |
| SEQ ID NO: 2498<br>SEQUENCE: 2498<br>000 | moltype = | length = |
| SEQ ID NO: 2499<br>SEQUENCE: 2499<br>000 | moltype = | length = |
| SEQ ID NO: 2500<br>SEQUENCE: 2500<br>000 | moltype = | length = |
| SEQ ID NO: 2501<br>SEQUENCE: 2501<br>000 | moltype = | length = |
| SEQ ID NO: 2502<br>SEQUENCE: 2502<br>000 | moltype = | length = |
| SEQ ID NO: 2503<br>SEQUENCE: 2503<br>000 | moltype = | length = |
| SEQ ID NO: 2504<br>SEQUENCE: 2504<br>000 | moltype = | length = |
| SEQ ID NO: 2505<br>SEQUENCE: 2505<br>000 | moltype = | length = |
| SEQ ID NO: 2506<br>SEQUENCE: 2506<br>000 | moltype = | length = |
| SEQ ID NO: 2507<br>SEQUENCE: 2507<br>000 | moltype = | length = |
| SEQ ID NO: 2508<br>SEQUENCE: 2508<br>000 | moltype = | length = |
| SEQ ID NO: 2509<br>SEQUENCE: 2509<br>000 | moltype = | length = |
| SEQ ID NO: 2510<br>SEQUENCE: 2510<br>000 | moltype = | length = |
| SEQ ID NO: 2511<br>SEQUENCE: 2511<br>000 | moltype = | length = |
| SEQ ID NO: 2512<br>SEQUENCE: 2512<br>000 | moltype = | length = |
| SEQ ID NO: 2513<br>SEQUENCE: 2513<br>000 | moltype = | length = |
| SEQ ID NO: 2514<br>SEQUENCE: 2514<br>000 | moltype = | length = |
| SEQ ID NO: 2515<br>SEQUENCE: 2515 | moltype = | length = |

```
000

SEQ ID NO: 2516        moltype =    length =
SEQUENCE: 2516
000

SEQ ID NO: 2517        moltype =    length =
SEQUENCE: 2517
000

SEQ ID NO: 2518        moltype =    length =
SEQUENCE: 2518
000

SEQ ID NO: 2519        moltype =    length =
SEQUENCE: 2519
000

SEQ ID NO: 2520        moltype =    length =
SEQUENCE: 2520
000

SEQ ID NO: 2521        moltype =    length =
SEQUENCE: 2521
000

SEQ ID NO: 2522        moltype =    length =
SEQUENCE: 2522
000

SEQ ID NO: 2523        moltype =    length =
SEQUENCE: 2523
000

SEQ ID NO: 2524        moltype =    length =
SEQUENCE: 2524
000

SEQ ID NO: 2525        moltype =    length =
SEQUENCE: 2525
000

SEQ ID NO: 2526        moltype =    length =
SEQUENCE: 2526
000

SEQ ID NO: 2527        moltype =    length =
SEQUENCE: 2527
000

SEQ ID NO: 2528        moltype =    length =
SEQUENCE: 2528
000

SEQ ID NO: 2529        moltype =    length =
SEQUENCE: 2529
000

SEQ ID NO: 2530        moltype =    length =
SEQUENCE: 2530
000

SEQ ID NO: 2531        moltype =    length =
SEQUENCE: 2531
000

SEQ ID NO: 2532        moltype =    length =
SEQUENCE: 2532
000

SEQ ID NO: 2533        moltype =    length =
SEQUENCE: 2533
000

SEQ ID NO: 2534        moltype =    length =
SEQUENCE: 2534
000

SEQ ID NO: 2535        moltype =    length =
```

| | | |
|---|---|---|
| SEQUENCE: 2535 000 | | |
| SEQ ID NO: 2536 SEQUENCE: 2536 000 | moltype = | length = |
| SEQ ID NO: 2537 SEQUENCE: 2537 000 | moltype = | length = |
| SEQ ID NO: 2538 SEQUENCE: 2538 000 | moltype = | length = |
| SEQ ID NO: 2539 SEQUENCE: 2539 000 | moltype = | length = |
| SEQ ID NO: 2540 SEQUENCE: 2540 000 | moltype = | length = |
| SEQ ID NO: 2541 SEQUENCE: 2541 000 | moltype = | length = |
| SEQ ID NO: 2542 SEQUENCE: 2542 000 | moltype = | length = |
| SEQ ID NO: 2543 SEQUENCE: 2543 000 | moltype = | length = |
| SEQ ID NO: 2544 SEQUENCE: 2544 000 | moltype = | length = |
| SEQ ID NO: 2545 SEQUENCE: 2545 000 | moltype = | length = |
| SEQ ID NO: 2546 SEQUENCE: 2546 000 | moltype = | length = |
| SEQ ID NO: 2547 SEQUENCE: 2547 000 | moltype = | length = |
| SEQ ID NO: 2548 SEQUENCE: 2548 000 | moltype = | length = |
| SEQ ID NO: 2549 SEQUENCE: 2549 000 | moltype = | length = |
| SEQ ID NO: 2550 SEQUENCE: 2550 000 | moltype = | length = |
| SEQ ID NO: 2551 SEQUENCE: 2551 000 | moltype = | length = |
| SEQ ID NO: 2552 SEQUENCE: 2552 000 | moltype = | length = |
| SEQ ID NO: 2553 SEQUENCE: 2553 000 | moltype = | length = |
| SEQ ID NO: 2554 SEQUENCE: 2554 000 | moltype = | length = |

| | | |
|---|---|---|
| SEQ ID NO: 2555<br>SEQUENCE: 2555<br>000 | moltype = | length = |
| SEQ ID NO: 2556<br>SEQUENCE: 2556<br>000 | moltype = | length = |
| SEQ ID NO: 2557<br>SEQUENCE: 2557<br>000 | moltype = | length = |
| SEQ ID NO: 2558<br>SEQUENCE: 2558<br>000 | moltype = | length = |
| SEQ ID NO: 2559<br>SEQUENCE: 2559<br>000 | moltype = | length = |
| SEQ ID NO: 2560<br>SEQUENCE: 2560<br>000 | moltype = | length = |
| SEQ ID NO: 2561<br>SEQUENCE: 2561<br>000 | moltype = | length = |
| SEQ ID NO: 2562<br>SEQUENCE: 2562<br>000 | moltype = | length = |
| SEQ ID NO: 2563<br>SEQUENCE: 2563<br>000 | moltype = | length = |
| SEQ ID NO: 2564<br>SEQUENCE: 2564<br>000 | moltype = | length = |
| SEQ ID NO: 2565<br>SEQUENCE: 2565<br>000 | moltype = | length = |
| SEQ ID NO: 2566<br>SEQUENCE: 2566<br>000 | moltype = | length = |
| SEQ ID NO: 2567<br>SEQUENCE: 2567<br>000 | moltype = | length = |
| SEQ ID NO: 2568<br>SEQUENCE: 2568<br>000 | moltype = | length = |
| SEQ ID NO: 2569<br>SEQUENCE: 2569<br>000 | moltype = | length = |
| SEQ ID NO: 2570<br>SEQUENCE: 2570<br>000 | moltype = | length = |
| SEQ ID NO: 2571<br>SEQUENCE: 2571<br>000 | moltype = | length = |
| SEQ ID NO: 2572<br>SEQUENCE: 2572<br>000 | moltype = | length = |
| SEQ ID NO: 2573<br>SEQUENCE: 2573<br>000 | moltype = | length = |
| SEQ ID NO: 2574<br>SEQUENCE: 2574<br>000 | moltype = | length = |

| | | |
|---|---|---|
| SEQ ID NO: 2575<br>SEQUENCE: 2575<br>000 | moltype = | length = |
| SEQ ID NO: 2576<br>SEQUENCE: 2576<br>000 | moltype = | length = |
| SEQ ID NO: 2577<br>SEQUENCE: 2577<br>000 | moltype = | length = |
| SEQ ID NO: 2578<br>SEQUENCE: 2578<br>000 | moltype = | length = |
| SEQ ID NO: 2579<br>SEQUENCE: 2579<br>000 | moltype = | length = |
| SEQ ID NO: 2580<br>SEQUENCE: 2580<br>000 | moltype = | length = |
| SEQ ID NO: 2581<br>SEQUENCE: 2581<br>000 | moltype = | length = |
| SEQ ID NO: 2582<br>SEQUENCE: 2582<br>000 | moltype = | length = |
| SEQ ID NO: 2583<br>SEQUENCE: 2583<br>000 | moltype = | length = |
| SEQ ID NO: 2584<br>SEQUENCE: 2584<br>000 | moltype = | length = |
| SEQ ID NO: 2585<br>SEQUENCE: 2585<br>000 | moltype = | length = |
| SEQ ID NO: 2586<br>SEQUENCE: 2586<br>000 | moltype = | length = |
| SEQ ID NO: 2587<br>SEQUENCE: 2587<br>000 | moltype = | length = |
| SEQ ID NO: 2588<br>SEQUENCE: 2588<br>000 | moltype = | length = |
| SEQ ID NO: 2589<br>SEQUENCE: 2589<br>000 | moltype = | length = |
| SEQ ID NO: 2590<br>SEQUENCE: 2590<br>000 | moltype = | length = |
| SEQ ID NO: 2591<br>FEATURE<br>source<br><br>SEQUENCE: 2591<br>SASTGAS | moltype = AA   length = 7<br>Location/Qualifiers<br>1..7<br>mol_type = protein<br>note = Dependovirus adeno-associated virus<br>organism = unidentified<br><br> | <br><br><br><br><br><br>7 |
| SEQ ID NO: 2592<br>FEATURE<br>source | moltype = AA   length = 10<br>Location/Qualifiers<br>1..10<br>mol_type = protein<br>note = Dependovirus adeno-associated virus | |

```
                                  -continued organism = unidentified
SEQUENCE: 2592
VFMIPQYGYL                                                       10

SEQ ID NO: 2593        moltype = AA  length = 9
FEATURE                Location/Qualifiers
source                 1..9
                       mol_type = protein
                       note = Dependovirus adeno-associated virus
                       organism = unidentified
SEQUENCE: 2593
NQSGSAQNK                                                         9

SEQ ID NO: 2594        moltype =     length =
SEQUENCE: 2594
000

SEQ ID NO: 2595        moltype = AA  length = 8
FEATURE                Location/Qualifiers
source                 1..8
                       mol_type = protein
                       note = Dependovirus adeno-associated virus
                       organism = unidentified
SEQUENCE: 2595
KTDNNNSN                                                          8

SEQ ID NO: 2596        moltype = AA  length = 7
FEATURE                Location/Qualifiers
source                 1..7
                       mol_type = protein
                       note = Dependovirus adeno-associated virus
                       organism = unidentified
SEQUENCE: 2596
KDDEDKF                                                           7

SEQ ID NO: 2597        moltype = AA  length = 6
FEATURE                Location/Qualifiers
source                 1..6
                       mol_type = protein
                       note = Dependovirus adeno-associated virus
                       organism = unidentified
SEQUENCE: 2597
SAGASN                                                            6

SEQ ID NO: 2598        moltype = AA  length = 10
FEATURE                Location/Qualifiers
source                 1..10
                       mol_type = protein
                       note = Dependovirus adeno-associated virus
                       organism = unidentified
SEQUENCE: 2598
STDPATGDVH                                                       10

SEQ ID NO: 2599        moltype =     length =
SEQUENCE: 2599
000

SEQ ID NO: 2600        moltype = AA  length = 7
FEATURE                Location/Qualifiers
source                 1..7
                       mol_type = protein
                       note = Dependovirus adeno-associated virus
                       organism = unidentified
SEQUENCE: 2600
DNNGLYT                                                           7

SEQ ID NO: 2601        moltype = AA  length = 6
FEATURE                Location/Qualifiers
source                 1..6
                       mol_type = protein
                       note = Dependovirus adeno-associated virus
                       organism = unidentified
SEQUENCE: 2601
SQSGAS                                                            6

SEQ ID NO: 2602        moltype = AA  length = 10
FEATURE                Location/Qualifiers
source                 1..10
                       mol_type = protein
```

```
                        note = Dependovirus adeno-associated virus
                        organism = unidentified
SEQUENCE: 2602
VFMVPQYGYL                                                              10

SEQ ID NO: 2603         moltype = AA  length = 9
FEATURE                 Location/Qualifiers
source                  1..9
                        mol_type = protein
                        note = Dependovirus adeno-associated virus
                        organism = unidentified
SEQUENCE: 2603
TPSGTTTQS                                                                9

SEQ ID NO: 2604         moltype =     length =
SEQUENCE: 2604
000

SEQ ID NO: 2605         moltype = AA  length = 8
FEATURE                 Location/Qualifiers
source                  1..8
                        mol_type = protein
                        note = Dependovirus adeno-associated virus
                        organism = unidentified
SEQUENCE: 2605
SADNNNSE                                                                 8

SEQ ID NO: 2606         moltype = AA  length = 7
FEATURE                 Location/Qualifiers
source                  1..7
                        mol_type = protein
                        note = Dependovirus adeno-associated virus
                        organism = unidentified
SEQUENCE: 2606
KDDEEKF                                                                  7

SEQ ID NO: 2607         moltype = AA  length = 6
FEATURE                 Location/Qualifiers
source                  1..6
                        mol_type = protein
                        note = Dependovirus adeno-associated virus
                        organism = unidentified
SEQUENCE: 2607
GSEKTN                                                                   6

SEQ ID NO: 2608         moltype = AA  length = 10
FEATURE                 Location/Qualifiers
source                  1..10
                        mol_type = protein
                        note = Dependovirus adeno-associated virus
                        organism = unidentified
SEQUENCE: 2608
NRQAATADVN                                                              10

SEQ ID NO: 2609         moltype =     length =
SEQUENCE: 2609
000

SEQ ID NO: 2610         moltype = AA  length = 7
FEATURE                 Location/Qualifiers
source                  1..7
                        mol_type = protein
                        note = Dependovirus adeno-associated virus
                        organism = unidentified
SEQUENCE: 2610
DTNGVYS                                                                  7

SEQ ID NO: 2611         moltype = AA  length = 6
FEATURE                 Location/Qualifiers
source                  1..6
                        mol_type = protein
                        note = Dependovirus adeno-associated virus
                        organism = unidentified
SEQUENCE: 2611
SQSGAS                                                                   6

SEQ ID NO: 2612         moltype = AA  length = 10
FEATURE                 Location/Qualifiers
source                  1..10
```

```
SEQ ID NO: 2612              moltype = AA  length = 10
                             mol_type = protein
                             note = Dependovirus adeno-associated virus
                             organism = unidentified
SEQUENCE: 2612
VFMVPQYGYL                                                          10

SEQ ID NO: 2613              moltype = AA  length = 9
FEATURE                      Location/Qualifiers
source                       1..9
                             mol_type = protein
                             note = Dependovirus adeno-associated virus
                             organism = unidentified
SEQUENCE: 2613
TTSGTTNQS                                                            9

SEQ ID NO: 2614              moltype =   length =
SEQUENCE: 2614
000

SEQ ID NO: 2615              moltype = AA  length = 8
FEATURE                      Location/Qualifiers
source                       1..8
                             mol_type = protein
                             note = Dependovirus adeno-associated virus
                             organism = unidentified
SEQUENCE: 2615
ANDNNNSN                                                             8

SEQ ID NO: 2616              moltype = AA  length = 7
FEATURE                      Location/Qualifiers
source                       1..7
                             mol_type = protein
                             note = Dependovirus adeno-associated virus
                             organism = unidentified
SEQUENCE: 2616
KDDEEKF                                                              7

SEQ ID NO: 2617              moltype = AA  length = 6
FEATURE                      Location/Qualifiers
source                       1..6
                             mol_type = protein
                             note = Dependovirus adeno-associated virus
                             organism = unidentified
SEQUENCE: 2617
GTTASN                                                               6

SEQ ID NO: 2618              moltype = AA  length = 10
FEATURE                      Location/Qualifiers
source                       1..10
                             mol_type = protein
                             note = Dependovirus adeno-associated virus
                             organism = unidentified
SEQUENCE: 2618
NTAPTTGTVN                                                          10

SEQ ID NO: 2619              moltype =   length =
SEQUENCE: 2619
000

SEQ ID NO: 2620              moltype = AA  length = 7
FEATURE                      Location/Qualifiers
source                       1..7
                             mol_type = protein
                             note = Dependovirus adeno-associated virus
                             organism = unidentified
SEQUENCE: 2620
DTNGVYS                                                              7

SEQ ID NO: 2621              moltype = AA  length = 8
FEATURE                      Location/Qualifiers
source                       1..8
                             mol_type = protein
                             note = Dependovirus adeno-associated virus
                             organism = unidentified
SEQUENCE: 2621
RLGESLQS                                                             8

SEQ ID NO: 2622              moltype = AA  length = 10
FEATURE                      Location/Qualifiers
```

| | | |
|---|---|---|
| source | 1..10<br>mol_type = protein<br>note = Dependovirus adeno-associated virus<br>organism = unidentified | |
| SEQUENCE: 2622<br>VFMVPQYGYC | | 10 |
| SEQ ID NO: 2623<br>FEATURE<br>source | moltype = AA  length = 9<br>Location/Qualifiers<br>1..9<br>mol_type = protein<br>note = Dependovirus adeno-associated virus<br>organism = unidentified | |
| SEQUENCE: 2623<br>GTTLNAGTA | | 9 |
| SEQ ID NO: 2624<br>SEQUENCE: 2624<br>000 | moltype =   length = | |
| SEQ ID NO: 2625<br>FEATURE<br>source | moltype = AA  length = 12<br>Location/Qualifiers<br>1..12<br>mol_type = protein<br>note = Dependovirus adeno-associated virus<br>organism = unidentified | |
| SEQUENCE: 2625<br>ANQNYKIPAT GS | | 12 |
| SEQ ID NO: 2626<br>FEATURE<br>source | moltype = AA  length = 7<br>Location/Qualifiers<br>1..7<br>mol_type = protein<br>note = Dependovirus adeno-associated virus<br>organism = unidentified | |
| SEQUENCE: 2626<br>GPADSKF | | 7 |
| SEQ ID NO: 2627<br>FEATURE<br>source | moltype = AA  length = 6<br>Location/Qualifiers<br>1..6<br>mol_type = protein<br>note = Dependovirus adeno-associated virus<br>organism = unidentified | |
| SEQUENCE: 2627<br>QNGNTA | | 6 |
| SEQ ID NO: 2628<br>FEATURE<br>source | moltype = AA  length = 10<br>Location/Qualifiers<br>1..10<br>mol_type = protein<br>note = Dependovirus adeno-associated virus<br>organism = unidentified | |
| SEQUENCE: 2628<br>SNLPTVDRLT | | 10 |
| SEQ ID NO: 2629<br>SEQUENCE: 2629<br>000 | moltype =   length = | |
| SEQ ID NO: 2630<br>FEATURE<br>source | moltype = AA  length = 7<br>Location/Qualifiers<br>1..7<br>mol_type = protein<br>note = Dependovirus adeno-associated virus<br>organism = unidentified | |
| SEQUENCE: 2630<br>DAAGKYT | | 7 |
| SEQ ID NO: 2631<br>FEATURE<br>source | moltype = AA  length = 10<br>Location/Qualifiers<br>1..10<br>mol_type = protein<br>note = Dependovirus adeno-associated virus<br>organism = unidentified | |
| SEQUENCE: 2631<br>EIKSGSVDGS | | 10 |
| SEQ ID NO: 2632 | moltype = AA  length = 10 | |

| | | |
|---|---|---|
| FEATURE | Location/Qualifiers | |
| source | 1..10 | |
| | mol_type = protein | |
| | note = Dependovirus adeno-associated virus | |
| | organism = unidentified | |
| SEQUENCE: 2632 | | |
| VFTLPQYGYA | | 10 |
| | | |
| SEQ ID NO: 2633 | moltype = AA length = 9 | |
| FEATURE | Location/Qualifiers | |
| source | 1..9 | |
| | mol_type = protein | |
| | note = Dependovirus adeno-associated virus | |
| | organism = unidentified | |
| SEQUENCE: 2633 | | |
| STNNTGGVQ | | 9 |
| | | |
| SEQ ID NO: 2634 | moltype = length = | |
| SEQUENCE: 2634 | | |
| 000 | | |
| | | |
| SEQ ID NO: 2635 | moltype = AA length = 7 | |
| FEATURE | Location/Qualifiers | |
| source | 1..7 | |
| | mol_type = protein | |
| | note = Dependovirus adeno-associated virus | |
| | organism = unidentified | |
| SEQUENCE: 2635 | | |
| SGVNRAS | | 7 |
| | | |
| SEQ ID NO: 2636 | moltype = AA length = 7 | |
| FEATURE | Location/Qualifiers | |
| source | 1..7 | |
| | mol_type = protein | |
| | note = Dependovirus adeno-associated virus | |
| | organism = unidentified | |
| SEQUENCE: 2636 | | |
| LQGSNTY | | 7 |
| | | |
| SEQ ID NO: 2637 | moltype = AA length = 8 | |
| FEATURE | Location/Qualifiers | |
| source | 1..8 | |
| | mol_type = protein | |
| | note = Dependovirus adeno-associated virus | |
| | organism = unidentified | |
| SEQUENCE: 2637 | | |
| ANPGTTAT | | 8 |
| | | |
| SEQ ID NO: 2638 | moltype = AA length = 10 | |
| FEATURE | Location/Qualifiers | |
| source | 1..10 | |
| | mol_type = protein | |
| | note = Dependovirus adeno-associated virus | |
| | organism = unidentified | |
| SEQUENCE: 2638 | | |
| TTAPATGTYN | | 10 |
| | | |
| SEQ ID NO: 2639 | moltype = length = | |
| SEQUENCE: 2639 | | |
| 000 | | |
| | | |
| SEQ ID NO: 2640 | moltype = AA length = 7 | |
| FEATURE | Location/Qualifiers | |
| source | 1..7 | |
| | mol_type = protein | |
| | note = Dependovirus adeno-associated virus | |
| | organism = unidentified | |
| SEQUENCE: 2640 | | |
| DSTGEYR | | 7 |
| | | |
| SEQ ID NO: 2641 | moltype = AA length = 7 | |
| FEATURE | Location/Qualifiers | |
| source | 1..7 | |
| | mol_type = protein | |
| | note = Dependovirus adeno-associated virus | |
| | organism = unidentified | |
| SEQUENCE: 2641 | | |
| SASTGAS | | 7 |

| | | |
|---|---|---|
| SEQ ID NO: 2642<br>FEATURE<br>source | moltype = AA  length = 10<br>Location/Qualifiers<br>1..10<br>mol_type = protein<br>note = Dependovirus adeno-associated virus<br>organism = unidentified | |
| SEQUENCE: 2642<br>VFMIPQYGYL | | 10 |
| SEQ ID NO: 2643<br>FEATURE<br>source | moltype = AA  length = 9<br>Location/Qualifiers<br>1..9<br>mol_type = protein<br>note = Dependovirus adeno-associated virus<br>organism = unidentified | |
| SEQUENCE: 2643<br>NQSGSAQNK | | 9 |
| SEQ ID NO: 2644<br>SEQUENCE: 2644<br>000 | moltype =   length = | |
| SEQ ID NO: 2645<br>FEATURE<br>source | moltype = AA  length = 8<br>Location/Qualifiers<br>1..8<br>mol_type = protein<br>note = Dependovirus adeno-associated virus<br>organism = unidentified | |
| SEQUENCE: 2645<br>KTDNNNSN | | 8 |
| SEQ ID NO: 2646<br>FEATURE<br>source | moltype = AA  length = 7<br>Location/Qualifiers<br>1..7<br>mol_type = protein<br>note = Dependovirus adeno-associated virus<br>organism = unidentified | |
| SEQUENCE: 2646<br>KDDKDKF | | 7 |
| SEQ ID NO: 2647<br>FEATURE<br>source | moltype = AA  length = 6<br>Location/Qualifiers<br>1..6<br>mol_type = protein<br>note = Dependovirus adeno-associated virus<br>organism = unidentified | |
| SEQUENCE: 2647<br>SAGASN | | 6 |
| SEQ ID NO: 2648<br>FEATURE<br>source | moltype = AA  length = 10<br>Location/Qualifiers<br>1..10<br>mol_type = protein<br>note = Dependovirus adeno-associated virus<br>organism = unidentified | |
| SEQUENCE: 2648<br>STDPATGDVH | | 10 |
| SEQ ID NO: 2649<br>SEQUENCE: 2649<br>000 | moltype =   length = | |
| SEQ ID NO: 2650<br>FEATURE<br>source | moltype = AA  length = 7<br>Location/Qualifiers<br>1..7<br>mol_type = protein<br>note = Dependovirus adeno-associated virus<br>organism = unidentified | |
| SEQUENCE: 2650<br>DNNGLYT | | 7 |
| SEQ ID NO: 2651<br>FEATURE<br>source | moltype = AA  length = 7<br>Location/Qualifiers<br>1..7<br>mol_type = protein<br>note = Dependovirus adeno-associated virus<br>organism = unidentified | |
| SEQUENCE: 2651<br>SETAGST | | 7 |

```
SEQ ID NO: 2652          moltype = AA  length = 10
FEATURE                  Location/Qualifiers
source                   1..10
                         mol_type = protein
                         note = Dependovirus adeno-associated virus
                         organism = unidentified
SEQUENCE: 2652
VFMIPQYGYL                                                              10

SEQ ID NO: 2653          moltype = AA  length = 9
FEATURE                  Location/Qualifiers
source                   1..9
                         mol_type = protein
                         note = Dependovirus adeno-associated virus
                         organism = unidentified
SEQUENCE: 2653
NPGGTAGNR                                                                9

SEQ ID NO: 2654          moltype =    length =
SEQUENCE: 2654
000

SEQ ID NO: 2655          moltype = AA  length = 8
FEATURE                  Location/Qualifiers
source                   1..8
                         mol_type = protein
                         note = Dependovirus adeno-associated virus
                         organism = unidentified
SEQUENCE: 2655
LDQNNNSN                                                                 8

SEQ ID NO: 2656          moltype = AA  length = 7
FEATURE                  Location/Qualifiers
source                   1..7
                         mol_type = protein
                         note = Dependovirus adeno-associated virus
                         organism = unidentified
SEQUENCE: 2656
KDDEDRF                                                                  7

SEQ ID NO: 2657          moltype = AA  length = 6
FEATURE                  Location/Qualifiers
source                   1..6
                         mol_type = protein
                         note = Dependovirus adeno-associated virus
                         organism = unidentified
SEQUENCE: 2657
GATNKT                                                                   6

SEQ ID NO: 2658          moltype = AA  length = 10
FEATURE                  Location/Qualifiers
source                   1..10
                         mol_type = protein
                         note = Dependovirus adeno-associated virus
                         organism = unidentified
SEQUENCE: 2658
NTAAQTQVVN                                                              10

SEQ ID NO: 2659          moltype =    length =
SEQUENCE: 2659
000

SEQ ID NO: 2660          moltype = AA  length = 7
FEATURE                  Location/Qualifiers
source                   1..7
                         mol_type = protein
                         note = Dependovirus adeno-associated virus
                         organism = unidentified
SEQUENCE: 2660
DSQGVYS                                                                  7

SEQ ID NO: 2661          moltype = AA  length = 8
FEATURE                  Location/Qualifiers
source                   1..8
                         mol_type = protein
                         note = Dependovirus adeno-associated virus
                         organism = unidentified
SEQUENCE: 2661
```

| | | |
|---|---|---|
| NGTSGGAT | | 8 |
| SEQ ID NO: 2662<br>FEATURE<br>source<br><br>SEQUENCE: 2662<br>VFMIPQYGYL | moltype = AA  length = 10<br>Location/Qualifiers<br>1..10<br>mol_type = protein<br>note = Dependovirus adeno-associated virus<br>organism = unidentified | <br><br><br><br><br>10 |
| SEQ ID NO: 2663<br>FEATURE<br>source<br><br>SEQUENCE: 2663<br>TTGGTANTQ | moltype = AA  length = 9<br>Location/Qualifiers<br>1..9<br>mol_type = protein<br>note = Dependovirus adeno-associated virus<br>organism = unidentified | <br><br><br><br><br>9 |
| SEQ ID NO: 2664<br>SEQUENCE: 2664<br>000 | moltype =   length = | |
| SEQ ID NO: 2665<br>FEATURE<br>source<br><br>SEQUENCE: 2665<br>TGQNNNSN | moltype = AA  length = 8<br>Location/Qualifiers<br>1..8<br>mol_type = protein<br>note = Dependovirus adeno-associated virus<br>organism = unidentified | <br><br><br><br><br>8 |
| SEQ ID NO: 2666<br>FEATURE<br>source<br><br>SEQUENCE: 2666<br>KDDEERF | moltype = AA  length = 7<br>Location/Qualifiers<br>1..7<br>mol_type = protein<br>note = Dependovirus adeno-associated virus<br>organism = unidentified | <br><br><br><br><br>7 |
| SEQ ID NO: 2667<br>FEATURE<br>source<br><br>SEQUENCE: 2667<br>NAARDN | moltype = AA  length = 6<br>Location/Qualifiers<br>1..6<br>mol_type = protein<br>note = Dependovirus adeno-associated virus<br>organism = unidentified | <br><br><br><br><br>6 |
| SEQ ID NO: 2668<br>FEATURE<br>source<br><br>SEQUENCE: 2668<br>NTAPQIGTVN S | moltype = AA  length = 11<br>Location/Qualifiers<br>1..11<br>mol_type = protein<br>note = Dependovirus adeno-associated virus<br>organism = unidentified | <br><br><br><br><br>11 |
| SEQ ID NO: 2669<br>SEQUENCE: 2669<br>000 | moltype =   length = | |
| SEQ ID NO: 2670<br>FEATURE<br>source<br><br>SEQUENCE: 2670<br>NTEGVYS | moltype = AA  length = 7<br>Location/Qualifiers<br>1..7<br>mol_type = protein<br>note = Dependovirus adeno-associated virus<br>organism = unidentified | <br><br><br><br><br>7 |
| SEQ ID NO: 2671<br>FEATURE<br>source | moltype = AA  length = 8<br>Location/Qualifiers<br>1..8<br>mol_type = protein<br>note = Dependovirus adeno-associated virus<br>organism = unidentified | |

| | | |
|---|---|---|
| SEQUENCE: 2671 NSTSGGSS | | 8 |
| SEQ ID NO: 2672 FEATURE source | moltype = AA  length = 10 Location/Qualifiers 1..10 mol_type = protein note = Dependovirus adeno-associated virus organism = unidentified | |
| SEQUENCE: 2672 VFMIPQYGYL | | 10 |
| SEQ ID NO: 2673 FEATURE source | moltype = AA  length = 9 Location/Qualifiers 1..9 mol_type = protein note = Dependovirus adeno-associated virus organism = unidentified | |
| SEQUENCE: 2673 INGSGQNQQ | | 9 |
| SEQ ID NO: 2674 SEQUENCE: 2674 000 | moltype =   length = | |
| SEQ ID NO: 2675 FEATURE source | moltype = AA  length = 8 Location/Qualifiers 1..8 mol_type = protein note = Dependovirus adeno-associated virus organism = unidentified | |
| SEQUENCE: 2675 VTQNNNSE | | 8 |
| SEQ ID NO: 2676 FEATURE source | moltype = AA  length = 7 Location/Qualifiers 1..7 mol_type = protein note = Dependovirus adeno-associated virus organism = unidentified | |
| SEQUENCE: 2676 KEGEDRF | | 7 |
| SEQ ID NO: 2677 FEATURE source | moltype = AA  length = 6 Location/Qualifiers 1..6 mol_type = protein note = Dependovirus adeno-associated virus organism = unidentified | |
| SEQUENCE: 2677 GTGRDN | | 6 |
| SEQ ID NO: 2678 FEATURE source | moltype = AA  length = 10 Location/Qualifiers 1..10 mol_type = protein note = Dependovirus adeno-associated virus organism = unidentified | |
| SEQUENCE: 2678 QAQAQTGWVQ | | 10 |
| SEQ ID NO: 2679 SEQUENCE: 2679 000 | moltype =   length = | |
| SEQ ID NO: 2680 FEATURE source | moltype = AA  length = 7 Location/Qualifiers 1..7 mol_type = protein note = Dependovirus adeno-associated virus organism = unidentified | |
| SEQUENCE: 2680 NTEGVYS | | 7 |
| SEQ ID NO: 2681 FEATURE source | moltype = AA  length = 8 Location/Qualifiers 1..8 mol_type = protein note = Dependovirus adeno-associated virus | |

```
                                    -continued
SEQUENCE: 2681                                          organism = unidentified
NGTSGGST                                                                       8

SEQ ID NO: 2682         moltype = AA  length = 10
FEATURE                 Location/Qualifiers
source                  1..10
                        mol_type = protein
                        note = Dependovirus adeno-associated virus
                        organism = unidentified
SEQUENCE: 2682
VFMVPQYGYL                                                                    10

SEQ ID NO: 2683         moltype = AA  length = 9
FEATURE                 Location/Qualifiers
source                  1..9
                        mol_type = protein
                        note = Dependovirus adeno-associated virus
                        organism = unidentified
SEQUENCE: 2683
QTTGTGGTQ                                                                      9

SEQ ID NO: 2684         moltype =  length =
SEQUENCE: 2684
000

SEQ ID NO: 2685         moltype = AA  length = 8
FEATURE                 Location/Qualifiers
source                  1..8
                        mol_type = protein
                        note = Dependovirus adeno-associated virus
                        organism = unidentified
SEQUENCE: 2685
TNQNNNSN                                                                       8

SEQ ID NO: 2686         moltype = AA  length = 7
FEATURE                 Location/Qualifiers
source                  1..7
                        mol_type = protein
                        note = Dependovirus adeno-associated virus
                        organism = unidentified
SEQUENCE: 2686
KDDDDRF                                                                        7

SEQ ID NO: 2687         moltype = AA  length = 6
FEATURE                 Location/Qualifiers
source                  1..6
                        mol_type = protein
                        note = Dependovirus adeno-associated virus
                        organism = unidentified
SEQUENCE: 2687
GAGNDG                                                                         6

SEQ ID NO: 2688         moltype = AA  length = 10
FEATURE                 Location/Qualifiers
source                  1..10
                        mol_type = protein
                        note = Dependovirus adeno-associated virus
                        organism = unidentified
SEQUENCE: 2688
NTQAQTGLVH                                                                    10

SEQ ID NO: 2689         moltype =  length =
SEQUENCE: 2689
000

SEQ ID NO: 2690         moltype = AA  length = 7
FEATURE                 Location/Qualifiers
source                  1..7
                        mol_type = protein
                        note = Dependovirus adeno-associated virus
                        organism = unidentified
SEQUENCE: 2690
NTEGVYS                                                                        7

SEQ ID NO: 2691         moltype = AA  length = 8
FEATURE                 Location/Qualifiers
source                  1..8
                        mol_type = protein
```

```
SEQUENCE: 2691
NGTSGGST                                                                 8

SEQ ID NO: 2692       moltype = AA  length = 10
FEATURE               Location/Qualifiers
source                1..10
                      mol_type = protein
                      note = Dependovirus adeno-associated virus
                      organism = unidentified
SEQUENCE: 2692
VFMIPQYGYL                                                              10

SEQ ID NO: 2693       moltype = AA  length = 9
FEATURE               Location/Qualifiers
source                1..9
                      mol_type = protein
                      note = Dependovirus adeno-associated virus
                      organism = unidentified
SEQUENCE: 2693
STGGTAGTQ                                                                9

SEQ ID NO: 2694       moltype =     length =
SEQUENCE: 2694
000

SEQ ID NO: 2695       moltype = AA  length = 8
FEATURE               Location/Qualifiers
source                1..8
                      mol_type = protein
                      note = Dependovirus adeno-associated virus
                      organism = unidentified
SEQUENCE: 2695
LSQNNNSN                                                                 8

SEQ ID NO: 2696       moltype = AA  length = 7
FEATURE               Location/Qualifiers
source                1..7
                      mol_type = protein
                      note = Dependovirus adeno-associated virus
                      organism = unidentified
SEQUENCE: 2696
KDDEERF                                                                  7

SEQ ID NO: 2697       moltype = AA  length = 6
FEATURE               Location/Qualifiers
source                1..6
                      mol_type = protein
                      note = Dependovirus adeno-associated virus
                      organism = unidentified
SEQUENCE: 2697
GAGKDN                                                                   6

SEQ ID NO: 2698       moltype = AA  length = 10
FEATURE               Location/Qualifiers
source                1..10
                      mol_type = protein
                      note = Dependovirus adeno-associated virus
                      organism = unidentified
SEQUENCE: 2698
NAAPIVGAVN                                                              10

SEQ ID NO: 2699       moltype =     length =
SEQUENCE: 2699
000

SEQ ID NO: 2700       moltype = AA  length = 7
FEATURE               Location/Qualifiers
source                1..7
                      mol_type = protein
                      note = Dependovirus adeno-associated virus
                      organism = unidentified
SEQUENCE: 2700
NTDGTYS                                                                  7

SEQ ID NO: 2701       moltype = AA  length = 8
FEATURE               Location/Qualifiers
source                1..8
```

```
                         mol_type = protein
                         note = Dependovirus adeno-associated virus
                         organism = unidentified
SEQUENCE: 2701
NGTSGGST                                                               8

SEQ ID NO: 2702          moltype = AA  length = 10
FEATURE                  Location/Qualifiers
source                   1..10
                         mol_type = protein
                         note = Dependovirus adeno-associated virus
                         organism = unidentified
SEQUENCE: 2702
VFMIPQYGYL                                                            10

SEQ ID NO: 2703          moltype = AA  length = 9
FEATURE                  Location/Qualifiers
source                   1..9
                         mol_type = protein
                         note = Dependovirus adeno-associated virus
                         organism = unidentified
SEQUENCE: 2703
STGGTQGTQ                                                              9

SEQ ID NO: 2704          moltype =     length =
SEQUENCE: 2704
000

SEQ ID NO: 2705          moltype = AA  length = 8
FEATURE                  Location/Qualifiers
source                   1..8
                         mol_type = protein
                         note = Dependovirus adeno-associated virus
                         organism = unidentified
SEQUENCE: 2705
LSQNNNSN                                                               8

SEQ ID NO: 2706          moltype = AA  length = 7
FEATURE                  Location/Qualifiers
source                   1..7
                         mol_type = protein
                         note = Dependovirus adeno-associated virus
                         organism = unidentified
SEQUENCE: 2706
KDDEERF                                                                7

SEQ ID NO: 2707          moltype = AA  length = 6
FEATURE                  Location/Qualifiers
source                   1..6
                         mol_type = protein
                         note = Dependovirus adeno-associated virus
                         organism = unidentified
SEQUENCE: 2707
GAGRDN                                                                 6

SEQ ID NO: 2708          moltype = AA  length = 10
FEATURE                  Location/Qualifiers
source                   1..10
                         mol_type = protein
                         note = Dependovirus adeno-associated virus
                         organism = unidentified
SEQUENCE: 2708
NTGPIVGNVN                                                            10

SEQ ID NO: 2709          moltype =     length =
SEQUENCE: 2709
000

SEQ ID NO: 2710          moltype = AA  length = 7
FEATURE                  Location/Qualifiers
source                   1..7
                         mol_type = protein
                         note = Dependovirus adeno-associated virus
                         organism = unidentified
SEQUENCE: 2710
NTEGTYS                                                                7

SEQ ID NO: 2711          moltype = AA  length = 8
FEATURE                  Location/Qualifiers
```

-continued

| | | |
|---|---|---|
| source | 1..8<br>mol_type = protein<br>note = Dependovirus adeno-associated virus<br>organism = unidentified | |
| SEQUENCE: 2711<br>RLGTTSSS | | 8 |
| SEQ ID NO: 2712<br>FEATURE<br>source | moltype = AA   length = 10<br>Location/Qualifiers<br>1..10<br>mol_type = protein<br>note = Dependovirus adeno-associated virus<br>organism = unidentified | |
| SEQUENCE: 2712<br>VFMVPQYGYC | | 10 |
| SEQ ID NO: 2713<br>FEATURE<br>source | moltype = AA   length = 9<br>Location/Qualifiers<br>1..9<br>mol_type = protein<br>note = Dependovirus adeno-associated virus<br>organism = unidentified | |
| SEQUENCE: 2713<br>GETLNQGNA | | 9 |
| SEQ ID NO: 2714<br>SEQUENCE: 2714<br>000 | moltype =    length = | |
| SEQ ID NO: 2715<br>FEATURE<br>source | moltype = AA   length = 12<br>Location/Qualifiers<br>1..12<br>mol_type = protein<br>note = Dependovirus adeno-associated virus<br>organism = unidentified | |
| SEQUENCE: 2715<br>ASQNYKIPAS GG | | 12 |
| SEQ ID NO: 2716<br>FEATURE<br>source | moltype = AA   length = 7<br>Location/Qualifiers<br>1..7<br>mol_type = protein<br>note = Dependovirus adeno-associated virus<br>organism = unidentified | |
| SEQUENCE: 2716<br>GPSDGDF | | 7 |
| SEQ ID NO: 2717<br>FEATURE<br>source | moltype = AA   length = 6<br>Location/Qualifiers<br>1..6<br>mol_type = protein<br>note = Dependovirus adeno-associated virus<br>organism = unidentified | |
| SEQUENCE: 2717<br>VTGNTT | | 6 |
| SEQ ID NO: 2718<br>FEATURE<br>source | moltype = AA   length = 10<br>Location/Qualifiers<br>1..10<br>mol_type = protein<br>note = Dependovirus adeno-associated virus<br>organism = unidentified | |
| SEQUENCE: 2718<br>TTAPITGNVT | | 10 |
| SEQ ID NO: 2719<br>SEQUENCE: 2719<br>000 | moltype =    length = | |
| SEQ ID NO: 2720<br>FEATURE<br>source | moltype = AA   length = 7<br>Location/Qualifiers<br>1..7<br>mol_type = protein<br>note = Dependovirus adeno-associated virus<br>organism = unidentified | |
| SEQUENCE: 2720<br>DTTGKYT | | 7 |
| SEQ ID NO: 2721 | moltype = AA   length = 8 | |

```
FEATURE                 Location/Qualifiers
source                  1..8
                        mol_type = protein
                        note = Dependovirus adeno-associated virus
                        organism = unidentified
SEQUENCE: 2721
RIGTTANS                                                              8

SEQ ID NO: 2722         moltype = AA  length = 10
FEATURE                 Location/Qualifiers
source                  1..10
                        mol_type = protein
                        note = Dependovirus adeno-associated virus
                        organism = unidentified
SEQUENCE: 2722
VFMVPQYGYC                                                           10

SEQ ID NO: 2723         moltype = AA  length = 9
FEATURE                 Location/Qualifiers
source                  1..9
                        mol_type = protein
                        note = Dependovirus adeno-associated virus
                        organism = unidentified
SEQUENCE: 2723
GNSLNQGTA                                                             9

SEQ ID NO: 2724         moltype =   length =
SEQUENCE: 2724
000

SEQ ID NO: 2725         moltype = AA  length = 12
FEATURE                 Location/Qualifiers
source                  1..12
                        mol_type = protein
                        note = Dependovirus adeno-associated virus
                        organism = unidentified
SEQUENCE: 2725
ANQNYKIPAS GG                                                        12

SEQ ID NO: 2726         moltype = AA  length = 7
FEATURE                 Location/Qualifiers
source                  1..7
                        mol_type = protein
                        note = Dependovirus adeno-associated virus
                        organism = unidentified
SEQUENCE: 2726
GAGDSDF                                                               7

SEQ ID NO: 2727         moltype = AA  length = 6
FEATURE                 Location/Qualifiers
source                  1..6
                        mol_type = protein
                        note = Dependovirus adeno-associated virus
                        organism = unidentified
SEQUENCE: 2727
PSGNTT                                                                6

SEQ ID NO: 2728         moltype = AA  length = 10
FEATURE                 Location/Qualifiers
source                  1..10
                        mol_type = protein
                        note = Dependovirus adeno-associated virus
                        organism = unidentified
SEQUENCE: 2728
TTAPHIANLD                                                           10

SEQ ID NO: 2729         moltype =   length =
SEQUENCE: 2729
000

SEQ ID NO: 2730         moltype = AA  length = 7
FEATURE                 Location/Qualifiers
source                  1..7
                        mol_type = protein
                        note = Dependovirus adeno-associated virus
                        organism = unidentified
SEQUENCE: 2730
DNAGNYH                                                               7
```

| | | |
|---|---|---|
| SEQ ID NO: 2731<br>FEATURE<br>source | moltype = AA   length = 8<br>Location/Qualifiers<br>1..8<br>mol_type = protein<br>note = Dependovirus adeno-associated virus<br>organism = unidentified | |
| SEQUENCE: 2731<br>RLGTTSNS | | 8 |
| SEQ ID NO: 2732<br>FEATURE<br>source | moltype = AA   length = 10<br>Location/Qualifiers<br>1..10<br>mol_type = protein<br>note = Dependovirus adeno-associated virus<br>organism = unidentified | |
| SEQUENCE: 2732<br>VFMVPQYGYC | | 10 |
| SEQ ID NO: 2733<br>FEATURE<br>source | moltype = AA   length = 9<br>Location/Qualifiers<br>1..9<br>mol_type = protein<br>note = Dependovirus adeno-associated virus<br>organism = unidentified | |
| SEQUENCE: 2733<br>GETLNQGNA | | 9 |
| SEQ ID NO: 2734<br>SEQUENCE: 2734<br>000 | moltype =   length = | |
| SEQ ID NO: 2735<br>FEATURE<br>source | moltype = AA   length = 12<br>Location/Qualifiers<br>1..12<br>mol_type = protein<br>note = Dependovirus adeno-associated virus<br>organism = unidentified | |
| SEQUENCE: 2735<br>ASQNYKIPAS GG | | 12 |
| SEQ ID NO: 2736<br>FEATURE<br>source | moltype = AA   length = 7<br>Location/Qualifiers<br>1..7<br>mol_type = protein<br>note = Dependovirus adeno-associated virus<br>organism = unidentified | |
| SEQUENCE: 2736<br>GPSDGDF | | 7 |
| SEQ ID NO: 2737<br>FEATURE<br>source | moltype = AA   length = 6<br>Location/Qualifiers<br>1..6<br>mol_type = protein<br>note = Dependovirus adeno-associated virus<br>organism = unidentified | |
| SEQUENCE: 2737<br>VTGNTT | | 6 |
| SEQ ID NO: 2738<br>FEATURE<br>source | moltype = AA   length = 10<br>Location/Qualifiers<br>1..10<br>mol_type = protein<br>note = Dependovirus adeno-associated virus<br>organism = unidentified | |
| SEQUENCE: 2738<br>TTAPITGNVT | | 10 |
| SEQ ID NO: 2739<br>SEQUENCE: 2739<br>000 | moltype =   length = | |
| SEQ ID NO: 2740<br>FEATURE<br>source | moltype = AA   length = 7<br>Location/Qualifiers<br>1..7<br>mol_type = protein<br>note = Dependovirus adeno-associated virus<br>organism = unidentified | |
| SEQUENCE: 2740<br>DTTGKYT | | 7 |

```
SEQ ID NO: 2741          moltype = AA  length = 8
FEATURE                  Location/Qualifiers
source                   1..8
                         mol_type = protein
                         note = Dependovirus adeno-associated virus
                         organism = unidentified
SEQUENCE: 2741
RLGSSNAS                                                                  8

SEQ ID NO: 2742          moltype = AA  length = 10
FEATURE                  Location/Qualifiers
source                   1..10
                         mol_type = protein
                         note = Dependovirus adeno-associated virus
                         organism = unidentified
SEQUENCE: 2742
VFMVPQYGYC                                                               10

SEQ ID NO: 2743          moltype = AA  length = 9
FEATURE                  Location/Qualifiers
source                   1..9
                         mol_type = protein
                         note = Dependovirus adeno-associated virus
                         organism = unidentified
SEQUENCE: 2743
GGTLNQGNS                                                                 9

SEQ ID NO: 2744          moltype =     length =
SEQUENCE: 2744
000

SEQ ID NO: 2745          moltype = AA  length = 12
FEATURE                  Location/Qualifiers
source                   1..12
                         mol_type = protein
                         note = Dependovirus adeno-associated virus
                         organism = unidentified
SEQUENCE: 2745
ASQNYKIPQG RN                                                            12

SEQ ID NO: 2746          moltype = AA  length = 7
FEATURE                  Location/Qualifiers
source                   1..7
                         mol_type = protein
                         note = Dependovirus adeno-associated virus
                         organism = unidentified
SEQUENCE: 2746
ANDATDF                                                                   7

SEQ ID NO: 2747          moltype = AA  length = 6
FEATURE                  Location/Qualifiers
source                   1..6
                         mol_type = protein
                         note = Dependovirus adeno-associated virus
                         organism = unidentified
SEQUENCE: 2747
ITGNTT                                                                    6

SEQ ID NO: 2748          moltype = AA  length = 10
FEATURE                  Location/Qualifiers
source                   1..10
                         mol_type = protein
                         note = Dependovirus adeno-associated virus
                         organism = unidentified
SEQUENCE: 2748
TTVPTVDDVD                                                               10

SEQ ID NO: 2749          moltype =     length =
SEQUENCE: 2749
000

SEQ ID NO: 2750          moltype = AA  length = 7
FEATURE                  Location/Qualifiers
source                   1..7
                         mol_type = protein
                         note = Dependovirus adeno-associated virus
                         organism = unidentified
SEQUENCE: 2750
```

```
DNAGAYK                                                                      7

SEQ ID NO: 2751         moltype = AA  length = 8
FEATURE                 Location/Qualifiers
source                  1..8
                        mol_type = protein
                        note = Dependovirus adeno-associated virus
                        organism = unidentified
SEQUENCE: 2751
RIQGPSGG                                                                     8

SEQ ID NO: 2752         moltype = AA  length = 10
FEATURE                 Location/Qualifiers
source                  1..10
                        mol_type = protein
                        note = Dependovirus adeno-associated virus
                        organism = unidentified
SEQUENCE: 2752
IYTIPQYGYC                                                                  10

SEQ ID NO: 2753         moltype = AA  length = 9
FEATURE                 Location/Qualifiers
source                  1..9
                        mol_type = protein
                        note = Dependovirus adeno-associated virus
                        organism = unidentified
SEQUENCE: 2753
VSQAGSSGR                                                                    9

SEQ ID NO: 2754         moltype =     length =
SEQUENCE: 2754
000

SEQ ID NO: 2755         moltype = AA  length = 12
FEATURE                 Location/Qualifiers
source                  1..12
                        mol_type = protein
                        note = Dependovirus adeno-associated virus
                        organism = unidentified
SEQUENCE: 2755
ASNITKNNVF SV                                                               12

SEQ ID NO: 2756         moltype = AA  length = 7
FEATURE                 Location/Qualifiers
source                  1..7
                        mol_type = protein
                        note = Dependovirus adeno-associated virus
                        organism = unidentified
SEQUENCE: 2756
FSGEPDR                                                                      7

SEQ ID NO: 2757         moltype = AA  length = 8
FEATURE                 Location/Qualifiers
source                  1..8
                        mol_type = protein
                        note = Dependovirus adeno-associated virus
                        organism = unidentified
SEQUENCE: 2757
VYDQTTAT                                                                     8

SEQ ID NO: 2758         moltype = AA  length = 10
FEATURE                 Location/Qualifiers
source                  1..10
                        mol_type = protein
                        note = Dependovirus adeno-associated virus
                        organism = unidentified
SEQUENCE: 2758
VTPGTRAAVN                                                                  10

SEQ ID NO: 2759         moltype =     length =
SEQUENCE: 2759
000
```

```
SEQ ID NO: 2760        moltype = AA  length = 7
FEATURE                Location/Qualifiers
source                 1..7
                       mol_type = protein
                       note = Dependovirus adeno-associated virus
                       organism = unidentified
SEQUENCE: 2760
SDTGSYS                                                                  7
```

What is claimed is:

1. An adeno-associated virus (AAV) vector comprising an AAV capsid protein, wherein the AAV capsid protein comprises the amino acid sequence of SEQ ID NO: 180.

2. The AAV vector of claim 1, wherein the AAV vector comprises a cargo nucleic acid, wherein the cargo nucleic acid is encapsidated by the AAV capsid protein.

3. The AAV vector of claim 2, wherein the cargo nucleic acid comprises at least one terminal repeat sequence.

4. The AAV vector of claim 3, wherein the cargo nucleic acid comprises a heterologous nucleic acid sequence.

5. The AAV vector of claim 4, wherein the cargo nucleic acid comprises inverted terminal repeat (ITR) sequences located 3' and 5' of the heterologous sequence.

6. The AAV vector of claim 4, wherein the heterologous nucleic acid sequence encodes a polypeptide.

7. The AAV vector of claim 6, wherein the polypeptide is a therapeutic polypeptide.

8. The AAV vector of claim 6, wherein the polypeptide is an immunogenic polypeptide.

9. The AAV vector of claim 6, wherein the polypeptide is nuclease.

10. The AAV vector of claim 9, wherein the nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, or a modified or truncated variant of any thereof.

11. The AAV vector of claim 4, wherein the heterologous nucleic acid sequence encodes an untranslated RNA.

12. The AAV vector of claim 11, wherein the untranslated RNA is a guide RNA.

13. The AAV vector of claim 11, wherein the untranslated RNA is an antisense RNA, a ribozyme, or an interfering RNA.

14. A pharmaceutical composition comprising the AAV vector of claim 2 and a pharmaceutically acceptable carrier.

15. A method of introducing a cargo nucleic acid molecule into a cell, comprising contacting the cell with the AAV vector of claim 2.

16. An adeno-associated virus (AAV) capsid protein comprising the amino acid sequence of SEQ ID NO: 180.

17. A nucleic acid comprising a nucleic acid sequence encoding the AAV capsid protein of claim 16.

18. A cell comprising the nucleic acid of claim 17.

19. An expression vector comprising a nucleic acid sequence encoding the AAV capsid protein of claim 16.

20. A method of producing an adeno-associated virus (AAV) vector, the method comprising:
   a. culturing a cell that comprises (i) the nucleic acid of claim 17, (ii) a cargo nucleic acid comprising a 5' inverted terminal repeat (ITR), a heterologous acid sequence, and a 3' ITR, and (iii) AAV sequences sufficient for replication and encapsidation of nucleic acid, wherein the cell is cultured under conditions such that it produces the AAV vector; and
   b. collecting the AAV vector from the cell.

* * * * *